US008293714B2

(12) United States Patent
Doppalapudi et al.

(10) Patent No.: US 8,293,714 B2
(45) Date of Patent: Oct. 23, 2012

(54) ANTI-ANGIOGENIC COMPOUNDS

(75) Inventors: Venkata Ramana Doppalapudi, San Diego, CA (US); Jing-Yu Lai, San Diego, CA (US); Bin Liu, San Diego, CA (US); Dingguo Liu, San Marcos, CA (US); Joel Desharnais, La Mesa, CA (US); Abhijit Suresh Bhat, Encinitas, CA (US); Yanwen Fu, San Diego, CA (US); Bryan Douglas Oates, Carlsbad, CA (US); Gang Chen, San Diego, CA (US); Curt William Bradshaw, San Diego, CA (US)

(73) Assignee: Covx Technology Ireland, Ltd., Dun Laoighaire, County Dublin (IE)

( * ) Notice: Subject to any disclaimer, the term of this patent is extended or adjusted under 35 U.S.C. 154(b) by 509 days.

(21) Appl. No.: 12/432,528

(22) Filed: Apr. 29, 2009

(65) Prior Publication Data

US 2010/0003267 A1    Jan. 7, 2010

Related U.S. Application Data

(60) Provisional application No. 61/050,544, filed on May 5, 2008, provisional application No. 61/050,569, filed on May 5, 2008, provisional application No. 61/050,574, filed on May 5, 2008.

(51) Int. Cl.
    *A61K 38/16* (2006.01)
(52) U.S. Cl. ................. 514/21.3; 514/8.1; 530/324
(58) Field of Classification Search .................. None
    See application file for complete search history.

(56) References Cited

U.S. PATENT DOCUMENTS

| | | | |
|---|---|---|---|
| 3,719,667 A | 3/1973 | Gutowski | |
| 3,840,556 A | 10/1974 | Kukolja | |
| 5,229,275 A | 7/1993 | Goroff et al. | |
| 5,567,610 A | 10/1996 | Borrebaeck et al. | |
| 5,733,757 A | 3/1998 | Barbas et al. | |
| 5,985,626 A | 11/1999 | Barbas et al. | |
| 6,013,625 A | 1/2000 | Pierschbacher et al. | |
| 6,210,938 B1 | 4/2001 | Barbas et al. | |
| 6,326,176 B1 | 12/2001 | Barbas et al. | |
| 6,368,839 B1 | 4/2002 | Barbas et al. | |
| 6,589,766 B1 | 7/2003 | Barbas et al. | |
| 2003/0045477 A1 | 3/2003 | Haviv et al. | |
| 2003/0190676 A1* | 10/2003 | Barbas et al. ............. | 435/7.1 |
| 2006/0205670 A1 | 9/2006 | Bradshaw et al. | |

FOREIGN PATENT DOCUMENTS

| | | | |
|---|---|---|---|
| WO | WO 00/24782 | * | 5/2000 |
| WO | WO 01/22922 | | 4/2001 |
| WO | WO0183525 | | 11/2001 |
| WO | WO2006010057 | | 1/2006 |
| WO | WO2006094269 | | 9/2006 |
| WO | WO2008056346 | | 5/2008 |
| WO | WO2008081418 | | 7/2008 |

OTHER PUBLICATIONS

Doppalapudi, V., et al., "Chemically Programmed Antibodies: Endothelin Receptor Targeting CovX-Bodies," Bioorganic & Medicinal Chemistry Letters, 2007, 501-506, vol. 17.
Barbas, C., et al., "Immune Versus Natural Selection: Antibody Aldolases With Enzymic Rates But Broader Scope," Science, 1997, 2085-2092, vol. 278.
Borrebaeck, C., et al., "Human Monoclonal Antibodies Produced by Primary in vitro Immunization of Peripheral Blood Lymphocytes," Proceedings of the National Academy of Science USA, 1988, 3995-3999, vol. 85.
Cahn, R., et al., "Specification of Molecular Chirality," Angew. Chem Int. Ed., 1966, 385-415, vol. 5, No. 4.
Caine, G., et al., Plasma Angiopoietin-I, Angiopoietin-2 and Tie-2 in Breast and Prostate Cancer: A Comparison With VEGF and Flt-1, European Journal of Clinical Investigation, 2003, 883-890, vol. 33.
De Haard, H., et al., "A Large Non-immunized Human Fab Fragment Phage Library That Permits Rapid Isolation and Kinetic Analysis of High Affinity Antibodies," Journal of Biological Chemistry, 1999, 18218-18230, vol. 274, No. 26.
Fairbrother, W., et al., "Novel Peptides Selected to Bind Vascular Endothelial Growth Factor Target the Receptor-Binding Site," Biochemistry, 1998, 17754-17764, vol. 37, No. 51.
Folkman, J., "How Is Blood Vessel Growth Regulated in Normal and Neoplastic Tissue?-G. H. A. Clowes Memorial Award Lecture," Cancer Research, 1986, 467-473, vol. 46.
Folkman, J., "What is the Evidence That Tumors are Angiogenesis Dependent?," Journal of The National Cancer Institute, 1990, 4-6, vol. 82, No. 1.
Francis, G., et al., "PEGylation of Cytokines and Other Therapeutic Proteins and Peptides: The Importance of Biological Optimisation of Coupling Techniques," International Journal of Hematology, 1998, 1-18, vol. 68.
Janda, K, et al., "Direct Selection for a Catalytic Mechanism From Combinatorial Antibody Libraries," Proceedings of The National Academy of Science USA, 1994, 2532-2536, vol. 91.
Karlstrom, A., et al., "Using Antibody Catalysis to Study the Outcome of Multiple Evolutionary Trials of a Chemical Task," Proceedings of the National Academy of Science USA, 2000, 3878-3883, vol. 97, No. 8.
Katre, N., "Immunogenicity of Recombinant IL-2 Modified by Covalent Attachment of Polyethylene Glycol," Journal of Immunology, 1990, 209-213, vol. 144, No. 1.
Knappik, A., et al., "Fully Synthetic Human Combinatorial Antibody Libraries (HuCAL) Based on Modular Consensus Frameworks and CDRs Randomized With Trinucleotides" Journal of Molecular Biology, 2000, 57-86, vol. 296.

(Continued)

*Primary Examiner* — Karlheinz R Skowronek
*Assistant Examiner* — Satyanarayana R Gudibande
(74) *Attorney, Agent, or Firm* — Pfizer Inc.; Wendy L. Hsu; Keith D. Hutchinson

(57) ABSTRACT

The present invention provides VEGF binding peptides. In addition, the invention provides VEGF peptides conjugated to antibodies alone and in conjunction with other anti-angiogenic molecules. Various uses of the peptides and compounds are provided, including methods to treat disorders associated with abnormal angiogenesis.

33 Claims, 20 Drawing Sheets

OTHER PUBLICATIONS

Kukolja, S., "Electrophilic Opening of The Thiazolidine Ring in Penicillins," Journal of The American Chemical Society, 1971, 6267-6269, vol. 93, No. 23.

Mc Cafferty, J., et al., "Phage Antibodies: Filamentous Phage Displaying Antibody Variable Domains," Nature, 1990, 552-553, vol. 348.

Oliner, J., et al., "Suppression of Angiogenesis and Tumor Growth by Selective Inhibition of Angiopoietin-2," Cancer Cell, 2004, 507-516, No. 6.

Rader, C., et al., "A Humanized Aldolase Antibody for Selective Chemotherapy and Adaptor Immunotherapy," Journal of Molecular Biology, 2003, 889-899, vol. 332.

Rader, C., et al., "Integrin αvβ3-targeted Therapy for Kaposi's Sarcoma With an in vitro-evolved Antibody," FASEB Journal, 2002, 2000-2028, vol. 16.

Rader, C., et al., "The Rabbit Antibody Repertoire as a Novel Source for the Generation of Therapeutic Human Antibodies," The Journal of Biological Chemistry, 2000, 13668-13676, vol. 275, No. 18.

Roche, E., Bioreversible Carriers in Drug Design: Theory and Application (E. B. Roche, ed.), 1987, Pergamon Press, New York, 14-21.

Wagner, J., et al., "Efficient Aldolase Catalytic Antibodies That Use the Enamine Mechanism of Natural Enzymes," Science, 1995, 1797-1800, vol. 270.

Weidner, N., et al., "Tumor Angiogenesis and Metastasis—Correlation in Invasive Breast Carcinoma," The New England Journal of Medicine, 1991, 1-8, vol. 324.

Wells, J., et al., "High-Resolution Epitope Mapping of hGH-Receptor Interactions by Alanine-Scanning Mutagenesis," Science, 1989, 1081-1085, vol. 244.

Wirsching, P., et al., "Reactive Immunization," Science, 1995, 1775-1782, vol. 270.

Zhong, G., et al., "Broadening the Aldolase Catalytic Antibody Repertoire by Combining Reactive Immunization and Transition State Theory: New Enantio- and Diastereoselectivities," Angew. Chem. Int. Ed., 1999, 3738-3741, vol. 38, No. 24.

* cited by examiner

P.G. = protecting group
● = solid-phase support
R = side chain of amino acid

FIGURE 2A

```
VL
                   FR1                          CDR1                      FR2            CDR2                    FR3                         CDR3         FR4
           1         2         3                              4         5              6         7         8                    9         1
       1234567890123 4567890123 4567890 1abcde234 5678901234 56789 0123456 789012345678901234567 8901234567 89 01234567
m38C2  DVVMTQTPLSLPVRLGDQASISC RSSQSLLHTYGSPYLN WYLQKPGQSPKLLIY KVSNRFS GVPDRFSGSGSGTDFTLRISRVEAEDLGVYFC SQGTHLPYT FGGGTKLEIK
       ***  * *  **** ***  *                *                 **            *     *      *   ****   **          *
h38C2  ELQMTQSPSSLSASVGDRVTITC RSSQSLLHTYGSPYLN WYLQKPGQSPKLLIY KVSNRFS GVPSRFSGSGSGTDFTLTISSLQPEDFAVYFC SQGTHLPYT FGGGTKVEIK
        **                                                    ** ***                                  * * *****          *
DPK-9  DIQMTQSPSSLSASVGDRVTITC RASQSISS-----YLN WYQQKPGKAPKLLIY AASSLQS GVPSRFSGSGSGTDFTLTISSLQPEDFATYYC QQSYSTP
JK4                                                                                                            LT FGGGTKVEIK VH
                   FR1                          CDR1               FR2                  CDR2                              FR3                                CDR3              FR4
           1         2         3                                4         5                  6         7         8                        9         1           1
       12345678901234567890 12345 678901234567890 1ab2345 6789012345 012abc345678901234 5 6789012345678901234 56789012abc3456789012 abc345678901234 3456789012 3456789012 3
m38C2  EVKLVESGGGLVQPGGSLRLSCAASGFTFS N--YWMS WVRQSPEKGLEWVA EIRLRSDNYATHYAESVKG KFTISRDDSKSRLYLQMNSLRTEDTGIYYCKT YFY-SFSY WGQGTLVTVSA
         *     *     *                 *            **  *            *       **                *     ***  ***             *                       *
h38C2  EVQLVESGGGLVQPGGSLRLSCAASGFTFS N--YWMS WVRQAPGKGLEWVS AISG--SGGSTYYADSVKG RFTISRDNSKNTLYLQMNSLRAEDTAVYYCKT YFY-SFSY WGQGTLVTVSS
         *                             *         *         * **   **** *  **                               *  **                     **
DP-47  EVQLLESGGGLVQPGGSLRLSCAASGFTFS S--YAMS WVRQAPGKGLEWVS AISG--SGGSTYYADSVKG RFTISRDNSKNTLYLQMNSLRAEDTAVYYCAK
JH4                                                                                                                            YFDY WGQGTLVTVSS
```

FIGURE 2B

| |
|---|
| Light Chain (219 amino acids): SEQ ID NO:1 |
| ELQMTQSPSSLSASVGDRVTITCRSSQSLLHTYGSPYLNWYLQKPGQSPKLLIYKVSNRFSGV PSRFSGSGSGTDFTLTISSLQPEDFAVYFCSQGTHLPYTFGGGTKVEIKRTVAAPSVFIFPPSDE QLKSGTASVVCLLNNFYPREAKVQWKVDNALQSGNSQESVTEQDSKDSTYSLSSTLTLSKA DYEKHKVYACEVTHQGLSSPVTKSFNRGEC |
| Heavy chain (448 amino acids): SEQ ID NO:2 |
| EVQLVESGGGLVQPGGSLRLSCAASGFTFSNYWMSWVRQSPEKGLEWVSEIRLRSDNYATH YAESVKGRFTISRDNSKNTLYLQMNSLRAEDTGIYYCKTYFYSFSYWGQGTLVTVSSASTKG PSVFPLAPSSKSTSGGTAALGCLVKDYFPEPVTVSWNSGALTSGVHTFPAVLQSSGLYSLSSV VTVPSSSLGTQTYICNVNHKPSNTKVDKRVEPKSCDKTHTCPPCPAPELLGGPSVFLFPPKPK DTLMISRTPEVTCVVVDVSHEDPEVKFNWYVDGVEVHNAKTKPREEQYNSTYRVVSVLTVL HQDWLNGKEYKCKVSNKALPAPIEKTISKAKGQPREPQVYTLPPSREEMTKNQVSLTCLVKG FYPSDIAVEWESNGQPENNYKTTPPVLDSDGSFFLYSKLTVDKSRWQQGNVFSCSVMHEALH NHYTQKSLSLSPGK |

FIGURE 3

Linker Reactive Groups

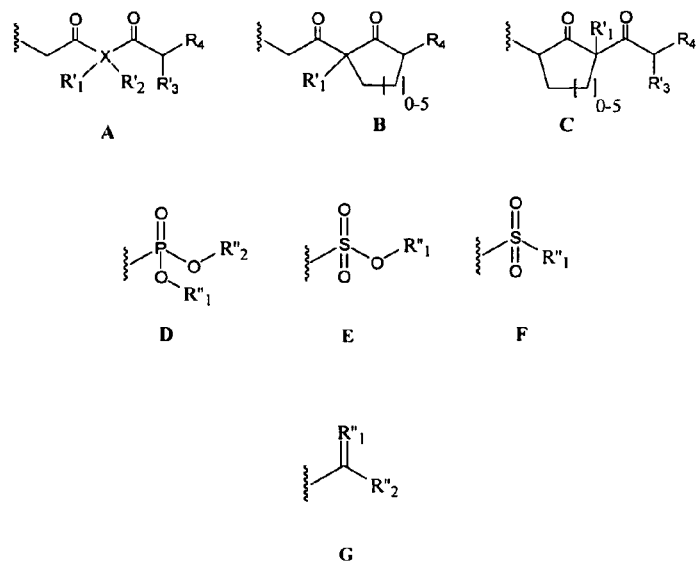

FIGURE 4
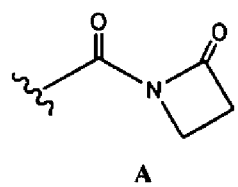
A
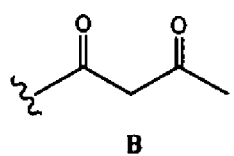
B
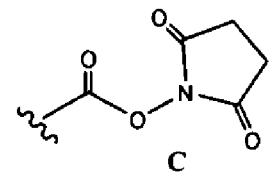
C
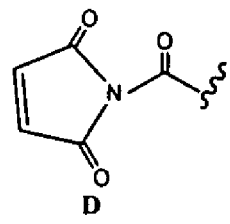
D
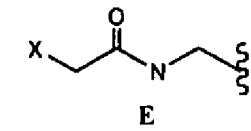
E
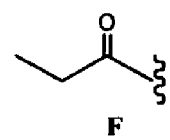
F
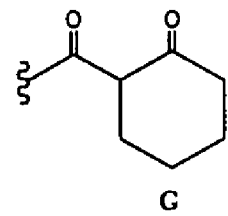
G
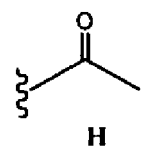
H Synthesis of [Ang2-Peptide]-[Ang2-Spacer]
SEQ ID NO:153

Synthesis of [VEGF-Peptide]-[VEGF-Spacer]
SEQ ID NO:195

Bifunctional Synthesis
SEQ ID NO:153 & SEQ ID NO:195

FIGURE 17
A. MDA-MB-435
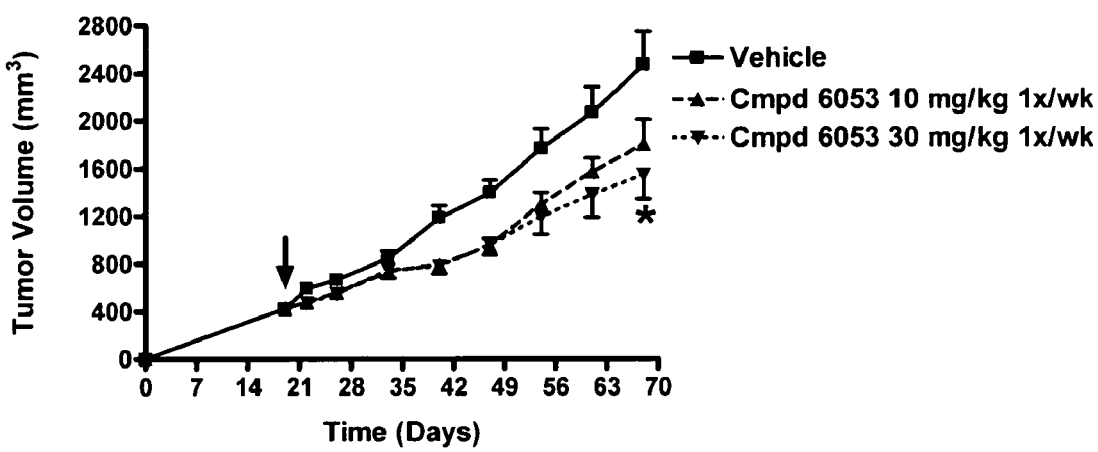
B. A431
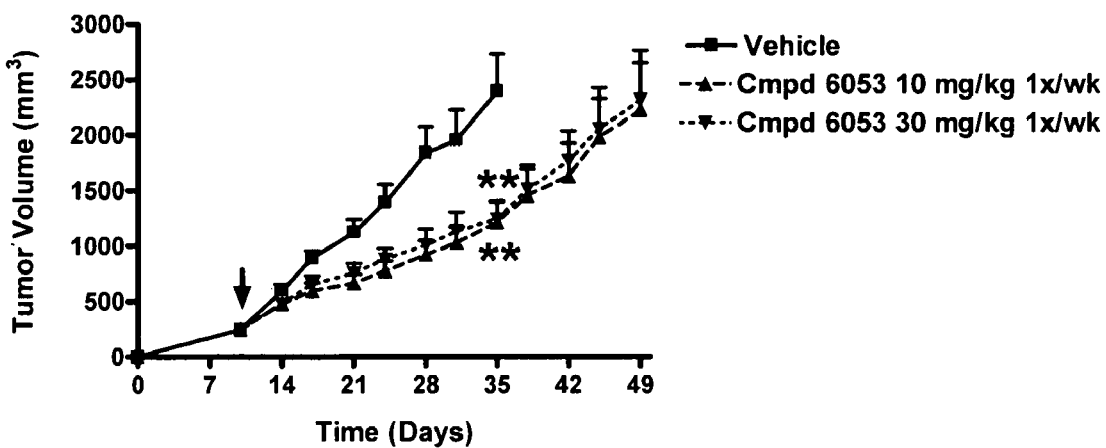

ANTI-ANGIOGENIC COMPOUNDS

This application claims the benefit of U.S. Provisional Application No. 61/050,544 filed May 5, 2008, U.S. Provisional Application No. 61/050,569 filed May 5, 2008 and U.S. Provisional Application No. 61/050,574 filed May 5, 2008, the contents of which are hereby incorporated by reference in their entireties.

REFERENCE TO SEQUENCE LISTING

This application is being filed electronically via EFS-Web and includes an electronically submitted sequence listing in .txt format. The .txt file contains a sequence listing entitled "PC33738 US Corrected Sequence Listing.txt" created on Aug. 19, 2009 and having a size of 97 KB. The sequence listing contained in this .txt file is part of the specification and is herein incorporated by reference in its entirety.

FIELD OF THE DISCLOSURE

The present invention relates to novel compounds that possess anti-angiogenic activity and methods of making and using these compounds. In particular, the present invention relates to peptides that bind to the vascular endothelial cell growth factor (VEGF) and macromolecules incorporating these peptides, and methods and uses associated thereof.

BACKGROUND

Angiogenesis is the fundamental process by which new blood vessels are formed and is essential to a variety of normal body activities such as reproduction, development and wound repair. Although angiogenesis is a highly regulated process under normal conditions, many diseases (characterized as "angiogenic diseases") are caused or exacerbated by unregulated angiogenesis. For example, ocular neovascularization has been implicated as the most common cause of blindness. In certain existing conditions such as arthritis, newly formed capillary blood vessels invade the joints and destroy cartilage. In diabetes, new capillaries formed in the retina invade the vitreous, bleed, and cause blindness. Growth and metastasis of solid tumors are also angiogenesis-dependent (J. Folkman, Cancer Res., 46:467-473 (1986), J. Folkman, J. Natl. Cancer Inst., 82:4-6 (1989)). It has been shown, for example, that tumors which enlarge to greater than 2 mm obtain their own blood supply by inducing the growth of new capillary blood vessels. Once these new blood vessels become embedded in the tumor, they provide a means for tumor cells to enter the circulation and metastasize to distant sites such as the liver, lungs, and bones (N. Weidner, et. al., N. Engl. J. Med., 324:1-8 (1991)).

Vascular endothelial growth factor (VEGF) has been identified as an extremely powerful angiogenic factor and is required for the growth and metastasis of many human tumours. Much research has focused on attempting to inhibit the VEGF pathway so as to limit or prevent angiogenesis or metastasis. Fairbrother et al: 'Novel peptides selected to bind vascular endothelial growth factor target the receptor-binding site' (Biochemistry, 1998, 37, 17754-17764) discloses peptides with varying abilities to bind to VEGF. Various peptides have been identified that bind to the angiogenesis related factor angiopoietin-2 ("Ang-2") (Oliner, J. et al., Cancer Cell, 204(6), 507-516 (2004)). The Ang-2 binding peptides have been shown to possess anti-angiogenic activity.

It would be desirable to provide compounds that show improved characteristics over known compounds, such as for example, improved binding to VEGF. It would be further desirable to provide compounds showing binding to both VEGF and Ang2.

The reference to any art in this specification is not, and should not be taken as, an acknowledgement of any form or suggestion that the referenced art forms part of the common general knowledge.

SUMMARY OF THE INVENTION

[VEGF-Peptides] of the Invention

The invention provides peptides, compounds, and pharmaceutical compositions capable of binding to human VEGF (as exemplified by SEQ ID NO:3). Accordingly, in some aspects, the present invention provides for a peptide including a sequence substantially homologous to the sequence: $V^1$-$E^2$-$P^3$—$N^4$—$C^5$-$D^6$-$I^7$—$H^8$—$V^9$-$M^{10}$-$W^{11}$—$V^{12}$—$W^{13}$—$X^{14}$—$C^{15}$—$F^{16}$-$E^{17}$-$R^{18}$—$X^{19}$ (SEQ ID NO:122), wherein $X^{14}$ is E or V, and $X^{19}$ is a natural or unnatural hydrophobic amino acid, or D-isomers thereof.

It has surprisingly been found that this class of peptides, and derivates thereof (as will be detailed further below) demonstrate improved binding to VEGF over peptides of related structure. In particular mutating position 12 to a neutral hydrophobic residue, especially valine, provides improved binding characteristics over peptides with a negatively charged groups at this position, such as glutamate. In some embodiments, the present invention provides for a peptide including a sequence substantially homologous to SEQ ID NO:122, provided that $V^{12}$ is not substituted with E. In some embodiments, $X^{19}$ is L. $X^{19}$ may be D-Leu. $X^{19}$ may be a conservative substitution of L, such as I, or other hydrophobic residue, such as A or V, or D-isomers of any of the preceding.

Further derivatives of the present invention provide for the addition of at least 1-4 residues at the C-terminus. Some embodiments provide for the addition of 2-4 residues at the C-terminus. Some embodiments provide for the addition of 2 residues at the C-terminus. Some embodiments provide for the addition of 3 residues at the C-terminus. Some embodiments provide for the addition of 4 residues at the C-terminus.

Accordingly, the invention also provides for a peptide including a sequence substantially homologous to the sequence:

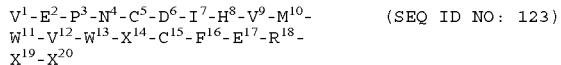

wherein $X^{20}$ is any neutral, hydrophobic or aromatic amino acid. $X^{20}$ may be any aromatic amino acid, such as Y, F, W, or D-isoforms thereof $X^{20}$ may be any neutral hydrophobic amino acid, such as M, I, L, Nle, A, or D-isoforms thereof.

In some aspects, the invention provides for a peptide including a sequence substantially homologous to the sequence:

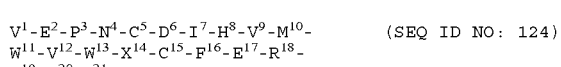

wherein $X^{21}$ is any amino acid. In some aspects, $x^{21}$ may be any neutral or positively charged amino acid, such as G, A, I, L, K, R, or K(ac), or D-isoforms thereof For example, $X^{21}$ may be D-Ala.

In some aspects, the invention provides for a peptide including a sequence substantially homologous to the sequence:

$V^1-E^2-P^3-N^4-C^5-D^6-I^7-H^8-V^9-M^{10}-$
$W^{11}-V^{12}-W^{13}-X^{14}-C^{15}-F^{16}-E^{17}-R^{18}-$ (SEQ ID NO: 125)
$X^{19}-X^{20}-X^{21}-X^{22}$ wherein $X^{22}$ is any aliphatic, polar, or negatively charged amino acid, such as V, L, P, E, G, I, S, T, W, F, E, or D-isomers thereof.

In some aspects, the invention provides for a peptide including a sequence substantially homologous to the sequence:

$V^1-E^2-P^3-N^4-C^5-D^6-I^7-H^8-V^9-M^{10}-$
$W^{11}-V^{12}-W^{13}-X^{14}-C^{15}-F^{16}-E^{17}-R^{18}-$ (SEQ ID NO: 126)
$X^{19}-X^{20}-X^{21}-X^{22}-X^{23}$,

NO: 126), wherein $X^{23}$ is any amino acid. $X^{23}$ may be selected from the group consisting of G, A, I, L, Q, E, F, T, W, S, and Y, and D-isomers thereof. $X^{23}$ may be selected from the group consisting of G, A, I, L, Q, E, F, T, S, and Y, and D-isomers thereof. In some aspects, $X^{23}$ does not comprise a side chain with a double ring. In some aspects, $X^{23}$ is not W. In some aspects, $X^{23}$ may be E, T, S, L, or F, or D-isomers thereof.

In some embodiments, it has been found that it can be preferred for at least one of the 5 residues at the carboxyl terminus to be a D-isomer. In some aspects, at least two of the five C-terminus located residues are D-isomers. In some aspects, no more than three of the of the five C-terminus located residues are D-isomers. In some aspects, between one and three of the five C-terminus located residues are D-isomers. In some aspects, at least one of the four residues at the carboxyl terminus is a D-isomer. In some aspects, at least two of the four C-terminus located residues are D-isomers. In some aspects, no more than three of the four C-terminus located residues are D-isomers. In some aspects, between one and three of the four C-terminus located residues are D-isomers. For each of these, it is preferred that there are at least two and preferably at least three additional residues after $X^{19}$. Providing an optimized number of D-isomers at the C-terminus has been found to provide the advantage of increased resistance to enzymatic degradation at the C-terminus, especially enzymatic degradation between residues $E^{17}$ and $R^{18}$, and enzymatic degradation between residues $R^{18}$ and $X^{19}$.

In some aspects of the invention, $X^{19}$ may be L, $X^{20}$ is present and may be Y, $X^{21}$ is present and may be an aliphatic hydrophobic amino acid (and may be selected from A, L, I, V, G), and $X^{22}$ is present, and is a hydrophobic amino acid (and may be selected from L, P, V). In certain embodiments, two of $X^{19}$, $X^{21}$ and $X^{22}$ are D-isomers. In some embodiments, $X^{23}$ may or may not be present.

In certain aspects, specific peptides, and compounds of the invention may include including a peptide sequence substantially homologous to one or more of SEQ ID NOs:36-106

In another aspect, the present invention provides for a peptide including a sequence substantially homologous to the sequence: $V^1-E^2-P^3-N^4-C^5-D^6-I^7-H^8-V^9-M^{10}-W^{11}-E^{12}-W^{13}-E^{14}-C^{15}-F^{16}-E^{17}-R^{18}-X^{19}-X^{20}-X^{21}-X^{22}-X^{23}$ (SEQ ID NO:127), wherein $X^{19}$ is a natural or unnatural hydrophobic amino acid, or D-isomers thereof, and $X^{20}$ is an aromatic amino acid, neutral amino acid, hydrophobic amino acid or polar amino acid, or D-isomers thereof, and $X^{21}$ is a hydrophobic amino acid or positively charged amino acid, or D-isomers thereof, and $X^{22}$ is absent, or is a hydrophobic amino acid, aromatic amino acid, negatively charged amino acid, or D-isomers thereof, and $X^{23}$ is absent, or is an aromatic amino acid, neutral aminioa acid, hydrophobic amino acid or D-isomers thereof. $X^{19}$ may be L. In alternative embodiments $X^{19}$ is D-Leu. $X^{19}$ may be a conservative substitution of L, such as I, or other hydrophobic residue, such as A or V, or D-isomers of any of the preceding. $X^{20}$ may be selected from the group consisting of A, V, I, L, Y, W, F, M, S, and T or D-isomer thereof. $X^{20}$ may be selected from the group consisting of A, Y, F, M, and S or D-isomer thereof. $X^{21}$ may be selected from the group consisting of K, R, H, Orthinine, Dap, Dab, G, A, V, I, and L or D-isomers thereof. $X^{21}$ may be selected from the group consisting of K, R, and G or D-isomer thereof. Where $X^{20}$ is hydrophobic or aromatic, $X^{21}$ may be a positively charged amino acid. Where $X^{20}$ is one of A, F or Y, $X^{21}$ may be one of K or R or D-isomer thereof. Where $X^{21}$ is hydrophobic, $X^{20}$ may be polar. $X^{22}$ if present may be selected from the group consisting of E, D, G, A, L, I, V, M, W, Y, and F or D-isomers thereof. $X^{22}$ if present may be selected from the group consisting of E, G and W or D-isomers thereof. Where $X^{21}$ is a positively charged residue, $X^{22}$ if present may be a negatively charged residue. Where $X^{21}$ is K, $X^{22}$ may be E. $X^{23}$ if present may be selected from the group consisting of W, Y, F, G, A, I, L, V, and M, or D-isomers thereof $X^{23}$ if present may be selected from the group consisting of W, F, G, A, L, and M, or D-isomers thereof.

In certain aspects, specific peptides, compounds and pharmaceutical compositions of the invention may include including a peptide sequence substantially homologous to one or more of the following: SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121.

Peptides of the invention can be used in a variety of applications, including diagnostis, screening and therapeutics. Peptides and compounds of the invention may be used directly in therapeutic applications, or may find use conjugated covalently or non-covalently to larger molecules which provide additional therapeutic value, such as increased half-life (PK). Examples of molecules which may provide increased half-life include proteins, polypeptides, antibodies, antibody fragments, in particular, the Fc domain of antibodies The invention provides for a compound of the formula: $R^1$-[VEGF-Peptide]-$R^2$ wherein [VEGF-Peptide] is a peptide including a sequence substantially homologous to the sequence: $X^1$—$X^2$—$P^3$—$N^4$—$C^5$—$X^6$—$X^7$—$X^8$—$V^9$—$X^{10}$—$X^{11}$—$X^{12}$—$W^{13}$—$X^{14}$—$C^{15}$—$F^{16}$-$E^{17}$-$R^{18}$-$X^{19}$—$X^{20}$—$X^{21}$—$X^{22}$—$X^{23}$ (SEQ ID NO:131) wherein $R^1$ is absent, $CH_3$, $C(O)CH_3$, $C(O)CH_3$, $C(O)CH_2CH_3$, $C(O)CH_2CH_2CH_3$, $C(O)CH(CH_3)CH_3$, $C(O)CH_2CH_2CH_2CH_3$, $C(O)CH(CH_3)CH_2CH_3$, $C(O)C_6H_5$, $C(O)CH_2CH_2(CH_2CH_2O)_{1-5}$Me, amido-2-PEG, N-acyl and N-alkyl an amino protecting group, a lipid fatty acid group or a carbohydrate; and $R^2$ is absent, OH, $NH_2$, $NH(CH_3)$, $NHCH_2CH_3$, $NHCH_2CH_2CH_3$, $NHCH(CH_3)CH_3$, $NHCH_2CH_2CH_2CH_3$, $NHCH(CH_3)CH_2CH_3$, $NHC_6H_5$, $NHCH_2CH_2OCH_3$, $NHOCH_3$, $NHOCH_2CH_3$, a carboxy protecting group, a lipid fatty acid group or a carbohydrate, and $X^1$ is a hydrophobic amino acid residue, $X^2$ is a negatively charged residue, $X^6$ is a negatively charged residue, $X^7$ is a hydrophobic amino acid residue, $X^8$ is a residue comprising a ring structure, $X^{10}$ may be M or any hydrophobic amino acid, $X^{11}$ is an aromatic amino acid, $X^{12}$ is selected from the group consisting of V, E and Kac, $X^{14}$ is E or V, $X^{19}$ may be any hydrophobic amino acid residue, or D-isomer thereof, $X^{20}$ may be absent, or may be any neutral, hydrophobic or aromatic amino acid or D-isomer thereof, $X^{21}$ may be absent, or may be any positively charged residue or any aliphatic non-polar residue or D-isoform thereof, $X^{22}$ may absent, or may be selected from the group consisting of G, V, L, I, P, S, T, W, F, E, Kac, or D-isomers thereof, $X^{23}$ may be absent, or is selected from the group consisting of G, A, I, L, Q, E, F, T, W, S, Y, and Kac and D-isomers thereof.

$X^1$ may be V. $X^2$ may be E. $X^6$ may be D. $X^7$ may be I. $X^8$ may be H. $X^{11}$ may be W. [VEGF-Peptide] may be a peptide including a sequence substantially homologous to the sequence: $V^1$-$E^2$-$P^3$—$N^4$—$C^5$-$D^6$-$I^7$—$H^8$—$V^9$—$X^{10}$—$W^{11}$—$X^{12}$—$W^{13}$—$X^{14}$—$C^{15}$—$F^{16}$-$E^{17}$-$R^{19}$—$X^{20}$—$X^{21}$—$X^{22}$—$X^{23}$ (SEQ ID NO:132), where $X^{10}$ may be M or any hydrophobic amino acid, $X^{12}$ is selected from the group consisting of V, E and Kac, $X^{14}$ is E or V, $X^{19}$ may be any hydrophobic amino acid residue, or D-isomer thereof, $X^{20}$ may be absent, or may be any neutral, hydrophobic or aromatic amino acid or D-isomer thereof, $X^{21}$ may be absent, or may be any positively charged residue or any aliphatic non-polar residue or D-isoform thereof, $X^{22}$ may absent, or may be selected from the group consisting of G, V, L, I, P, S, T, W, F, E, Kac, or D-isomers thereof, $X^{23}$ may be absent, or is selected from the group consisting of G, A, I, L, Q, E, F, T, W, S, Y, and Kac and D-isomers thereof.

[VEGF-Peptide] includes a sequence substantially homologous to one or more of the following:

| Sequence | |
|---|---|
| V-E-P-N-C-D-I-H-V-M-W-E-W-E-C-F-E-R-L | (SEQ ID NO: 34) |
| V-E-P-N-C-D-I-H-V-M-W-V-W-E-C-F-E-R-L-Y-G-G-W | (SEQ ID NO: 35) |
| V-E-P-N-C-D-I-H-V-M-W-V-W-V-C-F-E-R-L-F-R-E-A | (SEQ ID NO: 36 |
| V-E-P-N-C-D-I-H-V-M-W-V-W-V-C-F-E-R-L-F-K-E-A | (SEQ ID NO: 37) |
| V-E-P-N-C-D-I-H-V-M-W-V-W-V-C-F-E-R-L-M-K | (SEQ ID NO: 38) |
| V-E-P-N-C-D-I-H-V-M-W-V-W-E-C-F-E-R-L-Y-R-E-L | (SEQ ID NO: 39) |
| V-E-P-N-C-D-I-H-V-M-W-V-W-E-C-F-E-R-L-Y-G-I-F | (SEQ ID NO: 40) |
| V-E-P-N-C-D-I-H-V-M-W-V-W-E-C-F-E-R-L-Y | (SEQ ID NO: 41) |
| V-E-P-N-C-D-I-H-V-M-W-V-W-E-C-F-E-R-L-Y-G-W-G | (SEQ ID NO: 42) |
| V-E-P-N-C-D-I-H-V-M-W-V-W-V-C-F-E-R-L-Y-G-G-G | (SEQ ID NO: 43) |
| V-E-P-N-C-D-I-H-V-M-W-V-W-E-C-F-E-R-L-Y-G-L-Y | (SEQ ID NO: 44) |
| V-E-P-N-C-D-I-H-V-M-W-V-W-E-C-F-E-R-L-S-G-G-G | (SEQ ID NO: 45) |
| V-E-P-N-C-D-I-H-V-M-W-V-W-E-C-F-E-R-L-M-R-L-T | (SEQ ID NO: 46) |
| V-E-P-N-C-D-I-H-V-M-W-V-W-E-C-F-E-R-L-Y-G | (SEQ ID NO: 47) |
| V-E-P-N-C-D-I-H-V-M-W-V-W-E-C-F-E-R-L-V-K | (SEQ ID NO: 48) |
| V-E-P-N-C-D-I-H-V-M-W-V-W-E-C-F-E-R-L-M-R | (SEQ ID NO: 49) |
| V-E-P-N-C-D-I-H-V-M-W-V-W-E-C-F-E-R-L-Y-G-I-L | (SEQ ID NO: 50) |
| V-E-P-N-C-D-I-H-V-M-W-V-W-E-C-F-E-R-L-(Yome)-G-L-T | (SEQ ID NO: 51) |
| V-E-P-N-C-D-I-H-V-M-W-V-W-E-C-F-E-R-L-Y-G-G | (SEQ ID NO: 52) |
| V-E-P-N-C-D-I-H-V-M-W-V-W-E-C-F-E-R-L-F-K-E-A | (SEQ ID NO: 53) |
| V-E-P-N-C-D-I-H-V-M-W-V-W-E-C-F-E-R-L-(Nle)-K | (SEQ ID NO: 54) |
| V-E-P-N-C-D-I-H-V-M-W-V-W-E-C-F-E-R-L-Y-G-L-T | (SEQ ID NO: 55) |
| V-E-P-N-C-D-I-H-V-M-W-V-W-E-C-F-E-R-L-Y-G-G-F | (SEQ ID NO: 56) |
| V-E-P-N-C-D-I-H-V-M-W-V-W-E-C-F-E-R-L-I-K | (SEQ ID NO: 57) |
| V-E-P-N-C-D-I-H-V-M-W-V-W-E-C-F-E-R-L-Y-K | (SEQ ID NO: 58) |
| V-E-P-N-C-D-I-H-V-M-W-V-W-E-C-F-E-R-L-M-G-L-T | (SEQ ID NO: 59) |
| V-E-P-N-C-D-I-H-V-M-W-V-W-E-C-F-E-R-L-(D-Leu)-(Kac) | (SEQ ID NO: 60) |
| V-E-P-N-C-D-I-H-V-M-W-V-W-E-C-F-E-R-L-Y-G-G-G | (SEQ ID NO: 61) |
| V-E-P-N-C-D-I-H-V-M-W-V-W-E-C-F-E-R-L-M-K | (SEQ ID NO: 62) |
| V-E-P-N-C-D-I-H-V-M-W-V-W-E-C-F-E-R-L-M-R-E-L | (SEQ ID NO: 63) |
| V-E-P-N-C-D-I-H-V-M-W-V-W-E-C-F-E-R-L- | (SEQ ID NO: 64) |
| V-E-P-N-C-D-I-H-V-M-W-V-W-E-C-F-E-R-L-M-K-E-L | (SEQ ID NO: 65) |

-continued

| | |
|---|---|
| V-E-P-N-C-D-I-H-V-M-W-V-W-E-C-F-E-R-L-Y-G-P-W | (SEQ ID NO: 66) |
| V-E-P-N-C-D-I-H-V-M-W-V-W-E-C-F-E-R-L-L-K | (SEQ ID NO: 67) |
| V-E-P-N-C-D-I-H-V-M-W-V-W-E-C-F-E-R-L-L-(Kac) | (SEQ ID NO: 68) |
| V-E-P-N-C-D-I-H-V-M-W-V-W-E-C-F-E-R-L-Y-G-L-T | (SEQ ID NO: 69) |
| V-E-P-N-C-D-I-H-V-M-W-V-W-E-C-F-E-R-L-Y-G-E-F | (SEQ ID NO: 70) |
| V-E-P-N-C-D-I-H-V-M-W-V-W-E-C-F-E-R-L-Y-G-L-S | (SEQ ID NO: 71) |
| V-E-P-N-C-D-I-H-V-M-W-V-W-E-C-F-E-R-L-Y-G-L | (SEQ ID NO: 72) |
| V-E-P-N-C-D-I-H-V-M-W-V-W-E-C-F-E-R-L-Y-G-(D-Leu)-T | (SEQ ID NO: 73) |
| V-E-P-N-C-D-I-H-V-M-W-V-W-E-C-F-E-R-L-Y-G-V-Q | (SEQ ID NO: 74) |
| V-E-P-N-C-D-I-H-V-M-W-V-W-E-C-F-E-R-L-Y-G-L-E | (SEQ ID NO: 75) |
| V-E-P-N-C-D-I-H-V-M-W-V-W-E-C-F-E-R-L-Y-G-P-L | (SEQ ID NO: 76) |
| V-E-P-N-C-D-I-H-V-M-W-V-W-E-C-F-E-R-L-Y-G-P-F | (SEQ ID NO: 77) |
| V-E-P-N-C-D-I-H-V-M-W-V-W-E-C-F-E-R-L-Y-(D-Ala)-(D-Leu) | (SEQ ID NO: 78) |
| V-E-P-N-C-D-I-H-V-M-W-V-W-E-C-F-E-R-L-R-(D-Leu)-(Kac) | (SEQ ID NO: 79) |
| V-E-P-N-C-D-I-H-V-M-W-V-W-E-C-F-E-R-L-(D-Tyr)-G-(D-Pro)-L | (SEQ ID NO: 80) |
| V-E-P-N-C-D-I-H-V-M-W-V-W-E-C-F-E-R-L-(D-Tyr)-G-(D-Pro)-(D-Leu) | (SEQ ID NO: 81) |
| V-E-P-N-C-D-I-H-V-M-W-V-W-E-C-F-E-R-L-(D-Tyr)-G-(D-Leu)-(Kac) | (SEQ ID NO: 82) |
| V-E-P-N-C-D-I-H-V-M-W-V-W-E-C-F-E-R-(D-Leu)-Y-(Aib)-L-T | (SEQ ID NO: 83) |
| V-E-P-N-C-D-I-H-V-M-W-V-W-E-C-F-E-R-(D-Leu)-Y-(D-Ala)-V-(D-Gln) | (SEQ ID NO: 84) |
| V-E-P-N-C-D-I-H-V-M-W-V-W-E-C-F-E-R-(D-Leu)-Y-(D-Ala)-L-(D-Thr) | (SEQ ID NO: 85) |
| V-E-P-N-C-D-I-H-V-M-W-V-W-E-C-F-E-R-L-(Cha)-G-(DLeu)-T | (SEQ ID NO: 86) |
| V-E-P-N-C-D-I-H-V-M-W-V-W-E-C-F-E-R-L-Y-(Aib)-L-(D-Thr) | (SEQ ID NO: 87) |
| V-E-P-N-C-D-I-H-V-M-W-V-W-E-C-F-E-R-L-Y-(Sar)-(D-Leu)-T | (SEQ ID NO: 88) |
| V-E-P-N-C-D-I-H-V-M-W-V-W-E-C-F-E-R-L-Y-G-(D-Pro)-L | (SEQ ID NO: 89) |
| V-E-P-N-C-D-I-H-V-M-W-V-W-E-C-F-E-R-L-Y-(D-Ala)-V-(D-Gln) | (SEQ ID NO: 90) |
| V-E-P-N-C-D-I-H-V-M-W-V-W-E-C-F-E-R-L-Y-(Aib)-L-T | (SEQ ID NO: 91) |
| V-E-P-N-C-D-I-H-V-M-W-V-W-E-C-F-E-R-L-(D-Tyr)-G-(D-Leu)-T | (SEQ ID NO: 92) |
| V-E-P-N-C-D-I-H-V-M-W-V-W-E-C-F-E-R-L-(D-Tyr)-G-L-T | (SEQ ID NO: 93) |
| V-E-P-N-C-D-I-H-V-M-W-V-W-E-C-F-E-R-L-(D-Tyr)-D-L-(D-Thr) | (SEQ ID NO: 94) |
| V-E-P-N-C-D-I-H-V-M-W-V-W-E-C-F-E-R-L-(D-Leu)-(Aib) | (SEQ ID NO: 95) |
| V-E-P-N-C-D-I-H-V-M-W-V-W-E-C-F-E-R-L-Y-G-(D-Leu)-(D-Thr) | (SEQ ID NO: 96) |
| V-E-P-N-C-D-I-H-V-M-W-V-W-V-C-F-E-R-L | (SEQ ID NO: 97) |
| V-E-P-N-C-D-I-H-V-M-W-V-W-V-C-F-E-R-L-Y-G-P-F | (SEQ ID NO: 98) |
| V-E-P-N-C-D-I-H-V-M-W-V-W-V-C-F-E-R-L-Y-G-P- | (SEQ ID NO: 99) |
| V-E-P-N-C-D-I-H-V-M-W-V-W-V-C-F-E-R-L-Y-G-P-E | (SEQ ID NO: 100) |
| V-E-P-N-C-D-I-H-V-M-W-V-W-V-C-F-E-R-L-Y-G-P-Q | (SEQ ID NO: 101) |
| V-E-P-N-C-D-I-H-V-M-W-V-W-V-C-F-E-R-L-Y-G-(D-Leu)-T | (SEQ ID NO: 102) |
| V-E-P-N-C-D-I-H-V-M-W-V-W-V-C-F-E-R-L-Y-G-L | ((SEQ ID NO: 103) |
| V-E-P-N-C-D-I-H-V-M-W-V-W-V-C-F-E-R-L-(D-Leu)-Kac | (SEQ ID NO: 104) |
| V-E-P-N-C-D-I-H-V-M-W-V-W-V-C-F-E-R-L-Y-G-L-T | (SEQ ID NO: 105) |
| V-E-P-N-C-D-I-H-V-M-W-V-W-V-C-F-E-R-L-Y-(D-Ala)-(D-Leu) | (SEQ ID NO: 106) |

-continued

| | |
|---|---|
| V-E-P-N-C-D-I-H-V-M-W-E-W-E-C-F-E-R-L-Y-A-K | (SEQ ID NO: 108) |
| V-E-P-N-C-D-I-H-V-M-W-E-W-E-C-F-E-R-L-Y-F-K-E-W | (SEQ ID NO: 109) |
| V-E-P-N-C-D-I-H-V-M-W-E-W-E-C-F-E-R-L-Y-A-R | (SEQ ID NO: 110) |
| V-E-P-N-C-D-I-H-V-M-W-E-W-E-C-F-E-R-L-Y-F-K | (SEQ ID NO: 111) |
| V-E-P-N-C-D-I-H-V-M-W-E-W-E-C-F-E-R-L-Y-A-K-E-F | (SEQ ID NO: 112) |
| V-E-P-N-C-D-I-H-V-M-W-E-W-E-C-F-E-R-L-Y-S-G-W-G | (SEQ ID NO: 113) |
| V-E-P-N-C-D-I-H-V-M-W-E-W-E-C-F-E-R-L-Y-S-G-W-F | (SEQ ID NO: 114) |
| V-E-P-N-C-D-I-H-V-M-W-E-W-E-C-F-E-R-L-Y-A-K-E-A | (SEQ ID NO: 115) |
| V-E-P-N-C-D-I-H-V-M-W-E-W-E-C-F-E-R-L-Y-A-K-E-M | (SEQ ID NO: 116) |
| V-E-P-N-C-D-I-H-V-M-W-E-W-E-C-F-E-R-L-Y-A-K-E-L | (SEQ ID NO: 117) |
| V-E-P-N-C-D-I-H-V-M-W-E-W-E-C-F-E-R-L-Y-F-K-E-L | (SEQ ID NO: 118) |
| V-E-P-N-C-D-I-H-V-M-W-E-W-E-C-F-E-R-L-Y-F-K-E-A | (SEQ ID NO: 119) |
| V-E-P-N-C-D-I-H-V-M-W-E-W-E-C-F-E-R-L-Y-Y-G-G-G | (SEQ ID NO: 120) |
| V-E-P-N-C-D-I-H-V-M-W-E-W-E-C-F-E-R-L-Y-M-K | (SEQ ID NO: 121) |
| V-E-P-N-C-D-I-H-V-(Nle)-W-V-W-E-C-F-E-R-L-Y-(Aib)-L-T | (SEQ ID NO: 128) |
| V-E-P-N-C-D-I-H-V-L-W-V-W-E-C-F-E-R-L-Y-(Aib)-L-T | (SEQ ID NO: 129) |
| V-E-P-N-C-D-I-H-V-V-W-V-W-E-C-F-E-R-L-Y-(Aib)-L-T | (SEQ ID NO: 130) |
| V-E-P-N-C-D-I-H-V-M-W-(Kac)-W-E-C-F-E-R-L-Y-(D-Ala)-V-(D-Gln) | (SEQ ID NO: 136) |
| V-E-P-N-C-D-I-H-V-K-W-V-W-E-C-F-E-R-L-(D-Leu)-(Kac) | (SEQ ID NO: 192) |
| V-E-P-N-C-D-I-H-V-K-W-V-W-E-C-F-E-R-L-Y-G-(D-Leu)-T | (SEQ ID NO: 193) |
| V-E-P-N-C-D-I-H-V-K-W-V-W-E-C-F-E-R-L-Y-G-P-L | (SEQ ID NO: 194) |
| V-E-P-N-C-D-I-H-V-K-W-V-W-E-C-F-E-R-L-Y-(D-Ala)-(D-Leu) | (SEQ ID NO: 195) |
| V-E-P-N-C-D-I-H-V-M-W-V-W-E-C-F-E-R-L(-D-Leu)-K | (SEQ ID NO: 196) |
| V-E-P-N-C-D-I-H-V-M-W-V-W-E-C-F-E-R-L-Y-G-(D-Leu)-K | (SEQ ID NO: 197) |
| V-E-P-N-C-D-I-H-V-M-W-E-W-E-C-F-K-R-(D-Leu) | (SEQ ID NO: 198) |
| V-E-P-N-C-D-I-H-V-KW-E-W-E-C-F-(N-methyl glutamate)-R-L | (SEQ ID NO: 199) |
| V-E-P-N-C-D-I-H-V-KW-V-E-E-C-F-(D-Glu)-R-L | (SEQ ID NO: 200) |
| V-E-P-N-C-D-I-H-V-KW-E-W-E-C-F-E-R(N-methyl arginine) | (SEQ ID NO: 201) |
| V-E-P-N-C-D-I-H-V-KW-E-W-E-C-F-E-R-(D-Asn) | (SEQ ID NO: 202) |
| V-E-P-N-C-D-I-H-V-KW-E-W-E-C-F-E-R-(Aib) | (SEQ ID NO: 203) |
| V-E-P-N-C-D-I-H-V-KW-E-W-E-C-F-(Aib)-R-L | (SEQ ID NO: 204) |
| V-E-P-N-C-D-I-H-V-KW-E-W-E-C-(Napthaline)-E-R-L | (SEQ ID NO: 205) |
| V-E-P-N-C-D-I-H-V-M-W-V-E-C-F-K-R-L-Y-G-L-T | (SEQ ID NO: 206) |
| V-E-P-N-C-D-I-H-V-M-W-V-E-C-F-E-R-L-Y-K-L-E | (SEQ ID NO: 207) |
| V-E-P-N-C-D-I-H-V-M-W-E-W-E-C-F-E-R-(D-Leu) | (SEQ ID NO: 208) |
| V-E-P-N-C-D-I-H-V-E-W-E-W-E-C-F-K-R-L | (SEQ ID NO: 209) |
| V-E-P-N-C-D-I-H-V-K-W-V-W-E-C-F-E-(homoargenine)-L-Y-(D-Ala)-(D-Leu) | (SEQ ID NO: 210) |
| V-E-P-N-C-D-I-H-V-M-W-K-W-E-C-F-E-R-Y-G-(D-Leu)-E | (SEQ ID NO: 211) |
| V-E-P-N-C-D-I-H-V-K-W-V-W-E-C-F-E-R-L-Y-G-(D-Leu)-E | (SEQ ID NO: 212) |
| V-E-P-N-C-D-I-H-V-K-W-V-W-E-C-F-E-R-L-Y-(Aib)-L-E | (SEQ ID NO: 213) |

```
V-E-P-N-C-D-I-H-V-M-W-K-W-E-C-F-E-R-L-Y-(Aib)-L-E                    (SEQ ID NO: 214)

V-E-P-N-C-D-I-H-V-M-W-K-W-E-C-F-E-R-(D-Leu)-K                        (SEQ ID NO: 215)

V-E-P-N-C-D-I-H-V-K-W-V-W-E-C-F-E-(Kac)-L-Y-(D-Ala)-(D-Leu)          (SEQ ID NO: 216)

V-E-P-N-C-D-I-H-V-K-W-V-W-E-C-F-E-(Kac)-(cyclo-Leu)-Y-(D-Ala)-(D-Leu) (SEQ ID NO: 217)

V-E-P-N-C-D-I-H-V-K-W-V-W-E-C-F-E-(Kac)-(Tle)-Y-(D-Ala)-(D-Leu)      (SEQ ID NO: 218)
```

In some embodiments, the [VEGF-Peptide] of the invention is selected from the group consisting of SEQ ID NOs: 60, 73, 76, 78, 192, 193, 194, or 195.

$X^{10}$ may be M. [VEGF-Peptide] may be a peptide including a sequence substantially homologous to the sequence: $V^1$-$E^2$-$P^3$—$N^4$—$C^5$-$D^6$-$I^7$—$H^8$—$V^9$-$M^{10}$-$W^{11}$—$X^{12}$—$W^{13}$—$X^{14}$—$C^{15}$—$F^{16}$-$E^{17}$-$R^{18}$—$X^{19}$—$X^{20}$—$X^{21}$—$X^{22}$—$X^{23}$ (SEQ ID NO:133) where $X^{12}$ is selected from the group consisting of V, E and Kac, $X^{14}$ is E or V, $X^{19}$ may be any hydrophobic amino acid residue, or D-isomer thereof, $X^{20}$ may be absent, or may be any neutral, hydrophobic or aromatic amino acid or D-isomer thereof, $X^{21}$ may be absent, or may be any positively charged residue or any aliphatic non-polar residue or D-isomer thereof, $X^{22}$ may absent, or may be selected from the group consisting of G, V, L, I, P, S, T, W, F, E, Kac, or D-isomers thereof, $X^{23}$ may be absent, or is selected from the group consisting of G, A, I, L, Q, E, F, T, W, S, Y, and Kac and D-isomers thereof.

$X^{12}$ may be E. [VEGF-Peptide] may be a peptide including a sequence substantially homologous to the sequence: $V^1$-$E^2$-$P^3$—$N^4$—$C^5$-$D^6$-$I^7$—$H^8$—$V^9$-$M^{10}$-$W^{11}$-$E^{12}$-$W^{13}$—$X^{14}$—$C^{15}$—$F^{16}$-$E^{17}$-$R^{18}$—$X^{19}$—$X^{20}$—$X^{21}$—$X^{22}$—$X^{23}$ (SEQ ID NO:134) where $X^{14}$ is E or V, $X^{19}$ may be any hydrophobic amino acid residue, or D-isomer thereof, $X^{20}$ may be absent, or may be any neutral, hydrophobic or aromatic amino acid or D-isomer thereof, $X^{21}$ may be absent, or may be any positively charged residue or any aliphatic non-polar residue or D-isoform thereof, $X^{22}$ may absent, or may be selected from the group consisting of G, V, L, I, P, S, T, W, F, E, Kac, or D-isomers thereof, $X^{23}$ may be absent, or is selected from the group consisting of G, A, I, L, Q, E, F, T, W, S, Y, and Kac and D-isomers thereof.

[VEGF-Peptide] may include a sequence substantially homologous to one or more of the following: SEQ ID NO:34, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, ID NO:118, SEQ ID NO:119, SEQ ID NO:120, SEQ ID NO:121.

$X^{12}$ may be V. [VEGF-Peptide] may be a peptide including a sequence substantially homologous to the sequence: $V^1$-$E^2$-$P^3$—$N^4$—$C^5$-$D^6$-$I^7$—$H^8$—$V^9$-$M^{10}$-$W^{11}$—$V^{12}$—$W^{13}$—$X^{14}$—$C^{15}$—$F^{16}$-$E^{17}$-$R^{18}$—$R^{19}$—$X^{20}$—$X^{21}$—$X^{22}$—$X^{23}$ (SEQ ID NO:135) where $X^{14}$ is E or V, $X^{19}$ may be any hydrophobic amino acid residue, or D-isomer thereof, $X^{20}$ may be absent, or may be any neutral, hydrophobic or aromatic amino acid or D-isomer thereof, $X^{21}$ may be absent, or may be any positively charged residue or any aliphatic non-polar residue or D-isoform thereof, $X^{22}$ may absent, or may be selected from the group consisting of G, V, L, I, P, S, T, W, F, E, Kac, or D-isomers thereof, $X^{23}$ may be absent, or is selected from the group consisting of G, A, I, L, Q, E, F, T, W, S, Y, and Kac and D-isomers thereof.

[VEGF-Peptide] may include a sequence substantially homologous to one or more of the following: SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, ID NO:71, SEQ ID NO:72), SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, ID NO:83, SEQ ID NO:84, SEQ ID NO:85, SEQ ID NO:86, SEQ ID NO:87, ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:128, SEQ ID NO:129, SEQ ID NO:130

In relation to the various embodiments of [VEGF-Peptide] described herein, in some aspects of the invention, $R^1$ may be $C(O)CH_3$. In some aspects of the invention, $R^2$ is $NH_2$. $R^1$ and/or $R^2$ may be absent. $X^{19}$ may be selected from the group consisting of L, I, A, V, G or D-isomers thereof. $X^{19}$ may be L. $X^{19}$ may be D-Leu. $X^{20}$ may be Y. $X^{20}$ may be D-Tyr. $X^{21}$ may be selected from the group consisting of D-Ala, G, Aib and Kac. $X^{21}$ may be D-Ala. $X^{21}$ may be G. $X^{22}$ may be selected from the group consisting of L, V, P, D-Leu, D-Pro. $X^{22}$ may be D-Leu. $X^{22}$ may be D-Pro. $X^{22}$ may be L. $X^{23}$ may be absent.

In some embodiments of the invention, [VEGF-peptide] is (SEQ ID NO:78). In some embodiments, $R^1$-[VEGF-peptide]-$R^2$ is {$C(O)CH_3$}—V-E-P—N—C-D-I—H—V—K—W—V—W-E-C—F-E-R-L-Y-(D-Ala)-(D-Leu)-{$NH_2$} (SEQ ID NO:188) and $K^{11}$ is the linking residue.

Linking

The presence of the linking residue (both VEGF-linking residue and Ang2-linking residue respectively) provides the compounds of the invention with great flexibility for linkages to scaffolds, macromolecules and other moieties. In particular, the compounds of the invention may be reliably, securely and efficiently covalently linked to scaffolds, such as antibodies, antibody fragments, PEG molecules, albumin and so on. Surprisingly, it has been found that locating the linking residue at certain key positions in the respective peptide leads to increased stability and/or binding of the peptide. The linking residue can be selected so as to provide a side chain whose chemical characteristics permit specific, reliable, directional and efficient chemical covalent linkages at that location. In some aspects of the invention, the linking residue is covalently linked to the combining site of an antibody directly or via an intermediate linker. The linkage may be irreversible.

The compounds of the invention may be covalently linked to a linker moiety, L (or L', as later described) through the linking residue. Numerous linkers are possible; many suitable linkers are disclosed in US2006205670, the contents of which are incorporated herein by reference. In particular, aspects of US2006205670 pertaining to the general formulae describing linkers, specific linker structure, synthesis of linkers and combinations of different elements of X, Y and Z groups as specifically and generally described therein are herein included. The linker may be linear or branched, and optionally includes one or more carbocyclic or heterocyclic groups. Linker length may be viewed in terms of the number of linear atoms, with cyclic moieties such as aromatic rings and the like to be counted by taking the shortest route around the ring. In some embodiments, the linker has a linear stretch of between 5-15 atoms, in other embodiments 15-30 atoms, in still other embodiments 30-50 atoms, in still other embodiments 50-100 atoms, and in still other embodiments 100-200 atoms. Other linker considerations include the effect on physical or pharmacokinetic properties of the resulting compound, such as solubility, lipophilicity, hydrophilicity, hydrophobicity, stability (more or less stable as well as planned degradation), rigidity, flexibility, immunogenicity, modulation of antibody binding, the ability to be incorporated into a micelle or liposome, and the like.

In some aspects of the invention, the compound comprises a linker (L) or (L') covalently linked to the side chain of the linking residue. The linker may comprise the formula: -[Connector]-X—Y—Z; -[Connector]-X—Y—Z'; —X—Y—Z—; or —X—Y—Z'—; wherein: [Connector] is present where the linker is branched, and where present is covalently linked to the linking residue, and one or more additional Active Molecules, X is a biologically compatible connecting chain including any atom selected from the group consisting of C, H, N, O, P, S, F, CL, Br, and I, and may comprise a polymer or block co-polymer, and is covalently linked to the linking residue where the linker is linear, Y is an optionally present recognition group comprising at least a ring structure; and Z is a reactive group that is capable of forming a covalent bond with an amino acid side chain in a combining site of an antibody, and Z' is an attachment moiety comprising a covalent link to an amino acid side chain in a combining site of an antibody.

When present, Y may have the optionally substituted structure:

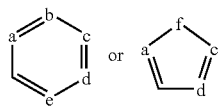

wherein a, b, c, d, and e are independently carbon or nitrogen; f is carbon, nitrogen, oxygen, or sulfur; Y is attached to X and Z independently at any two ring positions of sufficient valence; and no more than four of a, b, c, d, e, or f are simultaneously nitrogen and preferably a, b, c, d, and e in the ring structure are each carbon. In some aspects, Y may be phenyl. Although not wishing to be bound by any theory, it is believed that the Y group can assist in positioning the reactive group into an antibody combining site so that the Z group can react with a reactive amino acid side chain.

The linker may be designed such that it contains a reactive group capable of covalently or non-covalently forming a bond with a macromolecule, such as an antibody, protein, or fragment thereof. The reactive group is chosen for use with a reactive residue in a particular combining site. For example, a chemical moiety for modification by an aldolase antibody may be a ketone, diketone, beta lactam, active ester haloketone, lactone, anhydride, maleimide, alpha-haloacetamide, cyclohexyl diketone, epoxide, aldehyde, amidine, guanidine, imine, eneamine, phosphate, phosphonate, epoxide, aziridine, thioepoxide, masked or protected diketone (ketal for example), lactam, haloketone, aldehyde, and the like. In embodiments of the present invention linking a peptide of the invention with a linker L or L', the moieties Z (or Z' when attached to the macromolecule) is the reactive group.

In some embodiments, Z includes one or more C=O groups arranged to form an azitidinone, diketone, an acyl beta-lactam, an active ester, a haloketone, a cyclohexyl diketone group, an aldehyde, a maleimide, an activated alkene, an activated alkyne or, in general, a molecule comprising a leaving group susceptible to nucleophilic or electrophilic displacement. Other groups may include a lactone, an anhydride, an alpha-haloacetamide, an imine, a hydrazide, or an epoxide. Exemplary linker electrophilic reactive groups that can covalently bond to a reactive nucleophilic group (e.g., a lysine or cysteine side chain) in a combining site of antibody include acyl beta-lactam, simple diketone, succinimide active ester, maleimide, haloacetamide with linker, haloketone, cyclohexyl diketone, aldehyde, amidine, guanidine, imine, eneamine, phosphate, phosphonate, epoxide, aziridine, thioepoxide, a masked or protected diketone (a ketal for example), lactam, sulfonate, and the like, masked C=O groups such as imines, ketals, acetals, and any other known electrophilic group. In certain embodiments, the reactive group includes one or more C=O groups arranged to form an acyl beta-lactam, simple diketone, succinimide active ester, maleimide, haloacetamide with linker, haloketone, cyclohexyl diketone, or aldehyde. Z or Z' if present may be a substituted alkyl, substituted cycloalkyl, substituted aryl, substituted arylalkyl, substituted heterocyclyl, or substituted heterocyclylalkyl, wherein at least one substituent is a 1,3-diketone moiety, an acyl beta-lactam, an active ester, an alpha-haloketone, an aldehyde, a maleimide, a lactone, an anhydride, an alpha-haloacetamide, an amine, a hydrazide, or an epoxide. In some aspects, the Z group if present is covalently linked to the combining site of an antibody. In other aspects, the Z group is covalently linked to a macromolecule scaffold that can provide increased half-life to the peptides of the invention.

In some aspects, Z if present has the structure:

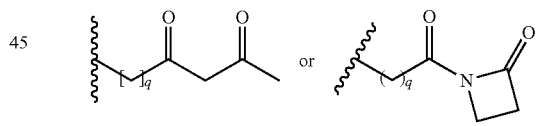

wherein q=0-5. q may be 1 or 2. q may be 1. In other aspects, q may be 2.

Z' if present may have the structure:

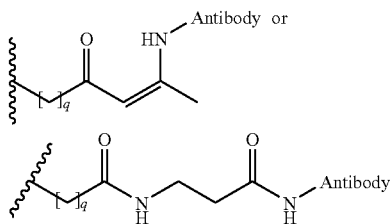

wherein q=0-5 and Antibody-N— is a covalent bond to a side chain in a combining site of an antibody. q may be 1 or 2. q may be 1. In other aspects, q may be 2.

X may be a group comprising three components; Xp-Xs-Xy, wherein Xp is a group specifically adapted to be combinable with the side chain of the linking residue, Xs is a spacer region of the X group, and Xy is a group adapted to bind to the Y group. In some aspects, Xy is selected from an amide bond, an einimine bond, or a guaninium bond. Xy may be selected so as to provide a hydrogen molecule adjacent (within two atoms) to the Y group. While not wishing to be bound be theory, it is believed that the H atom can assist the Y group recognition of a hydrophobic pocket through H-bond interaction, particularly in respect of the hydrophobic pocket of the binding cleft of a catalytic antibody, such as h38C2 (e.g. FIG. 2A). Thus the amide bond, for example, may be orientated such that the NH group is directly bonded to the Y group, providing the H of the NH group for hydrogen bonding. Alternatively, the C=O group of an amide may be bonded to the Y group, with the H of the NH group nay 2 atoms adjacent to the Y group, but still available for H-bonding. In some aspects, Xs is selected such that Xs does not provide any overly reactive groups. Xs may be selected so as to provide an overall length of the X groups of between 2-15 atoms. Xs may be selected so that the overall length of the X group is between 2 and 10 atoms. Xs may be selected so that the overall length of X group is 4-8 atoms. Xs may be selected so that the overall length of X group is 5 atoms. Xs may be selected so that the overall length of X group is 6 atoms. Xp ideally is selected so as to enable a specific directional covalent linking strategy to the linging residue. For example, where the linking residue comprises a nucleophillic group, Xp may be an electrophillic group and vice versa. For example, if the linking residue side chain comprises an amine group, such as K, H, Y, orthinine, Dap, or Dab, Xp may be COOH, or other similarily reactive electrophile. If the linking residue is D or E, Xp may comprise a nucleophilic group, such as an amine group. Either of these strategies permits a covalent bond to be formed between the Xp group and the linking reside by amide bond formation strategies. Where the linking group is C, homologs of C, or other thiol-group containing residues, Xp may comprise a malemide group, permitting a thiol-malemide addition reaction strategy to covalently link the Xp group to the linking residue. In some aspects, Xp may also comprise a thiol group, allowing a disulphide bridge to be formed between the linking residue and Xp group.

The backbone length of X may be 3-15 atoms.

X may be: and in some aspects, X—Y may be:

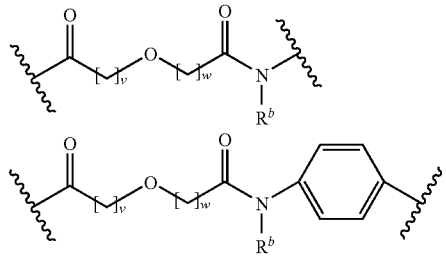

wherein v and w are selected such that the backbone length of X is 6-12 atoms, or 3-9 atoms, or 4-7 atoms, or 6 atoms, or 7 atoms, or 8 atoms. V and W may each be between 0-8. V may be 1 or 2. W may be 1 or 2. V and W may each be 1. $R^b$ may be hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. $R^b$ may be H. In some aspects, V and W are both 1, and $R^b$ is H.

Certain embodiments in accordance of the invention have the structure:

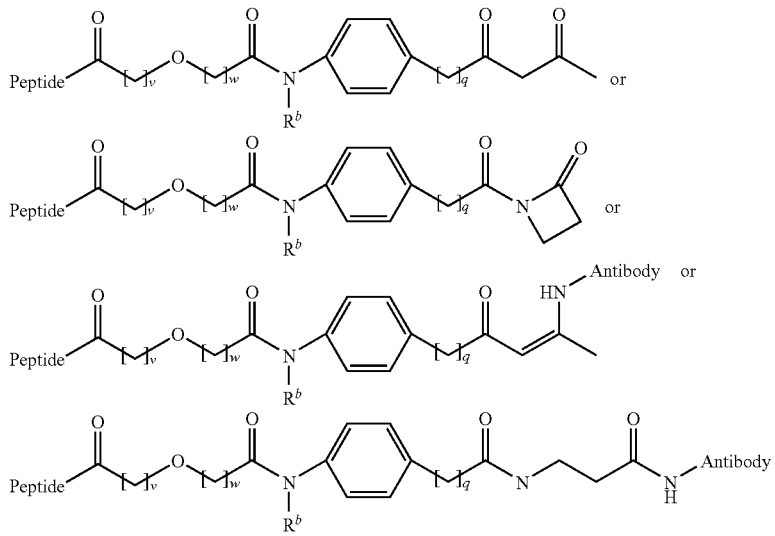

where Peptide is a [VEGF-Peptide] of the invention, and v is 1, 2, 3, 4, or 5; w is 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 1, 2, or 3; w is 1, 2, or 3; and q is 0, 1, 2, or 3. In some embodiments, v is 1 or 2; w is 1 or 2; and q is 1 or 2 and $R^b$ is H.

In some aspects, the invention provides for a compound selected from the group consisting of Compounds 2001-2010, Compounds 2014-2016, Compound 2018, Compound 2020, Compound 2022-2024, Compounds 2027-2033, Compound 2036, Compound 2038, Compounds 2041-2042, Compounds 2045-2046, Compounds 2048-2050, and Compound 2052-2053. These compounds may be covalently linked to the combining site of a catalytic antibody, for example an aldolase antibody, for example h38C2. In some aspects, the invention provides for a compound of the invention selected from the group consisting of Compounds 2018, 2036, 2045, and 2050. These compounds may be covalently linked to the combining site of a catalytic antibody, for example an aldolase antibody, for example h38C2. In some aspects, the invention provides for Compound 2018.

The present invention also provides for nucleic acid sequences (including DNA sequences, RNA sequences, and DNA-RNA sequences) encoding peptides of the invention, and their precursors.

Bifunctional Molecules

In some aspects, the invention provides a compound of the formula:

wherein [Active Molecule-1] is a [VEGF-Peptide] of the invention and [Connector] is a moiety covalently bonded to both [VEGF-Peptide] and [Active Molecule-2]. It will be appreciated that in some aspects of the invention, [Connector] may be covalently attached more than one other [Active Molecule] in addition to the [VEGF-Peptide].

$R^1$-[VEGF-peptide]-$R^2$ may be {C(O)CH$_3$}—V-E-P—N—C-D-I—H—V—K—W—V—W-E-C—F-E-R-L-Y-(D-Ala)-(D-Leu)-{NH$_2$} (SEQ ID NO:188) and $K^{11}$ may be the VEGF-linking residue covalently linked to the [Connector].

An Active Molecule may be any chemical, biochemical, or biological entity capable of being covalently bonded to [Connector] and interacting with biological systems. Examples include therapeutic agents, drugs, pro-drugs, targeting agents, toxins, proteins, peptides, nucleic acid molecules, and lipids. In some aspects of the invention, Active Molecules are Peptides, and may be anti-angiogenic peptides. In some aspects, Active Molecules are [VEGF-Peptides] of the invention and/or [Ang2-Peptides] of the invention as appropriate.

The [VEGF-Peptide] may be covalently linked to [Connector] through a nucleophilic side chain, or N-terminus amino group, or C-terminus carboxyl group of an VEGF-linking residue. Alternatively, where the linker is not branched, the [VEGF-peptide] may be covalently linked to the X-group of L or L' through a nucleophilic side chain or the N-terminus amino group or C-terminus carboxyl group of a VEGF-linking residue. The VEGF-linking residue may be selected from the group comprising K, R, Y, C, T, S, homologs of lysine, homocysteine, homoserine, Dap, Dab, the N-terminus residue and the C-terminus residue. The VEGF-linking residue may be selected from the group consisting of K, Y, T, Dap, and Dab. In some aspects of the invention, the VEGF-linking residue is K. The linking residue may be $K^{10}$. The linking residue may be $K^{12}$. In some aspects of the invention one of the group consisting of $V^1$, $E^2$, $P^3$, $N^4$, $V^9$, $M^{10}$, $V^{12}$, $X^{14}$, $E^{17}$ and the C-terminus residue of the [VEGF-peptide] is substituted with a (VEGF-)linking residue comprising a nucleophilic side chain or the N-terminus amino group or the C-terminus carboxyl group covalently linked to the combining site of an antibody directly or via an intermediate linker, the linking residue being selected from the group comprising K, R, Y, C, T, S, homologs of lysine, homocysteine, homoserine, Dap, Dab, the N-terminus residue and the C-terminus residue. In some aspects where the linking residue is located at the N-terminus or C-terminus, the linking may occur through the amino group of the N-terminus or carboxyl group of the C-terminus, rather than through the respective amino acid side chain. In some aspects of the invention, one of $V^1$, $N^4$, $M^{10}$, $V^{12}$, $X^{14}$, and $E^{17}$ is substituted with the VEGF-linking residue. In some aspects of the invention, one of $M^{10}$ and $V^{12}$ is substituted with the linking residue. In some aspects of the invention, $M^{10}$ is substituted with the VEGF-linking residue. In some aspects of the invention, $V^{12}$ is substituted with the VEGF-linking residue.

The [Connector] may comprise the formula: -[AM1-Spacer]-[Branch]-[AM2-Spacer]- wherein [AM-1-Spacer] and [AM-2-Spacer] are each independently a biologically compatible polymer, block copolymer C, H, N, O, P, S, halogen (F, Cl, Br, I), or a salt thereof, alkyl, alkenyl, alkynyl, oxoalkyl, oxoalkenyl, oxoalkynyl, aminoalkyl, aminoalkenyl, aminoalkynyl, sulfoalkyl, sulfoalkenyl, sulfoalkynyl, phosphoalkyl, phosphoalkenyl, or phosphoalkynyl group, covalently bonded to [Branch], and [Branch] is molecule with at least three reactive groups, and [AM-1-Spacer] is covalently linked to [Branch] and to the [Active Molecule-1], and [AM-2-Spacer] is covalently linked to [Branch] and to the [Active Molecule-2]. [AM-1-Spacer] and [AM-2-Spacer] may each independently be a neutal, water soluble molecule able to form covalent bonds with their respective Active Molecule and [Branch]. Where the Active Molecule comprises a peptide, [AM-1-Spacer] and [AM-2-Spacer] may be able to form peptide bonds to the respective Active Molecule.

[AM-1-Spacer] and [AM-2-Spacer] may each independently be selected from the group consisting of: amino polyethylene glycol acids, polyethylene glycol diacids, amino alkanoic acids, amino alkanoic acids, and poly glycine. [AM-1-Spacer] and [AM-2-Spacer] may each independently be selected from the group consisting of (representative molecules shown below merely to exemplify certain suitable species of Spacer):

Amino polyethylene glycol Acids

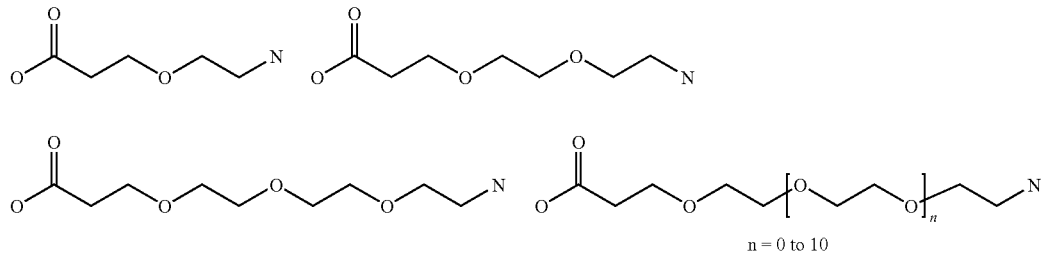

n = 0 to 10

-continued
Polyethylene glycol diacids
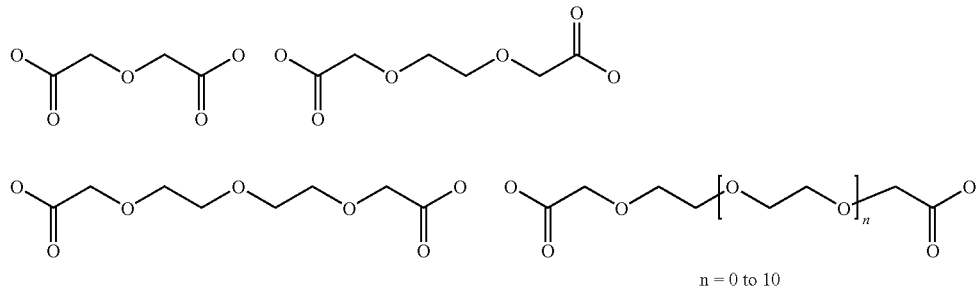
n = 0 to 10
Amino alkanoic acids
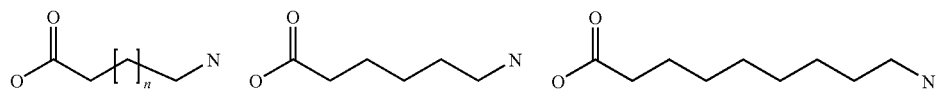
Amino alkanoic acids
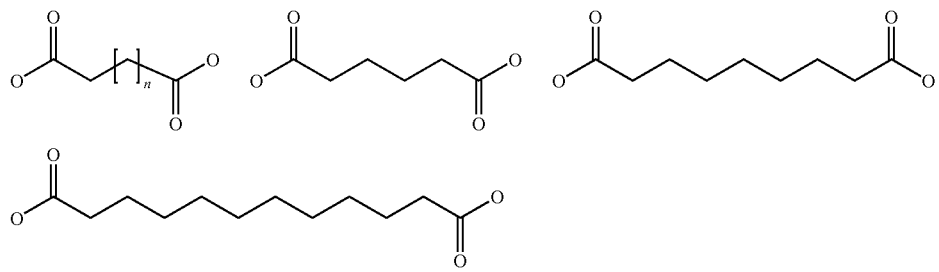
Polyglycine
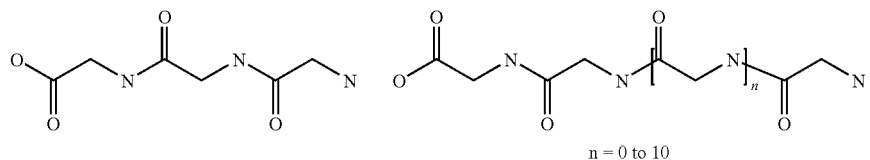
n = 0 to 10
PEG molecules
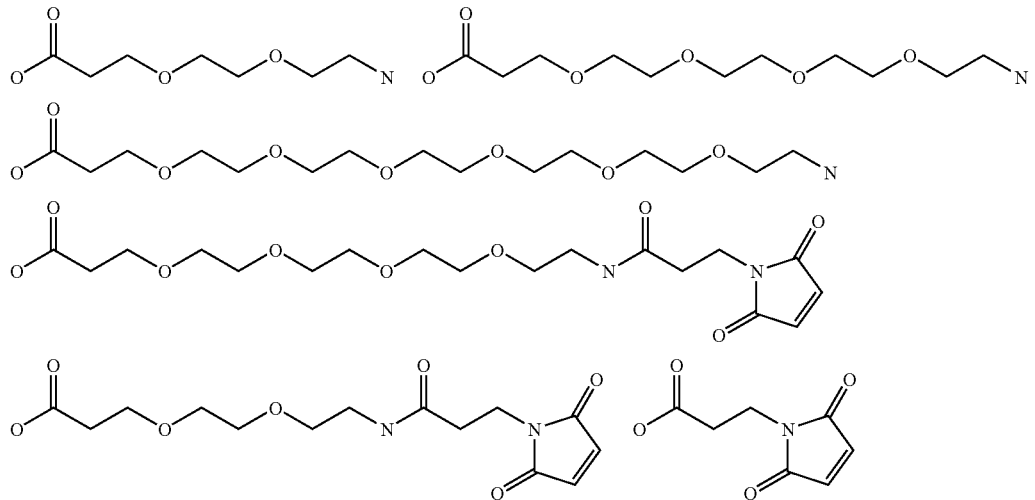

[AM-1-Spacer] and [AM-2-Spacer] may each independently be selected from the group consisting of: 2-PEG, 4-PEG, and 6-PEG:

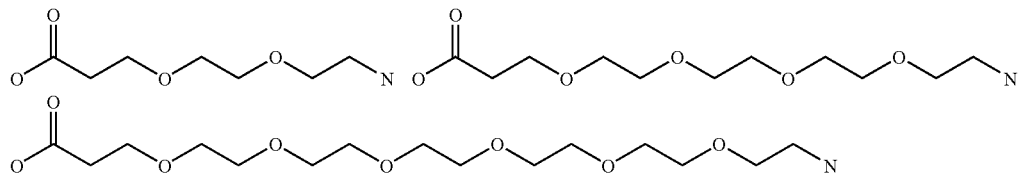

The [AM-1-Spacer] and [AM-2-Spacer] may each independently be between 6 atoms in length and 15 atoms in length. The [AM-1-Spacer] and [AM-2-Spacer] may each independently be a 4-PEG spacer. The [AM-1-Spacer] and [AM-2-Spacer] may each independently be a 2-PEG spacer. The [AM-1-Spacer] and [AM-2-Spacer] may each independently be a 1-PEG spacer. The [AM-1-Spacer] may be between 6 atoms and 15 atoms in length. [AM-1-Spacer] may be 4-PEG. [AM-2-Spacer] may be between 6 atoms and 15 atoms in length. [AM-2-Spacer] may be 4-PEG.

[Branch] may be a chemical moiety comprising three orthogonal reactive groups. [Branch] may be selected from the group consisting of: Cysteine, Diaminopropionic acid, Diaminobutanoic acid Ornithine, Lysine, Homocysteine, Bismaleimide, and Maleimide-acid, and derivitaves and homo logs thereof.

[Branch] may be selected from the group consisting of:

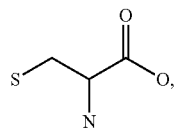 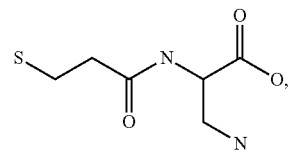

Cysteine branch     Diaminopropionic acid based branch

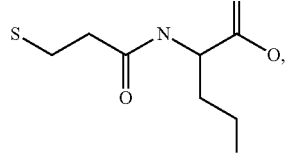

Diaminobutanoic acid based branch

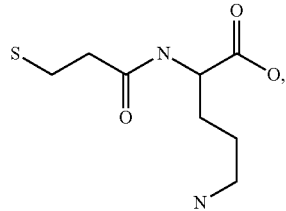

Ornithine based branch

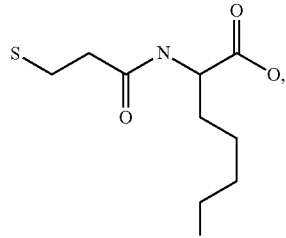

Lysine based branch     Homocysteine branch

-continued

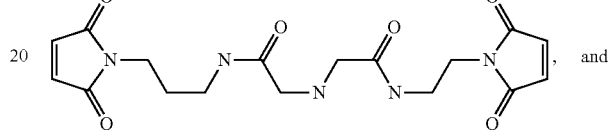

Bismaleimide branch

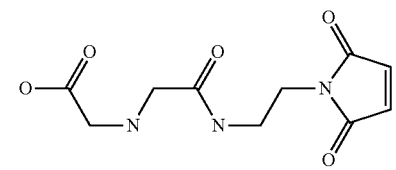

Maleimeide-acid branch and derivitaves and homologs thereof. [Branch] may be cycsteine:

Compounds of the invention may comprise the formula: [Branch]-L or [Branch]-L', wherein L is a linker, and L' is a linker covalently attached to an amino acid side chain in a combining site of an antibody, and [Branch] is covalently attached to L or L'. [Branch]-L may be selected from the group consisting of:

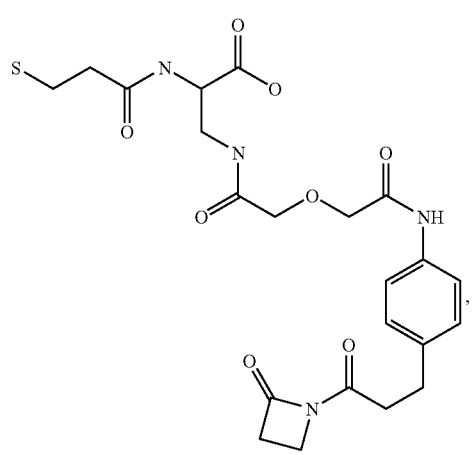

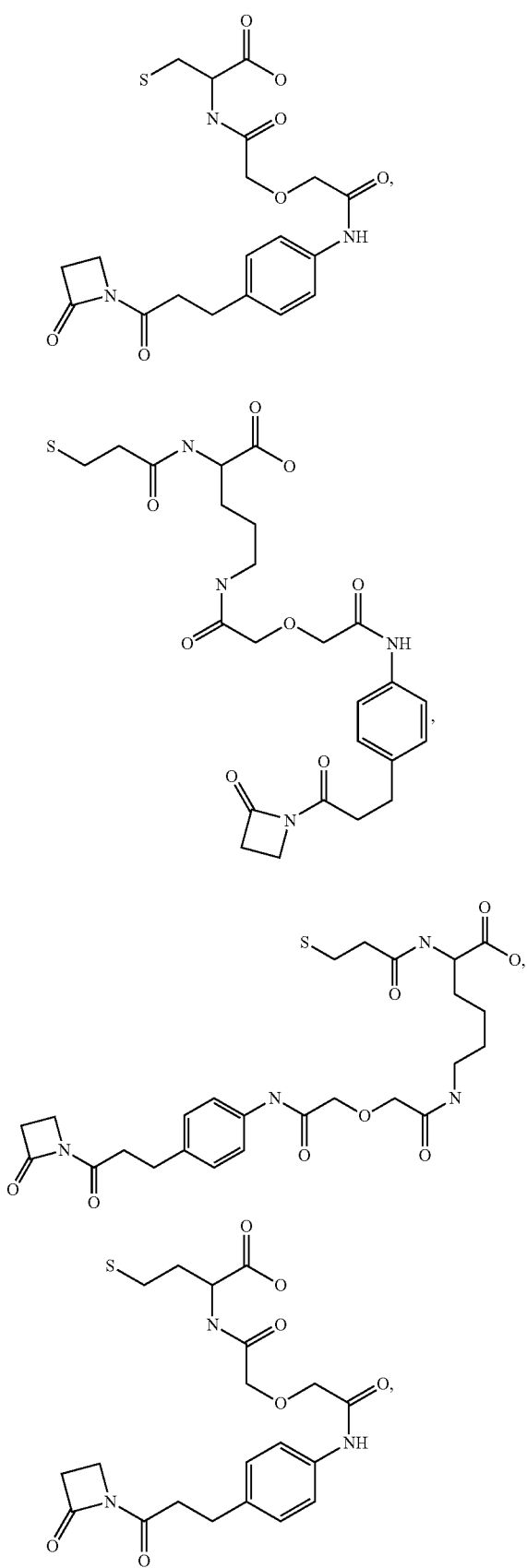

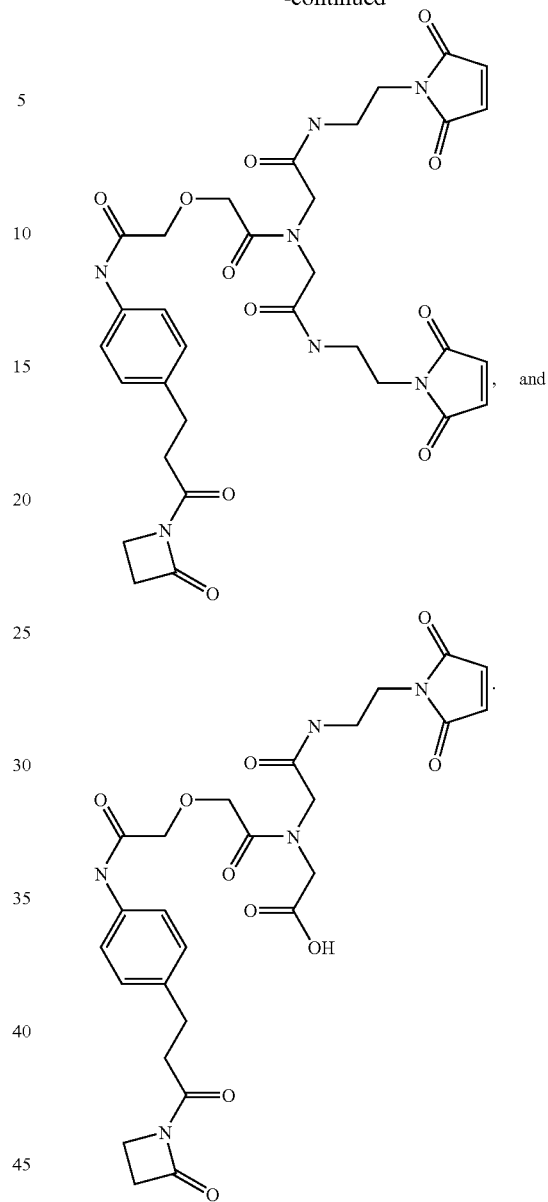

[Ang2 Peptides]

In some aspects of the invention, [Active Molecule 2] is an Ang-2 binding peptide [Ang2-peptide]. The [Ang2-Peptide] may be covalently linked to [Connector] through a nucleophilic side chain or N-terminus or C-terminus of an Ang2-linking residue, the Ang2-linking residue being selected from the group comprising K, R, Y, C, T, S, homologs of lysine, homocysteine, homoserine, Dap, Dab, the N-terminus residue and the C-terminus residue]. Where the Ang2-linking residue is located at the C-terminus or N-terminus, the linkage may be through the amino group of the N-terminus or the carboxyl group of the C-terminus, rather than the side chain of the particular amino acid at that position. The Ang2-linking residue may be selected from the group consisting of K, Y, T, Dap, and Dab. The Ang2-linking residue may be K.

In some aspects of the invention, the [Ang2-Peptide] comprises a sequence substantially homologous to: $Q^1X^2Y^3Q^4X^5L^6D^7E^8X^9D^{10}X^{11}X^{12}X^{13}X^{14}D^{15}X^{16}F^{17}M^{18}X^{19}Q^{20}Q^{21}G^{22}$ (SEQ ID NO:107) wherein $X^2$ is selected from the group consisting of K, N, R, H, Kac, Nick, and CbcK, and $X^5$ is selected from the group consisting of P, hP, dhP, and BnHP, and $X^9$ is selected from the group consisting of L, I, ThA, and Kac, and $x^{11}$ is selected from the group consisting of Q, N, C, K, Kac, Dab, and Dap, and $X^{12}$ is selected from the group consisting of L, HL, Nva, I, HchA, HF, and ThA, and $X^{13}$ is selected from the group consisting of L, HL, Nva, I, HchA, HF, and ThA, and $X^{14}$ is selected from the group consisting of aromatic residues, and $X^{16}$ is selected from the group consisting of Q and N, and $X^{19}$ is selected from the group consisting of L, and I, and wherein one of $Q^1$, $E^8$, $X^9$, $X^{11}$, $X^{12}$, $D^{15}$, $X^{16}$, $M^{18}$, $X^{19}$ or $G^{22}$ is substituted with the Ang2-linking residue.

In some aspects, $X^2$ is selected from the group consisting of K, N, and Kac. $X^2$ may be N. $X^2$ may be Kac. In some aspects, $X^5$ is selected from the group consisting of P, hP, and dhP. $X^5$ may be P. in some aspects, $X^9$ is L. in some aspects, $X^9$ is Kac. In some aspects, $X^{11}$ is selected from the group consisting of K, Kac. In some aspects, $X^{13}$ is selected from the group consisting of L, HL, Nva, I. $X^{13}$ may be L. In some aspects, $X^{14}$ is selected from the group consisting of F, Y, W, BPA, CF, NF. $X^{14}$ may be Y. In some aspects, $X^{16}$ is Q. The Ang2-linking residue may be substituted for one of the group consisting of $X^9$, $X^{11}$, $X^{12}$, $D^{15}$, $X^{16}$, $M^{18}$ and $X^{19}$, $X^{11}$ may be the location of the Ang2-linking residue.

The [Ang2-peptide] may comprise a sequence substantially homologous to one or more compounds selected from the group consisting of: SEQ ID NOs:137-191. The Ang-2 peptide may comprise a compound selected from the group consisting of SEQ ID NOs:137-172 and SEQ ID NO:182. The [Ang2-peptide] may comprise a sequence substantially homologous to one or more compounds selected from the group consisting of: SEQ ID NO:137, SEQ ID NO:138, SEQ ID NO:139, SEQ ID NO:140, SEQ ID NO:153, SEQ ID NO:154, SEQ ID NO:155, SEQ ID NO:157, SEQ ID NO:161, SEQ ID NO:174, and SEQ ID NO:181.

The [Ang2-peptide] may comprises a sequence substantially homologous to Q(Kac)YQPLDE(Kac)DKTLYDQFM-LQQG (SEQ ID NO:153). $R^1$ may be $C(O)CH_3$. $R^2$ may be $NH_2$. In some aspects, $R^1$-[Ang-peptide]-$R^2$ may be {C(O)CH$_3$}Q(Kac)YQPLDE(Kac)DKTLYDQFMLQQ G-{NH$_2$} (SEQ ID NO:153) and $K^{11}$ is the Ang2-linking residue covalently linked to the [Connector].

In some aspects of the invention, the compound may be selected from the group consisting of: compounds 5001-5028, and 5031-5062. In some aspects, the compound is selected from the group consisting of compounds 5001-5028 and compounds 5031-5074. In some aspects, the compound is selected from the group consisting of 5053, 5060, 5061 and 5062. In some aspects, the compound is compound 5053. In some aspects, the compound is 5037. In some aspects of the invention, the compound selected from the group consisting of: compounds 6001-6028, and 6031-6062. In some aspects, the compound is selected from the group consisting of compounds 6001-6026, 6029, 6031-6069. In some aspects, the compound is selected from the group consisting of compounds 6001-6028 and compounds 6031-6074. In some aspects, the compound is selected from the group consisting of compounds 6053, 6060, 6061 and 6062. In some aspects, the compound is compound 6053. In some aspects, the compound is compound 6037.

Antibodies

The contents of US2006205670 are incorporated herein by reference—in particular paragraphs [0153]-[0233], describing antibodies, useful fragments and variants and modifications thereof, combining sites and CDRs, antibody preparation, expression, humanization, aa modification, glycosylation, ADCC, CDC, increasing serum half life of antibodies, expression vectors, mammalian host systems, and folding, amongst other elements of antibody technology.

As discussed, in certain embodiments, certain antibodies that can be used in conjunction with compounds of the invention may require a reactive side chain in the antibody combining site. A reactive side chain may be present naturally or may be placed in an antibody by mutation. The reactive residue of the antibody combining site may be associated with the antibody, such as when the residue is encoded by nucleic acid present in the lymphoid cell first identified to make the antibody. Alternatively, the amino acid residue may arise by purposely mutating the DNA so as to encode the particular residue (see, e.g., WO 01/22922 to Meares et al.). The reactive residue may be a non-natural residue arising, for example, by biosynthetic incorporation using a unique codon, tRNA, and aminoacyl-tRNA as discussed herein. In another approach, the amino acid residue or its reactive functional groups (e.g., a nucleophilic amino group or sulfhydryl group) may be attached to an amino acid residue in the antibody combining site. Thus, covalent linkage with the antibody occurring "through an amino acid residue in a combining site of an antibody" as used herein means that linkage can be directly to an amino acid residue of an antibody combining site or through a chemical moiety that is linked to a side chain of an amino acid residue of an antibody combining site. In some embodiments, the amino acid is cysteine, and the reactive group of the side chain is a sulfhydryl group. In other embodiments, the amino acid residue is lysine, and the reactive group of the side chain is the ϵ-amino group.

Catalytic antibodies are one source of antibodies with suitable combining sites that comprise one or more reactive amino acid side chains. Such antibodies include aldolase antibodies, beta lactamase antibodies, esterase antibodies, amidase antibodies, and the like.

One embodiment comprises an aldolase antibody such as the mouse monoclonal antibodies mAb 33F12 and mAb 38C2, as well as suitably chimeric and humanized versions of such antibodies (e.g., h38C2, SEQ ID NOs:1 and 2). Mouse mAb 38C2 (andh38C2) has a reactive lysine near to but outside HCDR3, and is the prototype of a new class of catalytic antibodies that were generated by reactive immunization and mechanistically mimic natural aldolase enzymes. See C. F. Barbas 3$^{rd}$ et al., Science 278:2085-2092 (1997)). Other aldolase catalytic antibodies that may be used include the antibodies produced by the hybridoma 85A2, having ATCC accession number PTA-1015; hybridoma 85C7, having ATCC accession number PTA-1014; hybridoma 92F9, having ATCC accession number PTA-1017; hybridoma 93F3, having ATCC accession number PTA-823; hybridoma 84G3, having ATCC accession number PTA-824; hybridoma 84G11, having ATCC accession number PTA-1018; hybridoma 84H9, having ATCC accession number PTA-1019; hybridoma 85H6, having ATCC accession number PTA-825; hybridoma 90G8, having ATCC accession number PTA-1016. Through a reactive lysine, these antibodies catalyze aldol and retro-aldol reactions using the enamine mechanism of natural aldolases. See, e.g., J. Wagner et al., Science 270:1797-1800 (1995); C. F. Barbas 3$^{rd}$ et al., Science 278: 2085-2092 (1997); G. Zhong et al., Angew. Chem. Int. Ed. Engl. 38:3738-3741 (1999); A. Karlstrom et al., Proc. Natl. Acad. Sci. U.S.A., 97:3878-3883 (2000). Aldolase antibodies and methods of generating aldolase antibodies are disclosed in U.S. Pat. Nos. 6,210,938, 6,368,839, 6,326,176, 6,589,766, 5,985,626, and 5,733,75, which are incorporated herein by reference.

Compounds of the invention may also be formed by linking a compound of the invention to a reactive cysteine, such as those found in the combining sites of thioesterase and esterase catalytic antibodies. Suitable thioesterase catalytic antibodies are described by K. D. Janda et al., Proc. Natl. Acad. Sci. U.S.A. 91:2532-2536 (1994). Suitable esterase antibodies are described by P. Wirsching et al., Science 270: 1775-1782 (1995). Reactive amino acid-containing antibodies may be prepared by means well known in the art, including mutating an antibody combining site residue to encode for the reactive amino acid or chemically derivatizing an amino acid side chain in an antibody combining site with a linker that contains the reactive group.

Antibody may be a humanized antibody. Where compounds of the invention are covalently linked to the combining site of an antibody, and such antibodies are humanized, it is important that such antibodies be humanized with retention of high linking affinity for the Z group. Various forms of humanized murine aldolase antibodies are contemplated. One embodiment uses the humanized aldolase catalytic antibody h38c2 IgG1 or h38c2 Fab with human constant domains $C_\kappa$ and $C_{\gamma1}1$. C. Rader et al., J. Mol. Bio. 332:889-899 (2003) discloses the gene sequences and vectors that may be used to produce h38c2 Fab and h38c2 IgG1. Human germline Vk gene DPK-9 and human $J_\kappa$ gene JK4 were used as frameworks for the humanization of the kappa light chain variable domain of m38c2, and human germline gene DP-47 and human $J_H$ gene JH4 were used as frameworks for the humanization of the heavy chain variable domain of m38c2. FIG. 2A illustrates a sequence alignment between the variable light and heavy chains in m38c2, h38c2, and human germlines. h38c2 may utilize IgG1, IgG2, IgG3, or IgG4 constant domains, including any of the allotypes thereof.

FIG. 2B illustrates one embodiment of h38c2 IgG1 using the Glm(f) allotype, where the light and heavy chain amino acid sequences of this h38c2 IgG1 are set forth in the figure. In certain embodiments of compounds of the invention wherein Antibody is h38c2 IgG1 with the Glm(f) allotype, Z binds to the side chain of the lysine residue at position 99 of the heavy chain. This residue is denoted by bold print in FIG. 2B. Another embodiment uses a chimeric antibody comprising the variable domains ($V_L$ and $V_H$) of h38c2 and the constant domains from an IgG1, IgG2, IgG3, or IgG4. Antibody may be a full-length antibody, Fab, Fab', $F(ab')_2$, $F_v$, $dsF_v$, $scF_v$, $V_H$, $V_L$, diabody, or minibody comprising $V_H$ and $V_L$ domains from h38c2. Antibody may be an antibody comprising the $V_H$ and $V_L$ domains from h38c2 and a constant domain selected from the group consisting of IgG1, IgG2, IgG3, and IgG4. Antibody may be h38C2 IgG1. Antibody may be a humanized version of a murine aldolase antibody comprising a constant region from a human IgG, IgA, IgM, IgD, or IgE antibody. In another embodiment, the Antibody is a chimeric antibody comprising the variable region from a murine aldolase antibody and a constant region from a human IgG, IgA, IgM, IgD, or IgE antibody. In further embodiments, the Antibody is a fully human version of a murine aldolase antibody comprising a polypeptide sequence from natural or native human IgG, IgA, IgM, IgD, or IgE antibody.

Various forms of humanized aldolase antibody fragments are also contemplated. One embodiment uses h38c2 $F(ab')_2$. h38c2 $F(ab')_2$ may be produced by the proteolytic digestion of h38c2 IgG1. Another embodiment uses an h38c2 scFv comprising the $V_L$ and $V_H$ domains from h38c2 which are optionally connected by the intervening linker $(Gly_4Ser)_3$. As an alternative to humanization, human antibodies can be generated. For example, it is now possible to produce transgenic animals (e.g., mice) that are capable, upon immunization (or reactive immunization in the case of catalytic antibodies) of producing a full repertoire of human antibodies in the absence of endogenous immunoglobulin production.

Alternatively, phage display technology (see, e.g., J. McCafferty et al., Nature 348:552-553 (1990); H. J. de Haard et al., J Biol Chem 274, 18218-18230 (1999); and A. Kanppik et al., J Mol Biol, 296, 57-86 (2000)) can be used to produce human antibodies and antibody fragments in vitro using immunoglobulin variable (V) domain gene repertoires from unimmunized donors. As indicated above, human antibodies may also be generated by in vitro activated B cells. See, e.g., U.S. Pat. Nos. 5,567,610 and 5,229,275; and C. A. K. Borrebaeck et al., Proc. Natl. Acad. Sci. U.S.A. 85:3995-3999 (1988).

Amino acid sequence modification(s) of the antibodies described herein are contemplated. For example, it may be desirable to improve the binding affinity and/or other biological properties of the antibody. Amino acid sequence variants of an antibody are prepared by introducing appropriate nucleotide changes into the antibody nucleic acid, or by peptide synthesis. Such modifications include, for example, deletions from, insertions into, and/or substitutions of residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites. A useful method for identification of certain residues or regions of an antibody that are preferred locations for mutagenesis is called "alanine scanning mutagenesis," as described in B. C. Cunningham and J. A. Wells, Science 244:1081-1085 (1989).

Exemplary Uses of Compounds and Compositions of the Invention

The invention provides for the use of compounds of the invention or pharmaceutical compositions of the invention in a method of inhibiting or reducing angiogenesis or for treating or preventing a disease or symptom associated with an angiogenic disorder. The invention provides methods of inhibiting or reducing angiogenesis or treating or preventing a disease or symptom associated with an angiogenic disorder comprising administering to a patient a therapeutically effective dose of compounds and compositions of the invention. Also provided are methods of delivering or administering compounds and compositions of the invention and methods of treatment using compounds and compositions of the invention. As used herein, an angiogenesis-mediated condition is a condition that is caused by abnormal angiogenesis activity or one in which compounds that modulate angiogenesis activity have therapeutic use. One aspect of the invention provides methods for modulating VEGF activity in vivo comprising administering an effective amount of a compound or composition as described herein to a subject. Another aspect of the invention includes methods of using compounds and compositions of the invention for diagnostic purposes. Diseases and conditions that may be treated and/or diagnosed with compounds and compositions of the invention include cancer, arthritis, hypertension, kidney disease, psoriasis, angiogenesis of the eye associated with ocular disorder, infection or surgical intervention, macular degeneration, diabetic retinopathy, and the like.

More specifically, examples of "cancer" when used herein in connection with the present invention include cancer selected from lung cancer (NSCLC and SCLC), cancer of the head or neck, ovarian cancer, colon cancer, rectal cancer, prostate cancer, cancer of the anal region, stomach cancer, breast cancer, cancer of the kidney or ureter, renal cell carcinoma, carcinoma of the renal pelvis, neoplasms of the central nervous system (CNS), primary CNS lymphoma, non-Hodgkins's lymphoma, spinal axis tumors, carcinomas of the, oropharynx, hypopharynx, esophagus, pancreas, liver, gallbladder and bile ducts, small intestine, urina; or lymphoma or a combination of one or more of the foregoing cancers. Still more specifically, examples of "cancer" when used herein in connection with the present invention include cancer selected from lung cancer (NSCLC and SCLC), breast cancer, ovarian cancer, colon cancer, rectal cancer, prostate cancer, cancer of the anal region, or a combination of one or more of the foregoing cancers.

In some aspects, compounds of the invention may be uysed in the treatment and/or prevention of ophthalmic diseases such as age-related macular degeneration (both wet and dry), glaucoma, diabetic retinopathy (including diabetic macular edema), choroidal neovascular membrane (CNV), uveitis, myopic degeneration, ocular tumors, central retinal vein occlusion, rubeosis, ocular neovascularization, central serous retinopathy, ocular surface discus such as dry eye, central retinal artery occlusion, cystoid macular edema and other retinal degenerative disease. In some embodiments, it may be advantageous to employ molecules with high binding affinity for the respective target(s), but with a lower PK or half-life, as there will be little enzymatic degradation of the molecule while in the eye, but once the molecule clears the eye, it may be desirable for the molecule to be degraded and undergo renal clearance as soon as possible so as to minimize potential direct effect or side-effects outside the eye. In some aspects of the invention Compounds 6037 is used for the treatment of opthalmic diseases. In some aspects of the invention Compounds 6044 is used for the treatment of opthalmic diseases. In some aspects of the invention Compounds 6053 is used for the treatment of opthalmic diseases.

The compounds according to the invention may be solvated, especially hydrated. Hydration may occur during manufacturing of the compounds or compositions comprising the compounds, or the hydration may occur over time due to the hygroscopic nature of the compounds.

In another aspect, the present invention includes methods of altering at least one physical or biological characteristic of a compounds and compositions. The methods include covalently linking a [VEGF-Peptide] of the invention to a combining site of an antibody, either directly or though a linker. Characteristics of compounds of the invention that may be modified include, but are not limited to, binding affinity, susceptibility to degradation (e.g., by proteases), pharmacokinetics, pharmacodynamics, immunogenicity, solubility, lipophilicity, hydrophilicity, hydrophobicity, stability (either more or less stable, as well as planned degradation), rigidity, flexibility, modulation of antibody binding, and the like. Also, the biological potency of a particular compound of the invention may be increased by the addition of the effector function(s) provided by the antibody. For example, an antibody provides effector functions such as complement mediated effector functions. Without wishing to be bound by any theory, the antibody portion of a compound of the invention may generally extend the half-life of a smaller sized [VEGF-Peptide] in vivo. Thus, in one aspect, the invention provides a method for increasing the effective circulating half-life of a [VEGF-Peptide].

In another aspect, the present invention includes methods of modifying a combining site of an antibody to generate binding specificity for VEGF, or VEGF and one or more other Active Molecules, including Ang2. Such methods include covalently linking a reactive amino acid side chain in a combining site of the antibody to a chemical moiety on a linker of [VEGF-Peptide]-linker compound as described herein. The chemical moiety of the linker is sufficiently distanced from the [VEGF-Peptide] so that the [VEGF-Peptide] can bind its cognate when the [VEGF-Peptide]-linker compound is covalently linked to an antibody combining site (similar constraints will exist for tethering to other half-life increasing macromolecules). Typically, the antibody will not be considered specific for the target molecule. In certain embodiments, an antibody prior to covalent linking would have an affinity for VEGF of less than about $1 \times 10^{-5}$ moles/liter. However, after the antibody is covalently linked to the [VEGF-Peptide], the modified antibody preferably has an affinity for the target molecule of at least about $1 \times 10^{-6}$ moles/liter, alternatively, at least about $1 \times 10^{-7}$ moles/liter, alternatively, at least $1 \times 10^{-8}$ moles/liter, alternatively at least $1 \times 10^{-9}$ moles/liter, or alternatively least about $1 \times 10^{-10}$ moles/liter.

The administration of [VEGF-Peptide] of the invention to an immunocompetent individual may result in the production of antibodies against the conjugate. Such antibodies may be directed to the variable region, including the antibody idiotype, as well as to the targeting agent or any linker used to conjugate the targeting agent to the antibody. Reducing the immunogenicity of a [VEGF-Peptide]can be accomplished by methods well known in the art, such as by attaching long chain polyethylene glycol (PEG)-based spacers and the like to the [VEGF-Peptide]. Long chain PEG and other polymers are known for their ability to mask foreign epitopes, resulting in the reduced immunogenicity of therapeutic proteins that display foreign epitopes (N. V. Katre, J. Immunol. 144:209-213 (1990); G. E. Francis et al., Int. J. Hematol. 68:1-18 (1998). Alternatively, or in addition, the individual administered the antibody-[VEGF-Peptide] conjugate may be administered an immunosuppressant such as cyclosporin A, anti-CD3 antibody, and the like. The above also applies *muatis mutandis* when other Active Molecules, such as Ang2, are covalently linked, via a branched linker, to the compounds of the invention The invention also provides for stereoisomers, tautomers, solvates, prodrugs, and pharmaceutically acceptable salts of compounds of the invention.

Pharmaceutical Compositions, Methods of Administration and Combination Therapies The invention also provides pharmaceutical compositions comprising a therapeutically effective amount of one or more compounds of the invention. The invention also provides methods of treatment using such compositions, and methods of preparing pharmaceutical compositions of the invention. The contents of US2006205670 are incorporated herein by reference—in particular paragraphs [0497]-[0510], describing administration ([0498], [0499]; formulations ([0499], [0500], [0501], [0502]); preparations ([0503], [504]); kits ([0505]); dosage strategies ([0506], [0507], [0508], [0509]); as per the respective targeting agent/AA argeting agent/[Peptide] of the invention, and methods of visualizing or localizing the biolological target to which the [Peptide] of the invention is directed.

The invention also includes administration of one or more compounds or compositions of the invention in combination with one or more oncology therapeutics, each being administered according to a regimen suitable for that therapeutic. The components of the combination therapy may be administered concurrently or non-concurrently. Components may be administered in the same or in separate compositions, and by the same or different routes of administration. Examples of suitable oncology therapeutics and combinations that may be used in combination with peptides and compounds of the invention are listed in Tables 4-6 of US2006205670 (which is incorporated herein by reference). The pharmaceutical compositions of the invention may further comprise a therapeutically effective amount of one or more chemotherapeutic agent, the chemotherapeutic agent preferably being a compound selected from the group consisting of 5-Flurouracil, Irinotecan, Taxotere, Sunitinib, Axitinib, oxilaplatin, bevacizumab, cetuximab, or chemical equivelants thereof. In some aspects, the chemotherapeutic agent is selected from the group consisting of 5-Flurouracil, Irinotecan, Taxotere, Sunitinib, and Axitinib; or chemical equivelants thereof.

Examples of Synthesis of Compounds of the Invention

Compounds of the invention can be prepared using techniques known in the art. Typically, synthesis of the [VEGF-Peptide] or [Ang2-Peptide] (or other Active Molecule) is the first step and is carried out as described herein. The Active Molecule is then derivatized for linkage to a connecting component (the linker), which is then combined with the antibody. One of skill in the art will readily appreciate that the specific synthetic steps used depend upon the exact nature of the three components. Thus, [VEGF-Peptide]—linker conjugates and compounds of the invention described herein can be readily synthesized. [VEGF-Peptides] and [Ang2-Peptides] may be synthesized by many techniques that are known to those skilled in the art. For solid phase peptide synthesis, a summary of exemplary techniques may be found in *Chemical Approaches to the Synthesis of Peptides and Proteins* (Williams et al., eds.), CRC Press, Boca Raton, Fla. (1997).

Typically, the desired peptidic Active Molecule is synthesized sequentially on solid phase according to procedures well known in the art. See, e.g., U.S. Patent Application No. 2003/0045477). The linker may be attached to the peptide in part or in full on the solid phase, or may be added using solution phase techniques after the removal of the peptide from the resin (see FIGS. 1A and 1B). For example, an N-protected amino and carboxylic acid-containing linking moiety may be attached to a resin such as 4-hydroxymethyl-phenoxymethyl-poly(styrene-1% divinylbenzene). The N-protecting group may be removed by the appropriate acid (e.g., TFA for Boc) or base (e.g., piperidine for Fmoc), and the peptide sequence developed in the normal C-terminus to N-terminus fashion (see FIG. 1A). Alternatively, the peptide sequence may be synthesized first and the linker added to the N-terminal amino acid residue last (see FIG. 1B). Yet another method entails deprotecting an appropriate side chain during synthesis and derivatizing with a suitably reactive linker. For example, a lysine side chain may be deprotected and reacted with a linker having an active ester. Alternatively, an amino acid derivative with a suitably protected linker moiety already attached to the side chain (see FIG. 1B) or, in some cases, the alpha-amino nitrogen, may be added as part of the growing peptide sequence.

At the end of the solid phase synthesis, the targeting agent-linker conjugate is removed from the resin and deprotected, either in succession or in a single operation. Removal of the targeting agent-linker conjugate and deprotection can be accomplished in a single operation by treating the resin-bound peptide-linker conjugate with a cleavage reagent, for example, trifluoroacetic acid containing scavengers such as thianisole, water, or ethanedithiol. After deprotection and release of the targeting agent, further derivatization of the targeting agent peptide may be carried out. The fully deprotected peptidyl Active Molecule-linker conjugate is purified by a sequence of chromatographic steps employing any or all of the following types: ion exchange on a weakly basic resin in the acetate form; hydrophobic adsorption chromatography on underivatized polystyrene-divinylbenzene (e.g., AMBERLITE XAD); silica gel adsorption chromatography; ion exchange chromatography on carboxymethylcellulose; partition chromatography, e.g., on SEPHADEX G-25, LH-20 or countercurrent distribution; high performance liquid chromatography (HPLC), especially reverse-phase HPLC on octyl- or octadecylsilyl-silica bonded phase column packing.

BRIEF DESCRIPTION OF THE DRAWINGS

FIG. 2A illustrates the amino acid sequence alignment of the variable domains of m38c2, h38c2, and human germlines. Framework regions (FR) and complementarity determining regions (CDR) are defined according to Kabat et al. Asterisks mark differences between m38c2 and h38c2 or between h38c2 and the human germlines. FIG. 2B illustrates the amino acid sequence of the light and heavy chains (SEQ ID NOs:1 and 2, respectively) of one embodiment of a humanized 38c2 IgG1.

FIG. 3 shows various structures that may serve as linker reactive groups. Structures A-C form reversible covalent bonds with surface accessible reactive nucleophilic groups (e.g., lysine or cysteine side chain) of a combining site of an antibody. $R'_1$, $R'_2$, $R'_3$, and $R_4$ in structures A-C represent substituents which include, for example, C, H, N, O, P, S, halogen (F, Cl, Br, I) or a salt thereof X is N, C, or any other heteroatom. These substituents may also include a group such as an alkyl, alkenyl, alkynyl, oxoalkyl, oxoalkenyl, oxoalkynyl, aminoalkyl, aminoalkenyl, aminoalkynyl, sulfoalkyl, sulfoalkenyl, or sulfoalkynyl group, phosphoalkyl, phosphoalkenyl, phosphoalkynyl group. $R'_2$ and $R'_3$ could be cyclic as exemplified in structures B and C while X could be a heteroatom. For example, structure A could form an irreversible covalent bond with a reactive nucleophile if X is N and if $R'_1$ and $R_3$ form part of a cyclic structure. Structures D-G may form nonreversible covalent bonds with reactive nucleophilic groups in a combining site of an antibody. In these structures, $R'''^1$ and $R'''^2$ represent C, O, N, halide or leaving groups such as mesyl or tosyl.

FIG. 4 shows various electrophiles that are suitable for reactive modification with a reactive amino acid side chain in a combining site of an antibody and thus may serve as linker reactive groups. Key: (A) acyl beta-lactam; (B) simple diketone; (C) succinimide active ester; (D) maleimide; (E) haloacetamide with linker; (F) haloketone; (G) cyclohexyl diketone; and (H) aldehyde. The squiggle line indicates the point of attachment to the rest of the linker or targeting agent. X refers to a halogen.

FIG. 7 shows a synthesis of:

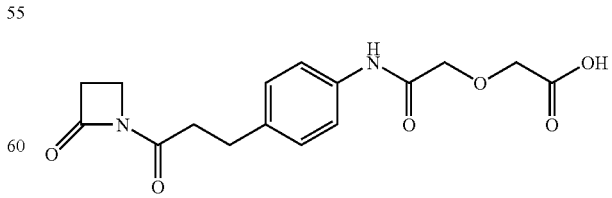

Figure 8:
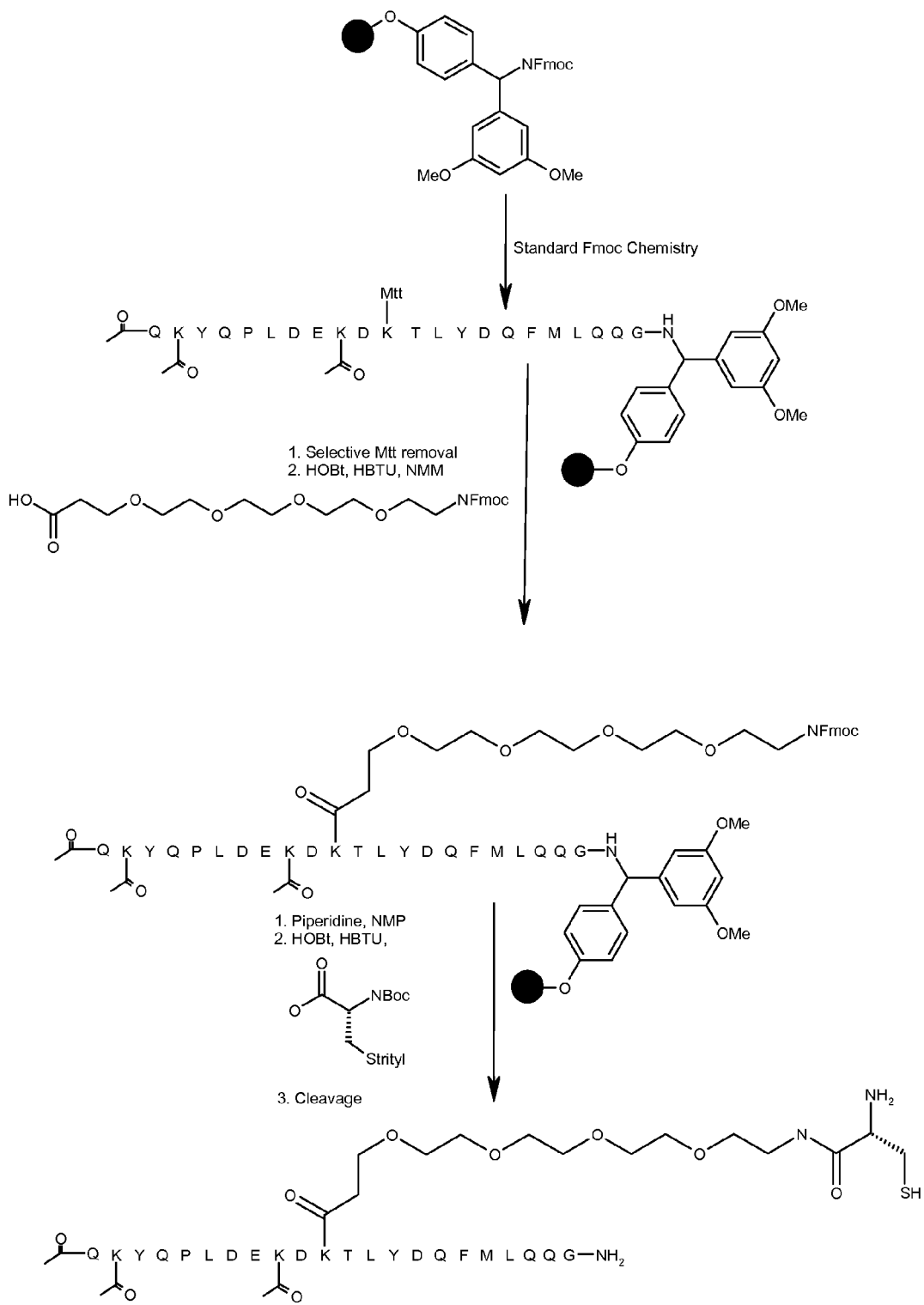

FIG. 8: Exemplary synthesis of [Ang2-peptide]-[Ang2-Spacer], using SEQ ID NO:153 as example.

Figure 9:
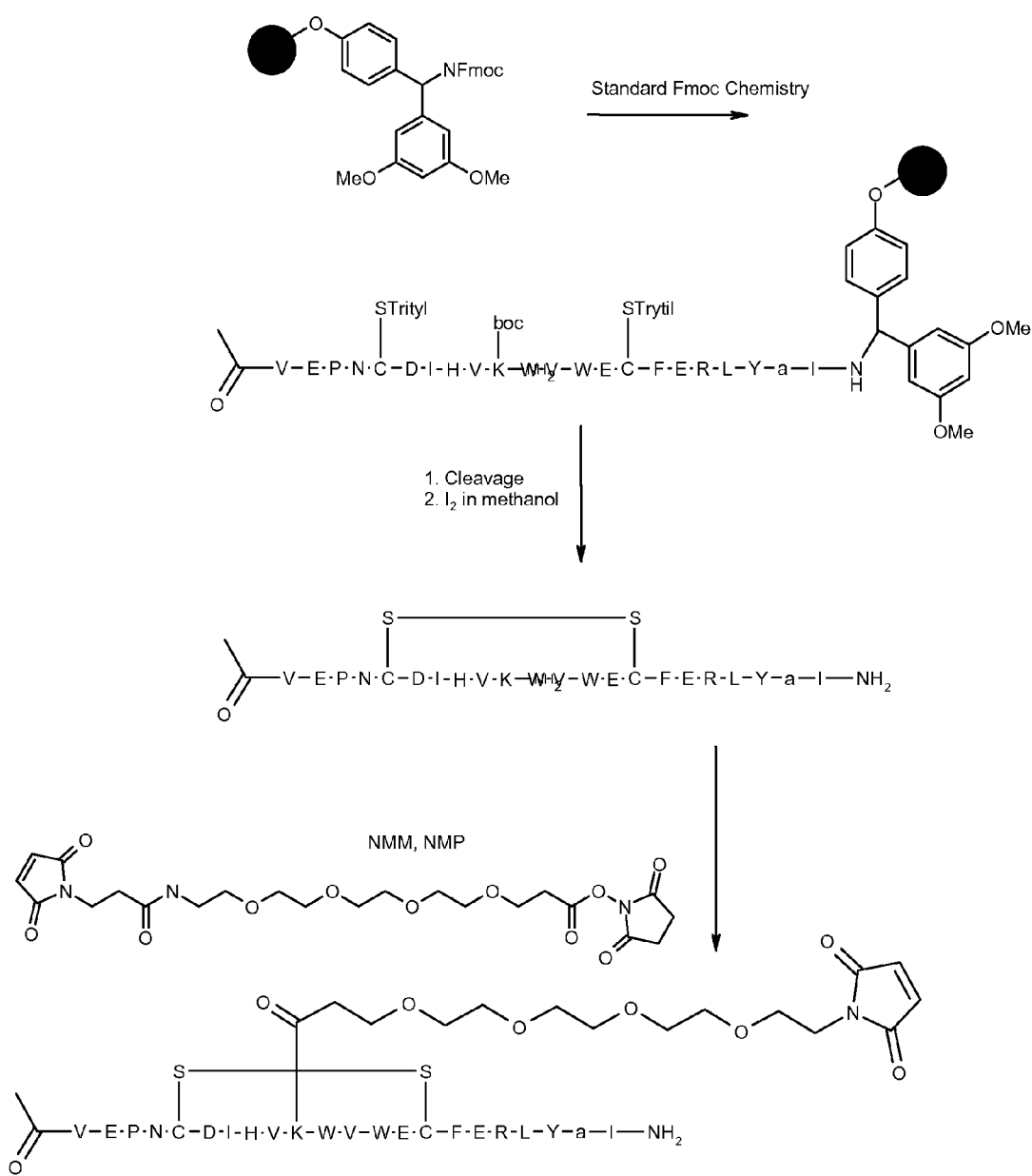

FIG. 9: Exemplary synthesis of [VEGF-Peptide]-[VEGF-Spacer], using SEQ ID NO:188 as example.

Figure 10:
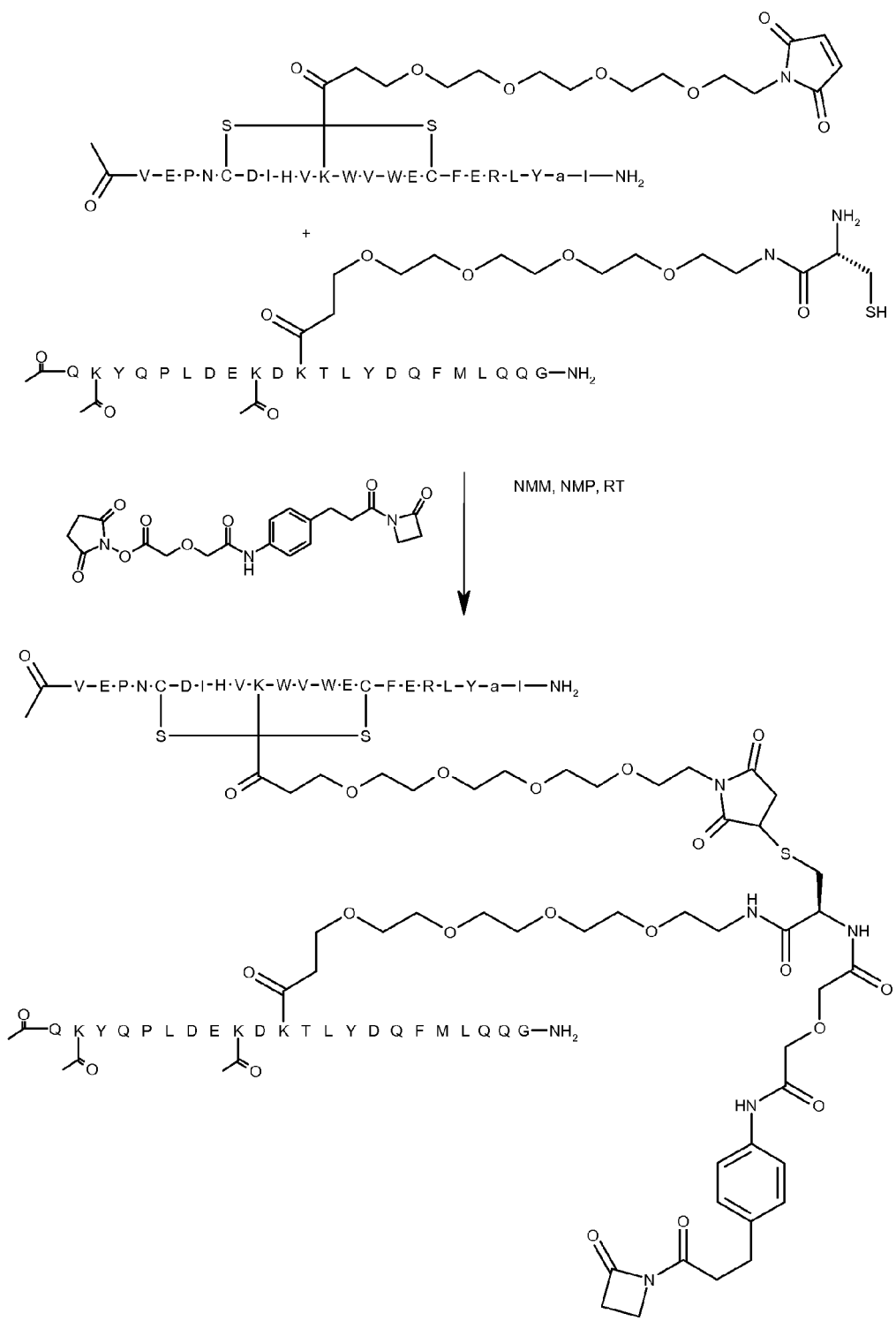

FIG. 10: Exemplary synthesis of compound 5053.

Figure 11:
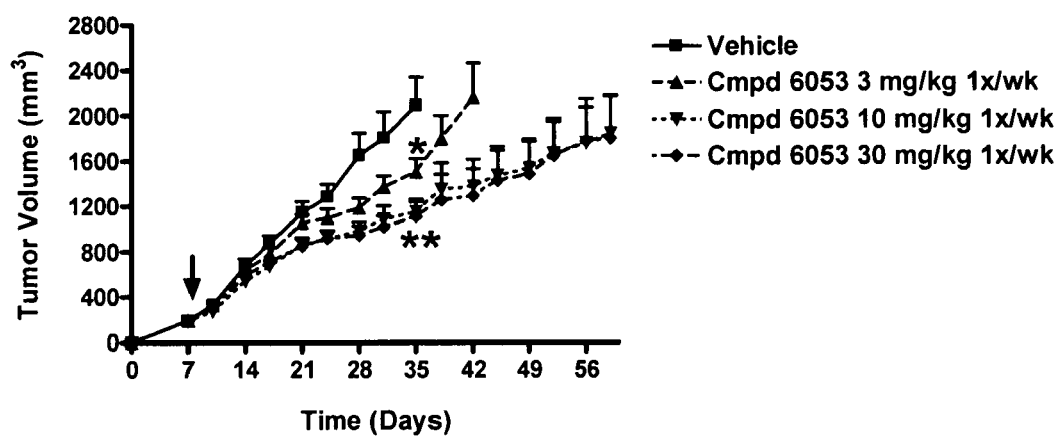

FIG. 11: Tumor volume of Colo205 colon adenocarcinoma xenografts after treatment with Vehicle or Compound 6053 (IP, 1x/wk). Data are depicted as the mean and SE of n=20/group for days 0-35 (n=10 for all groups beyond day 35), vertical arrow indicates first dosing day. *P<0.05, **P<0.01 versus Vehicle at day 35 (One-way ANOVA with Dunnett's Multiple Comparison Test).

Figure 12:
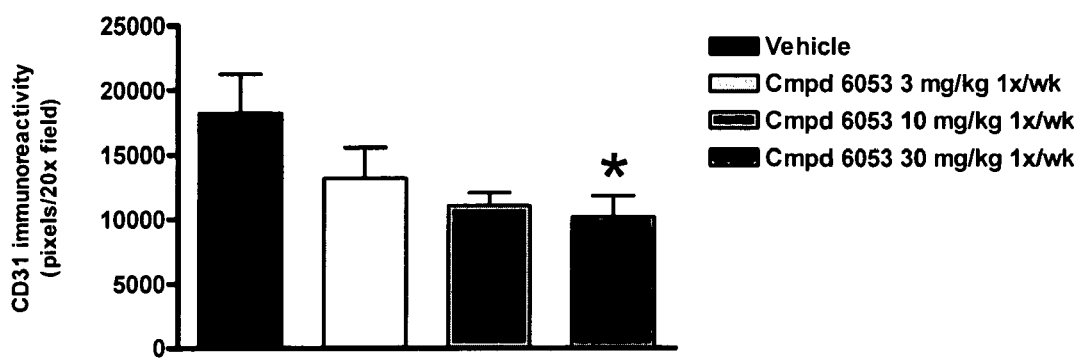

FIG. 12: Tumor microvessel density of Colo205 colon adenocarcinoma xenografts after treatment with Vehicle or Compound 6053 (IP, 1x/wk). Data are depicted as the mean and SE of n=9-10/group. *P<0.05 versus Vehicle (One-way ANOVA with Dunnett's Multiple Comparison Test).

Figure 13:
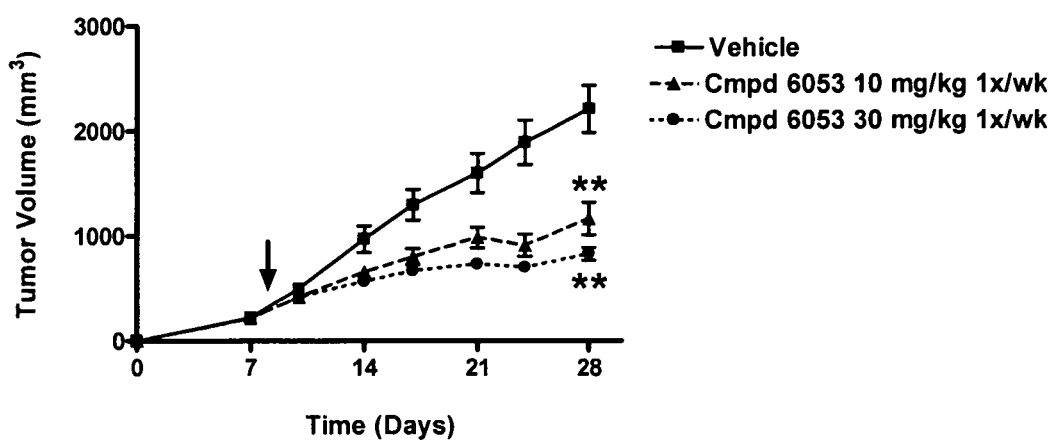

FIG. 13: Tumor volume of Colo205 colon adenocarcinoma xenografts after treatment with Vehicle or Compound 6053 (IP, 1x/wk). Data are depicted as the mean and SE of n=10/group, vertical arrow indicates first dosing day. **P<0.01 versus Vehicle (One-way ANOVA with Dunnett's Multiple Comparison Test).

Figure 14:
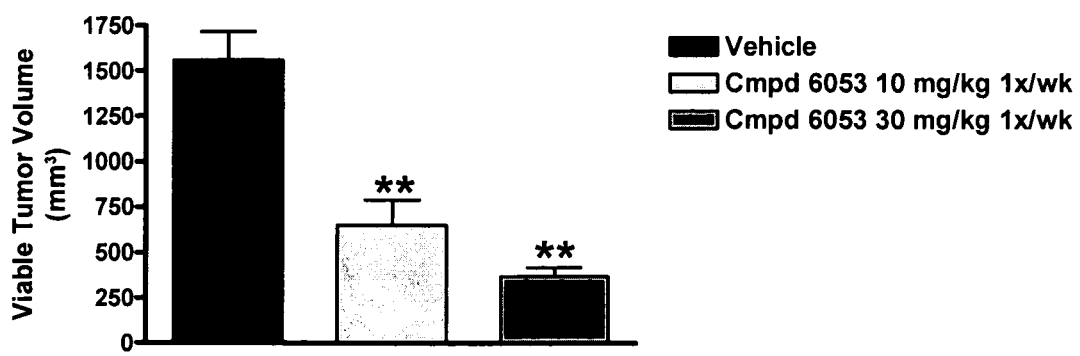

FIG. 14: Viable tumor volume of Colo205 colon adenocarcinoma xenografts after treatment with Vehicle or Compound 6053 (IP, 1x/wk). Data are depicted as the mean and SE of n=9-10/group. **P<0.01 versus Vehicle (One-way ANOVA with Dunnett's Multiple Comparison Test).

Figure 15:
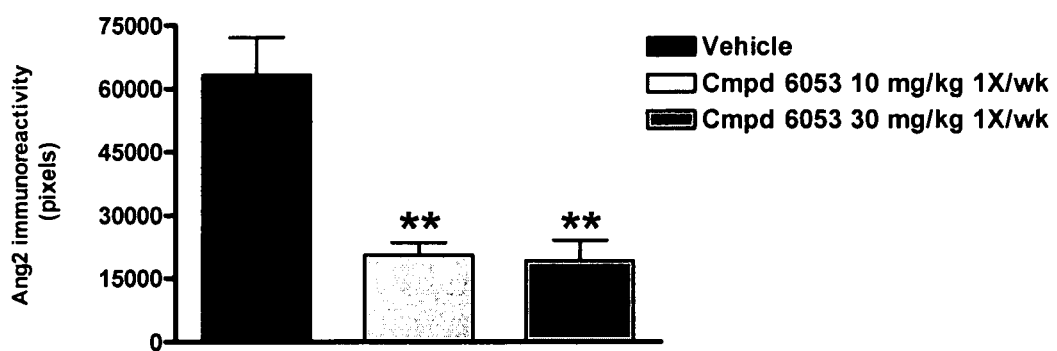

FIG. 15: Ang2 immunoreactivity of Colo205 colon adenocarcinoma xenografts after treatment with Vehicle or Compound 6053 (IP, 1x/wk). Data are depicted as the mean and the SE of n=9-10/group. **P<0.01 versus Vehicle (One-way ANOVA with Dunnett's Multiple Comparison Test).

Figure 16:
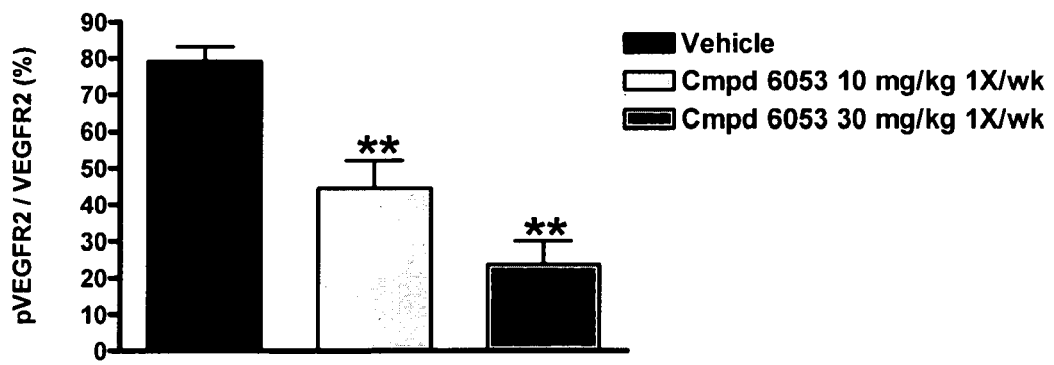

FIG. 16: Phosphorylated VEGFR2 (pVEGFR2) immunoreactivity as a percentage of total VEGFR2 immunoreactivity of Colo205 colon adenocarcinoma xenografts after treatment with Vehicle or Compound 6053 (IP, 1x/wk). Data are depicted as the mean and the SE of n=9-10/group. **P<0.01 versus Vehicle (One-way ANOVA with Dunnett's Multiple Comparison Test).

FIG. 17: Tumor volume of MDA-MB-435 breast adenocarcinoma (A) and A431 skin carcinoma (B) after weekly treatment with Vehicle or Compound 6053 (IP, 1x/wk). Data are depicted as the mean and SE of n=9-10/group, vertical arrow indicates first dosing day. *P<0.05 vs Vehicle at day 68; **P<0.01 versus Vehicle at day 35 (One-way ANOVA with Dunnett's Multiple Comparison Test).

Figure 18:
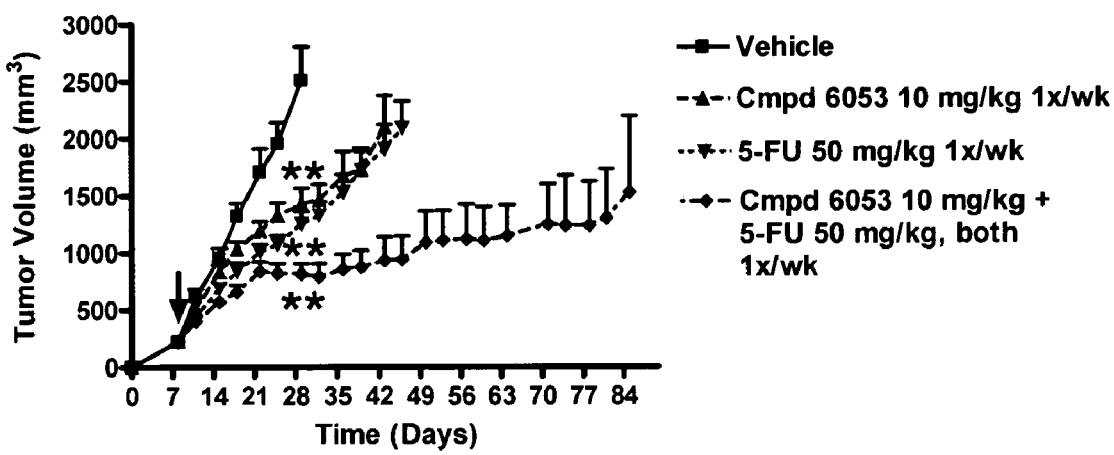

FIG. 18: Tumor volume of Colo205 colon adenocarcinoma xenografts after once weekly treatment with Vehicle, Compound 6053 alone (IP), 5-FU alone (IP), or Compound 6053 in combination with 5-FU (both IP). Data are depicted as the mean and SE of n=9-10/group, vertical arrow indicates first dosing day. **P<0.01 vs Vehicle at day 29 (One-way ANOVA with Bonferroni's Multiple Comparison Test).

Figure 19:
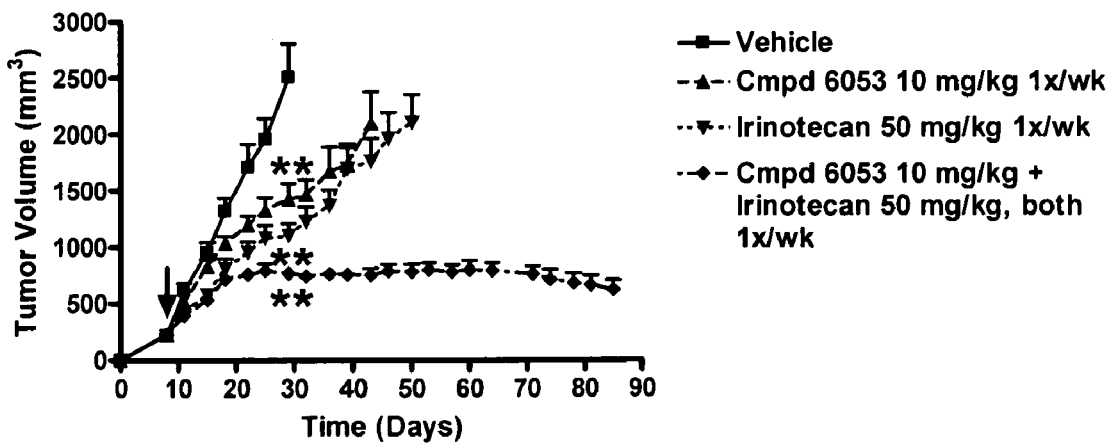

FIG. 19: Tumor volume of Colo205 colon adenocarcinoma xenografts after weekly treatment with Vehicle, Compound 6053 alone (IP), Irinotecan alone (IP), or Compound 6053 in combination with Irinotecan (both IP). Data are depicted as the mean and SE of n=9-10/group, vertical arrow indicates first dosing day. **P<0.01 vs Vehicle at day 29 (One-way ANOVA with Bonferroni's Multiple Comparison Test).

Figure 20:
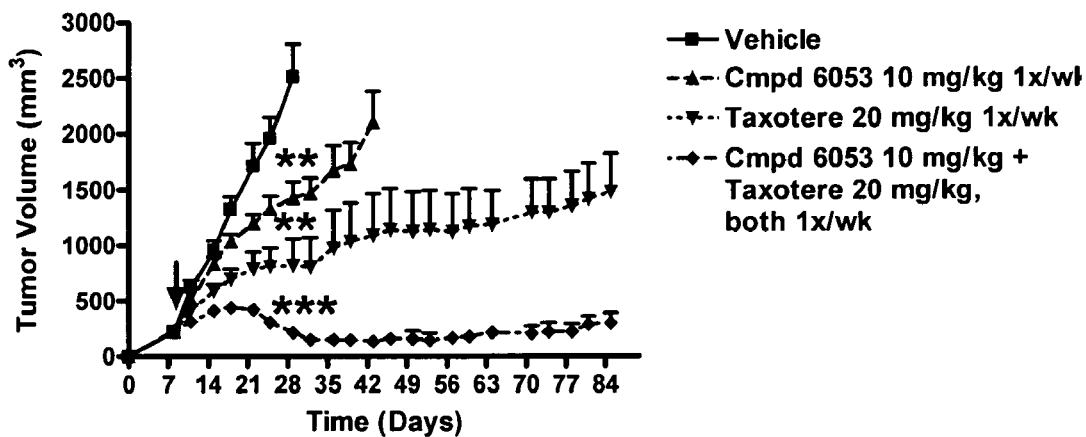

FIG. 20: Tumor volume of Colo205 colon adenocarcinoma xenografts after once weekly treatment with Vehicle, Compound 6053 alone (IP), Taxotere alone (IP), or Compound 6053 in combination with Taxotere (both IP). Data are depicted as the mean and SE of n=9-10/group, vertical arrow indicates first dosing day. P<0.01 vs Vehicle, *P<0.01 vs Vehicle and vs Compound 6053 alone at day 29 (One-way ANOVA with Bonferroni's Multiple Comparison Test).

Figure 21:
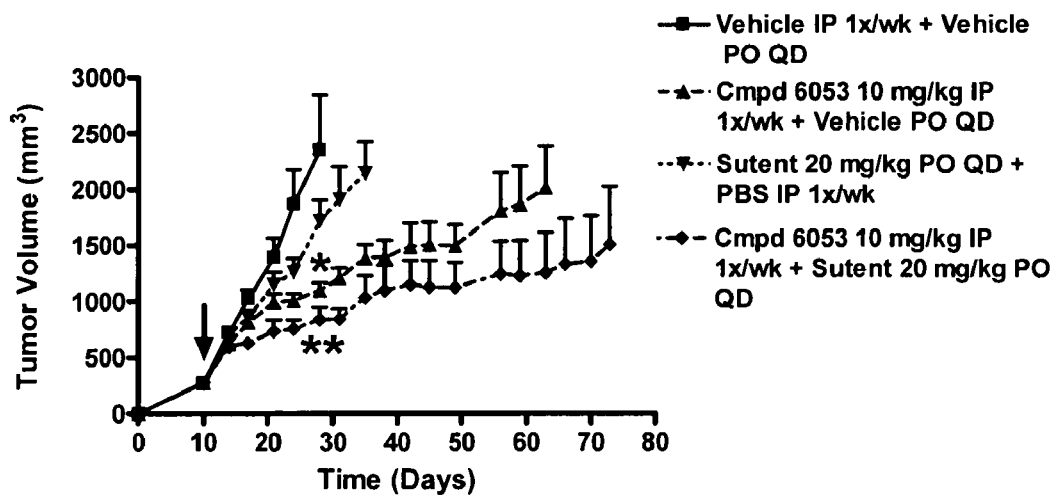

FIG. 21: Tumor volume of Colo205 colon adenocarcinoma xenografts after once weekly treatment with Vehicle, Compound 6053 alone (IP), daily Sunitinib (PO), or Compound 6053 (IP) in combination with Sunitinib (PO). Data are depicted as the mean and SE of n=9-10/group, vertical arrow indicates first dosing day. *P<0.05, **P<0.01 vs Vehicle at day 28 (One-way ANOVA with Bonferroni's Multiple Comparison Test).

Figure 22:
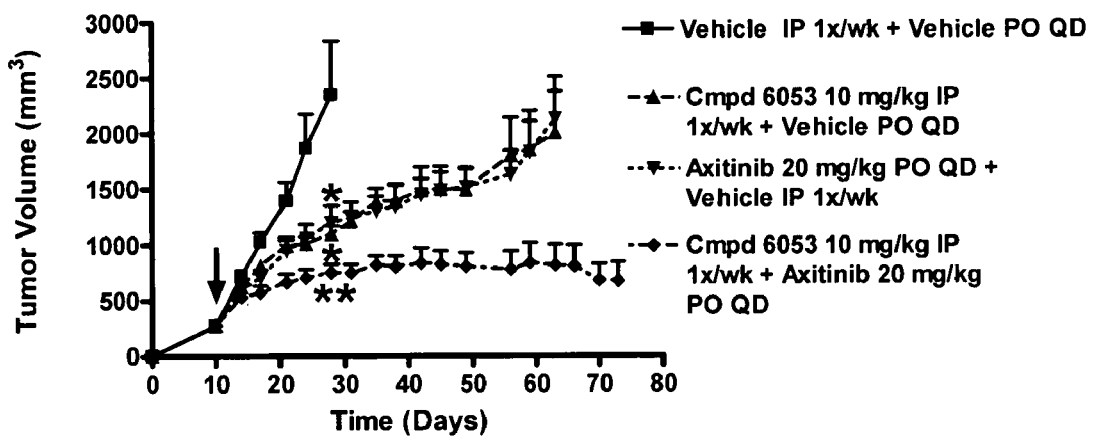

FIG. 22: Tumor volume of Colo205 colon adenocarcinoma xenografts after once weekly treatment with Vehicle, Compound 6053 alone (IP), daily Axitinib (PO), or Compound 6053 (IP) in combination with Axitinib (PO). Data are depicted as the mean and SE of n=9-10/group, vertical arrow indicates first dosing day. *P<0.05, **P<0.01 vs Vehicle at day 28 (One-way ANOVA with Bonferroni's Multiple Comparison Test).

Figure 23:
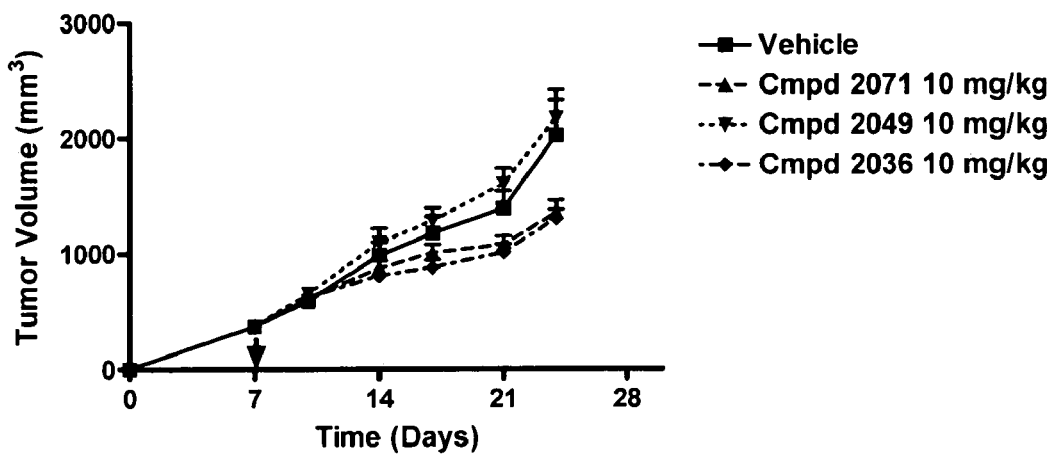

FIG. 23: Tumor volume of Colo205 colon adenocarcinoma xenografts after once weekly treatment with Vehicle, Compound 2071, Compound 2049, or Compound 2046 (all IP). Data are depicted as the Mean and SE of n=10/group, vertical arrow indicates first dosing day.

Figure 24:
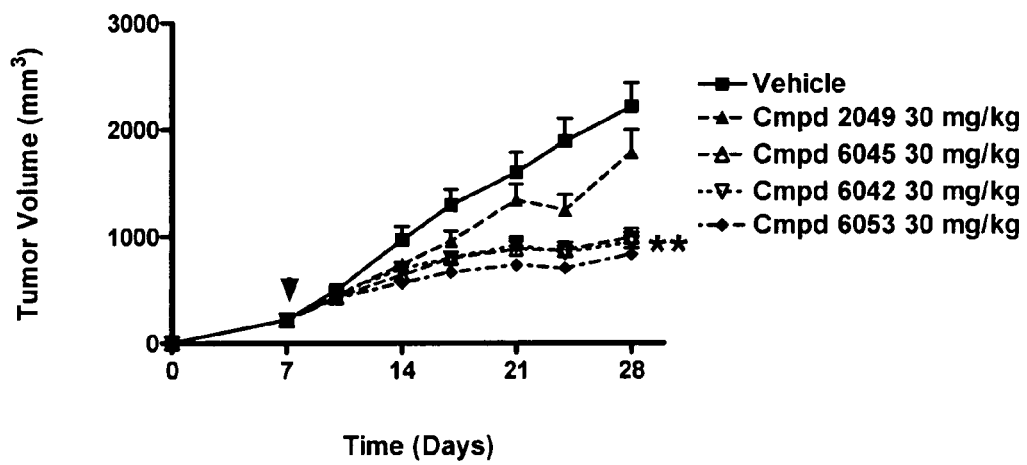

FIG. 24: Tumor volume of Colo205 colon adenocarcinoma xenografts after once weekly treatment with Vehicle, Compound 2049, Compound 6045, Compound 6042, or Compound 6053 (all IP). Data are depicted as the Mean and SE of n=10/group, vertical arrow indicates first dosing day. **P<0.01 versus Vehicle on day 28 (Compounds 6045, 6042, and 6053).

Figure 25:
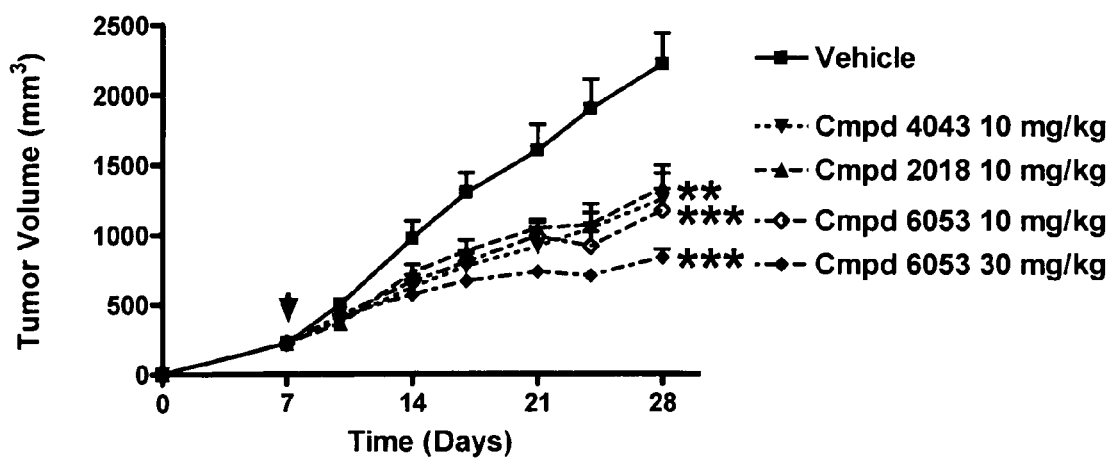

FIG. 25: Tumor volume of Colo205 colon adenocarcinoma xenografts after once weekly treatment with Vehicle, Compound 4043, Compound 2018, or Compound 6053 (all IP). Data are depicted as the Mean and SE of n=10/group, vertical arrow indicates first dosing day. P<0.01 versus Vehicle on day 28 (Compounds 4043 and 2018), *P<0.001 versus Vehicle on day 28 (Compound 6053, 10 and 30 mg/kg weekly doses).

Figure 26:
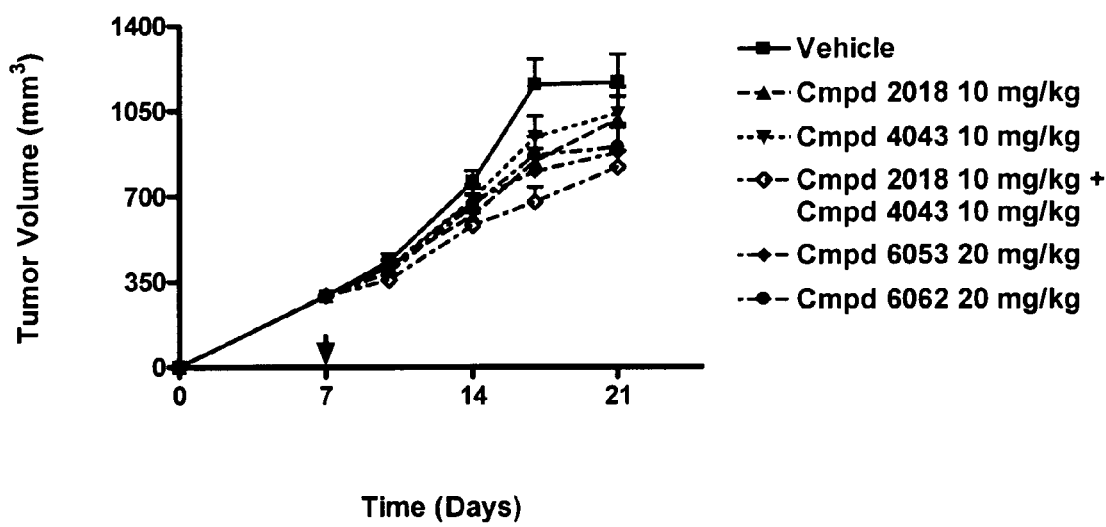

FIG. 26: Tumor volume of Colo205 colon adenocarcinoma xenografts after once weekly treatment with Vehicle, Compound 2018, Compound 4043, Compound 6053, Compound 6062, or the combination of Compounds 2018 and 4043 (all IP). Data are depicted as the Mean and SE of n=9/group, vertical arrow indicates first dosing day.

Figure 27:
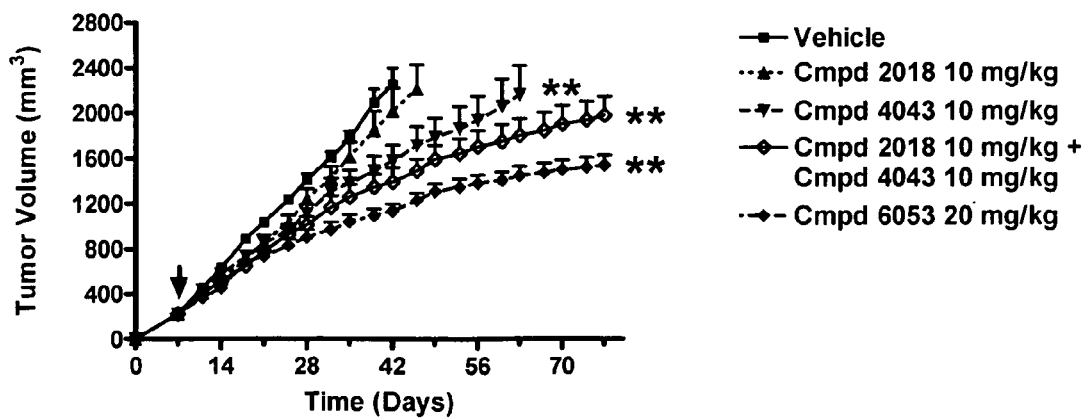

FIG. 27: Tumor volume of Colo205 colon adenocarcinoma xenografts after once weekly treatment with Vehicle, Compound 4043, Compound 2018, Compound 6053, or the combination of Compounds 4043 and 2018 (all IP). Data are depicted as the Mean and SE of n=10/group, vertical arrow indicates first dosing day. **P<0.01 versus Vehicle on day 42 (Compounds 4043 and 6053, and the combination of Compounds 4043 and 2018).

Figure 28:
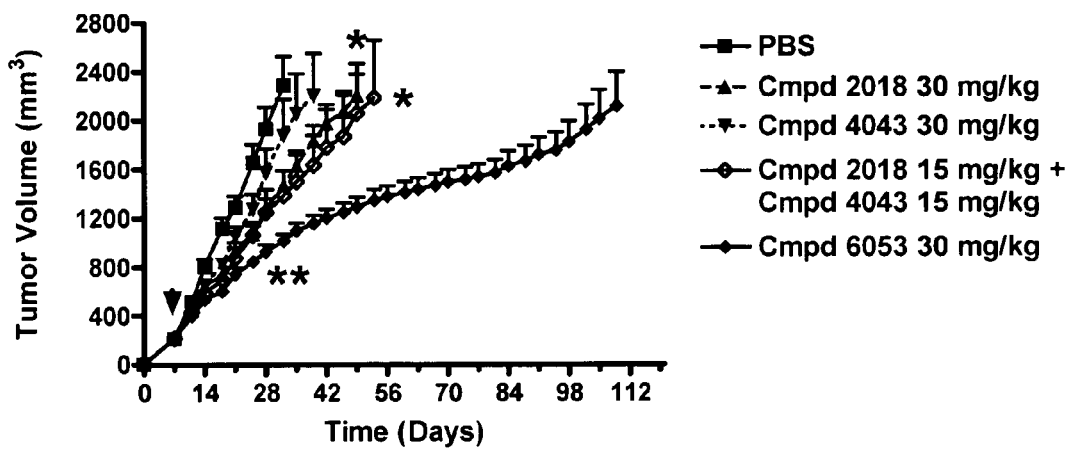

FIG. 28: Tumor volume of Colo205 colon adenocarcinoma xenografts after once weekly treatment with Vehicle, Compound 4043, Compound 2018, Compound 6053, or the combination of Compounds 4043 and 2018 (all IP). Data are depicted as the Mean and SE of n=10/group, vertical arrow indicates first dosing day. *P<0.05 versus Vehicle on day 32 (Compounds 2018, and the combination of Compounds 4043 and 2018), **P<0.01 versus Vehicle on day 32 (Compound 6053).

Figure 29:
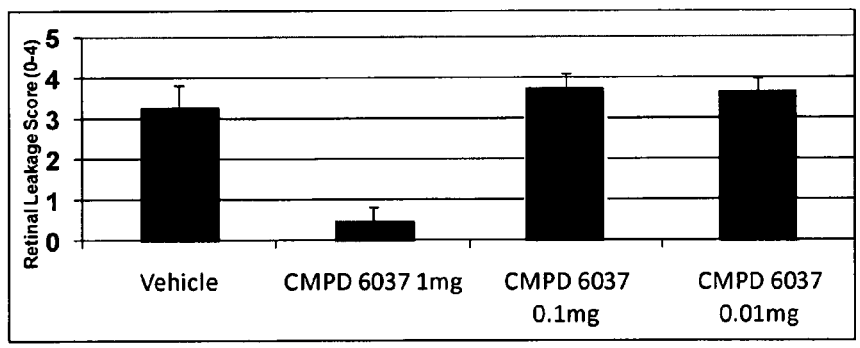

FIG. 29: Fluorescein angiography grading in rabbit VEGF induced retinal leakage 3 days post IVT injection and 48 hrs post VEGF dose. Compound 6037 dose response study.

Figure 30:
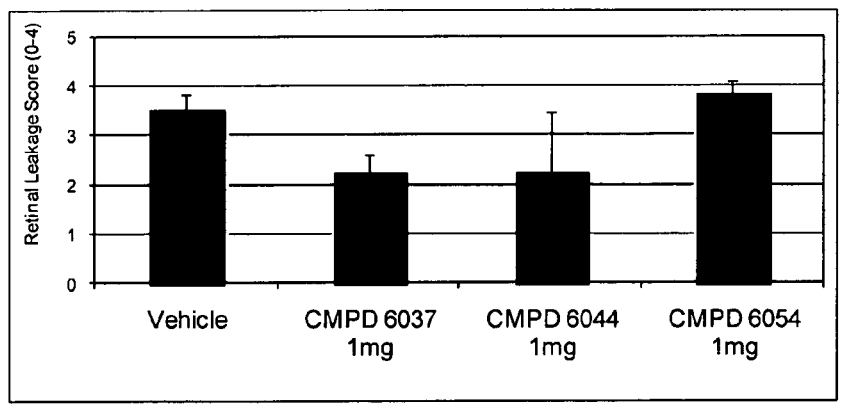

FIG. 30: Fluorescein angiography grading in rabbit VEGF induced retinal leakage 7 days post IVT injection and 48 hrs post VEGF dose

DEFINITIONS

The following abbreviations, terms and phrases are used herein as defined below.

Non-Natural Amino Acid Abbreviations

BnHP refers to (2S,4R)-4-Hydroxyproline

Tle refers to tertbutylGlycine

Methyl tyrosine or Tyr-OMe (Yme) refers to:

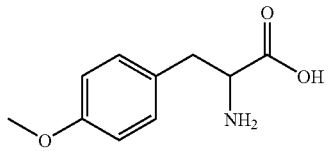

Norvaline or Nva refers to:

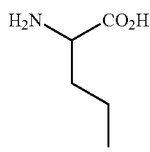

Dehydroproline or DHP refers to

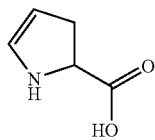

Hydroxyproline or HP refers to:

Homocyclohexyl alanine or HChA refers to:

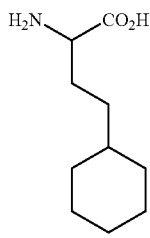

Homophenyl alanine or HF refers to:

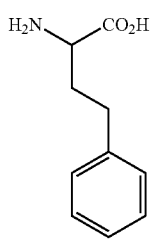

Thiazolyl alanine or Tha refers to:

Homoleucine or HL refers to or Kac (also Ack) refers to:

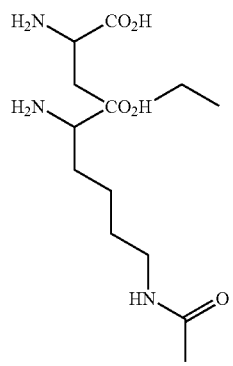

alanine or BPA refers to:

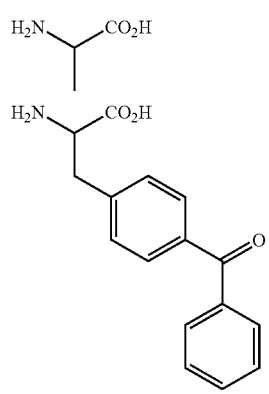

Epsilon chloro benzyl carbamate lysine or (ClBnCarbamate) K or CbcK refers to:

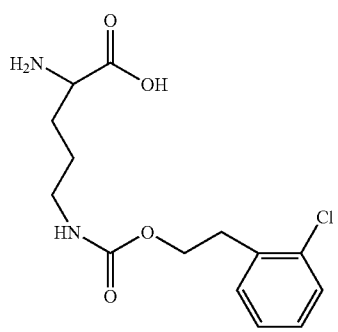

Thienyl Alanine or TA refers to

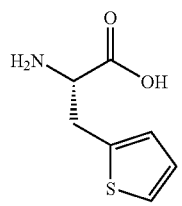

Diaminobutyric acid or Dab refers to:

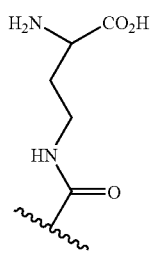

Diaminopropionic acid or Dab refers to:

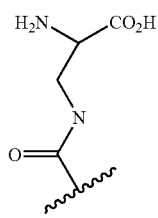

4-Nitro phenylalanine or NO2F or NF:

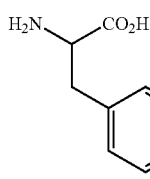

4-Carboxy phenylalanine or (CO2H)F or CF

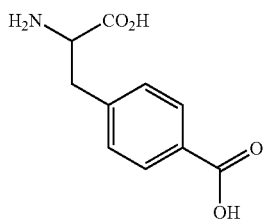

Amido 2-PEG refers to:

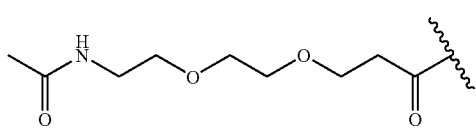

Nicotinyl Lysine (NicK) refers to:

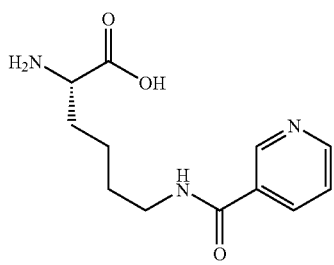

Difluorobenzoyl or DFB refers to:

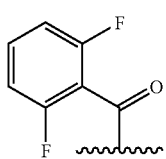

Dichlorobenzoyl or DCB refers to:

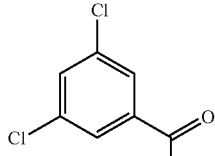

"O" PEG or OP refers to:

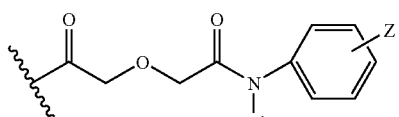

Pyridinyl carboxylate or PyC refers to:

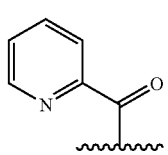

"4" PEG or 4P (shown attached to a lysine residue) refers to:

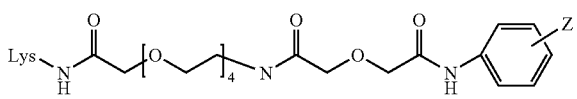

Sarcosine or Sar refers to:

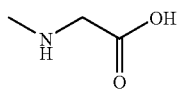

Norleucine (Nle) refers to:

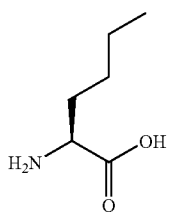

2-Aminobutyric Acid (Aib) refers to:

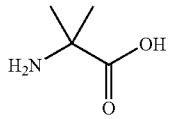

O-methyl-L-tyrosine (Yme) refers to:

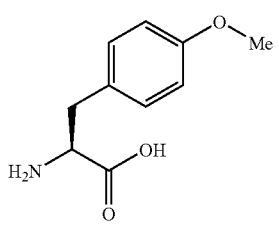

beta-cyclohexyl-L-alanine (Cha) refers to:

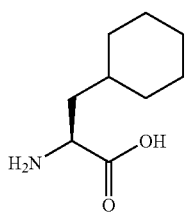

-continued

L-Tyrosine methyl ester (YOMe) refers to:

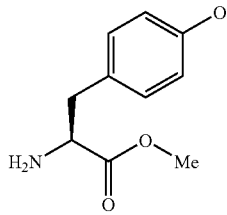

Unless indicated otherwise by a "D" prefix, e.g., D-Ala or N-Me-D-Ile, or written in lower case format, e.g., a, i, 1, (D versions of Ala, Ile, Leu), the stereochemistry of the alpha-carbon of the amino acids and aminoacyl residues in peptides described in this specification and the appended claims is the natural or "L" configuration. The Cahn-Ingold-Prelog "R" and "S" designations are used to specify the stereochemistry of chiral centers in certain acyl substituents at the N-terminus of the peptides. The designation "R,S" is meant to indicate a racemic mixture of the two enantiomeric forms. This nomenclature follows that described in R. S. Cahn, et al., Angew. Chem. Int. Ed. Engl., 5:385-415 (1966).

"Polypeptide," "peptide," and "protein" are used interchangeably to refer to a polymer of amino acid residues. As used herein, these terms apply to amino acid polymers in which one or more amino acid residues is an artificial chemical analog of a corresponding naturally occurring amino acid. These terms also apply to naturally occurring amino acid polymers. Amino acids can be in the L or D form as long as the binding function of the peptide is maintained. Peptides may be cyclic, having an intramolecular bond between two non-adjacent amino acids within the peptide, e.g., backbone to backbone, side-chain to backbone and side-chain to side-chain cyclization. Cyclic peptides can be prepared by methods well know in the art. See e.g., U.S. Pat. No. 6,013,625.

All peptide sequences are written according to the generally accepted convention whereby the alpha-N-terminal amino acid residue is on the left and the alpha-C-terminal amino acid residue is on the right. As used herein, the term "N-terminus" refers to the free alpha-amino group of an amino acid in a peptide, and the term "C-terminus" refers to the free α-carboxylic acid terminus of an amino acid in a peptide. A peptide which is N-terminated with a group refers to a peptide bearing a group on the alpha-amino nitrogen of the N-terminal amino acid residue. An amino acid which is N-terminated with a group refers to an amino acid bearing a group on the alpha-amino nitrogen.

In general, the term "hydrophobic amino acids" or "non-polar amino acids" means amino acid residues that do not contain an ionized group(s) at physiological pH. Examples of hydrophobic amino acid residues include, but are not limited to, Gly, Allylglycine, Cyclohexylglycine (Chg), Dpg, Hydroxyproline, HoLeu, alloIle, Ala, Abu (Aminobutyric acid), Homocycloleucine, Acpc (1-Aminocyclopropane-1-carboxylic acid), Aib, Aic, Val, Leu, Nle, Ile, Met, Phe, Cys, Pro, Gln, Asn, Cha (beta-cyclohexylalanine), Cyclopentylalanine, beta-Cyclopropyl alanine, 3,3-Diphenylalanine, beta-2-Furylalanine, Homocyclohexylalanine (HoCha) 3-(1-Naphthylalanine, 2-Furylalanine, Pyridylalanine, Quinolylalanine, Thiazolylalanine, Theinylalanine, Val, Nva, Ring substituted phenylanaline, Sar, HoSer, Tic, Tic(OH), Ring substituted Tryptophan, Ring substituted Tyrosine, and derivatives thereof.

In general, the term "aliphatic amino acids" and "non-polar aliphatic amino acids" means amino acids with a non-aromatic hydrophobic side chain. Examples include but not limited to Ala, AllylGly, Nva, Chg, Abu, Aib, Aic, Acpc, Homocycloleucine, Cyclopentylalanine, beta-Cyclopropyl alanine, Cha, HoCha, Val, Ile, Leu, and Met and derivatives thereof.

In general, the term "Aromatic amino acids" means amino acids with an aromatic ring side chain. Examples include Phe, Tyr, Trp, His, 2-Furylalanine, Tyr(Me) and derivatives thereof.

In general, the term "Polar amino acids" includes polar and uncharged amino acids, negatively charged amino acids and positively charged amino acids. Examples include Arg, HoArg, Cit, Glu, Asp, Lys, Gln, Asn, Ser, Thr, His, Trp, Tyr, Lys(Ac), and derivatives thereof.

In general, the term "Positively charged amino acids" (or basic amino acids) means amino acids whose side chains are protonated or may be protonated at physiological conditions. Examples include but not are limited to Lys, Ornathine (Orn), Arg, HoArg, Dab, Dap, Trp, His and derivatives thereof.

In general, the term "Negatively charged amino acids" (or acidic amino acids) means amino acids whose side chains may be deprotonated at physiological conditions. Examples include but not limited to Asp, Asu, Glu, Aad, and derivatives thereof.

In general, "Polar, uncharged amino acids" means amino acids with uncharged side chains capable of forming H-bonds with water at physiological conditions. Examples include but are not limited to Gln, Asn, Lys(Ac), Ser, Thr, Cit, and HoCit derivatives thereof.

"Substantially homologous" means at least about 75% (preferably at least about 80%, and more preferably at least about 90% or most preferably at least about 95%, of the amino-acid residues match over the defined length of the peptide sequences. Sequences that are substantially homologous can be identified by comparing the sequences using standard software available in sequence data banks, such as BLAST programs available from the National Cancer Center for Biotechnology Information at ncbi.nlm.nih.gov.

In general, "substituted" refers to a group as defined below in which one or more bonds to a hydrogen atom contained therein are replaced by a bond to non-hydrogen or non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups and also substituted cycloalkyl groups and others also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles. As employed herein, a group which is "optionally substituted" may be substituted or unsubstituted. Thus, e.g., "optionally substituted alkyl" refers to both substituted alkyl groups and unsubstituted alkyl groups.

The phrase "unsubstituted alkyl" refers to alkyl groups that do not contain heteroatoms. Thus, the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH($CH_3$)$_2$, —CH($CH_3$)($CH_2CH_3$), —CH($CH_2CH_3$)$_2$, —C($CH_3$)$_3$, —C($CH_2CH_3$)$_3$, —$CH_2$CH($CH_3$)$_2$, —$CH_2$CH($CH_3$)($CH_2CH_3$), —$CH_2$CH($CH_2CH_3$)$_2$, —$CH_2$C($CH_3$)$_3$, —$CH_2$C($CH_2CH_3$)$_3$, —CH($CH_3$)CH($CH_3$)($CH_2CH_3$), —$CH_2CH_2$CH($CH_3$)$_2$, —$CH_2CH_2$CH($CH_3$)($CH_2CH_3$), —$CH_2CH_2$CH($CH_2CH_3$)$_2$, —$CH_2CH_2$C($CH_3$)$_3$, —$CH_2CH_2$C($CH_2CH_3$)$_3$, —CH($CH_3$)$CH_2$CH($CH_3$)$_2$, —CH($CH_3$)CH($CH_3$)CH($CH_3$)$_2$, —CH($CH_2CH_3$)CH($CH_3$)CH($CH_3$)($CH_2CH_3$), and others. The phrase does not include cycloalkyl groups. Thus, the phrase unsubstituted alkyl groups includes primary alkyl groups, secondary alkyl groups, and tertiary alkyl groups. Unsubstituted alkyl groups may be bonded to one or more carbon atom(s), oxygen atom(s), nitrogen atom(s), and/or sulfur atom(s) in the parent compound. Possible unsubstituted alkyl groups include straight and branched chain alkyl groups having 1 to 20 carbon atoms. Alternatively, such unsubstituted alkyl groups have from 1 to 10 carbon atoms or are lower alkyl groups having from 1 to about 6 carbon atoms. Other unsubstituted alkyl groups include straight and branched chain alkyl groups having from 1 to 3 carbon atoms and include methyl, ethyl, propyl, and —CH($CH_3$)$_2$.

The phrase "substituted alkyl" refers to an alkyl group in which one or more bonds to a carbon(s) or hydrogen(s) are replaced by a bond to non-hydrogen and non-carbon atoms such as, but not limited to, a halogen atom in halides such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles. Substituted alkyl groups include, among others, alkyl groups in which one or more bonds to a carbon or hydrogen atom is/are replaced by one or more bonds to fluorine atoms. One example of a substituted alkyl group is the trifluoromethyl group and other alkyl groups that contain the trifluoromethyl group. Other alkyl groups include those in which one or more bonds to a carbon or hydrogen atom is replaced by a bond to an oxygen atom such that the substituted alkyl group contains a hydroxyl, alkoxy, aryloxy group, or heterocyclyloxy group. Still other alkyl groups include alkyl groups that have an amine, alkylamine, dialkylamine, arylamine, (alkyl)(aryl)amine, diarylamine, heterocyclylamine, (alkyl)(heterocyclyl)amine, (aryl)(heterocyclyl) amine, or diheterocyclylamine group.

The phrase "unsubstituted alkylene" refers to a divalent unsubstituted alkyl group as defined above. Thus methylene, ethylene, and propylene are each examples of unsubstituted alkylenes. The phrase "substituted alkylene" refers to a divalent substituted alkyl group as defined above. Substituted or unsubstituted lower alkylene groups have from 1 to about 6 carbons.

The phrase "unsubstituted cycloalkyl" refers to cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo [2.2.2]octyl and the like, as well as such rings substituted with straight and branched chain alkyl groups as defined above. Thus, the phrase would include methylcylcohexyl groups among others. The phrase does not include cyclic alkyl groups containing heteroatoms. Unsubstituted cycloalkyl groups may be bonded to one or more carbon atom(s), oxygen atom(s), nitrogen atom(s), and/or sulfur atom(s) in the parent compound. In some embodiments unsubstituted cycloalkyl groups have from 3 to 20 carbon atoms. In other embodiments, such unsubstituted alkyl groups have from 3 to 8 carbon atoms while in others, such groups have from 3 to 7 carbon atoms.

The phrase "substituted cycloalkyl" has the same meaning with respect to unsubstituted cycloalkyl groups that substituted alkyl groups have with respect to unsubstituted alkyl groups. Thus, the phrase includes, but is not limited to, oxocyclohexyl, chlorocyclohexyl, hydroxycyclopentyl, and chloromethylcyclohexyl groups.

The phrase "unsubstituted aryl" refers to aryl groups that do not contain heteroatoms. Thus the phrase includes, but is not limited to, groups such as phenyl, biphenyl, anthracenyl, and naphthenyl by way of example. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. Typically, an unsubstituted aryl may be a lower aryl, having from 6 to about 10 carbon atoms. One unsubstituted aryl group is phenyl. Unsubstituted aryl groups may be bonded to one or more carbon atom(s), oxygen atom(s), nitrogen atom(s), and/or sulfur atom(s) in the parent compound, however.

The phrase "substituted aryl group" has the same meaning with respect to unsubstituted aryl groups that substituted alkyl groups have with respect to unsubstituted alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g., dihydronaphthyl or tetrahydronaphthyl). Thus, the phrase "substituted aryl" includes, but is not limited to tolyl and hydroxyphenyl among others.

The phrase "unsubstituted alkenyl" refers to straight and branched chain and cyclic groups such as those described with respect to unsubstituted alkyl groups as defined above, except that at least one double bond exists between two carbon atoms. Examples include, but are not limited to vinyl, —CH=C(H)($CH_3$), —CH=C($CH_3$)$_2$, —C($CH_3$)=C(H)$_2$, —C($CH_3$)=C(H)($CH_3$), —C($CH_2CH_3$)=$CH_2$, cyclohexenyl, cyclopentenyl, cyclohexadienyl, butadienyl, pentadienyl, and hexadienyl among others. Lower unsubstituted alkenyl groups have from 1 to about 6 carbons.

The phrase "substituted alkenyl" has the same meaning with respect to unsubstituted alkenyl groups that substituted alkyl groups have with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon. For example, —CH═CH—OCH$_3$ and —CH═CH—CH$_2$—OH are both substituted alkenyls. Oxoalkenyls wherein a CH$_2$ group is replaced by a carbonyl, such as —CH═CH—C(O)—CH$_3$, are also substituted alkenyls. The phrase "unsubstituted alkenylene" refers to a divalent unsubstituted alkenyl group as defined above. For example, —CH═CH— is an exemplary unsubstituted alkenylene. The phrase "substituted alkenylene" refers to a divalent substituted alkenyl group as defined above.

The phrase "unsubstituted alkynyl" refers to straight and branched chain groups such as those described with respect to unsubstituted alkyl groups as defined above, except that at least one triple bond exists between two carbon atoms. Examples include, but are not limited to, —C≡C(H), —C≡C(CH$_3$), —C≡C(CH$_2$CH$_3$), —C(H$_2$)C≡C(H), —C(H)$_2$C≡C(CH$_3$), and —C(H)$_2$C≡C(CH$_2$CH$_3$) among others. Unsubstituted lower alkynyl groups have from 1 to about 6 carbons.

The phrase "substituted alkynyl" has the same meaning with respect to unsubstituted alkynyl groups that substituted alkyl groups have with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon. Examples include, but are not limited to, oxoalkynyls wherein a CH$_2$ group is replaced by a carbonyl, such as —C(O)—CH≡CH—CH$_3$ and —C(O)—CH$_2$—CH≡CH.

The phrase "unsubstituted alkynylene" refers to a divalent unsubstituted alkynyl group as defined above. A-C≡C— is an example of an unsubstituted alkynylene. The phrase "substituted alkynylene" refers to a divalent substituted alkynyl group as defined above.

The phrase "unsubstituted aralkyl" refers to unsubstituted alkyl groups as defined above in which a hydrogen or carbon bond of the unsubstituted alkyl group is replaced with a bond to an aryl group as defined above. For example, methyl (—CH$_3$) is an unsubstituted alkyl group. If a hydrogen atom of the methyl group is replaced by a bond to a phenyl group, such as if the carbon of the methyl were bonded to a carbon of benzene, then the compound is an unsubstituted aralkyl group (i.e., a benzyl group). Thus, the phrase includes, but is not limited to, groups such as benzyl, diphenylmethyl, and 1-phenylethyl (—CH(C$_6$H$_5$)(CH$_3$)).

The phrase "substituted aralkyl" has the same meaning with respect to unsubstituted aralkyl groups that substituted aryl groups have with respect to unsubstituted aryl groups. However, substituted aralkyls also include groups in which a carbon or hydrogen bond of the alkyl part of the group is replaced by a bond to a non-carbon or a non-hydrogen atom. Examples of substituted aralkyl groups include, but are not limited to, —CH$_2$C(═O)(C$_6$H$_5$), and —CH$_2$(2-methylphenyl).

The phrase "unsubstituted aralkenyl" refers to unsubstituted alkenyl groups as defined above in which a hydrogen or carbon bond of the unsubstituted alkenyl group is replaced with a bond to an aryl group as defined above. For example, vinyl is an unsubstituted alkenyl group. If a hydrogen atom of the vinyl group is replaced by a bond to a phenyl group, such as if a carbon of the vinyl were bonded to a carbon of benzene, then the compound is an unsubstituted aralkenyl group (i.e., a styryl group). Thus, the phrase includes, but is not limited to, groups such as styryl, diphenylvinyl, and 1-phenylethenyl (—C(C$_6$H$_5$)(CH$_2$)).

The phrase "substituted aralkenyl" has the same meaning with respect to unsubstituted aralkenyl groups that substituted aryl groups have with respect to unsubstituted aryl groups. A substituted aralkenyl group also includes groups in which a carbon or hydrogen bond of the alkenyl part of the group is replaced by a bond to a non-carbon or a non-hydrogen atom. Examples of substituted aralkenyl groups include, but are not limited to, —CH═C(Cl)(C$_6$H$_5$), and —CH═CH (2-methylphenyl). The phrase "unsubstituted aralkynyl" refers to unsubstituted alkynyl groups as defined above in which a hydrogen or carbon bond of the unsubstituted alkynyl group is replaced with a bond to an aryl group as defined above. For example, acetylene is an unsubstituted alkynyl group. If a hydrogen atom of the acetylene group is replaced by a bond to a phenyl group, such as if a carbon of the acetylene were bonded to a carbon of benzene, then the compound is an unsubstituted aralkynyl group. Thus, the phrase includes, but is not limited to, groups such as —C≡C-phenyl and —CH$_2$—C≡C-phenyl. The phrase "substituted aralkynyl" has the same meaning with respect to unsubstituted aralkynyl groups that substituted aryl groups have with respect to unsubstituted aryl groups. However, a substituted aralkynyl group also includes groups in which a carbon or hydrogen bond of the alkynyl part of the group is replaced by a bond to a non-carbon or a non-hydrogen atom. Examples of substituted aralkynyl groups include, but are not limited to, —C≡C—C(Br)(C$_6$H$_5$) and —C≡C(2-methylphenyl).

The phrase "unsubstituted heteroalkyl" refers to unsubstituted alkyl groups as defined above in which the carbon chain is interrupted by one or more heteroatoms chosen from N, O, and S. Unsubstituted heteroalkyls containing N may have NH or N (unsubstituted alkyl) in the carbon chain. For example, unsubstituted heteroalkyls include alkoxy, alkoxyalkyl, alkoxyalkoxy, thioether, alkylaminoalkyl, aminoalkyloxy, and other such groups. Typically, unsubstituted heteroalkyl groups contain 1-5 heteroatoms, and particularly 1-3 heteroatoms. In some embodiments unsubstituted heteroalkyls include, for example, alkoxyalkoxyalkoxy groups such as ethyloxyethyloxyethyloxy. The phrase "substituted heteroalkyl" has the same meaning with respect to unsubstituted heteroalkyl groups that substituted alkyl groups have with respect to unsubstituted alkyl groups.

The phrase "unsubstituted heteroalkylene" refers to a divalent unsubstituted heteroalkyl group as defined above. For example, —CH$_2$—O—CH$_2$— and —CH$_2$—NH—CH$_2$CH$_2$— are both exemplary unsubstituted heteroalkylenes. The phrase "substituted heteroalkylene" refers to a divalent substituted heteroalkyl group as defined above.

The phrase "unsubstituted heteroalkenyl" refers to unsubstituted alkene groups as defined above in which the carbon chain is interrupted by one or more heteroatoms chosen from N, O, and S. Unsubstituted heteroalkenyls containing N may have NH or N (unsubstituted alkyl or alkene) in the carbon chain. The phrase "substituted heteroalkenyl" has the same meaning with respect to unsubstituted heteroalkenyl groups that substituted heteroalkyl groups have with respect to unsubstituted heteroalkyl groups.

The phrase "unsubstituted heteroalkenylene" refers to a divalent unsubstituted heteroalkenyl group as defined above. Thus —CH$_2$—O—CH═CH— is an example of an unsubstituted heteroalkenylene. The phrase "substituted heteroalkenylene" refers to a divalent substituted heteroalkenyl group as defined above.

The phrase "unsubstituted heteroalkynyl" refers to unsubstituted alkynyl groups as defined above in which the carbon chain is interrupted by one or more heteroatoms chosen from N, O, and S. Unsubstituted heteroalkynyls containing N may have NH or N (unsubstituted alkyl, alkene, or alkyne) in the carbon chain. The phrase "substituted heteroalkynyl" has the same meaning with respect to unsubstituted heteroalkynyl groups that substituted heteroalkyl groups have with respect to unsubstituted heteroalkyl groups.

The phrase "unsubstituted heteroalkynylene" refers to a divalent unsubstituted heteroalkynyl group as defined above. Thus —CH$_2$—O—CH$_2$—C≡C— is an example of an unsubstituted heteroalkynylene. The phrase "substituted heteroalkynylene" refers to a divalent substituted heteroalkynyl group as defined above.

The phrase "unsubstituted heterocyclyl" refers to both aromatic and nonaromatic ring compounds including monocyclic, bicyclic, and polycyclic ring compounds such as, but not limited to, quinuclidyl, containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members as compounds such as 2-methylbenzimidazolyl are substituted heterocyclyl groups. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl (e.g., 4H-1,2,4-triazolyl, 1H-1,2,3-triazolyl, 2H-1,2,3-triazolyl etc.), tetrazolyl, (e.g., 1H-tetrazolyl, 2H tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e.g., 1,2,4-oxadiazolyl, 1,3,4-oxadiazolyl, 1,2,5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g., 2H-1,4-benzoxazinyl, etc.); unsaturated 3 to 8 membered rings containing 1 to 3 sulfur atoms and 1 to 3 nitrogen atoms such as, but not limited to, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g., 2H-1,4-benzothiazinyl, etc.), dihydrobenzothiazinyl (e.g., 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e.g., 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 3 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 3 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1,1-dioxide. In some embodiments heterocyclyl groups contain 5 or 6 ring members. In other embodiments heterocyclyl groups include morpholine, piperazine, piperidine, pyrrolidine, imidazole, pyrazole, 1,2,3-triazole, 1,2,4-triazole, tetrazole, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

The phrase "substituted heterocyclyl" refers to an unsubstituted heterocyclyl group as defined above in which one of the ring members is bonded to a non-hydrogen atom such as described above with respect to substituted alkyl groups and substituted aryl groups. Examples include, but are not limited to, 2-methylbenzimidazolyl, 5-methylbenzimidazolyl, 5-chlorobenzthiazolyl, 1-methyl piperazinyl, and 2-chloropyridyl.

The phrase "unsubstituted heteroaryl" refers to unsubstituted aromatic heterocyclyl groups as defined above. Thus, unsubstituted heteroaryl groups include but are not limited to furyl, imidazolyl, oxazolyl, isoxazolyl, pyridinyl, benzimidazolyl, and benzothiazolyl. The phrase "substituted heteroaryl" refers to substituted aromatic heterocyclyl groups as defined above. The phrase "unsubstituted heterocyclylalkyl" refers to unsubstituted alkyl groups as defined above in which a hydrogen or carbon bond of the unsubstituted alkyl group is replaced with a bond to a heterocyclyl group as defined above. For example, methyl (—CH$_3$) is an unsubstituted alkyl group. If a hydrogen atom of the methyl group is replaced by a bond to a heterocyclyl group, such as if the carbon of the methyl were bonded to carbon 2 of pyridine (one of the carbons bonded to the N of the pyridine) or carbons 3 or 4 of the pyridine, then the compound is an unsubstituted heterocyclylalkyl group.

The phrase "substituted heterocyclylalkyl" has the same meaning with respect to unsubstituted heterocyclylalkyl groups that substituted aralkyl groups have with respect to unsubstituted aralkyl groups. A substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group. The phrase "unsubstituted heterocyclylalkenyl" refers to unsubstituted alkenyl groups as defined above in which a hydrogen or carbon bond of the unsubstituted alkenyl group is replaced with a bond to a heterocyclyl group as defined above. For example, vinyl is an unsubstituted alkenyl group. If a hydrogen atom of the vinyl group is replaced by a bond to a heterocyclyl group, such as if the carbon of the vinyl were bonded to carbon 2 of pyridine or carbons 3 or 4 of the pyridine, then the compound is an unsubstituted heterocyclylalkenyl group.

The phrase "substituted heterocyclylalkenyl" has the same meaning with respect to unsubstituted heterocyclylalkenyl groups that substituted aralkenyl groups have with respect to unsubstituted aralkenyl groups. However, a substituted heterocyclylalkenyl group also includes groups in which a non-hydrogen atom is bonded to a heteroatom in the heterocyclyl group of the heterocyclylalkenyl group such as, but not limited to, a nitrogen atom in the piperidine ring of a piperidinylalkenyl group. The phrase "unsubstituted heterocyclylalkynyl" refers to unsubstituted alkynyl groups as defined above in which a hydrogen or carbon bond of the unsubstituted alkynyl group is replaced with a bond to a heterocyclyl group as defined above. For example, acetylene is an unsubstituted alkynyl group. If a hydrogen atom of the acetylene group is replaced by a bond to a heterocyclyl group, such as if the carbon of the acetylene were bonded to carbon 2 of pyridine or carbons 3 or 4 of the pyridine, then the compound is an unsubstituted heterocyclylalkynyl group.

The phrase "substituted heterocyclylalkynyl" has the same meaning with respect to unsubstituted heterocyclylalkynyl groups that substituted aralkynyl groups have with respect to unsubstituted aralkynyl groups. A substituted heterocyclylalkynyl group also includes groups in which a non-hydrogen atom is bonded to a heteroatom in the heterocyclyl group of the heterocyclylalkynyl group such as, but not limited to, a nitrogen atom in the piperidine ring of a piperidinylalkynyl group. The phrase "unsubstituted alkoxy" refers to a hydroxyl group (—OH) in which the bond to the hydrogen atom is replaced by a bond to a carbon atom of an otherwise unsubstituted alkyl group as defined above.

The phrase "substituted alkoxy" refers to a hydroxyl group (—OH) in which the bond to the hydrogen atom is replaced by a bond to a carbon atom of an otherwise substituted alkyl group as defined above. A "pharmaceutically acceptable salt" includes a salt with an inorganic base, organic base, inorganic acid, organic acid, or basic or acidic amino acid. Salts of inorganic bases include, for example, alkali metals such as sodium or potassium; alkaline earth metals such as calcium and magnesium or aluminum; and ammonia. Salts of organic bases include, for example, trimethylamine, triethylamine, pyridine, picoline, ethanolamine, diethanolamine, and triethanolamine. Salts of inorganic acids include for example, hydrochloric acid, hydroboric acid, nitric acid, sulfuric acid, and phosphoric acid. Salts of organic acids include for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. Salts of basic amino acids include, for example, arginine, lysine and orthinine. Acidic amino acids include, for example, aspartic acid and glutamic acid.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, ketones are typically in equilibrium with their enol forms. Thus, ketones and their enols are referred to as tautomers of each other. As readily understood by one skilled in the art, a wide variety of functional groups and other structures may exhibit tautomerism, and all tautomers of compounds the invention are within the scope of the present invention.

Certain embodiments are derivatives referred to as prodrugs. The expression "prodrug" denotes a derivative of a pharmaceutically or therapeutically active drug, e.g., esters and amides, wherein the derivative has an enhanced characteristic such as, for example, enhanced delivery and therapeutic value as compared to the drug and can be transformed into the drug by an enzymatic or chemical process. See, for example, R. E. Notari, Methods Enzymol. 112:309-323 (1985); N. Bodor, Drugs of the Future 6:165-182 (1981); H. Bundgaard, Chapter 1 in *Design of Prodrugs* (H. Bundgaard, ed.), Elsevier, N.Y. (1985); and A. G. Gilman et al., *Goodman And Gilman's The Pharmacological Basis of Therapeutics*, 8th ed., McGraw-Hill (1990). Thus, the prodrug may be designed to alter the metabolic stability or transport characteristics of a drug, mask side effects or toxicity of a drug, improve the flavor of a drug, or to alter other characteristics or properties of a drug. Compounds of the present invention include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners. All such stereoisomers are within the scope of the invention.

The term "carboxy protecting group" as used herein refers to a carboxylic acid protecting ester group employed to block or protect the carboxylic acid functionality while the reactions involving other functional sites of the compound are carried out. Carboxy protecting groups are disclosed in, for example, Greene, *Protective Groups in Organic Synthesis*, pp. 152-186, John Wiley & Sons, New York (1981), which is hereby incorporated herein by reference. In addition, a carboxy protecting group can be used as a prodrug, whereby the carboxy protecting group can be readily cleaved in vivo by, for example, enzymatic hydrolysis to release the biologically active parent. T. Higuchi and V. Stella provide a discussion of the prodrug concept in "Pro-drugs as Novel Delivery Systems", Vol. 14 of the A.C.S. Symposium Series, American Chemical Society (1975), which is hereby incorporated herein by reference. Such carboxy protecting groups are well known to those skilled in the art, having been extensively used in the protection of carboxyl groups in the penicillin and cephalosporin fields, as described in U.S. Pat. Nos. 3,840,556 and 3,719,667, S. Kukolja, J. Am. Chem. Soc. 93:6267-6269 (1971), and G. E. Gutowski, Tetrahedron Lett. 21:1779-1782 (1970), the disclosures of which are hereby incorporated herein by reference. Examples of esters useful as prodrugs for compounds containing carboxyl groups can be found, for example, at pp. 14-21 in *Bioreversible Carriers in Drug Design: Theory and Application* (E. B. Roche, ed.), Pergamon Press, New York (1987), which is hereby incorporated herein by reference. Representative carboxy protecting groups are $C_1$ to $C_8$ alkyl (e.g., methyl, ethyl or tertiary butyl and the like); haloalkyl; alkenyl; cycloalkyl and substituted derivatives thereof such as cyclohexyl, cyclopentyl and the like; cycloalkylalkyl and substituted derivatives thereof such as cyclohexylmethyl, cyclopentylmethyl and the like; aralkyl, for example, phenethyl or benzyl and substituted derivatives thereof such as alkoxybenzyl or nitrobenzyl groups and the like; arylalkenyl, for example, phenylethenyl and the like; aryl and substituted derivatives thereof, for example, 5-indanyl and the like; dialkylaminoalkyl (e.g., dimethylaminoethyl and the like); alkanoyloxyalkyl groups such as acetoxymethyl, butyryloxymethyl, valerytoxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl, such as benzoyloxymethyl, benzoyloxyethyl and the like; arylalkylcarbonyloxyalkyl, such as benzylcarbonyloxymethyl, 2-benzylcarbonyloxyethyl and the like; alkoxycarbonylalkyl, such as methoxycarbonylmethyl, cyclohexyloxycarbonylmethyl, 1-methoxycarbonyl-1-ethyl, and the like; alkoxycarbonyloxyalkyl, such as methoxycarbonyloxymethyl, t-butyloxycarbonyloxymethyl, 1-ethoxycarbonyloxy-1-ethyl, 1-cyclohexyloxycarbonyloxy-1-ethyl and the like; alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocycliccarbonyloxyalkyl, such as 4-methylpiperazinylcarbonyloxymethyl and the like; dialkylaminocarbonylalkyl, such as dimethylaminocarbonylmethyl, diethylaminocarbonylmethyl and the like; (5-(alkyl)-2-oxo-1,3-dioxolen-4-yl)alkyl, such as (5-t-butyl-2-oxo-1,3-dioxolen-4-yl)methyl and the like; and (5-phenyl-2-oxo-1,3-dioxolen-4-yl)alkyl, such as (5-phenyl-2-oxo-1,3-dioxolen-4-yl)methyl and the like. The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in, for example, Greene, *Protective Groups in Organic Synthesis*, John Wiley & Sons, New York (1981), which is hereby incorporated by reference. For example, N-protecting groups can comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, a-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-di methyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. In some embodiments N-protecting groups are formyl, acetyl, benzoyl, pivaloyl, t-butylacetyl, phenylsulfonyl, benzyl, 9-fluorenylmethyloxycarbonyl (Fmoc), t-butyloxycarbonyl (Boc), and benzyloxycarbonyl (Cbz).

As used herein, "halo," "halogen" or "halide" refers to F, Cl, Br or I.

As used herein, the abbreviations for any protective groups, amino acids or other compounds, are, unless indicated otherwise, in accord with their common usage, recognized abbreviations, or the IUPAC-IUB Commission on Biochemical Nomenclature, Biochem. 11:942-944 (1972). As used herein, "substantially pure" means sufficiently homogeneous to appear free of readily detectable impurities as determined by standard methods of analysis, such as thin layer chromatography (TLC), gel electrophoresis, and high performance liquid chromatography (HPLC), used by those of skill in the art to assess such purity, or sufficiently pure such that further purification would not detectably alter the physical and chemical properties, such as enzymatic and biological activities, of the substance. Substantially pure includes compositions in which the compound of the invention forms the major component of the composition, such as constituting about 50%, about 60%, about 70%, about 80%, about 90%, or about 95% or more of the substances in the composition. Methods for purification of compounds to produce substantially chemically pure compounds are known to those of skill in the art. A substantially chemically pure compound may, however, be a mixture of stereoisomers. In such instances, further purification may increase the specific activity of the compound. However, a compound of the invention need not always be provided in a specific purified state. Partially purified compositions will have utility in certain embodiments and depending on the desired use. For example, purification methods that may yield a greater total recovery of a compound of the invention may produce a lower degree of relative purification.

As used herein, "biological activity" refers to the in vivo activities of a compound, composition, or other mixture, or physiological responses that result upon in vivo administration of a compound, composition or other mixture. Biological activity thus encompasses therapeutic effects, diagnostic effects and pharmaceutical activity of such compounds, compositions, and mixtures. The term "biologically active" or "functional" when used as a modifier of a composition of the invention containing polypeptides or compositions thereof refers to a polypeptide that exhibits at least one activity that is characteristic of or similar to a compound of the invention.

As used herein, "pharmacokinetics" refers to the concentration of an administered compound in the serum over time. Pharmacodynamics refers to the concentration of an administered compound in target and nontarget tissues over time and the effects on the target tissue (e.g., efficacy) and the non-target tissue (e.g., toxicity). Improvements in, for example, pharmacokinetics or pharmacodynamics can be designed for a particular targeting agent or biological agent, such as by using labile linkages or by modifying the chemical nature of any linker (e.g., changing solubility, charge, and the like).

As employed herein, the phrases "an effective amount" and "therapeutically effective amount" refer to an amount of a compound of the invention that is useful or able to support an observable change in the level of one or more biological activity characteristic of a composition of the invention, or a dose sufficient to impart a beneficial effect, e.g., an amelioration of a symptom on the recipient thereof. The specific therapeutically effective dose level for any particular subject will depend upon a variety of factors including the symptom or disorder being treated, the severity of the symptom or disorder, the activity of the specific compound, the route of administration, the rate of clearance of the compound, the duration of treatment, the drugs used in combination or coincident with the compound, the age, body weight, sex, diet, and general health of the subject, and like, as well as other factors well known in the medical arts and sciences. A therapeutically effective amount can be an amount of a compound of the invention sufficient to produce a measurable inhibition of angiogenesis in the tissue being treated, i.e., an angiogenesis-inhibiting amount. Inhibition of angiogenesis can be measured in situ by immunohistochemistry, or by other methods known to one skilled in the art. Various general considerations taken into account in determining the "therapeutically effective amount" are known to those of skill in the art and are described, e.g., in Gilman, A. G., et al., *Goodman And Gilman's The Pharmacological Basis of Therapeutics*, 8th ed., McGraw-Hill (1990); and *Remington's Pharmaceutical Sciences*, 17th ed., Mack Publishing Co., Easton, Pa. (1990).

As used herein, the terms "concurrently administered" and "concurrent administration" encompass substantially simultaneous administration of one or more compounds of the invention and one other oncology therapeutic.

As used herein, the term, "non-concurrent" administration encompasses administering one or more compounds of the invention at different times, in any order, whether overlapping or not. This includes, but is not limited to, sequential treatment (such as pretreatment, post-treatment, or overlapping treatment) with the components of the combination, as well as regimens in which the drugs are alternated, or wherein one component is administered long-term and the other(s) are administered intermittently.

EXAMPLES

The versatility of the invention is illustrated by the following Examples, which illustrate typical embodiments of the invention and are not limiting of the claims or specification in any way.

Example 1

Synthesis of a Compound of the Invention

Peptides of the invention can be linked to antibody 38C2 by the following procedure: One mL antibody 38C2 in phosphate buffered saline (10 mg/mL) is added to 12 µL of a 10 mg/mL stock solution of Peptide and the resulting mixture maintained at room temperature for 2 hours prior to use.

Example 2

C. Rader, et al., J. Mol. Biol. 332:889-899 (2003) details one method of making h38c2. The following details the results, materials and methods in this reference. Humanization Human Vκ gene DPK-9 and human Jκ gene JK4 were used as frameworks for the humanization of the kappa light chain variable domain, and human $V_H$ gene DP-47 and human $J_H$ gene $J_H4$ are used as frameworks for the humanization of the heavy chain variable domain of m38C2. All complementarity determining region (CDR) residues as defined by Kabat et al., as well as defined framework residues in both light chain and heavy chain variable domain, were grafted from m38C2 onto the human framework. The selection of grafted framework residues may be based on the crystal structure of mouse mAb 33F12 Fab (PDB 1AXT). mAb 33F12 Fab shares a 92% sequence homology with m38c2 in the variable domains and identical CDR lengths. Furthermore, both 33F12 and m38C2 have similar catalytic activity. Framework residues consisted of five residues in the light chain and seven residues in the heavy chain (FIG. 7A) and encompassed the residues that are likely to participate directly or indirectly in the catalytic activity of m38C2. These include the reactive lysine of m38C2, $Lys^{H93}$, which is positioned in framework region 3 (FR3) of the heavy chain. Six residues, $Ser^{H35}$ $Val^{H37}$, $Trp^{H47}$, $Trp^{H103}$, and $Phe^{L98}$, which are conserved between mouse mAbs 33F12 and 38C2, are within a 5-Å radius of the ε amino group of $Lys^{H93}$. These residues were also conserved in the humanization. $Lys^{H93}$ lies at the bottom of a highly hydrophobic substrate binding sites of mouse mAbs 33F12 and 38C2. In addition to CDR residues, a number of framework residues line this pocket. Among these, $Leu^{L37}$ $Gln^{L42}$, $Ser^{L43}$, $Val^{L85}$, $Phe^{L87}$, $Val^{H5}$, $Ser^{H40}$, $Glu^{H42}$, $Gly^{H88}$, $Ile^{H89}$, and $Thr^{H94}$ were grafted onto the human framework.

Expression

By fusing the humanized variable domains to human constant domains $C_κ$ and $C_{γ1}$, h38C2 was initially generated as Fab expressed in E. coli. Next, h38c2 IgG was formed from h38c2 Fab using the PIGG vector engineered for human IgG1 expression in mammalian cells. Supernatants from transiently transfected human 293T cells were subjected to affinity chromatography on recombinant protein A, yielding approximately 1 mg/L h38C2 IgG1. Purity was established by SDS-PAGE followed by Coomassie blue staining.

β-Diketone Compounds-

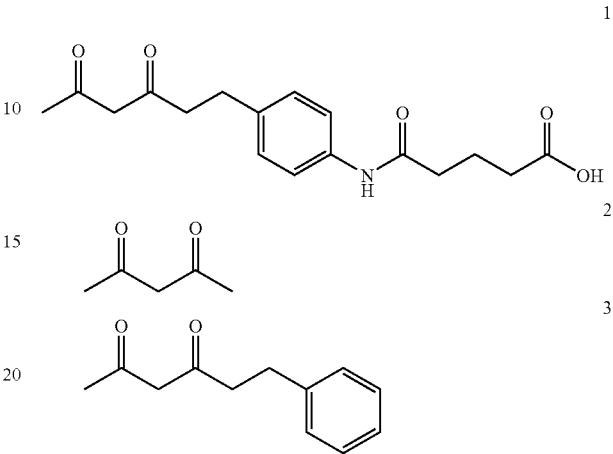

Figure 6:
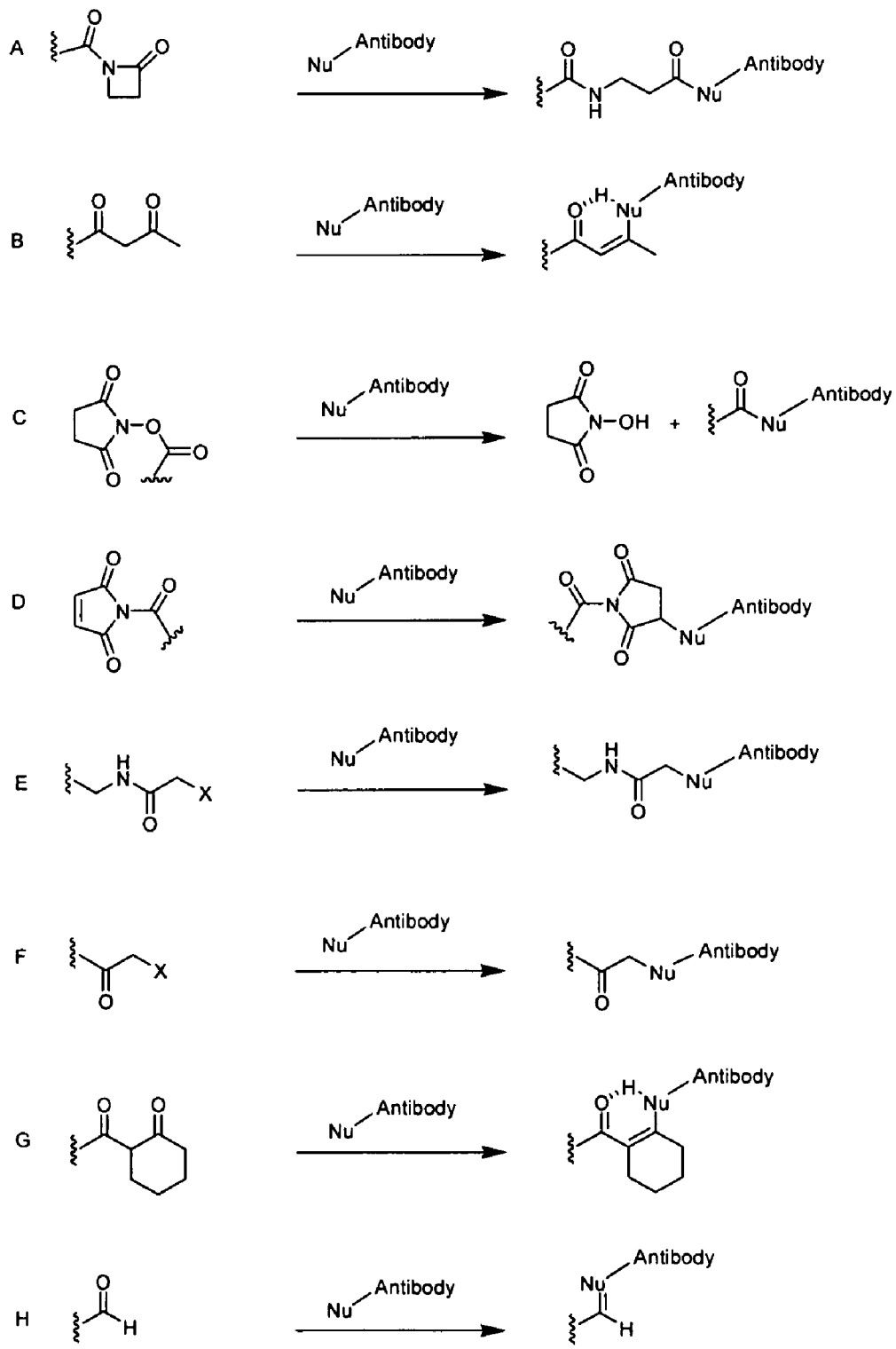
FIG. 6 shows the addition of a nucleophilic side chain in an antibody combining to compounds A-H in FIG. 5. Antibody-Nu- refers to a covalent bond to an amino acid side chain bearing a nucleophile in a combining site of an antibody.

The enaminone formed by the covalent addition of a β-diketone with m38c2 has a characteristic UV absorbance at $λ_{max}$=318 nm. Like m38C2 IgG, h38C2 IgG showed the characteristic enaminone absorbance after incubation with β-diketone. As a negative control, recombinant human anti-HIV-1 gp120 mAb b12 with the same IgG1 isotype as h38C2 but without reactive lysine, did not reveal enaminone absorbance after incubation with β-diketone 2. For a quantitative comparison of the binding of β-diketones to m38C2 and h38C2, the authors used a competition ELISA. The antibodies were incubated with increasing concentrations of β-diketones 2 and 3 and assayed against immobilized BSA-conjugated β-diketone 1. The apparent equilibrium dissociation constants were 38 µM (m38C2) and 7.6 µM (h38C2) for β-diketone 2 and 0.43 µM (m38C2) and 1.0 µM (h38C2) for β-diketone 3, revealing similar β-diketone binding properties for mouse and humanized antibody (FIG. 6).

Molecular modeling—A molecular model of h38C2 Fab was constructed by homology modeling using the crystal structure of a related aldolase antibody, mouse 33F12 Fab (Protein Data Bank ID: 1AXT), as a template. The crystal structure of mouse 33F12 Fab was previously determined at a resolution of 2.15 Å.[4] Alignment of mouse 33F12 and 38C2 amino acid sequences using the HOMOLOGY module within INSIGHT II software (Accelrys) confirmed that both sequences are highly homologous. They differ from each other by 19 out of 226 amino acids in the two variable domains, and their CDRs share the same lengths. In addition to the high sequence homology, both structures exhibit considerable structural similarity, as observed by a low-resolution crystal structure of 38C2. Residues in the model were mutated to conform to the h38C2 amino acid sequence and sidechains were placed based on standard rotamers. This model was then minimized with the DISCOVER module in INSIGHT II using 100 steps each of steepest descent minimization followed by conjugate gradient minimization.

Construction of h38C2 Fab—

The sequences of the variable light and heavy chain domains of m38C2 (SEQ ID NOs:4 and 5 respectively) as well as the sequences of human germline sequences DPK-9 (SEQ ID NO:6), JK4 (SEQ ID NO:7), DP-47 (SEQ ID NO:8), and JH4 (SEQ ID NOs:9, 10, and 11) (V BASE; http:// vbase.mrc-cpe.cam.ac.uk/) were used to design overlapping oligonucleotides for the synthetic assembly of humanized $V_\kappa$ and $V_H$, respectively. N-glycosylation sites with the sequence NXS/T as well as internal restriction sites HindIII, XbaI, SacI, ApaI, and SfiI were avoided. PCR was carried out by using the Expand High Fidelity PCR System (Roche Molecular Systems). The humanized V, oligonucleotides were: L flank sense (Rader, C., Ritter, G., Nathan, S., Elia, M., Gout, I., Junbluth, A. A., J. Biol. Chem. 275:13668-13676 (2000)) (sense 5'-GAGGAGGAGGAGGAGGGCCCAGGC GGC-CGAGCTCCAGATGACCCAGTCTCTCCA-3' SEQ ID NO:12); h38C2L1 (sense; 5'-GAGCT CCAGATGAC-CCAGTCTCCATCCTCCCTGTCTGCATCT-GTAGGTGACCGCGTCACCATCAC TTG-3') (SEQ ID NO:13); h38C2L2 (antisense; 5'-ATTCAGATATGGGCT-GCCATAAGTGTGCA GGAGGCTCTGACTGGAGCG-GCAAGTGATGGTGACGCGGTC-3') (SEQ ID NO:14); h38C2L3 (sense; 5'-TATGGCAGCCCATATCTGAATTGG-TATCTCCAGAAACCAGGCCAGTCTCCTAAG CTCCT-GATCTAT-3') (SEQ ID NO:15); h38C2L4 (antisense; 5'-CT-GAAACGTGATGGGACACC ACTGAAACGATTGGACACTTTATAGAT-CAGGAGCTTAGGAGACTG-3') (SEQ ID NO:16); h38C2L5 (sense; 5'-AGTGGTGTCCCAT-CACGTTTCAGTGGCAGTGGTTCTGGCACAGATTTC ACTCTCACCATCAGCAGTCTGCAACCT-GAAGATTTTGCAGTG-3') (SEQ ID NO:17); h38C2L6 (antisense; 5'-GATCTCCACCTTGGTCCCTCCGC-CGAAAGTATAAGGGAGGTGGGTGCCCTGA CTACA-GAAGTACACTGCAAAATCTTCAGGTTGCAG-3') (SEQ ID NO:18); L antisense flank (C. Rader et al., J. Biol. Chem. 275:13668-13676 (2000)) (antisense5'-GACAGATGGTG-CAGCCAC AGTTCGTTTGATCTCCACCTTGGTC-CTCC-3' SEQ ID NO:19). The humanized $V_H$ oligonucleotides were: H flank sense (C. Rader et al., J. Biol. Chem. 275:13668-13676 (2000))(sense 5'-GCTGCCCAACCAGC-CATGGCCGAGGTGCAGCTGGTGGAGTCTGGGGGA-3' SEQ ID NO:20); h38C2H1 (sense; 5'-GAGGTG-CAGCTGGTGGAGTCTGGCGGTGGCTTGGTACAGCCT GGCGGTTCCCTGCGCCTCTCCTGTG-CAGCCTCTGGCT-3') (SEQ ID NO:21); h38C2H2 (antisense; 5'-CTCCAGGCCCTTCTCTGGAGACTGGCG-GACCCAGCTCATCCAATAGTTGCTA AAGGTGAAGCCAGAGGCTGCACAGGAGAG-3') (SEQ ID NO:22); h38C2H3 (sense; 5'-TCTCC AGAGAAGGGC-CTGGAGTGGGTCTCAGAGATTCGTCT-GCGCAGTGACAACTACGCCACGC ACTATGCA-GAGTCTGTC-3') (SEQ ID NO:23); h38C2H4 (antisense; 5'-CAGATACAGCGTGTTC TTGGAATTGTCACGG-GAGATGGTGAAGCGGCCCTTGACA-GACTCTGCATAGTGCGTG-3') (SEQ ID NO:24); h38C2H5 (sense; 5'-CAATTCCAAGAACACGCTG-TATCTGCAAATGAACAGC CTGCGCGCCGAGGA-CACGGGCATTTATTACTGTAAAACG-3') (SEQ ID NO:25); h38C2H6 (antisense; 5'-TGAGGAGACGGTGAC-CAGGGTGCCCTGGCCCCAGTAGCT-GAAACTGTAGAA GTACGTTTTACAGTAATAAATGC-CCGTG-3') (SEQ ID NO:26); H flank antisense (C. Rader et al., J. Biol. Chem. 275:13668-13676 (2000))(antisense 5'-GACCGATGGGCCCTTGGTGGAGGCT GAG-GAGACGGTGACCAGGGTGCC-3' SEQ ID NO:27). Following assembly, humanized $V_\kappa$ and $V_H$ were fused to human $C_\kappa$ and $C_{\gamma1}$, respectively, and the resulting light chain and heavy chain fragment were fused and SfiI-cloned into phagemid vector pComb3X as described (C. Rader et at, J. Biol. Chem. 275:13668-13676(2000); C. F. Barbas 3$^{rd}$ et al., Phage Display: A laboratory manual, Cold Spring Harbor Laboratory, Cold Spring Harbor N.Y. (2001)). To enrich for clones with the correct h38C2 sequence, Fab were displayed on phage and selected by one round of panning against the immobilized β-diketone 1 (JW) conjugated to BSA. Soluble Fab were produced from single clones and tested for binding to immobilized JW-BSA by ELISA using donkey anti-human F(ab')$_2$ polyclonal antibodies conjugated to horseradish peroxidase (Jackson ImmunoResearch Laboratories) as secondary antibody. Light chain and heavy chain encoding sequences of positive clones were analyzed by DNA sequencing using the primers OMPSEQ (5'-AAGACAGCTATCGC-GATTGCAG-3' SEQ ID NO:28) and PELSEQ (5'-CTAT-TGCCTACGGCAGCCGCTG-3' SEQ ID NO:29) (C. F. Barbas 3$^{rd}$ et al., Phage Display: A laboratory manual, Cold Spring Harbor Laboratory, Cold Spring Harbor N.Y., (2001)), respectively, to confirm the assembled $V_\kappa$ and $V_H$ sequences of h38C2.

Construction, production, and purification of h38C2 IgG1—The recently described vector PIGG (C. Rader et al, FASEB J., 16:2000-2002 (2002)) was used for mammalian expression of h38C2 IgG1. The mammalian expression vector PIGG-h38c2 is illustrated in FIG. 23. The 9 kb vector comprises heavy chain γ1 and light chain κ expression cassettes driven by a bidirectional CM promoter construct. Using primers PIGG-h38C2H (sense; 5'-GAGGAGGAGGAG-GAGGAGCTCAC TCCGAGGTGCAGCTGGTG-GAGTCTG-3') (SEQ ID NO:30) and GBACK (5'-GC-CCCCTTATTA GCGTTTGCCATC-3' SEQ ID NO:31) (C. F. Barbas 3$^{rd}$ et al., Phage Display: A laboratory manual, Cold Spring Harbor Laboratory, Cold Spring Harbor N.Y. (2001)), the VH coding sequence from h38C2 Fab in phagemid vector pComb3X was amplified, digested with SacI and ApaI, and cloned into the appropriately digested vector PIGG. Using primers PIGG-h38C2L (sense; 5'-GAG-GAGGAG GAGGAGAAGCTTGTTGCTCTG-GATCTCTGGTGCCTACGGGGAGCTCCA-GATGACCCAGTC TCC-3') (SEQ ID NO:32) and LEADB (5'-GCCATGGCTGGTTGGGCAGC-3' SEQ ID NO:33) ((C. F. Barbas 3$^{rd}$ et at, Phage Display: A laboratory manual, Cold Spring Harbor Laboratory, Cold Spring Harbor N.Y. (2001)) the light chain coding sequence from h38C2 Fab in phagemid vector pComb3X was amplified, digested with HindIII and XbaI, and cloned into the appropriately digested vector PIGG that already contained the h38C2 heavy chain. Intermediate and final PIGG vector constructs were amplified in E. coli strain SURE (Stratagene) and prepared with the QIAGEN Plasmid Maxi Kit. h38C2 IgG1 were produced from the prepared final PIGG vector construct by transient transfection of human 293T cells using Lipofectamine 2000 (Invitrogen). Transfected cells were maintained in GIBCO 10% ultra-low IgG (<0.1%) FCS (Invitrogen) in RPMI 1640 (Hyclone) for 2 weeks. During this time, the medium was collected and replaced three times. The collected medium was subjected to affinity chromatography on a recombinant Protein A HiTrap column (Amersham Biosciences). This purification step yielded 2.45 mg h38C2 IgG1 from 2,300 mL collected medium as determined by measuring the optical density at 280 nm using an Eppendorf BioPhotometer. Following dialysis against PBS in a Slide-A-Lyzer 10K dialysis cassette (Pierce), the antibody was concentrated to 760 µg/mL using an Ultrafree-15 Centrifugal Filter Device (UFV2BTK40; Millipore), and sterile filtered through a 0.2-µm Acrodisc 13MM S-200 Syringe Filter (Pall). The final yield was 2.13 mg (87%). Purified h38C2 IgG1 was confirmed by nonreducing SDS-PAGE followed by Coomassie Blue staining.

Enaminone formation—Antibody (h38C2 IgG1 or b12 IgG1) was added to β-diketone 2 to a final concentration of 25 μM antibody binding site and 125 μM β-diketone. This mixture was incubated at room temperature for 10 minutes before a UV spectrum was acquired on a SpectraMax Plus 384 UV plate reader (Molecular Devices) using SOFTmax Pro software (version 3.1.2).

Binding assays—Unless noted otherwise, all solutions were phosphate buffered saline (pH 7.4). A 2× solution of either β-diketone 2 or 3 (50 μL) was added to 50 μL of the antibody (either h38C2 or m38C2) and allowed to incubate at 37° C. for 1 hr. Solutions were mixed by pipetting. Final concentrations of antibody were 0.4 to 8 nM antibody binding site, and final concentrations of β-diketones 2 and 3 were $10^{-9}$ to $10^{-2}$ M and $10^{-10}$ to $10^{-4}$ M, respectively. Each well of a Costar 3690 96-well plate (Corning) was coated with 100 ng of the BSA conjugate of β-diketone 1 in TBS. Wells were then blocked with 3% (w/v) BSA in TBS. Then, 50 μL of the antibody/β-diketone mixture was added, followed by 50 μL of a 1:1,000 dilution of either goat anti-human Fc IgG polyclonal antibodies (Pierce) or rabbit anti-mouse Fc IgG polyclonal antibodies (Jackson ImmunoResearch Laboratories) conjugated to horseradish peroxidase. This was followed by 50 μL ABTS substrate solution. Between each addition, the plate was covered, incubated at 37° C. for 1 hr, and then washed five times with deionized $H_2O$. The absorbance at 405 nm was monitored as described above until the reaction with no β-diketone reached an appropriate value ($0.5 < A_{405} < 1.0$). For each well, the fractional inhibition of ELISA signal ($v_i$) was calculated using equation i:

$$v_i = (A_o - A_i)/(A_o) \qquad (i)$$

where $A_o$ is the ELISA absorbance obtained in the absence of β-diketone and $A_i$ is the absorbance obtained in the presence of β-diketone. For monovalent binding proteins, the fraction of antibody bound to soluble β-diketone (f) is equal to $v_i$. However, the IgG antibody is bivalent, and the ELISA signal is inhibited only by the presence of doubly liganded antibody and not by monovalent binding. Therefore, the Stevens correction for a bivalent antibody was used:

$$f_i = (v_i)^{1/2} \qquad (ii)$$

The following relationship was used to determine the apparent equilibrium dissociation constant (modified from [ref 37]):

$$f_i = f_{min} + (f_{max} - f_{min})(1 + K_D/a_0)^{-1} \qquad (iii)$$

where $a_0$ corresponds to the total β-diketone concentration, $K_D$ is the equilibrium dissociation constant, and $f_{min}$ and $f_{max}$ represent the experimentally determined values when the antibody binding sites are unoccupied or saturated, respectively. Because this equation is only valid when the $K_D$ values are at least 10× higher than the antibody concentration, it was verified that the $K_D$ values determined from equation iii met this criterion. Data were fit using a nonlinear least-squares fitting procedure of KaleidaGraph (version 3.0.5, Abelbeck software) with $K_D$, $f_{max}$, and $f_{min}$ as the adjustable parameters and normalized using equation iv:

$$f_{norm} = (f_i - f_{min})/(f_{max} - f_{min}) \qquad (iv)$$

Example 3

Linking Peptides of the Invention with Linkers of the Invention

Compounds of the invention may be prepared by several approaches. In one approach, a [Peptide]-linker compound is synthesized with a linker that includes one or more reactive groups designed for covalent reaction with a side chain of an amino acid in a combining site of an antibody. The targeting agent-linker compound and antibody are combined under conditions where the linker reactive group forms a covalent bond with the amino acid side chain.

In another approach, linking can be achieved by synthesizing an antibody-linker compound comprising an antibody and a linker wherein the linker includes one or more reactive groups designed for covalent reaction with an appropriate chemical moiety of the [Peptide]. A [Peptide] may need to be modified to provide the appropriate moiety for reaction with the linker reactive group. The antibody-linker and [Peptide] are combined under conditions where the linker reactive group covalently links to the targeting and/or biological agent.

A further approach for forming an antibody-[Peptide]-conjugate uses a dual linker design. In certain embodiments, a [Peptide]-linker compound is synthesized which comprises a [Peptide]-linker and a linker with a reactive group. An antibody-linker compound is synthesized which comprises an antibody and a linker with a chemical group susceptible to reactivity with the reactive group of the [Peptide]-linker of the first step. These two linker containing compounds are then combined under conditions whereby the linkers covalently link, forming the antibody-[Peptide] compound. Table 9 shows exemplary compounds of the invention comprising [VEGF-Peptides] covalently linked to linkers: D-amino acids are indicated by the use of lower case type script: for example, Compound 2018 (comprising SEQ ID NO:78, substituted with $K^{10}$ as linking residue, also equal to SEQ ID NO:195) includes the residues "R-L-Y-(D-Ala)-(D-Leu)", which are written "R-L-Y-a-l". Disulphide bonds are depicted as connecting lines between two cysteine residues.

Z may be a group that forms a reversible or irreversible covalent bond. In some embodiments, reversible covalent bonds may be formed using diketone Z groups such as those shown in FIG. 3. Thus, structures A-C may form reversible covalent bonds with reactive nucleophilic groups (e.g. lysine or cysteine side chain) in a combining site of an antibody. $R'_1$, $R'_2$, $R'_3$, and $R_4$ in structures A-C of FIG. 3 represent substituents which can be C, H, N, O, P, S, halogen (F, Cl, Br, I) or a salt thereof. These substituents also may include a group such as an alkyl, alkenyl, alkynyl, oxoalkyl, oxoalkenyl, oxoalkynyl, aminoalkyl, aminoalkenyl, aminoalkynyl, sulfoalkyl, sulfoalkenyl, or sulfoalkynyl group, phosphoalkyl, phosphoalkenyl, phosphoalkynyl group. $R'_2$ and $R'_3$ also could from a ring structure as exemplified in structures B and C. X in FIG. 3 could be a heteroatom. Other Z groups that form reversible covalent bonds include the amidine, imine, and other reactive groups encompassed by structure G of FIG. 3. FIG. 4 includes the structures of other linker reactive groups that form reversible covalent bonds, e.g., structures B, G, H, and, where X is not a leaving group, E and F.

Figure 1A:
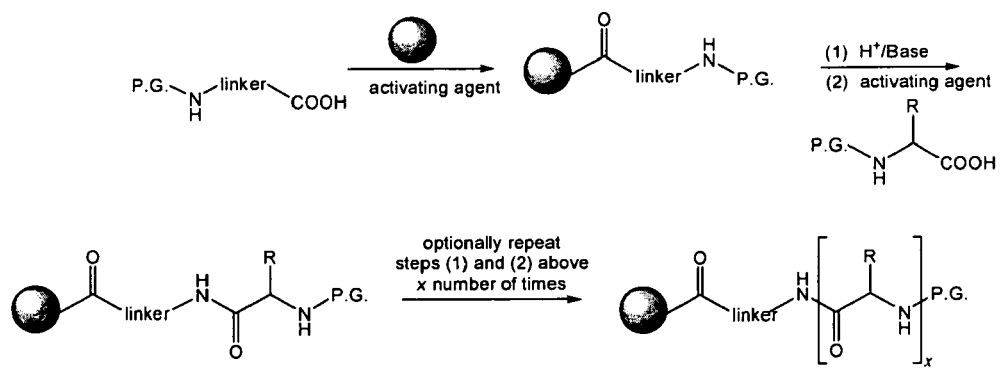
FIG. 1A and FIG. 1B illustrate the solid phase synthesis of targeting agent-linker conjugates of the present invention.
Figure 1B:
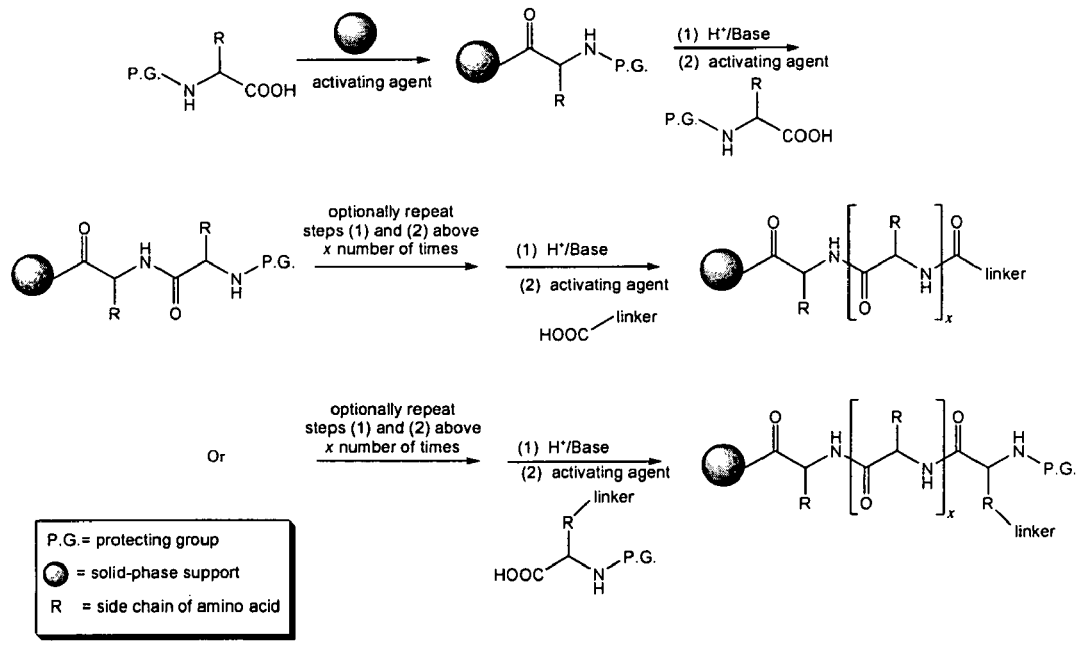
Figure 5:
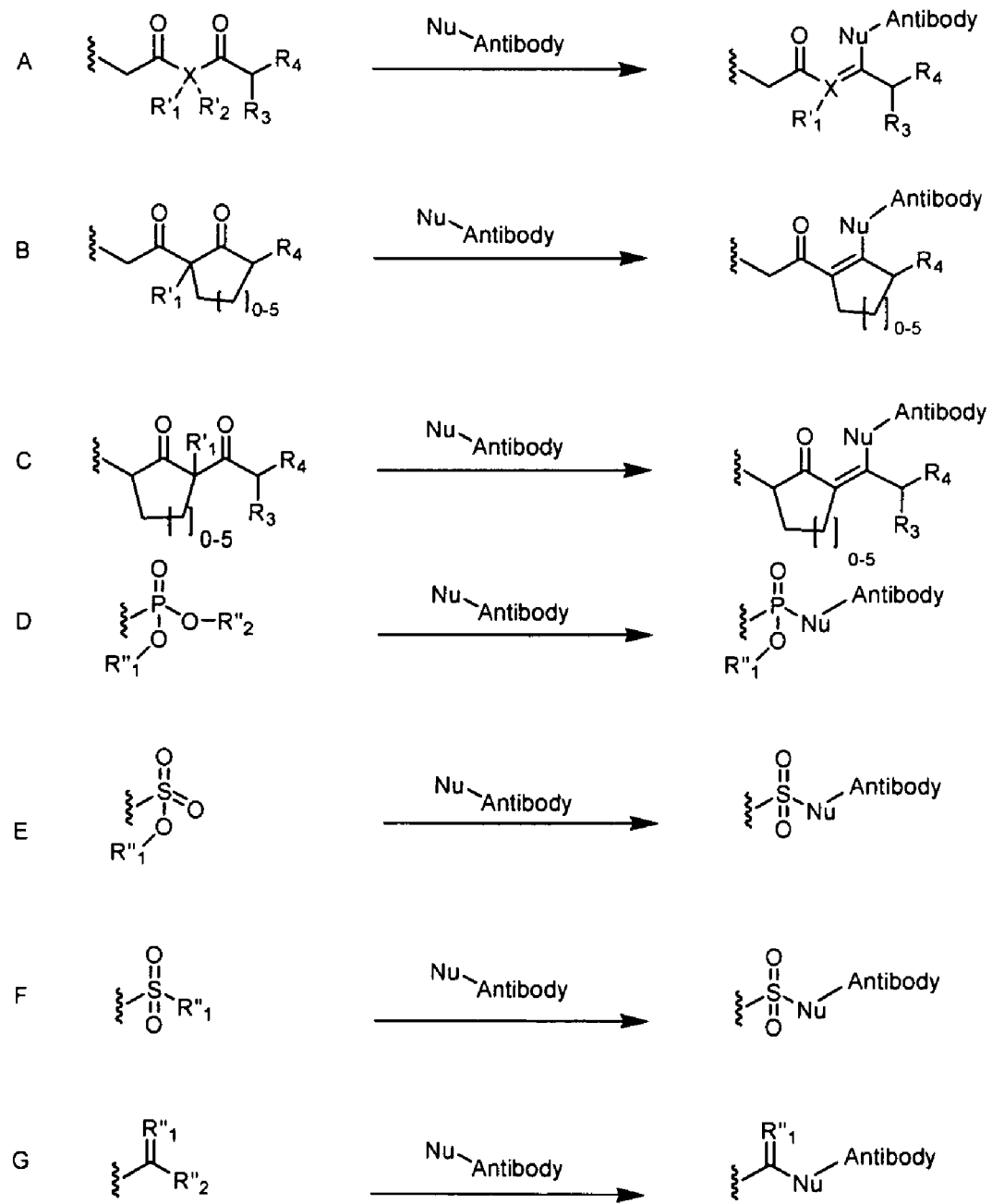
FIG. 5 shows the addition of a nucleophilic ("nu") side chain in an antibody combining site to compounds A-G in FIG. 3. Antibody-Nu- refers to a covalent bond to an amino acid side chain bearing a nucleophile in a combining site of an antibody.

Z reactive groups that form an irreversible covalent bond with a combining site of an antibody include structures D-G in FIG. 3 (e.g., when G is an imidate) and structures A, C and D of FIG. 4. When X is a leaving group, structures E and F of FIG. 4 may also form irreversible covalent bonds. Such structures are useful for irreversibly attaching a targeting agent-linker to a reactive nucleophilic group to a combining site of an antibody. As used herein, L' is a linker moiety linking an antibody to the targeting agent and having the formula —X—Y—Z'—. FIGS. 5 and 6, respectively, illustrate the addition mechanism of a reactive, nucleophilic side chain in a combining site of an antibody to the Z moieties illustrated in FIGS. 3 and 4.

This is shown below for the case where the linker has a diketone moiety as the reactive group and linkage occurs with the side chain amino group of a lysine residue in the antibody combining site. The Antibody is shown schematically as bivalent with a reactive amino acid side chain for each combining site indicated.

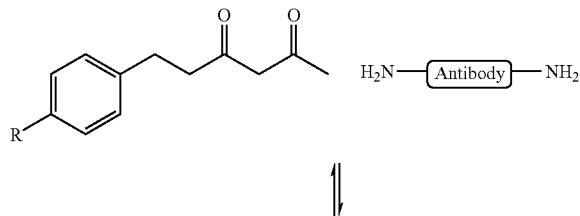

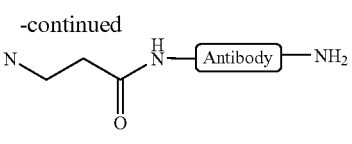

Compounds of the invention may also be readily synthesized by covalently linking a [Peptide]-linker compound as described herein to a combining site of a multivalent antibody. For example, a [Peptide]-linker conjugate, where the linker includes a diketone reactive moiety, can be incubated with 0.5 equivalents of an aldolase antibody, such as h38C2 IgG1 to produce a compound of the invention.

A further example of a reaction mechanism combining a [Linker]-[Antibody] to a peptide is shown below, employing 'click chemistry' to combine an alkyne and an azide (where R may be attached to a [Peptide] of the invention.

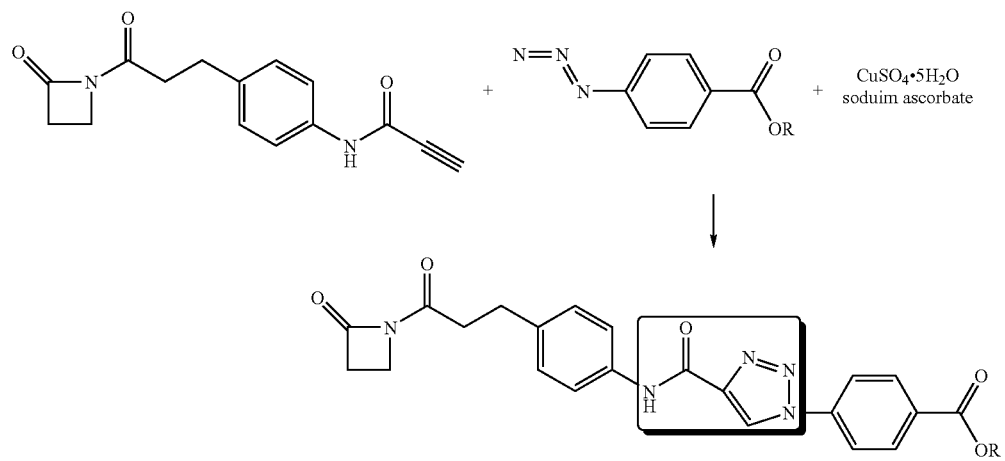

-continued

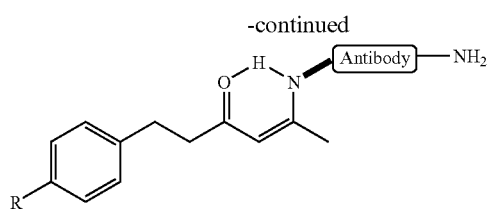

Another embodiment shown below is for the case where the linker has a beta lactam moiety as the reactive group and linkage occurs with the side chain amino group of a lysine residue in the antibody combining site. The Antibody is shown schematically as bivalent with a reactive amino acid side chain for each combining site indicated.

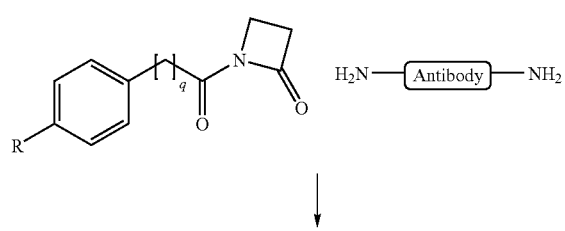

Example 4

Figure 7:
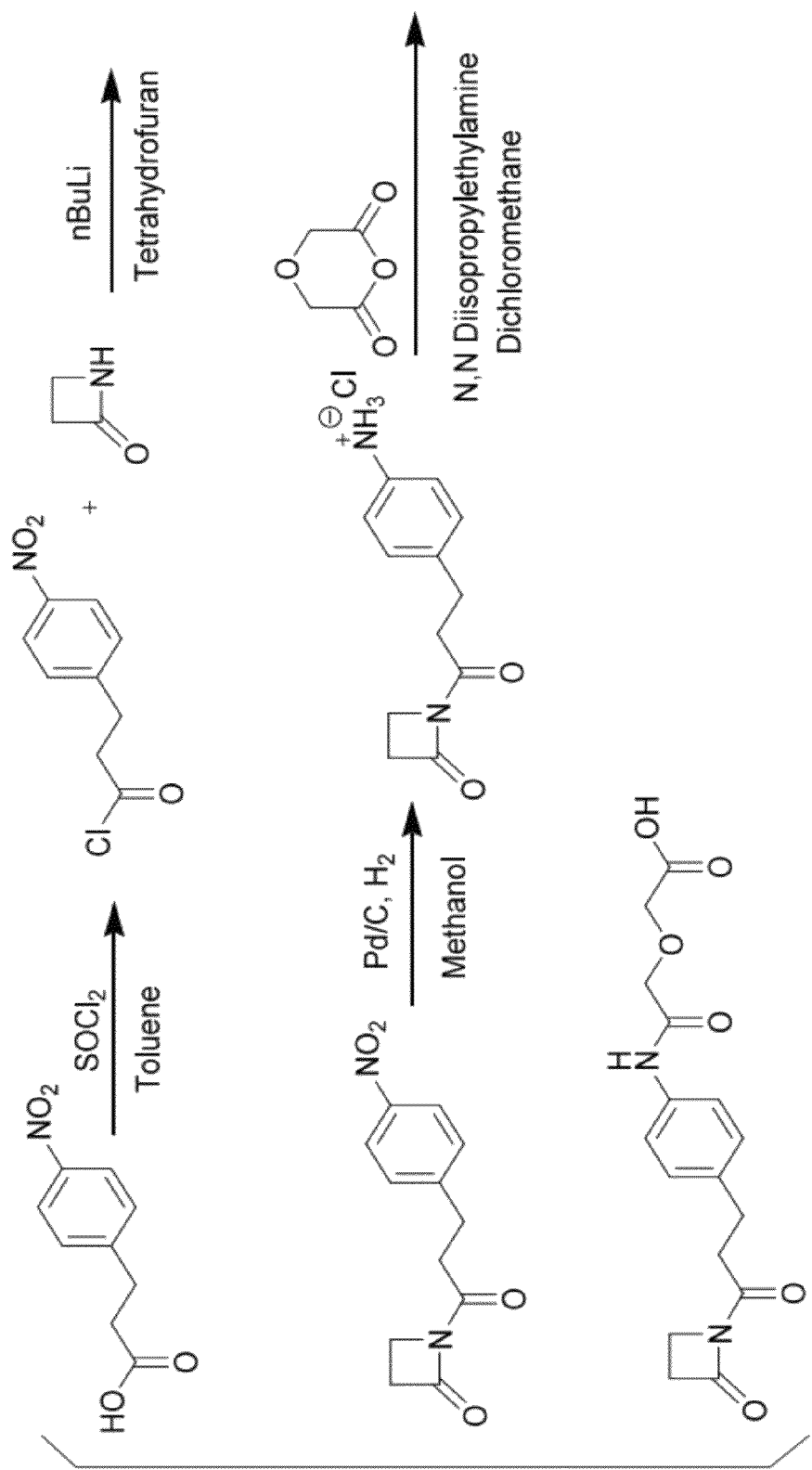

Synthesis of:

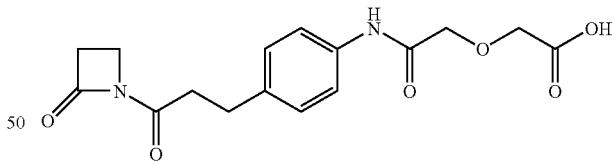

is provided in FIG. 7.

Example 5

The ability of Ang2 binding compounds to interact with Ang2 was measured by competition with Tie-2. These tests were described in US2008166364 (and also in PCT/IE2007/000110), whose contents are herein incorporated by reference in their entirety. In particular, those portions of PCT/IE2007/000110 and US2008166364 detailing the advantages and disadvantages of various Ang2-binding peptides, and the advantages and disadvantages of covalently linking certain Ang2-binding peptides to catalytic antibodies (and those portions specifically relating to linking to h38C2), as well as the advantages and disadvantages of using specific residues of the respective Ang2-specific peptide as the linking residue (in this context, linking residue meaning the residue covalently linked to the linker (for example as used herein in Example 4)). For competitive ELISA, human angiopoietin-2 protein and Tie-2-Fc (R&D Systems) were reconstituted without carrier protein. Mouse anti-human Tie-2 (Pharmingen) was used as the primary antibody and goat anti-mouse-IgG1-HRP (Pierce) was used as the secondary antibody. TMB substrate from Pierce was used.

High-binding half-well plates were coated with Ang-2 (100 ng/well) in 50 µl PBS and incubated at 4° C. overnight. Plates were washed three times with washing buffer (0.1% Tween 20, PBS, pH 7.4) and blocked with Superblock (Scytek), 100 µl/well at room temperature ("RT") for 1 hour. After removing the blocking solution, 50 µl of an Ang-2 binding peptide compound (1 uM and 5× serial dilution) in the presence of 0.25 nM hTie-2-Fc using Superblock as diluent was added and incubated at RT for 2 hours. Plates were washed 3 times with washing buffer. Then, 50 ul of 0.1 ug/ml mouse anti-human Tie-2 diluted in Superblock added and incubated at RT for 1 hour. Following incubation, 50 ul of 1:5,000 dilution of goat anti-mouse IgG-HRP in Superblock was then added and incubated at RT for one hour. After washing 3 times, 50 µl (25 µl TMB+25 µl $H_2O_2$) was added, and incubated for 3-5 minutes. Color development was monitored and stopped with 25 µl of 2 M $H_2SO_4$. OD450 nm with a correction wavelength of 540 nm was measured. IC50 values (50% inhibition of Ang-2-Tie-2 binding) were calculated using non-linear Sigmoidal dose-response curve fitting function in the Prism 4 software (GraphPad).

For reverse competition ELISA, human Tie-2-Fc, angiopoietin-2 protein, biotinylated anti-human Ang-2 antibody, and streptavidin HRP (R&D Systems) and TMB substrate from Pierce were used. High-binding half-well plates were coated with Tie-2-Fc (50 ng/well) in 50 µl PBS and incubated at 4° C. overnight. Plates were washed three times with washing buffer (0.1% Tween 20, PBS, pH 7.4) and blocked with Superblock, 150 µl/well at RT for 1 hour. Plates were washed three times. Following washing, 50 µl of an Ang-2 binding peptide compound (50 nM, 5x serial dilution) in the presence of 50 ng/ml (0.83 nM) Ang-2 in Superblock were added and incubated at RT for 1 hour. Plates were washed 3 times, 50 µl of 1 µg/ml biotinylated anti-Ang-2 detection antibody in Superblock was added and incubated at RT for 2 hours. Plates were washed 3 times, and 50 µl of streptavidin HRP (1:200 dilution in Superblock) was added at RT for 20 minutes. Plates were washed 3 times, and 50 µl (25 µl TMB+25 µl $H_2O_2$) substrate solution was added and incubated for 20-30 minutes. Color development was stopped with 25 µl of 2 M $H_2SO_4$. OD450 nm with a correction wavelength of 540 nm was measured. IC50 values (50% inhibition of Ang-2-Tie-2 binding) were calculated using non-linear Sigmoidal dose-response curve fitting function in the Prism 4 software.

IC50 values for exemplary Ang-2 binding peptide compounds as determined by competitive ELISA are presented in Table 5. IC50 values are provided for the Ang2-binding peptide covalently linked to the Linker as shown in Example 4 via the side chain of the Ang2-linking residue (T) and the Ang2-binding peptide covalently linked to the linker of Example 4 via the side chain of the Ang2-linking residue, wherein the Z group of the linker is covalently linked to the combining site of h38C2 (P).

In Table 5, compounds 4021, 4022 and 4023 are Ang-2 binding peptides alone, not conjugated to either a linker or linker-antibody; compounds 4024 and 4025 are Ang-2 binding peptides conjugated to a linker-antibody, where the linker is 4P ("4" PEG); and compounds 4026-4063 are Ang-2 binding peptides conjugated to a linker-antibody, where the linker is OP ("O" PEG) and has the structure of the linker shown in Example 4. Compounds 4024-4063 were conjugated to humanized aldolase antibody when obtaining the data shown below, except where otherwise indicated. All compounds of the invention shown in the Tables were capped with an acyl group at the N-terminus and an amino group at the C-terminus, except where otherwise indicated (e.g. compounds 4026, 4049, 4050, 4051 and 4052). In Table 5, amino acid sequences of peptide compounds are shown with the position of linker OP or 4P indicated in parentheses following the internal amino acid residue to which the linker is attached. For compound 4026, the N-terminal "OP" linker is indicated at the beginning of the peptide sequence.

For example, compound 4024 in Table 5 has the following sequence: Q(Kac)Y QPL DEL DK(4P)T LYD QFM LQQ G (parent SEQ ID is SEQ ID NO:138). In this example, the second amino acid residue is epsilon acyl lysine, followed by tyrosine, and the linking position (in this case a 4P linker) is the lysine residue 11, followed by threonine. Also, compound 4052 has the following sequence: (Amido 2-PEG)QKacY QPL DEL DK(OP)T LYD QFMLQQ G (SEQ ID NO:162). In this case, the N-terminal glutamine residue is capped by an amido-2-PEG group, the second amino acid residue is epsilon acyl lysine, and the OP linker is attached to lysine residue 11.

Tables 5 and 6 also show half-life (T ½) and "screening" half life (results in parentheses), an alternative method of determining T ½, based on a shorter test period. For "screening" T ½, test compounds were intravenously administered into male Swiss Webster mice. Blood samples were taken from 4 mice per time point via retroorbital sinus bleed at the following time points: 0.08, 5, and 32 hours. Blood level of test compounds were determined by ELISA. The data were reported as the percentage of test compounds at 32 hours versus 5 min. Normal T ½ was calculated in a similar fashion, after undergoing additional data analysis using WinNonlin version 4.1 (Pharsight Corporation). The data was fit to a model based upon the shape of the curve (i.e. a bi-exponential decline will be fit to a two compartment model, etc.) The criteria for best fit (i.e. lowest % CV) was based on iterative re-weighted least squares.

IC50 values for exemplary Ang-2 binding peptide compounds as determined by reverse competitive ELISA are presented in Table 5. IC50 values are provided for the targeting peptide plus linker and the targeting peptide linked to an antibody (P) via the linker of Example 4, unless otherwise specified. In Table 5, compounds are conjugated to humanized aldolase antibody h38c2 and the linker structures shown in Example 4 (OP).

Xenograft Studies

Colo205 cells were cultured with 10% FBS RPMI medium and $3 \times 10^6$ cells in 0.1 ml Hank's balanced salt solution (HBSS) were injected subcutaneously into the upper right flank of nude mice. After 7-9 days, animals were randomized into appropriate number of groups with average tumor size of 200-300 mm³. Mice were then treated with the requisite amount of compounds of the invention and tumor volumes were measured twice a week. Animals were terminated once their average tumor volume reached 2000 mm³. Upon termination, tumors were weighed and saved for further histological studies. Treatment efficacy was evaluated by measuring the difference in the tumor volumes of treated versus control groups. Results are reported as % T/C, where % T/C was calculated as: % T/C=$(V_t-V_0)/(C_t-C_0) \times 100$, where, $V_0$ and $V_t$ were the average tumor volumes of treated groups at the beginning and termination of the group. $C_0$ and $C_t$ were the average tumor volumes of the control group at the beginning and termination of the group (Table 7).

Example 6

Exemplary [VEGF-Peptide]-[Linker] compounds are shown in Table 9 and exemplary [VEGF-Peptide]-[Linker]-Antibody compounds are shown in Table 10.

Example 7

VEGF Peptide Binding Assay

High-binding half-well 96-well plates (Costar #3690) were coated with recombinant human VEGFR2/Fc (50 ng/well) in 50 µl PBS, and incubated at 4° C. overnight. After washing the plates three times with 1× washing buffer (KPL Cat #50-65-00) and blocking with Superblock (Scytek #AAA500) at room temperature (RT) for 1 hour, VEGF-peptides of the invention were serially diluted (concentrations: 0.128-10,000 nM) in the presence of 25 ng/ml of recombinant human VEGF165 in 50 µl Superblock, and were then added to the 96-well plates and incubated at RT for 1 hour. Peptides of the invention tested in this fashion were all capped at the amino terminus with a $C(O)CH_3$ group and at the carboxyl terminus with a $NH_2$ group. The plates were then washed three times with washing buffer, and a diluted (1:500) biotinylated anti-human VEGF antibody (R&D systems, Cat #BAF293) was added and incubated at RT for 2 hours. After washing the plates, streptavidin HRP conjugate (1:200 in Superblock) (R&D systems, Cat #DY998) was added to detect the bound anti-VEGF antibody, followed by addition of tetramethylbenzidine (TMB) substrate (Pierce, Cat #34021) for color development. The reaction was stopped with 2 M $H_2SO_4$. OD450 was measured using SpectraMax (Molecular Device) with a correction wavelength of 540 nM. The data were analyzed using Prism software. OD450 values were plotted as a function of the concentrations of the VEGF peptides. IC50 values, indicative of the potency of the VEGF peptides to inhibit VEGF-VEGFR2 interaction, were obtained using a sigmoid dose-response curve fit in Prism. Results of the VEGF binding assays are shown in Tables 1 and 2 (Table 1 features VEGF Peptides with $V^{12}$ (excepting SEQ ID NO:34) and Table 2 features VEGF peptides with $E^{12}$). Tables 1 and 2 indicate the compounds of the invention tested by the parent SEQ ID NO, although the N' and C' termini of the tested compounds were capped as described above. Not all compounds were tested at the same instance: IC50 values given in parantheses have been normalized.

Example 8

Peptide Tethering

A solution of linker (as shown in Example 4) (0.1 g, 0.3 mmol), HBTU (O-Benzotriazole-N,N,N',N'-tetramethyl-uronium-hexafluoro-phosphate) (0.11 g, 0.3 mmol) in anhydrous DMF (Dimethylformamide) (2 mL) was cooled to 2-5° C. in an ice bath under argon atmosphere. NMM (N-methylmorpholine) (0.12 g, 0.9 mmol) was introduced via syringe and stirred for 5 minutes. Another cold solution of Peptide (SEQ ID NO:64) (0.24 g, 0.1 mmol) in anhydrous DMF (2 ml) was added to the first reaction vessel and stirred for 30 minutes. After the completion of reaction as monitored by LCMS (Liquid Chromatography/Mass Spectrometry), water (1 ml) was added and the reaction mixture was purified using HPLC (High Performance Liquid Chromatography) to get a pure product (145 mg) with a mass of 2785. In the figure below, full structures of non-natural amino acids and residues involved any bonding other than peptide binding are depicted. Thus the N of both cysteines is shown. Other Compounds of the invention were formed by covalent linkage

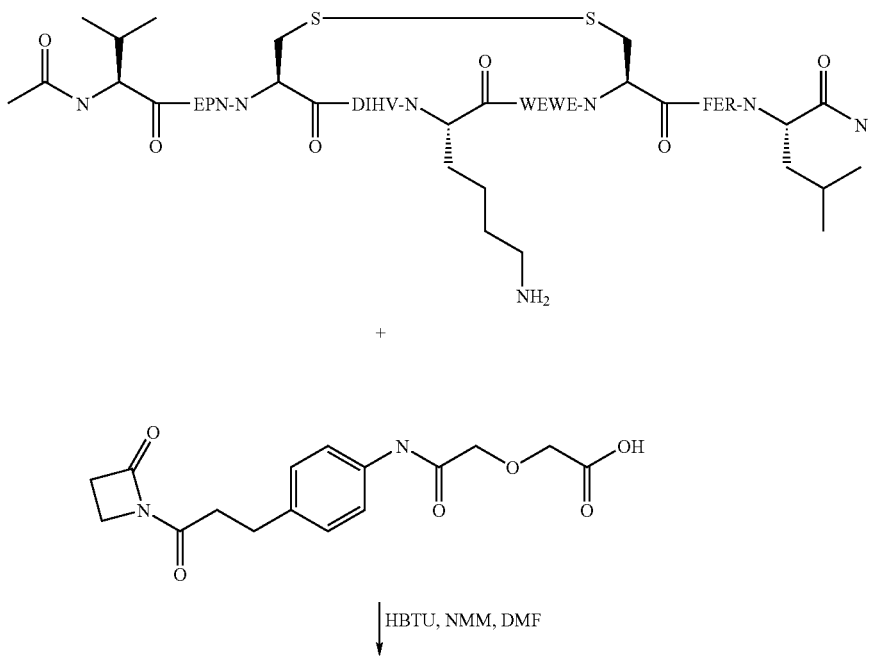

-continued

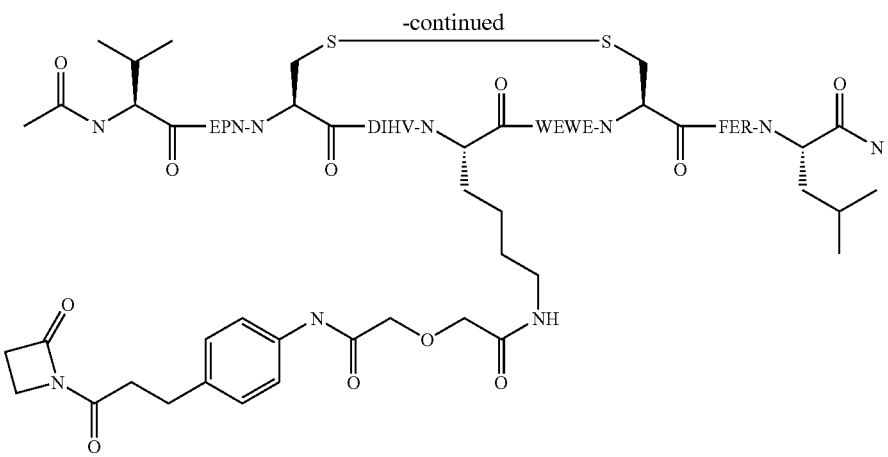

Example 9

Covalently Linking [Peptide]-[Linker] Moiety to [Antibody]

Programming and Purification of [Peptide]-[Linker]-[Antibody] Complexes

Tethered peptides were programmed at a 3:1 ratio with h38C2 at room temperature, overnight. The resultant [Peptide]-[Linker]-[Antibody] macromolecules were purified by PD-10 desalting columns. Protein concentrations were measured by UV A280. [Peptide]-[Linker]-[Antibody] macromolecules were characterized by LCMS analysis for programming efficiency.

Example 10

Mouse PK Assays

Reverse ELISA Format

PK studies were conducted using male Swiss Webster mice (CFW, Charles Rivers Hollister, Calif.) weighing approximately 20-22 grams at the start of dosing. [VEGF-Peptide]-[Linker]-[Antibody] complexes were given by IV administration through the tail vein, blood samples were taken from 3 mice per time point via retro orbital sinus bleed at the following time points: 0.08, 0.5, 1, 3, 5, 7 and 24 hours. For time points up to 32 hours mice were anesthetized with isoflurane and bleed volumes did not exceed 0.1 mL/bleed. For the remaining time points (32-120 hrs), mice were killed by $CO_2$ inhalation and terminal cardiac samples were drawn. Protease Inhibitor cocktail was added to all blood tubes prior to sample collection. Blood was allowed to clot on ice for 30 minutes and then centrifuged at 12000 rpm for 5-10 minutes at 4° C. to collect serum and immediately stored at −80° C. until analysis via ELISA. Dosing solutions were used to establish the standard curves for serum sample analysis by VEGF Reverse ELISA. Aliquots of each serum sample were analyzed by either VEGF Reverse ELISA (also described herein as IgG Coated ELISA) or VEGF ELISA (VEGF Coated ELISA).

VEGF Reverse ELISA

High-binding half-well 96-well plates (Costar #3690) were coated with 1:100 goat anti-human IgG in coating buffer (Bethyl Laboratories ELISA kit, Cat #E80-104) at 4° C. overnight. After washing the plates three times with 1× washing buffer (KPL Cat #50-65-00) and blocking with Superblock (Scytek #AAA500) at room temperature (RT) for 1 hour, prepared dosing solution standards (range: 3.91-500 ng/ml) and serum samples were added to the plate and incubated for 1 hour on a plate shaker to allow binding of [VEGF-Peptide]-[Linker]-[Antibody] complexes to the plates. A fixed concentration of VEGF (3 nM) was then added and incubated for 1 hour on a plate shaker. The plates were then washed three times with washing buffer, and a diluted (1:500) biotinylated anti-human VEGF antibody (R&D systems, Cat #BAF293) was added and incubated at RT for 2 hours. After washing the plates, streptavidin HRP conjugate (1:200 in Superblock) (R&D systems, Cat #DY998) was added to detect the bound anti-VEGF antibody, followed by addition of tetramethylbenzidine (TMB) substrate (Pierce, Cat #34021) for color development. The reaction was stopped with 2 M $H_2SO_4$. OD450 was measured using SpectraMax (Molecular Device) with a correction wavelength of 540 nM. Serum concentrations of the [VEGF-Peptide]-[Linker]-[Antibody] complexes were calculated using the standard curves. Serum compound concentrations, as determined by ELISA, were plotted as a function of time. Further data analysis was undertaken using WinNonlin version 4.1 (Pharsight Corporation) to determine the β half life ($T_{1/2}$) and the area under the curve (AUC) for [Peptide]-[Linker]-[Antibody] complexes.

VEGF Elisa

High-binding half-well 96-well plates (Costar #3690) were coated with rhVEGF165 (6.25 ng/well) in 50 μl PBS/well and incubated at 4° C. overnight. After washing the plates three times with 1× washing buffer (KPL Cat #50-65-00) and blocking with Superblock (Scytek #AAA500) at room temperature (RT) for 1 hour, prepared dosing solution standards (range: 3.91-500 ng/ml) and serum samples were added to the plate and incubated for 1 hour to allow binding of [VEGF-Peptide]-[Linker]-[Antibody] complexes to the coated VEGF on the plates. The plates were then washed three times with washing buffer, diluted goat anti-human IgG-HRP (1:5000) (Bethyl A80-104P-52) was added and incubated at RT for 1 hour, followed by addition of tetramethylbenzidine (TMB) substrate (Pierce, Cat #34021) for color development. The reaction was stopped with 2 M $H_2SO_4$. OD450 was measured using SpectraMax (Molecular Device) with a correction wavelength of 540 nM. Serum concentrations of the [VEGF-Peptide]-[Linker]-[Antibody] complexes were calculated using the standard curves. Serum [VEGF-Peptide]-[Linker]-[Antibody] complexes concentrations, as determined by ELISA, were plotted as a function of time. Further data analysis was undertaken using WinNonlin version 4.1 (Pharsight Corporation) to determine the β half life ($T_{1/2}$) and the area under the curve (AUC) for [VEGF-Peptide]-[Linker]-[Antibody] complexes.

Table 3 shows the binding of a series of [VEGF-Peptide]-[Linker]-[Antibody] complexes. The [VEGF-Peptide] portion of each complex was based on SEQ ID NO:34, and with one of the residues from $X^1$ through to $X^{19}$ substituted by K as a linking residue, with the exception of $C^5$ and $C^{15}$. In each case, the [VEGF-Peptide] was capped at the amino terminus with a $C(O)CH_3$ group and at the carboxly terminus with a $NH_2$ group. The [Linker] portion of each complex was that depicted in Example 4. The [Antibody] portion of each complex was h38C2: comprising SEQ ID NO:1 and SEQ ID NO:2. Table 6 also shows half-life data for certain [VEGF-Peptide]-[Linker]-[Antibody] complexes, as well as data representing area under the curve (AUC). The AUC data represents the total area unde the curve, taking into account both the α-half life and the β-half life.

Table 4 shows the binding of a series of [VEGF-Peptide]-[Linker]-[Antibody] complexes. The [VEGF-Peptide] portion of each complex was based on the SEQ ID NO indicated, and with the indicated residue substituted by K as a linking residue. In each case, the [VEGF-Peptide] was capped at the amino terminus with a $C(O)CH_3$ group and at the carboxly terminus with a $NH_2$ group. Residues 1 to 18 of the peptides are not depicted in Table 4, but were as described elsewhere, with the exception of the respective substitution of the lniking residue (in each case of these embodiments, the linking residue being K). The [Linker] portion of each complex was that depicted in Example 4. The [Antibody] portion of each complex was h38C2: comprising SEQ ID NO:1 and SEQ ID NO:2. Table 4 shows also shows some half life data for certain [Peptide]-[Linker]-[Antibody] complexes. Results were obtained from both VEGF ELISA and from VEGF Reverse ELISA (results in parentheses).

Example 11

Synthesis of compounds of the invention of the formula: [Ang2-Peptide]-[Connector]-[VEGF-Peptide] is shown in FIGS. 8-10.

Example 12

Exemplary compounds of the invention of the formula: [Ang2-Peptide]-[Connector]-[VEGF-Peptide] are shown in Table 11.

Example 13

Table 12 shows exemplary compounds of the invention of the formula:

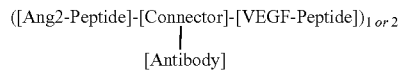

Example 14

Compounds of Example 13 were tested for VEGF binding (IC50), VEGF T½, Ang2 binding (IC50), and Ang2 T½. Testing methods were as described above. Results are shown in Table 8. Compounds of the invention exemplified in Example 13 contains a fixed ratio of [Ang-2-Peptide] and [VEGF-Peptide]. The circulating levels of Ang-2 is reported to be about 10 times higher than VEGF circulating levels in prostate (2.5 ng/ml Ang-2 and 0.2 ng/ml VEGF) and breast cancer (2 ng/ml Ang-2 and 0.3 ng/ml VEGF) patients (Ref. *European Journal of Clinical Investigation* (2003) 33, 883-890). It will be apparent that some compounds of the invention (e.g. see Example 14) demonstrate a great variety of binding IC50s and in vivo half lives of both Ang2 and VEGF relative to each other within the same molecule, and also relative to other molecules. Thus, for certain applications, it may be desirable to use a Compound whose binding affinity for Ang2 is between about 3 to about 15 times greater than its binding affinity for VEGF, so as to allow for the greater circulating amounts of the respective targets. Naturally, different therapeutic applications may require or permit or favour different Compounds of the invention.

For example, Compound 6053 showed a $K_D$ of 3E-10 for VEGF binding and a $K_D$ of 9E-11 for Ang-2 binding in Biacore assay. The higher affinity for Ang-2 binding may be advantageous as the plasma concentration Ang-2 has been reported as being higher in certain cancer patients. Compound 6053 shows similar VEGF inhibition IC50 (0.7 nM) and Ang-2 inhibition IC50 (0.6 nM). In addition, the stability (T½) in mice of both the [Ang2-Peptide] and the [VEGF-Peptide] components of Compound 6053 is very similar. A subsequent assay was conducted comparing Compound 2018, Compound 4043 and Compound 6053 (Table 8).

In Vivo Pharmacology

The anti-tumor activity of Compound 6053 was evaluated in human xenograft models. Xenografts were induced by subcutaneous (SC) implantation of tumor cells into 5-7 week old female nu/nu mice and allowed to establish to a volume of 200~400 mm prior to initiation of treatment. Once tumors were established, mice were randomized to treatment groups with identical tumor volumes (n=9-10/group), and Compound 6053 treatment was administered once weekly by intraperitoneal (IP) injection. In combination studies, additional anti-cancer agents were administered either weekly by IP injection or daily by oral gavage (PO), with treatments initiated concomitant with Compound 6053. Tumor volumes were measured once or twice weekly, using calipers, and body weights were measured weekly, during the treatment period. In some studies, all mice were killed by $CO_2$ asphyxiation and tumors were excised once tumor volume in the Vehicle-treated control group reached 2000 mm. In pseudo-survival studies, mice were killed by $CO_2$ asphyxiation and tumors were excised, weighed, and processed for further histological and/or immunochemical evaluation once the mean tumor volume of each treatment group exceeded 2000 $mm^3$.

Example 15

Single Agent Studies

An experiment conducted in the Colo205 (human colon adenocarcinoma) xenograft model is illustrated in FIG. 11. Weekly administration of Compound 6053 dose-dependently inhibited Colo205 tumor growth. At day 35, Compound 6053 at 3 mg/kg (IP, 1x/wk) resulted in a significant ~30% reduction in tumor growth, whereas at 10 or 30 mg/kg (IP, 1x/wk) a significant ~50% reduction in tumor growth was seen when compared with the Vehicle-treated controls. Ten or 30 mg/kg Compound 6053 treatment also led to sustained tumor inhibition compared with the control group. Compound 6053 treatment did not affect body weight gain (data not shown) and mice appeared to be in good health throughout the study.

At day 35, Vehicle-treated mice and half of each the Compound 6053-treated groups were killed, and tumors were excised and snap frozen. To assess the anti-angiogenic effect of Compound 6053, tumor microvessel density was assessed immunohistochemically on frozen sections of Colo205 colon adenocarcinoma xenograft tumors treated with Vehicle or Compound 6053. Tumors were stained with a mouse-specific monoclonal antibody to CD31, and immunoreactivity was quantified from 5 areas of 3 sections from each tumor. Tumor microvessel density was significantly reduced ~44% by Compound 6053 treatment (30 mg/kg, 1x/wk) in comparison with the Vehicle-treated group (FIG. 12) confirming the anti-angiogenic activity of the molecule.

In an independent Colo205 xenograft study, weekly administration of Compound 6053 again dose-dependently inhibited Colo205 tumor growth. At the 30 mg/kg weekly dose, Compound 6053 resulted in a significant ~70% reduction in tumor growth at day 28 compared with the Vehicle-treated controls (killed by $CO_2$ asphyxiation (FIG. 13). Excised tumors were sectioned and stained with Hematoxylin and Eosin (H&E), and viable tumor area was assessed using standard image analysis computation methods and software. The viable tumor area was determined for 4 sections from each tumor, and the mean value of these measurements was then multiplied by the tumor volume at study termination to yield an estimate of viable tumor volume for each tumor. Viable tumor volume data from the experiment in Colo205 colon adenocarcinoma xenografts are shown in FIG. 14. Viable tumor volume significantly decreased ~60% and ~76% in Compound 6053-treated mice at 10 mg/kg and 30 mg/kg dose, respectively, in comparison with the Vehicle-treated group.

To investigate whether Compound 6053 targets both Ang2 and VEGF in vivo, the effects of Compound 6053 on Ang2 expression and phosphorylated VEGFR2 (pVEGFR2) levels were assessed using immunofluorescense in Colo205 xenograft tumors treated with Vehicle or Compound 6053. Frozen sections of these tumors were stained with FITC-labeled anti-Ang2 monoclonal antibody, and Ang2 immunoreactivity was quantified from 3 images of 1 section from each tumor. Ang2 immunoreactivity was significantly reduced by ~70% in Compound 6053-treated groups (10 and 30 mg/kg) in comparison with the Vehicle-treated group (FIG. 15). Frozen sections of these tumors were also double-stained with FITC-labeled VEGFR antibody and a rodamine-labeled pVEGFR2 antibody, and the pVEGFR2 immunoreactivity was quantified from 3 images of 1 section from each tumor and expressed as a percentage of total VEGFR2 immunoreactivity (pVEGFR2/VEGFR2). pVEGFR2/VEGFR2 was significantly reduced by Compound 6053 treatment in a dose-dependent manner in comparison with the Vehicle-treated group, being ~43% and ~70% at 10 and 30 mg/kg, respectively (FIG. 16). These data demonstrate that Compound 6053 affects both Ang2 and VEGF pathways in Colo205 xenograft model.

The anti-tumor efficacy of Compound 6053 was also evaluated in an MDA-MB-435 breast carcinoma xenograft model and an A431 skin carcinoma xenograft model. Weekly administration of Compound 6053 (30 mg/kg IP) resulted in a significant 45% reduction (day 68) in tumor growth in MDA-MB-435 model (FIG. 17A), and a significant 54% reduction (day 35) in tumor growth of A431 model (FIG. 17B). Thus, Compound 6053 demonstrates significant anti-tumor efficacy in three different human xenograft tumor models.

Further single agent studies were conducted with Compounds 2018, 2036, 2049, 2071, 4043, and 6053, and are shown in FIGS. 23-28.

Example 16

Combination Studies

The anti-tumor efficacy of Compound 6053 was further evaluated in combination therapy studies conducted in the Colo205 xenograft model, comparing the anti-tumor efficacy of Compound 6053 (10 mg/kg IP, weekly) alone and in combination with 5-flurouracil (5-FU, FIG. 18), Irinotecan (FIG. 19), Taxotere (FIG. 20), Sunitinib (FIG. 21), and Axitinib (FIG. 22). Combination of Compound 6053 with these chemotherapy agents (5-FU, Irinotecan, Taxotere) or multiple tyrosine kinase inhibitors tested (Sunitinib, Axitinib) resulted in significantly greater inhibition of tumor growth rate than either of the monotherapy alone ($p<0.05$ by Two-way ANOVA with Bonferroni Multiple Comparison Test). In the Compound 6053+Taxotere combination study (FIG. 17), one tumor was an outlier (attained a tumor volume >2000 $mm^3$ at day 57, requiring euthanasia), and was therefore removed from the analysis. In conclusion, these data provide excellent preclinical rationale for broad application of Compound 6053 in combination with multiple anti-cancer therapeutics targeting both tumor and angiogenic mechanisms of action.

Summary of Preclinical Efficacy

Compound 6053 inhibited human Ang2 and human VEGF binding to their cognate receptors with sub-nanomolar potentcies, and demonstrated a prolonged and balanced pharmacokinetic profile across preclinical species. Compound 6053 was efficacious across multiple human xenograft tumor models, and provided additional benefit in combination with multiple standard therapeutic agents, including anti-angiogenics and anti-tumor cell therapeutics, as evidenced by delayed tumor growth and time-to-progression. Taken in total, these data suggest that the high potency of Compound 6053 for Ang2 and VEGF significantly impacts tumor growth and viability alone and in combination with standard chemotherapeutic agents.

Example 17

Anti-Angiogenic Activity in VEGF Induced Rabbit Eye Retinal Leakage Assay

The anti-angiogenic activity of compounds 6054, 6037, and 6044 was evaluated in the VEGF induced rabbit eye retinal leakage assay. This assay was performed in a 3 day or 7 day format. In a 3 day assay format the right eye of each rabbit (3 rabbits/group) was injected (IVT) with compound (1 mg/eye) or vehicle on day 0 followed by an injection (IVT) of VEGF (1 µg/eye) into the same eye on the next day or day 1. On day 3, fluorescein was injected by IV and angiography of the eye was taken. In a 7 day assay format compounds (1 mg/eye) were injected on day 0, VEGF (1 µg/eye) was injected on day 5 and fluorecein was injected by IV on day 7. In addition, binding and half-life were assayed as described above and are shown in Table 14. As a reference, the VEGF half-life of Compound 6037 is indicated as approximately 36 hours in Table 14, this figure being the VEGF half-life of the analogous molecule, Compound 2053 (see Table 4).

After the fluorescein angiography was taken each eye was a given grading of 0 to 4 based on the fluorescence intensity between retinal vessels compared to background. A grading of 0 indicates fluorescence intensity between retinal vessels equivalent to background not induced by VEGF and represents minimal or no retinal leakage. A grading of 4 indicates fluorescene intensity equivalent to VEGF induced retinal leakage background and indicates heavy retinal leakage of fluorescein. In the 3 day VEGF induced retinal leakage assay Compound 6037 showed efficacy with a retinal leakage grading of 1 at 1 mg/eye dose (FIG. 29). The 0.1 mg and 0.01 mg doses showed no efficacy.

Compounds 6037, 6044 and 6054 were evaluated in the 7 day rabbit leakage assay. Compound 6037 showed efficacy at 1 mg dose with a grading of 2 (FIG. 30).

The invention thus has been disclosed broadly and illustrated in reference to representative embodiments described above. Those skilled in the art will recognize that various modifications can be made to the present invention without departing from the spirit and scope thereof. All publications, patent applications, and issued patents, are herein incorporated by reference to the same extent as if each individual publication, patent application or issued patent were specifically and individually indicated to be incorporated by reference in its entirety. Definitions that are contained in text incorporated by reference are excluded to the extent that they contradict definitions in this disclosure.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. In particular, any aspect of the invention described in the claims, alone or in combination with one or more additional claims and/or aspects of the description, is to be understood as being combinable with other aspects of the invention set out elsewhere in the claims and/or description.

The use of the term "or" in the claims is used to mean "and/or" unless explicitly indicated to refer to alternatives only or the alternative are mutually exclusive, although the disclosure supports a definition that refers to only alternatives and "and/or."

As used herein the specification, "a" or "an" may mean one or more, unless clearly indicated otherwise. As used herein in the claim (s), when used in conjunction with the word "comprising," the words "a" or "an" may mean one or more than one. As used herein "another" may mean at least a second or more.

The words "comprises/comprising" and the words "having/including" when used herein with reference to the present invention are used to specify the presence of stated features, integers, steps or components but does not preclude the presence or addition of one or more other features, integers, steps, components or groups thereof.

TABLE 1

| | | | | | | | | | | | [VEGF-Peptide] Binding | | | | | | | | | | | | | |
|---|---|---|---|---|---|---|---|---|---|---|---|---|---|---|---|---|---|---|---|---|---|---|---|---|
| SEQ ID NO: | VEGF Binding IC$_{50}$ nM | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
| 34 | (188) | V | E | P | N | C | D | I | H | V | M | W | E | W | E | C | F | E | R | L | | | | |
| 35 | (325) | V | E | P | N | C | D | I | H | V | M | W | V | W | E | C | F | E | R | L | Y | G | G | W |
| 36 | (172) | V | E | P | N | C | D | I | H | V | M | W | V | W | V | C | F | E | R | L | F | R | E | A |
| 37 | (59) | V | E | P | N | C | D | I | H | V | M | W | V | W | V | C | F | E | R | L | F | K | E | A |
| 38 | 92.6 | V | E | P | N | C | D | I | H | V | M | W | V | W | V | C | F | E | R | L | M | K | | |
| 39 | (70) | V | E | P | N | C | D | I | H | V | M | W | V | W | E | C | F | E | R | L | Y | R | E | L |
| 40 | 78.3 | V | E | P | N | C | D | I | H | V | M | W | V | W | E | C | F | E | R | L | Y | G | I | F |
| 41 | 69.9 | V | E | P | N | C | D | I | H | V | M | W | V | W | E | C | F | E | R | L | Y | | | |
| 42 | 68.2 | V | E | P | N | C | D | I | H | V | M | W | V | W | E | C | F | E | R | L | Y | G | W | G |
| 43 | 66 | V | E | P | N | C | D | I | H | V | M | W | V | W | V | C | F | E | R | L | Y | G | G | G |
| 44 | 54.6 | V | E | P | N | C | D | I | H | V | M | W | V | W | E | C | F | E | R | L | Y | G | L | Y |
| 45 | 51 | V | E | P | N | C | D | I | H | V | M | W | V | W | E | C | F | E | R | L | S | G | G | G |
| 46 | 44.1 | V | E | P | N | C | D | I | H | V | M | W | V | W | E | C | F | E | R | L | M | R | L | T |
| 47 | 43.3 | V | E | P | N | C | D | I | H | V | M | W | V | W | E | C | F | E | R | L | Y | G | | |
| 48 | 42.4 | V | E | P | N | C | D | I | H | V | M | W | V | W | E | C | F | E | R | L | V | K | | |
| 49 | 34.5 | V | E | P | N | C | D | I | H | V | M | W | V | W | E | C | F | E | R | L | M | R | | |
| 50 | 34.4 | V | E | P | N | C | D | I | H | V | M | W | V | W | E | C | F | E | R | L | Y | G | I | L |
| 51 | 32.8 | V | E | P | N | C | D | I | H | V | M | W | V | W | E | C | F | E | R | L | YMe | G | L | T |
| 52 | 32.3 | V | E | P | N | C | D | I | H | V | M | W | V | W | E | C | F | E | R | L | Y | G | G | |
| 53 | 31.4 | V | E | P | N | C | D | I | H | V | M | W | V | W | E | C | F | E | R | L | F | K | E | A |
| 54 | 28.6 | V | E | P | N | C | D | I | H | V | M | W | V | W | E | C | F | E | R | L | Nle | K | | |
| 55 | 27 | V | E | P | N | C | D | I | H | V | M | W | V | W | E | C | F | E | R | dL | Y | G | L | T |
| 56 | 26.2 | V | E | P | N | C | D | I | H | V | M | W | V | W | E | C | F | E | R | L | Y | G | G | F |
| 57 | 25.4 | V | E | P | N | C | D | I | H | V | M | W | V | W | E | C | F | E | R | L | I | K | | |
| 58 | 25.1 | V | E | P | N | C | D | I | H | V | M | W | V | W | E | C | F | E | R | L | Y | K | | |
| 59 | 25 | V | E | P | N | C | D | I | H | V | M | W | V | W | E | C | F | E | R | L | M | G | L | T |
| 60 | 25 | V | E | P | N | C | D | I | H | V | M | W | V | W | E | C | F | E | R | L | dL | Kac | | |
| 61 | 23.6 | V | E | P | N | C | D | I | H | V | M | W | V | W | E | C | F | E | R | L | Y | G | G | G |
| 62 | 25 | V | E | P | N | C | D | I | H | V | M | W | V | W | E | C | F | E | R | L | M | K | | |
| 63 | 24 | V | E | P | N | C | D | I | H | V | M | W | V | W | E | C | F | E | R | L | M | R | E | L |
| 64 | 24 | V | E | P | N | C | D | I | H | V | M | W | V | W | E | C | F | E | R | L | | | | |
| 65 | 18 | V | E | P | N | C | D | I | H | V | M | W | V | W | E | C | F | E | R | L | M | K | E | L |
| 66 | 18.7 | V | E | P | N | C | D | I | H | V | M | W | V | W | E | C | F | E | R | L | Y | G | P | W |
| 67 | 10.1 | V | E | P | N | C | D | I | H | V | M | W | V | W | E | C | F | E | R | L | L | K | | |
| 68 | 10 | V | E | P | N | C | D | I | H | V | M | W | V | W | E | C | F | E | R | L | L | Kac | | |
| 69 | 9.4 | V | E | P | N | C | D | I | H | V | M | W | V | W | E | C | F | E | R | L | Y | G | L | T |
| 70 | 9.3 | V | E | P | N | C | D | I | H | V | M | W | V | W | E | C | F | E | R | L | Y | G | E | F |
| 71 | 5.4 | V | E | P | N | C | D | I | H | V | M | W | V | W | E | C | F | E | R | L | Y | G | L | S |
| 72 | 4.8 | V | E | P | N | C | D | I | H | V | M | W | V | W | E | C | F | E | R | L | Y | G | L | |

TABLE 1-continued

[VEGF-Peptide] Binding

| SEQ ID NO: | VEGF Binding IC$_{50}$ nM | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|
| 73 | 4.3 | V | E | P | N | C | D | I | H | V | M | W | V | W | E | C | F | E | R | L | Y | G | d-L | T |
| 74 | 4 | V | E | P | N | C | D | I | H | V | M | W | V | W | E | C | F | E | R | L | Y | G | V | Q |
| 75 | 3 | V | E | P | N | C | D | I | H | V | M | W | V | W | E | C | F | E | R | L | Y | G | L | E |
| 76 | 2.3 | V | E | P | N | C | D | I | H | V | M | W | V | W | E | C | F | E | R | L | Y | G | P | L |
| 77 | 1.8 | V | E | P | N | C | D | I | H | V | M | W | V | W | E | C | F | E | R | L | Y | G | P | F |

TABLE 2

[VEGF-Peptide] Binding

| SEQ ID NO # | VEGF Binding IC$_{50}$ nM | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|
| 34 | (188) | V | E | P | N | C | D | I | H | V | M | W | E | W | E | C | F | E | R | L | | | | |
| 108 | 362 | V | E | P | N | C | D | I | H | V | M | W | E | W | E | C | F | E | R | L | A | K | | |
| 109 | 325 | V | E | P | N | C | D | I | H | V | M | W | E | W | E | C | F | E | R | L | F | K | E | W |
| 110 | (188) | V | E | P | N | C | D | I | H | V | M | W | E | W | E | C | F | E | R | L | A | R | | |
| 111 | 265 | V | E | P | N | C | D | I | H | V | M | W | E | W | E | C | F | E | R | L | F | K | | |
| 112 | 115 | V | E | P | N | C | D | I | H | V | M | W | E | W | E | C | F | E | R | L | A | K | E | F |
| 113 | 137 | V | E | P | N | C | D | I | H | V | M | W | E | W | E | C | F | E | R | L | S | G | W | G |
| 114 | 127 | V | E | P | N | C | D | I | H | V | M | W | E | W | E | C | F | E | R | L | S | G | G | F |
| 115 | 122 | V | E | P | N | C | D | I | H | V | M | W | E | W | E | C | F | E | R | L | A | K | E | A |
| 116 | 69 | V | E | P | N | C | D | I | H | V | M | W | E | W | E | C | F | E | R | L | A | K | E | M |
| 117 | 73 | V | E | P | N | C | D | I | H | V | M | W | E | W | E | C | F | E | R | L | A | K | E | L |
| 118 | 79 | V | E | P | N | C | D | I | H | V | M | W | E | W | E | C | F | E | R | L | F | K | E | L |
| 119 | 51 | V | E | P | N | C | D | I | H | V | M | W | E | W | E | C | F | E | R | L | F | K | E | A |
| 120 | 32 | V | E | P | N | C | D | I | H | V | M | W | E | W | E | C | F | E | R | L | Y | G | G | G |
| 121 | 26 | V | E | P | N | C | D | I | H | V | M | W | E | W | E | C | F | E | R | L | M | K | | |

TABLE 3

[VEGF-Peptide]-Antibody Complex Binding, Half-life and AUC

| Compound | VEGF Binding IC$_{50}$ nM | Half life (Hrs) | AUC | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|---|---|---|
| 2077 | 147 | | | V | E | P | N | C | D | I | H | V | M | W | E | W | E | C | F | E | R | K |
| 2076 | 40.5 | | | V | E | P | N | C | D | I | H | V | M | W | E | W | E | C | F | E | K | L |
| 2073 | 5.6 | 83 | 7 × 10$^5$ | V | E | P | N | C | D | I | H | V | M | W | E | W | E | C | F | K | R | L |
| 2072 | >50,000 | | | V | E | P | N | C | D | I | H | V | M | W | E | W | E | C | K | E | R | L |
| 2075 | 3.2 | | | V | E | P | N | C | D | I | H | V | M | W | E | W | K | C | F | E | R | L |
| 2074 | 625 | | | V | E | P | N | C | D | I | H | V | M | W | E | K | E | C | F | E | R | L |
| 2071 | 1 | 43 | 2.8 × 10$^6$ | V | E | P | N | C | D | I | H | V | M | W | K | W | E | C | F | E | R | L |
| 2070 | 1372.5 | | | V | E | P | N | C | D | I | H | V | M | K | E | W | E | C | F | E | R | L |
| 2069 | 6 | 52 | 2.5 × 10$^6$ | V | E | P | N | C | D | I | H | V | K | W | E | W | E | C | F | E | R | L |
| 2068 | 9 . . . 3 | | | V | E | P | N | C | D | I | H | K | M | W | E | W | E | C | F | E | R | L |
| 2067 | 166.8 | | | V | E | P | N | C | D | I | K | V | M | W | E | W | E | C | F | E | R | L |
| 2066 | 423.5 | | | V | E | P | N | C | D | K | H | V | M | W | E | W | E | C | F | E | R | L |
| 2065 | 220 | | | V | E | P | N | C | K | I | H | V | M | W | E | W | E | C | F | E | R | L |
| 2064 | 4.5 | | | V | E | P | N | K | D | I | H | V | M | W | E | W | E | C | F | E | R | L |
| 2063 | 2.5 | | | V | E | P | K | C | D | I | H | V | M | W | E | W | E | C | F | E | R | L |
| 2062 | 2 | | | V | E | K | N | C | D | I | H | V | M | W | E | W | E | C | F | E | R | L |
| 2028 | 1.25 | 32 | 1.8 × 10$^6$ | K | E | P | N | C | D | I | H | V | M | W | E | W | E | C | F | E | R | L |

TABLE 4

[VEGF-Peptide]-Antibody Complex:
Binding & Half-life-Linking Residue and $X^{19}$-$X^{23}$ modifications

| Cmpd # | SEQ ID NO: | VEGF Binding IC$_{50}$ nM | Half Life(Hrs) VEGF [IgG] Coated | X1-X19 variations from SEQ ID NO: 64 *= linking residue | 19 | 20 | 21 | 22 | 23 |
|---|---|---|---|---|---|---|---|---|---|
| 2043 | 76 | | | K1* | L | Y | G | P | L |
| 2017 | 60 | 2.4 | 58 | K1* | L | D-leu | Kac | | |
| 2020 | 79 | 0.5 | 25 | K4* | L | R | D-leu | Kac | |
| 2081 | 60 | 0.8 | | K4* | L | D-leu | Kac | | |
| 2082 | 60 | 2 | | K9* | L | D-leu | Kac | | |
| 2019 | 97 | 2.8 | | K10* | L | | | | |
| 2006 | 136 | 2 | | K10*, (Kac)12 | L | Y | D-Ala | V | D-Gln |
| 2013 | 80 | 2 | | K10* | L | D-Tyr | G | D-Pro | L |
| 2025 | 60 | 1.65 | | K10* | L | D-leu | Kac | | |
| 2011 | 82 | 1.6 | | K10* | L | D-Tyr | G | D-leu | Kac |
| 2012 | 81 | 1.5 | | K10* | L | D-Tyr | G | D-Pro | D-leu |
| 2026 | 83 | 1.5 | | K10* | D-leu | Y | Aib | L | T |
| 2007 | 85 | 1.1 | | K10* | D-leu | Y | D-Ala | V | D-Gln |
| 2010 | 85 | 1 | | K10* | D-leu | Y | D-Ala | L | D-Thr |
| 2016 | 86 | 0.8 | | K10* | L | Cha | G | D-leu | T |
| 2027 | 87 | 0.7 | | K10* | L | Y | Aib | L | D-Thr |
| 2009 | 88 | 0.7 | | K10* | L | Y | Sar | D-leu | T |
| 2002 | 74 | 0.6 | | K10* | L | Y | G | V | Q |
| 2003 | 74 | 0.6 | | K10* | L | Y | G | V | Q |
| 2048 | 77 | 0.5 | [23] | K10* | L | Y | G | P | F |
| 2014 | 89 | 0.5 | | K10* | L | Y | G | D-Pro | L |
| 2008 | 90 | 0.5 | | K10* | L | Y | D-Ala | V | D-Gln |
| 2005 | 74 | 0.5 | | K10* | L | Y | G | V | Q |
| 2031 | 91 | 0.45 | [15] | K10* | L | Y | Aib | L | T |
| 2004 | 74 | 0.4 | | K10* | L | Y | G | V | Q |
| 2001 | 74 | 0.4 | | K10* | L | Y | G | V | Q |
| 2049 | 73 | 0.4 | [35] | K10* | L | Y | G | D-leu | T |
| 2018 | 78 | 0.4 | 109 | K10* | L | Y | D-Ala | D-leu | |
| 2053 | 75 | 0.35 | 36 | K10* | L | Y | G | L | E |
| 2046 | 76 | 0.2 | [19] | K10* | L | Y | G | P | L |
| 2022 | 84 | 0.7 | | K12* | D-leu | Y | D-Ala | V | D-Gln |
| 2083 | 128 | 0.6 | | (Nle)10, K12* | L | Y | Aib | L | T |
| 2028 | 83 | 0.5 | | K12* | D-leu | Y | Aib | L | T |
| 2084 | 129 | 0.5 | | L10, K12* | L | Y | Aib | L | T |
| 2036 | 60 | 0.45 | [134] | K12* | L | D-leu | Kac | | |
| 2024 | 74 | 0.4 | | K12* | L | Y | G | V | Q |
| 2085 | 130 | 0.4 | | V10, K12* | L | Y | Aib | L | T |
| 2023 | 90 | 0.3 | | K12* | L | Y | D-Ala | V | D-Gln |
| 2030 | 91 | 0.25 | [37] | K12* | L | Y | Aib | L | T |
| 2042 | 75 | 0.2 | | K12* | L | Y | G | L | E |
| 2029 | 87 | 0.1 | | K12* | L | Y | Aib | L | D-Thr |
| 2015 | 73 | 1.1 | | K14* | L | Y | G | D-leu | T |
| 2033 | 92 | 9.4 | | K17* | L | D-Tyr | G | D-leu | T |
| 2040 | 93 | 8.8 | | K17* | L | d-Tyr | G | L | T |
| 2037 | 94 | 8.1 | | K17* | L | D-Tyr | D | L | D-Thr |
| 2039 | 55 | 7.2 | | K17* | D-leu | Y | G | L | T |
| 2035 | 60 | 6.3 | | K17* | L | D-leu | Kac | | |
| 2038 | 95 | 4.2, 4.2 | | K17* | L | D-leu | Aib | | |
| 2047 | 77 | 2.6 | | K17* | L | Y | G | P | F |
| 2038 | 96 | 0.9 | | K17* | L | Y | G | D-leu | D-Thr |
| 2050 | 73 | 0.6 | [58] | K17* | L | Y | G | D-leu | T |
| 2045 | 76 | 0.6 | [50 | K17* | L | Y | G | P | L |
| 2052 | 75 | 0.4 | [38] | K17* | L | Y | G | L | E |
| 2079 | | | | K17* | L | Y | G | L | D-Thr |
| 2021 | | 7.2 | | K21* | L | R | K | K | |
| 2051 | 88 | 1.4 | 33 | K21* | L | Y | K | D-leu | T |
| 2041 | 77 | | | K21* | L | Y | K | P | F |
| 2080 | | | | K21* | L | Y | K | L | E |
| 2032 | 73* | 0.25 | [<10] | K23* | L | Y | G | D-leu | K |
| 2086 | 73* | | 8 | K23* | L | Y | G | D-leu | K |

TABLE 5

[Ang2-Peptide] and [Ang2-Peptide]-Antibody-Complex: Binding and Half-life

| Compound | Sequence showing position of linker (0P or 4P) and parent SEQ ID NO | Ang-2 T IC50 nM | Ang-2 P IC50 nM | T$^{1}/_{2}$ (Sc) hours |
|---|---|---|---|---|
| 4021 | QKY QPL DEL DKT LYD QFM LQQ G (SEQ ID NO: 137) | 25.81 | | |
| 4022 | Q(Kac)Y QPL DEL DKT LYD QFM LQQ G (SEQ ID NO: 138) | 41.9 | | |
| 4023 | QNY QPL DEL DKT LYD QFM LQQ G (SEQ ID NO: 139) | 27.83 | | |
| 4024 | Q(Kac)Y QPL DEL DK(4P)T LYD QFM LQQ G (SEQ ID NO: 138) | 206.7 | 17.4 | 104 (27) |
| 4025 | QNY QPL DEL DK(4P)T LYD QFM LQQ G (SEQ ID NO: 139) | 300.3 | 40.456 | |
| 4026 | (0P)QKY QPL DEL DKT LYD QFM LQQ G (SEQ ID NO: 137) | 32.3 | 58.77 | (7) |
| 4027 | QKY QPL DEL DK(0P)T LYD QFM LQQ G (SEQ ID NO: 137) | 29 | 55.876 | 117 (32) |
| 4028 | QNY QPL DEL DK(0P)T LYD QFM LQQ G (SEQ ID NO: 139) | 175 | 28.63 | 100 (57) |
| 4029 | Q(Kac)Y QPL DEL DK(0P)T LYD QFM LQQ G (SEQ ID NO: 138) | 83.3 | 13.195 | 77 (33) |
| 4030 | Q(Kac)Y QPL DEK(0P) D(Kac)T LYD QFM LQQ G (SEQ ID NO: 140) | 279 | 65.4 | (17) |
| 4031 | Q(Kac)Y QPL DEL DET K(0P)YD QFM LQQ G (SEQ ID NO: 141) | >5K | >1000 | |
| 4032 | Q(Kac)Y QPL DEL D(Kac)T K(0P)YD QFM LQQ G (SEQ ID NO: 142) | >5K | >1000 | |
| 4033 | Q(Kac)Y QPL DEK(0P) DET LYD QFM LQQ G (SEQ ID NO: 143) | 369.6 | 88.81 | |
| 4034 | Q(Kac)Y QD(HP)L DEL DK(0P) T LYD QFM LQQ G (SEQ ID NO: 144) | 224.5 | 19.75 | (31) |
| 4035 | Q(Kac)Y Q(HP)L DEL DK(0P)T LYD QFM LQQ G (SEQ ID NO: 145) | 121 | 16.68 | |
| 4036 | Q(Kac)Y QPL DEL DK(0P)T IYD QFM LQQ G (SEQ ID NO: 146) | 2410 | 152.9 | |
| 4037 | Q(Kac)Y QPL DEI DK(0P)T LYD QFM LQQ G (SEQ ID NO: 147) | 1273 | 80.05 | |
| 4038 | Q(Kac)Y QPL DEL DK(0P)T(HChA)YD QFM LQQ G (SEQ ID NO: 148) | >5K | 702.6 | |
| 4039 | Q(Kac)Y QPL DEL DK(0P)T(HF)YD QFM LQQ G (SEQ ID NO: 149) | 4894 | 258.1 | |
| 4040 | Q(Kac)Y QPL DEL DK(0P)T(ThA)YD QFM LQQ G (SEQ ID NO: 150) | >5K | 357.8 | |
| 4041 | Q(Kac)Y QPL DEL DK(0P)T(Nva)YD QFM LQQ G (SEQ ID NO: 151) | 1339 | 23.32 | (36) |
| 4042 | Q(Kac)Y QPL DEL DK(0P)T(HL)YD QFM LQQ G (SEQ ID NO: 152) | 1342 | 38.15 | (42) |
| 4043 | Q(Kac)Y QPL DE(Kac) DK(0P)T LYD QFM LQQ G (SEQ ID NO: 153) | 240 | 14.515 | 110 (38) |
| 4044 | Q(Kac)Y QPL DEL DK(0P)T LFD QFM LQQ G (SEQ ID NO: 154) | 36.9 | 11.68 | 58 (31) |
| 4045 | Q(Kac)Y Q(HP)L DE(ThA) DK(0P)T L(NO2)FD QFM LQQ G (SEQ ID NO: 155) | 24.7 | 12.7 | 68 (30) |
| 4046 | Q(Kac)Y QHPL DE(ThA) DK(0P)T L(BPA)D QFM LQQ G (SEQ ID NO: 156) | 82.7 | 25.21 | (32) |
| 4047 | Q(Kac)Y Q(HP)L DE(ThA) DK(0P)T L(CO2H)FD QFM LQQ G (SEQ ID NO: 157) | 43.3 | 20.65 | (47) |
| 4048 | Q(Kac)Y QPL DE(Kac) DK(0P)T L(NO2)FD QFM LQQ G (SEQ ID NO: 158) | 82.4 | 15.75 | 64 (35) |
| 4049 | (DCB)Q(Kac)Y QPL DEL DK(0P)T LYD QFMLQQ G (SEQ ID NO: 159) | 28.4 | 12.45 | (24) |
| 4050 | (DFB)Q(Kac)Y QPL DEL DK(0P)T LYD QFMLQQ G (SEQ ID NO: 160) | 33 | 13.56 | (23) |
| 4051 | (PyC)Q(Kac)Y QPL DEL DK(0P)T LYD QFMLQQ G (SEQ ID NO: 161) | 14.3 | 19.38 | (18) |
| 4052 | (Amido 2-PEG)Q(Kac)Y QPL DEL DK(0P)T LYDQFMLQQ G (SEQ ID NO: 162) | 133.8 | 18.14 | (31) |
| 4053 | Q(ClBnCarbamate)KY QPL DEL DK(0P)T LYD QFM LQQ G (SEQ ID NO: 163) | 146.9 | | |
| 4054 | Q(Kac)Y QPL DEL D(Dab)(0P)T LYD QFM LQQ G (SEQ ID NO: 164) | 291.7 | 22 | |
| 4055 | Q(Kac)Y QPL DEL D(Dap)(0P)T LYD QFM LQQ G (SEQ ID NO: 165) | 598 | 34.54 | |

TABLE 5-continued

[Ang2-Peptide] and [Ang2-Peptide]-Antibody-Complex: Binding and Half-life

| Compound | Sequence showing position of linker (0P or 4P) and parent SEQ ID NO | Ang-2 T IC50 nM | Ang-2 P IC50 nM | T½ (Sc) hours |
|---|---|---|---|---|
| 4056 | QNY QPL DEL DK(0P)T L(BPA)D QFM LQQ G (SEQ ID NO: 166) | 92.2 | 17.2 | (29) |
| 4057 | QNY QPL DEL DK(0P)T L(CF)D QFM LQQ G (SEQ ID NO: 167) | 110 | 15.3 | (11) |
| 4058 | QNY QPL DEL DK(0P)T LYD QFM LQQ G (SEQ ID NO: 139) | 36.9 | 12.9 | (24) |
| 4059 | QRY QPL DEL DK(0P)T LYD QFM LQQ G (SEQ ID NO: 168) | 176.8 | 16.1 | |
| 4060 | QHY QPL DEL DK(0P)T LYD QFM LQQ G (SEQ ID NO: 169) | 214 | 14.4 | |
| 4061 | Q(Nick)Y QPL DEL DK(0P)T LYD QFM LQQ G (SEQ ID NO: 170) | 83.9 | | |
| 4062 | Q(Kac)Y QPL DE(Kac) DK(0P)T L(CF)D QFM LQQ G (SEQ ID NO: 171) | 499 | 41.3 | |
| 4063 | Q(Kac)Y QPL DE(Kac) DK(0P)T LFD QFM LQQ G (SEQ ID NO: 153) | | | |

TABLE 6

[Ang2-Peptide]-Antibody-Complex: Binding and Half-life

| Compound No. | Sequence | Ang-2 P IC50 nM | Ang-2 T½ Hours |
|---|---|---|---|
| 4021 | QKY QPL DEL DKT LYD QFM LQQ G (SEQ ID NO: 137) | 36.39 | |
| 4022 | Q(Kac)Y QPL DEL DKT LYD QFM LQQ G (SEQ ID NO: 138) | 14.41 | |
| 4027 | QKY QPL DEL DK(0P)T LYD QFM LQQ G (SEQ ID NO: 137) | 0.59 | |
| 4028 | QNY QPL DEL DK(0P)T LYD QFM LQQ G (SEQ ID NO: 139) | 0.15 | |
| 4029 | Q(Kac)Y QPL DEL DK(0P)T LYD QFM LQQ G (SEQ ID NO: 138) | 0.41 | |
| 4030 | Q(Kac)Y QPL DEK(0P) D(Kac)T LYD QFM LQQ G (SEQ ID NO: 140) | 1.27 | 72 |
| 4032 | Q(Kac)Y QPL DEL D(Kac)T K(0P)YD QFM LQQ G (SEQ ID NO: 142) | >100 | |
| 4043 | Q(Kac)Y QPL DE(Kac) DK(0P)T LYD QFM LQQ G (SEQ ID NO: 153) | 0.92 | |
| 4044 | Q(Kac)Y QPL DEL DK(0P)T LFD QFM LQQ G (SEQ ID NO: 154) | 0.41 | |
| 4048 | Q(Kac)Y QPL DE(Kac) DK(0P)T L(NO2F)D QFM LQQ G (SEQ ID NO: 158) | 0.33 | |
| 4054 | Q(Kac)Y QPL DEL D(Dab)(0P)T LYD QFM LQQ G (SEQ ID NO: 164) | 0.09 | |
| 4055 | Q(Kac)Y QPL DEL D(Dap)(0P)T LYD QFM LQQ G (SEQ ID NO: 165) | 1.61 | |
| 4064 | K(0P)(Kac)Y QPL DEL D(Kac)T LYD QFM LQQ G (SEQ ID NO: 172) | 1.92 | 24 |
| 4065 | QK(0P)Y QPL DEL D(Kac)T LYD QFM LQQ G (SEQ ID NO: 173) | 0.31 | 12 |
| 4066 | Q(Kac)K(0P) QPL DEL D(Kac)T LYD QFM LQQ G (SEQ ID NO: 174) | 0.23 | 17 |
| 4067 | Q(Kac)Y K(0P)PL DEL D(Kac)T LYD QFM LQQ G (SEQ ID NO: 175) | N.I. | |
| 4068 | Q(Kac)Y QK(0P)L DEL D(Kac)T LYD QFM LQQ G (SEQ ID NO: 176) | 44.21 | |
| 4069 | Q(Kac)Y QPK(0P) DEL D(Kac)T LYD QFM LQQ G (SEQ ID NO: 177) | N.I | |
| 4070 | Q(Kac)Y QPL K(0P)EL D(Kac)T LYD QFM LQQ G (SEQ ID NO: 178) | N.I. | |
| 4071 | Q(Kac)Y QPL DK(0P)L D(Kac)T LYD QFM LQQ G (SEQ ID NO: 179) | 0.288 | 35 |
| 4072 | Q(Kac)Y QPL DEL K(0P)(Kac)T LYD QFM LQQ G (SEQ ID NO: 180) | N.I | |
| 4073 | Q(Kac)Y QPL DEL D(Kac)K(0P) LYD QFM LQQ G (SEQ ID NO: 181) | 0.11 | 56 |
| 4074 | Q(Kac)Y QPL DEL D(Kac)T LK(0P)D QFM LQQ G (SEQ ID NO: 182) | 32.82 | |

TABLE 6-continued

[Anq2-Peptide]-Antibody-Complex: Binding and Half-life

| Compound No. | Sequence | Ang-2 P IC50 nM | Ang-2 T½ Hours |
|---|---|---|---|
| 4075 | Q(Kac)Y QPL DEL D(Kac)T LYK(0P) QFM LQQ G (SEQ ID NO: 183) | 0.19 | 65 |
| 4076 | Q(Kac)Y QPL DEL D(Kac)T LYD K(0P)FM LQQ G (SEQ ID NO: 184) | 0.27 | 94 |
| 4077 | Q(Kac)Y QPL DEL D(Kac)T LYD QK(0P)M LQQ G (SEQ ID NO: 185) | 19.53 | |
| 4078 | Q(Kac)Y QPL DEL D(Kac)T LYD QFK(0P) LQQ G (SEQ ID NO: 186) | 0.74 | 72 |
| 4079 | Q(Kac)Y QPL DEL D(Kac)T LYD QFM K(0P)QQ G (SEQ ID NO: 187) | 0.077 | 65 |
| 4080 | Q(Kac)Y QPL DEL D(Kac)T LYD QFM LK(0P)Q G (SEQ ID NO: 188) | 0.11 | 35 |
| 4081 | Q(Kac)Y QPL DEL D(Kac)T LYD QFM LQK(0P) G (SEQ ID NO: 189) | 0.27 | 27 |
| 4082 | Q(Kac)Y QPL DEL D(Kac)T LYD QFM LQQ K(0P) (SEQ ID NO: 190) | 0.21 | 20 |

TABLE 7

| Compound | Sequence | % TC 10 mg/kg 1x/wk | % TC 3 mg/kg 1x/wk | % TC 1 mg/kg 1x/wk |
|---|---|---|---|---|
| 4027 | QKY QPL DEL DK(0P)T LYD QFM LQQ G (SEQ ID NO: 137) | 52 | | |
| 4028 | QNY QPL DEL DK(0P)T LYD QFM LQQ G (SEQ ID NO: 139) | 38 | 34 | |
| 4029 | Q(Kac)Y QPL DEL DK(0P)T LYD QFM LQQ G (SEQ ID NO: 138) | 60 | 28 | 9 |
| 4043 | Q(Kac)Y QPL DE(Kac) DK(0P)T LYD QFM LQQ G (SEQ ID NO: 153) | 53 | 27 | 34 |
| 4044 | Q(Kac)Y QPL DEL DK(0P)T LFD QFM LQQ G (SEQ ID NO: 154) | 40 | 22 | |
| 4045 | Q(Kac)Y Q(HP)L DE(ThA) DK(0P)T L(NO2)FD QFM LQQ G (SEQ ID NO: 155) | 47 | | |
| 4048 | Q(Kac)Y QPL DE(Kac) DK(0P)T L(NO2)FD QFM LQQ G (SEQ ID NO: 158) | 45 | | |
| 4058 | QNY QPL DEL DK(0P)T LYD QFM LQQ G (SEQ ID NO: 39) | 51 | | |
| 4092 | PL DEL DK(0P)T LYD QFM LQQ G (SEQ ID NO: 191) | 60 | | |

TABLE 8

| Compound No. | VEGF Part | | | | Ang-2 Part | | | |
|---|---|---|---|---|---|---|---|---|
| | Tethering Spot | PEG Length from Branch | VEGF Binding IC50 | βHalf Life (hrs) | Tethering Spot | PEG Length From Branch | Ang-2 Binding IC50 | βHalf Life (hrs) |
| 6001 | 1 | 4 | 4 | | 1 | 0 | | |
| 6002 | 1 | 2 | | | 1 | 0 | | |
| 6003 | 1 | 2 | | | 1 | 0 | | |
| 6004 | 1 | N/A | | | C-Ter | N/A | 0.5 | |
| 6005 | 1 | N/A | | | C-Ter | N/A | 1 | |
| 6006 | 10 | 0 | 71 | | 11 | 2 | 0.2 | |
| 6007 | 10 | 0 | 138 | | 11 | 0 | 0.3 | |
| 6008 | 10 | 2 | 79 | | 11 | 0 | 0.4 | |
| 6009 | 10 | 2 | 39 | | 11 | 2 | 0.2 | |
| 6010 | 10 | 0 | 344 | | 11 | 0 | | |
| 6011 | 12 | 0 | 84 | | 11 | 2 | 0.2 | |
| 6012 | 10 | 0 | 278 | | 11 | 0 | 0.6 | |
| 6013 | 17 | 0 | 2 | 67, 91 | 11 | 2 | 0.3 | 40, 34 |
| 6014 | 10 | 0 | 240 | | 11 | 2 | 0.1 | |
| 6015 | 1 | 0 | 2.8 | | 1 | 0 | 0.1 | |
| 6016 | 1 | 0 | 6, 8 | | 1 | 0 | 0.3 | |

TABLE 8-continued

| Compound No. | VEGF Part | | | | Ang-2 Part | | | |
|---|---|---|---|---|---|---|---|---|
| | Tethering Spot | PEG Length from Branch | VEGF Binding IC50 | βHalf Life (hrs) | Tethering Spot | PEG Length From Branch | Ang-2 Binding IC50 | βHalf Life (hrs) |
| 6017 | 10 | 4 | 26 | | 11 | 4 | 0.2 | |
| 6018 | 12 | 4 | 24 | | 11 | 4 | 0.2 | |
| 6019 | 17 | 4 | 1.3 | 68 | 11 | 4 | 0.13 | |
| 6020 | 1 | 0 | 356 | | 11 | 0 | 0.8 | |
| 6021 | 10 | 0 | 75 | | 11 | 4 | 0.3 | |
| 6022 | 12 | 4 | 120, 140 | | 18 | 4 | 0.5 | |
| 6023 | 10 | 4 | 60 | | 18 | 4 | 0.3 | |
| 6024 | 10 | 4 | 5584 | | 11 | 4 | 0.1 | |
| 6025 | 10 | 4 | 210, 227 | | 11 | 4 | 0.1 | |
| 6026 | 1 | 4 | 553, 1129 | | 11 | 4 | 0.2 | |
| 6027 | 17 | 0 | 2 | 65 | 11 | 0 | 0.3 | 32 |
| 6028 | 17 | 4 | 4 | | 11 | 4 | 0.2. 0.3 | |
| 6031 | 17 | 0 | | | 11 | 4 | | |
| 6032 | 1 | 0 | | | 11 | 0 | | |
| 6033 | 1 | 0 | | | 11 | 4 | | |
| 6034 | 17 | 0 | 0.6 | 42 | 11 | 0 | 1.3 | 39 |
| 6035 | 1 | 4 | | | 11 | 4 | | |
| 6036 | 17 | 4 | 0.5 | 27 | 11 | 4 | 0.4 | 41 |
| 6037 | 10 | 4 | 0.6 | | 11 | 4 | 1.6 | |
| 6038 | 17 | 0 | 0.5 | | 11 | 4 | 0.8 | |
| 6039 | 17 | 4 | 0.6 | | 11 | 4 | 1.1 | |
| 6040 | 17 | 0 | 0.4 | | 11 | 0 | 2.5 | |
| 6041 | 12 | 4 | 2.2 | | 11 | 4 | 0.8 | |
| 6042 | 12 | 4 | 3.3 | 56 | 11 | 4 | 0.8 | 49 |
| 6043 | 10 | 4 | 0.6 | 36 | 11 | 4 | 0.4 | 72 |
| 6044 | 10 | 4 | 0.7 | 43 | 11 | 4 | 0.9 | 82 |
| 6045 | 10 | 0 | 1.8 | 52 | 11 | 0 | 1.2 | 47 |
| 6046 | 12 | 0 | 3.3 | | 11 | 0 | 1 | |
| 6047 | 10 | 4 | 2.5 | | 11 | 4 | 0.5 | |
| 6048 | 12 | 4 | 4.4 | | 11 | 4 | 0.7 | |
| 6049 | 12 | 4 | 45 | | 11 | 0 | 0.6 | |
| 6050 | 12 | 4 | 33 | | 11 | 4 | 0.6 | |
| 6051 | 12 | 4 | Not Active | | 11 | 4 | 0.7 | |
| 6052 | 10 | 4 | 18 | | 11 | 4 | 0.5 | |
| 6053 | 10 | 4 | 0.7 | 68 | 11 | 4 | 0.6 | 68 |
| 6054 | 1 | 4 | 0.3 | 18 | 11 | 4 | 0.4 | |
| 6055 | 1 | 4 | | | 11 | 4 | | |
| 6056 | 12 | 4 | 94, 64 | | 18 | 4 | 0.8 | |
| 6057 | 12 | 0 | 32, 44 | | 11 | 12 | 0.7 | |
| 6058 | 12 | 12 | 18 | | 11 | 0 | 0.7 | |
| 6059 | 12 | | 15 | | 11 | | 0.6 | |
| 6060 | 10 | 4 | 1.2, 1.0 | | 11 | 0 | | |
| 6061 | 10 | 0 | 2.9 | | 11 | 0 | | |
| 6062 | 10 | 0 | 2.3, 2.2 | | 11 | 4 | | |
| 6063 | 10 | 4 | | | 11 | 4 | | |
| 6064 | 10 | 4 | | | 11 | 4 | | |
| 6065 | 12 | 4 | 36 | | 1 | 0 | | |
| 6066 | 4 | 0 | 3.1, 7.4 | | 11 | 4 | | |
| 6067 | 1 | 0 | 0.6, 0.4 | | 11 | 4 | | |
| 6068 | 9 | 4 | 22, 12 | | 11 | 4 | | |
| 6070 | 10 | 4 | 1 | 52 (rat) | 11 | 4 | 0.07 | 71 (rat) |
| 6071 | 10 | 4 | 0.8 | 66 (rat) | 11 | 4 | 0.05 | 61 (rat) |
| 6072 | 10 | 4 | 1.4 | 41 (rat) | 11 | 4 | 0.1 | 74 (rat) |
| 6073 | 10 | 4 | 0.6 | 80 (rat) | 11 | 4 | 0.08 | 91 (rat) |

TABLE 9
[VEGF-Peptide]-Linker Compounds
| SEQ ID | Compound # | Structure |
|---|---|---|
| 74 | 1001 | 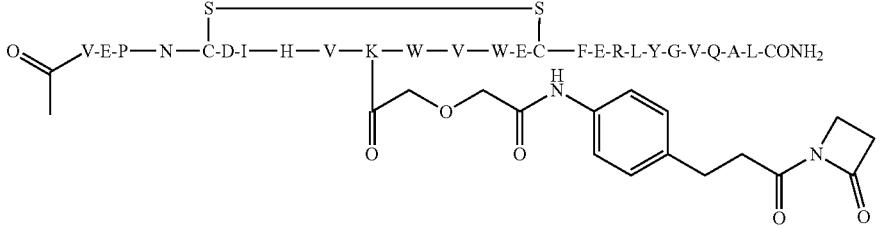 |
| 74 | 1002 | 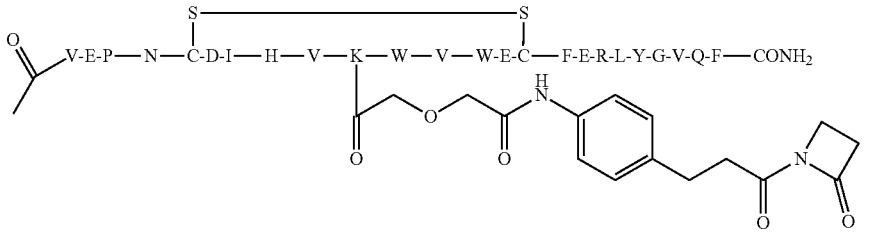 |
| 74 | 1003 | 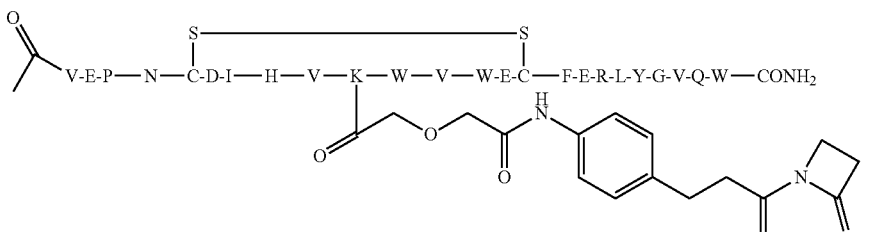 |
| 74 | 1004 | 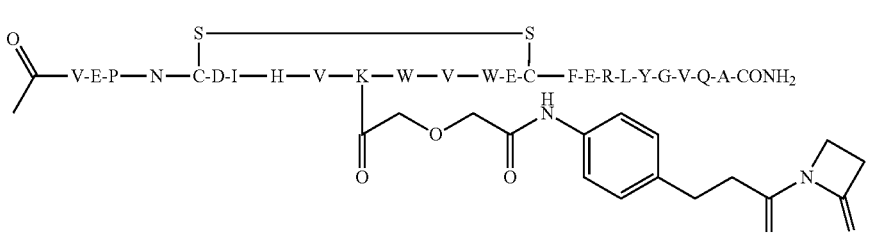 |
| 74 | 1005 | 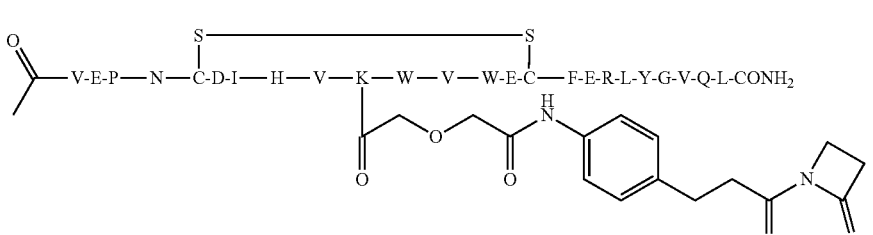 |
| 90 | 1006 | 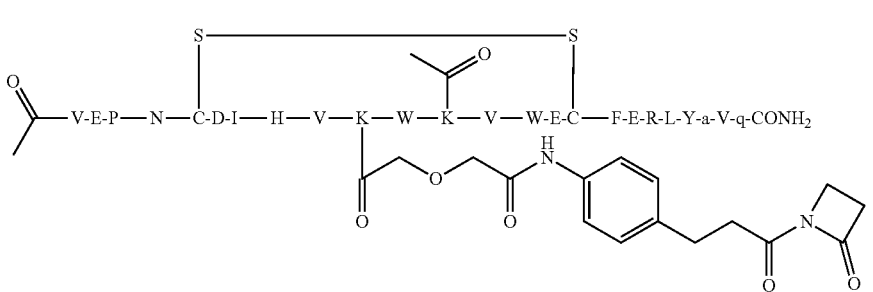 |

TABLE 9-continued
[VEGF-Peptide]-Linker Compounds
| SEQ ID | Compound # | Structure |
|---|---|---|
| 84 | 1007 | 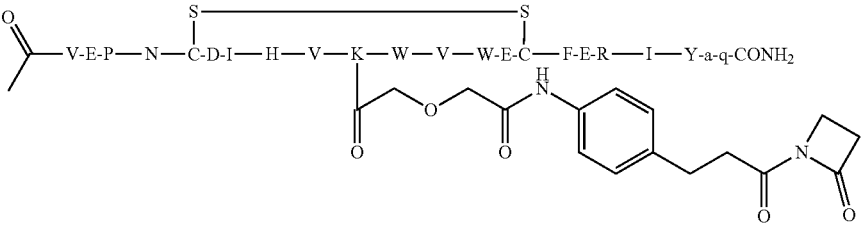 |
| 90 | 1008 | 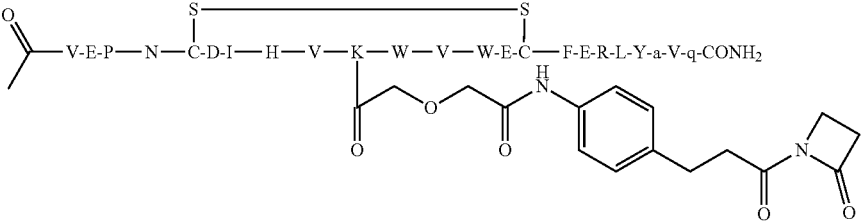 |
| 88 | 1009 | 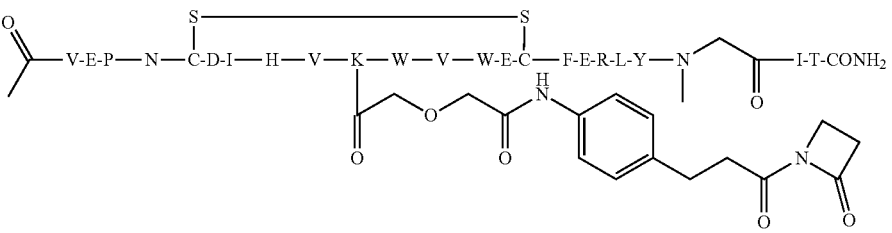 |
| 85 | 1010 | 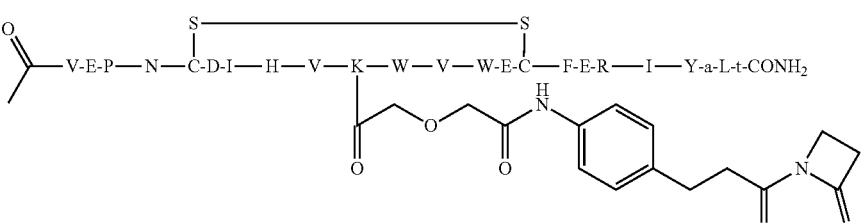 |
| 82 | 1011 | 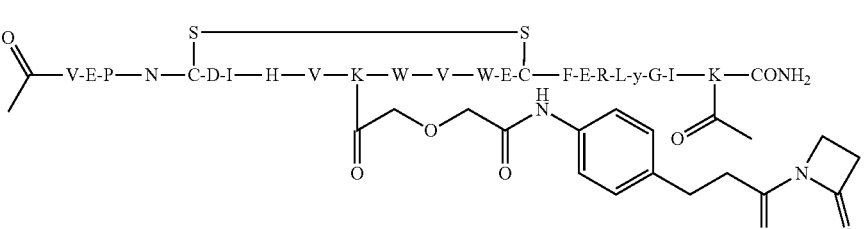 |
| 81 | 1012 | 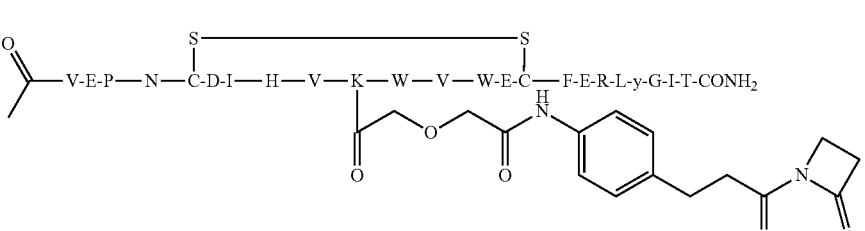 |

TABLE 9-continued
[VEGF-Peptide]-Linker Compounds
| SEQ ID | Compound # | Structure |
|---|---|---|
| 80 | 1013 | 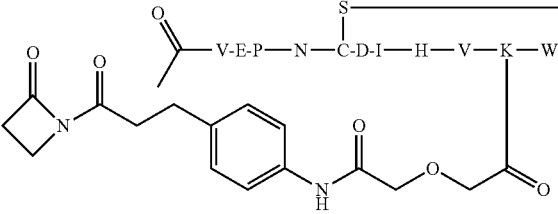 |
| 89 | 1014 | 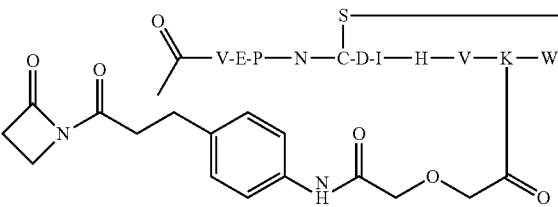 |
| 73 | 1015 | 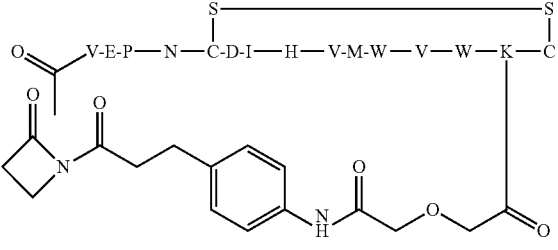 |
| 86 | 1016 | 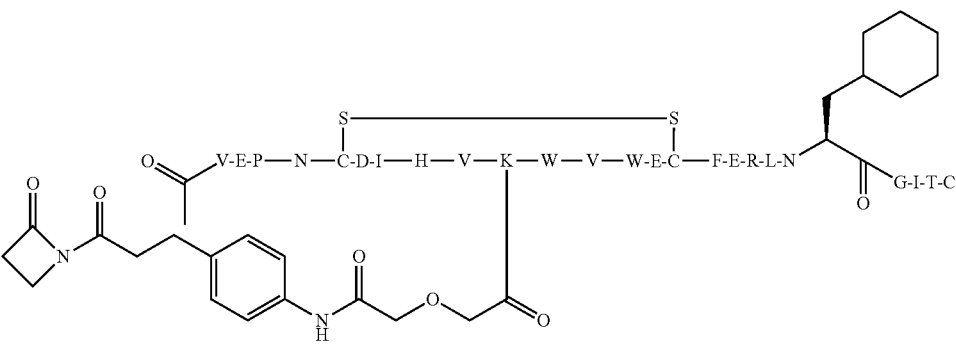 |
| 60 | 1017 | 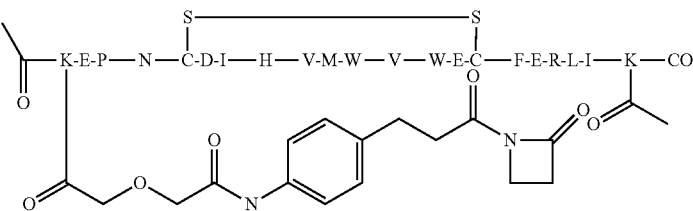 |
| 78 | 1018 | 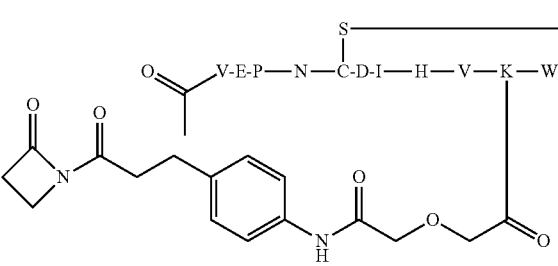 |

TABLE 9-continued
[VEGF-Peptide]-Linker Compounds
| SEQ ID | Compound # | Structure |
|---|---|---|
| 97 | 1019 | 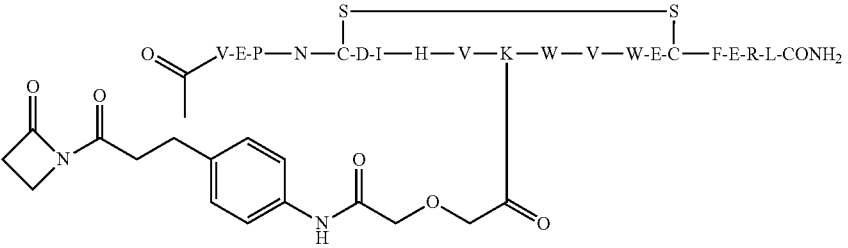 |
| 79 | 1020 | 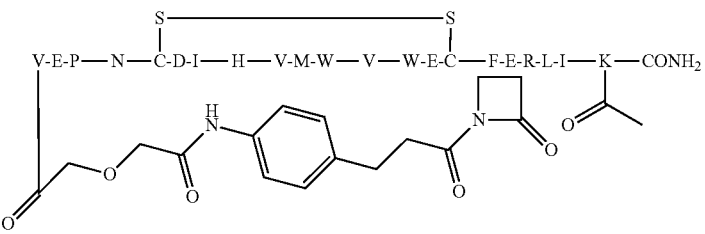 |
| 196 | 1021 | 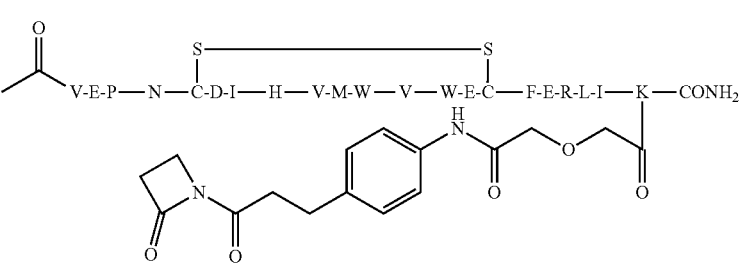 |
| 84 | 1022 | 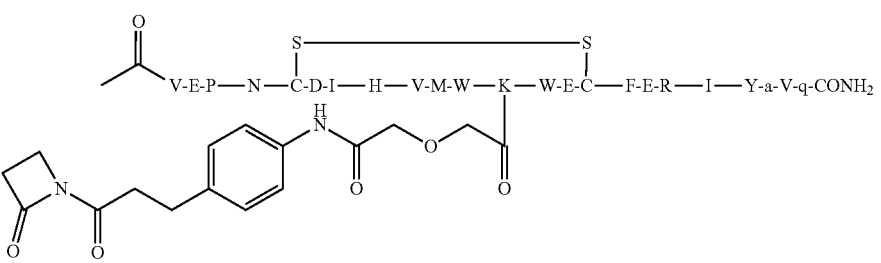 |
| 90 | 1023 | 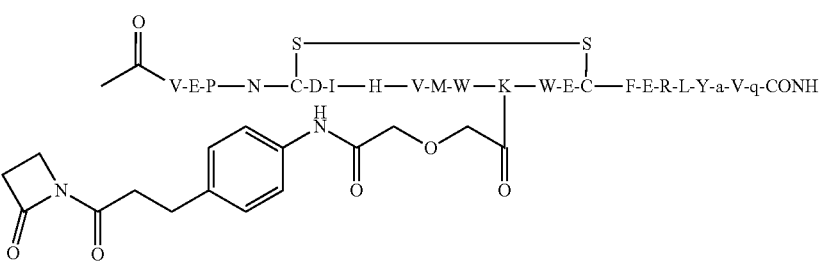 |
| 74 | 1024 | 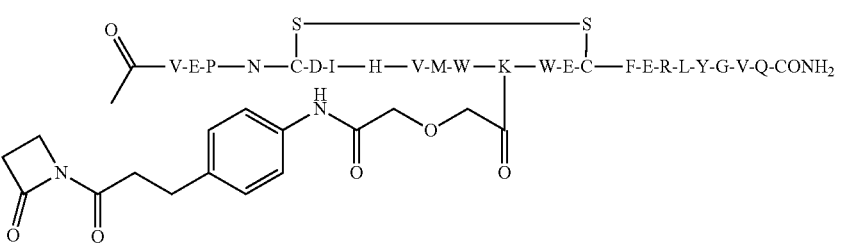 |

TABLE 9-continued
[VEGF-Peptide]-Linker Compounds
| SEQ ID | Compound # | Structure |
|---|---|---|
| 60 | 1025 | 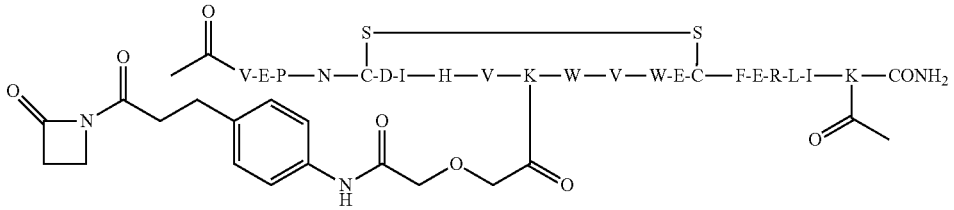 |
| 83 | 1026 | 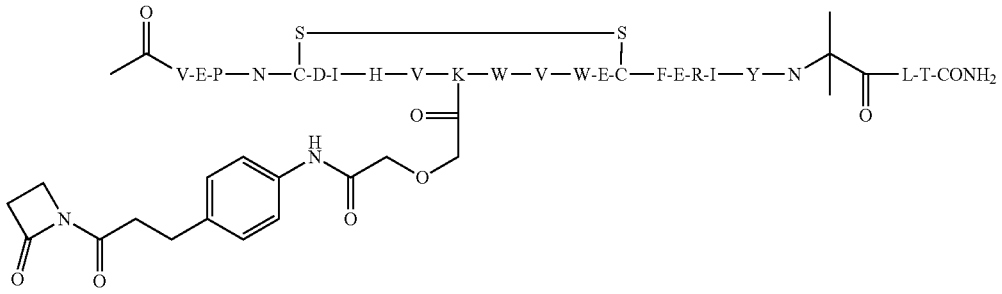 |
| 87 | 1027 | 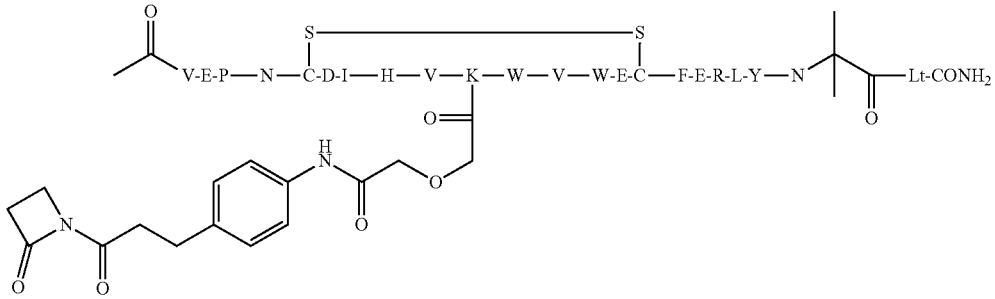 |
| 83 | 1028 | 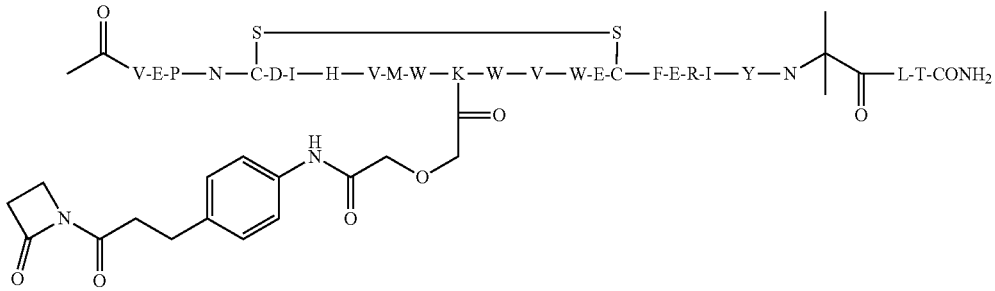 |
| 87 | 1029 | 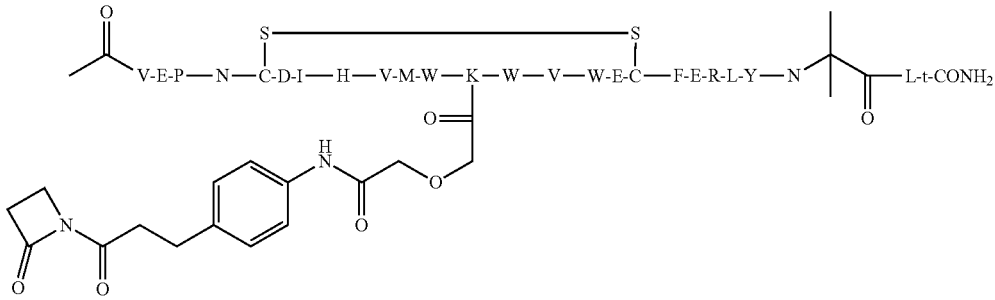 |

TABLE 9-continued
[VEGF-Peptide]-Linker Compounds
| SEQ ID | Compound # | Structure |
|---|---|---|
| 91 | 1030 | 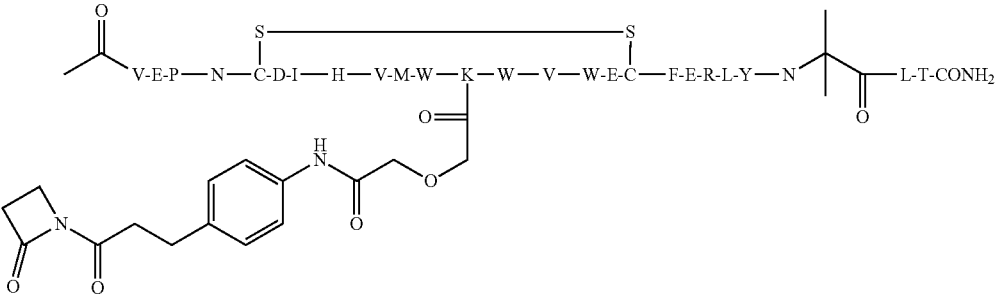 |
| 91 | 1031 | 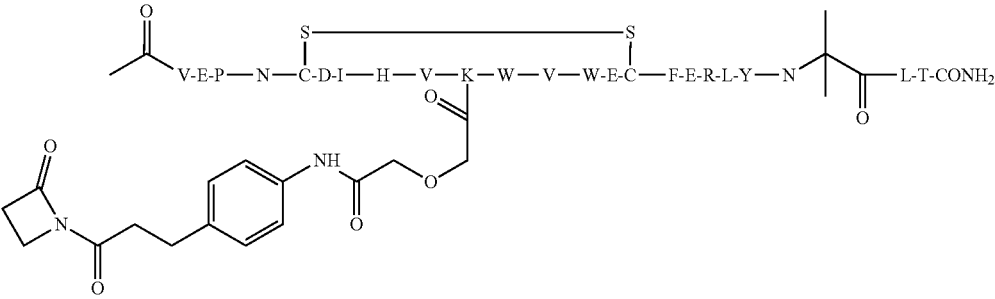 |
| 197 | 1032 | 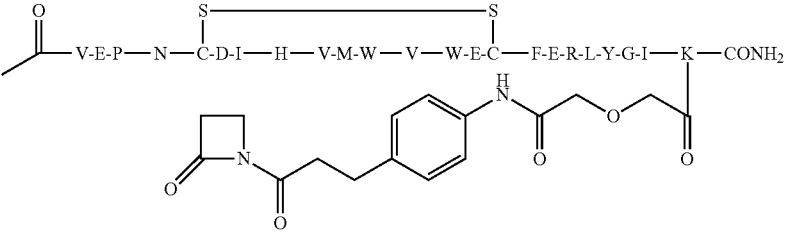 |
| 92 | 1033 | 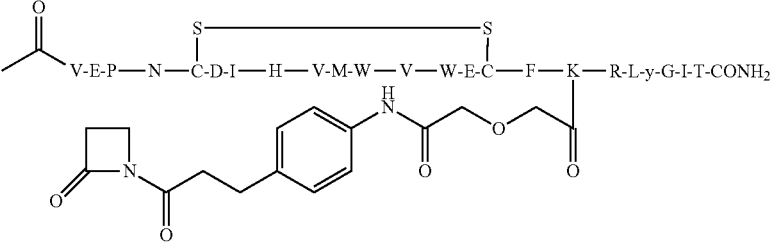 |
| 95 | 1034 | 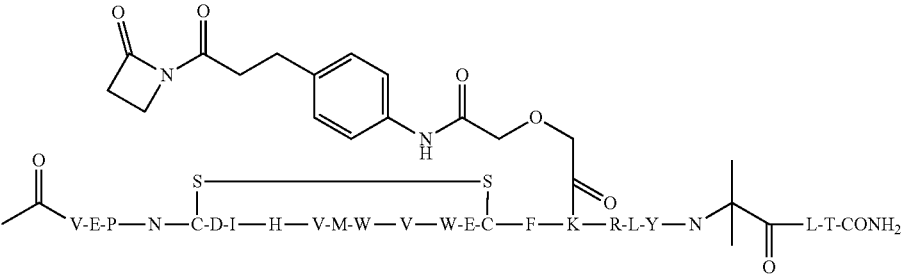 |

TABLE 9-continued

[VEGF-Peptide]-Linker Compounds

| SEQ ID | Compound # | Structure |
|---|---|---|
| 60 | 1035 | Ac-V-E-P-N-C-D-I-H-V-M-W-V-W-E-C-F-K-R-L-I-K-CONH₂, disulfide between the two C residues; N side chain linked to azetidinone-CO-CH₂CH₂-(p-C₆H₄)-NH-CO-CH₂-O-CH₂-CO-; K (between I and CONH₂) side chain acetylated |
| 60 | 1036 | Ac-V-E-P-N-C-D-I-H-V-M-W-K-W-E-C-F-E-R-L-I-K-CONH₂, disulfide between the two C residues; N side chain linked to azetidinone-CO-CH₂CH₂-(p-C₆H₄)-NH-CO-CH₂-O-CH₂-CHO |
| 94 | 1037 | Ac-V-E-P-N-C-D-I-H-V-M-W-V-W-E-C-F-K-R-L-y-G-L-t-CONH₂, disulfide between the two C residues; N side chain linked to azetidinone-CO-CH₂CH₂-(p-C₆H₄)-NH-CO-CH₂-O-CH₂-CO- |
| 96 | 1038 | Ac-V-E-P-N-C-D-I-H-V-M-W-V-W-E-C-F-K-R-L-Y-G-I-t-CONH₂, disulfide between the two C residues; N side chain linked to azetidinone-CO-CH₂CH₂-(p-C₆H₄)-NH-CO-CH₂-O-CH₂-CO- |
| 55 | 1039 | Ac-V-E-P-N-C-D-I-H-V-M-W-V-W-E-C-F-K-R-I-Y-G-L-T-CONH₂, disulfide between the two C residues; N side chain linked to azetidinone-CO-CH₂CH₂-(p-C₆H₄)-NH-CO-CH₂-O-CH₂-CO- |
| 93 | 1040 | Ac-V-E-P-N-C-D-I-H-V-M-W-V-W-E-C-F-K-R-L-y-G-L-T-CONH₂, disulfide between the two C residues; N side chain linked to azetidinone-CO-CH₂CH₂-(p-C₆H₄)-NH-CO-CH₂-O-CH₂-CO- |

TABLE 9-continued
[VEGF-Peptide]-Linker Compounds
| SEQ ID | Compound # | Structure |
|---|---|---|
| 77 | 1041 | 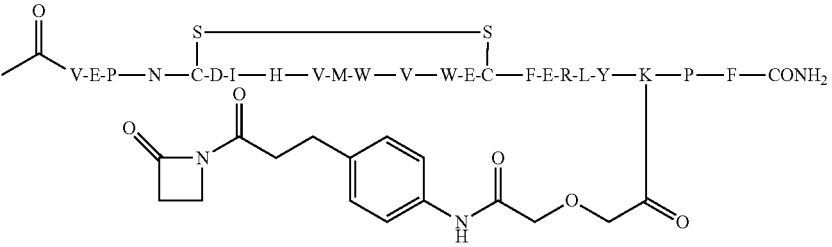 |
| 75 | 1042 | 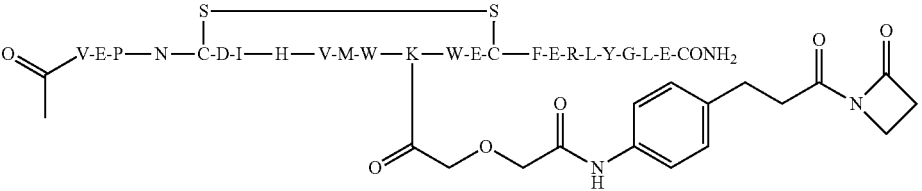 |
| 76 | 1043 | 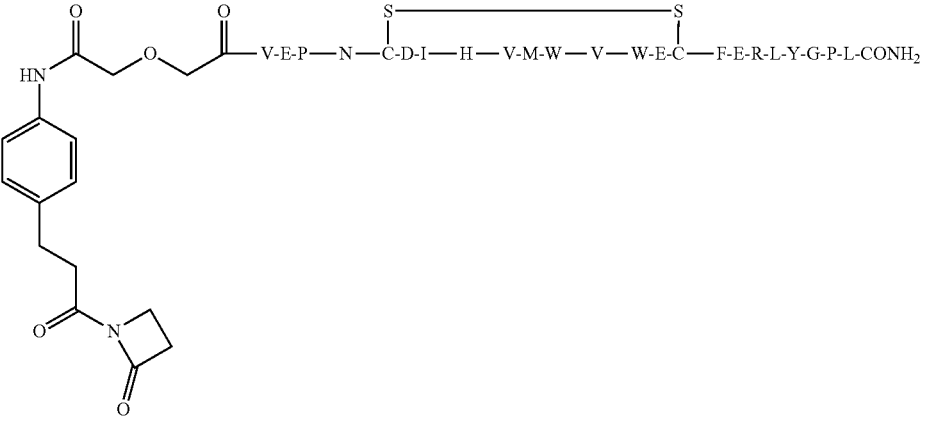 |
| 76 | 1044 | 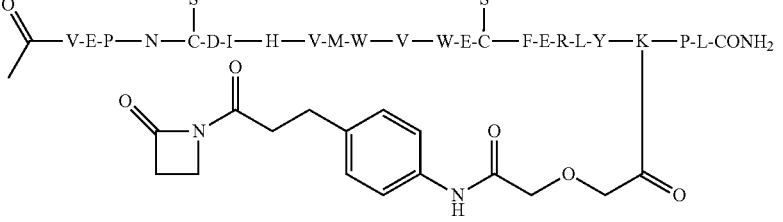 |
| 76 | 1045 | 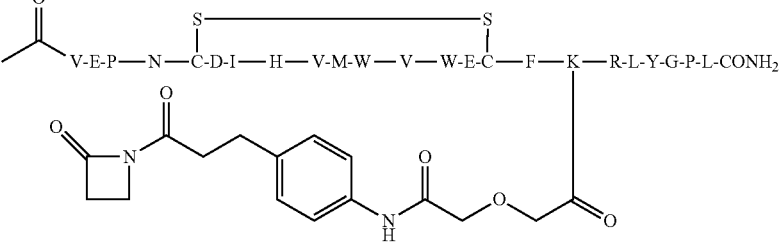 |

TABLE 9-continued

[VEGF-Peptide]-Linker Compounds

| SEQ ID | Compound # | Structure |
|---|---|---|
| 76 | 1046 | Ac-V-E-P-N-C-D-I-H-V-K(linker)-W-V-W-E-C-F-E-R-L-Y-G-P-L-CONH (disulfide C-C); linker = -CO-CH2-O-CH2-CO-NH-C6H4-CH2CH2-CO-N(2-oxoazetidine) |
| 77 | 1047 | Ac-V-E-P-N-C-D-I-H-V-M-W-V-W-E-C-F-K(linker)-R-L-Y-G-P-F-CONH (disulfide C-C); linker = 2-oxoazetidine-N-CO-CH2CH2-C6H4-NH-CO-CH2-O-CH2-CO- |
| 77 | 1048 | Ac-V-E-P-N-C-D-I-H-V-K(linker)-W-V-W-E-C-F-E-R-L-Y-G-P-F-CONH (disulfide C-C); linker = -CO-CH2-O-CH2-CO-NH-C6H4-CH2CH2-CO-N(2-oxoazetidine) |
| 73 | 1049 | Ac-V-E-P-N-C-D-I-H-V-K(linker)-W-V-W-E-C-F-E-R-L-Y-G-I-T-CONH2 (disulfide C-C); linker = -CO-CH2-O-CH2-CO-NH-C6H4-CH2CH2-CO-N(2-oxoazetidine) |
| 73 | 1050 | Ac-V-E-P-N-C-D-I-H-V-M-W-V-W-E-C-F-K(linker)-R-L-Y-G-I-T-CONH2 (disulfide C-C); linker = 2-oxoazetidine-N-CO-CH2CH2-C6H4-NH-CO-CH2-O-CH2-CO- |

TABLE 9-continued

[VEGF-Peptide]-Linker Compounds

| SEQ ID | Compound # | Structure |
|---|---|---|
| 73 | 1051 | Ac-V-E-P-N-C-D-I-H-V-M-W-V-W-E-C-F-E-R-L-Y-K-I-T-CONH₂ (disulfide between the two C residues; linker with 2-oxoazetidine-propanoyl-phenyl-NH-CH₂-O-CH₂-C(O)- attached at Y) |
| 75 | 1052 | Ac-V-E-P-N-C-D-I-H-V-M-W-V-W-E-C-F-K-R-L-Y-G-L-E-CONH₂ (disulfide between the two C residues; linker with 2-oxoazetidine-propanoyl-phenyl-NH-CH₂-O-CH₂-C(O)- attached at K) |
| 75 | 1053 | Ac-V-E-P-N-C-D-I-H-V-M-W-V-W-E-C-F-K-R-L-Y-G-L-E-CONH₂ (disulfide between the two C residues; linker with 2-oxoazetidine-propanoyl-phenyl-NH-CH₂-O-CH₂-C(O)- attached at K) |
| 198 | 1054 | Ac-V-E-P-N-C-D-I-H-V-M-W-E-W-E-C-F-K-R-I-CONH₂ (disulfide between the two C residues; linker with 2-oxoazetidine-propanoyl-phenyl-NH-CH₂-O-CH₂-C(O)- attached at K) |
| 199 | 1055 | Ac-V-E-P-N-C-D-I-H-V-K-W-E-W-E-C-F-N(Me)-E(R-L-CONH₂)-... (disulfide between the two C residues; linker with -C(O)-CH₂-O-CH₂-C(O)-NH-phenyl-CH₂CH₂-C(O)-N-(2-oxoazetidine) attached at K side chain) |

TABLE 9-continued
[VEGF-Peptide]-Linker Compounds
| SEQ ID | Compound # | Structure |
|---|---|---|
| 200 | 1056 | 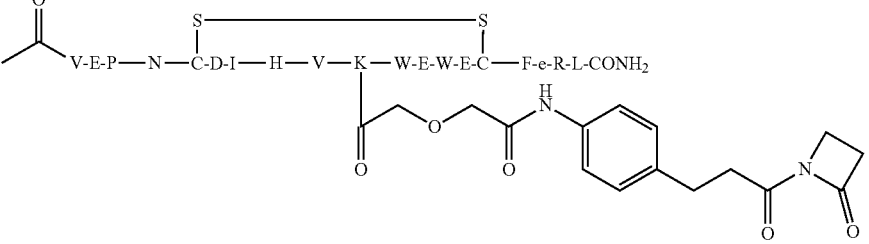 |
| 201 | 1057 | 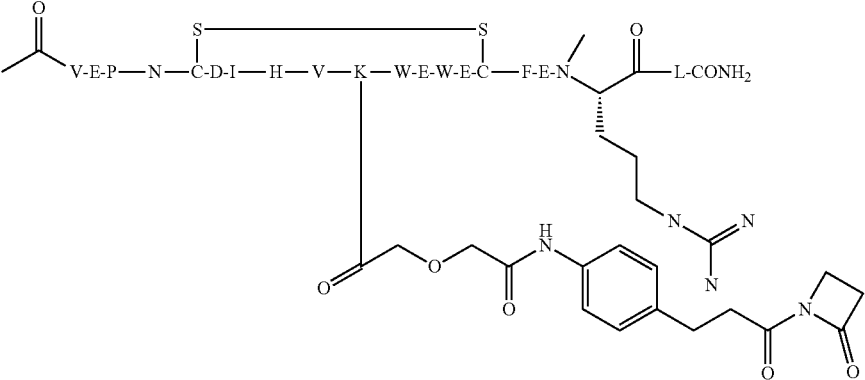 |
| 202 | 1058 | 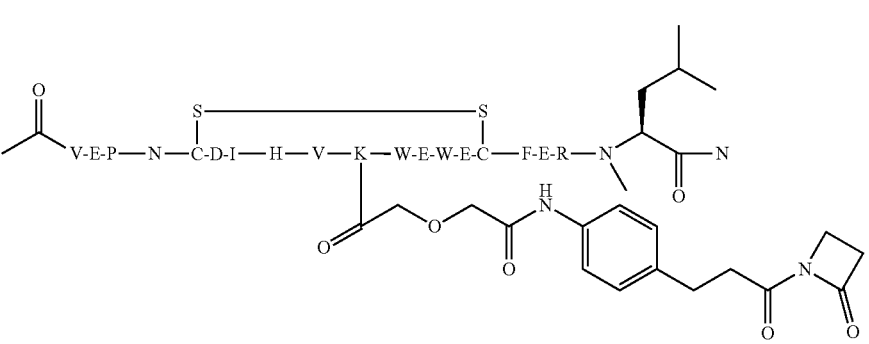 |
| 203 | 1059 | 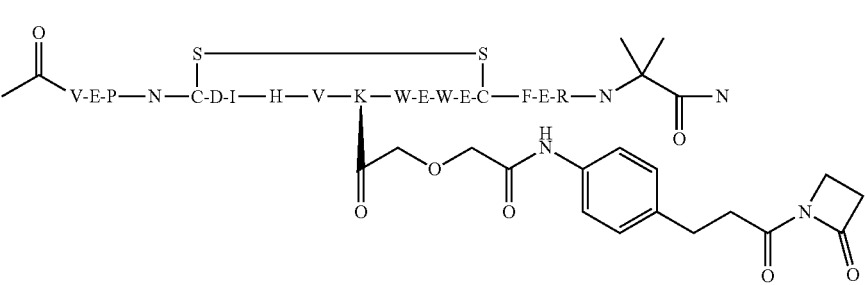 |

TABLE 9-continued
[VEGF-Peptide]-Linker Compounds
| SEQ ID | Compound # | Structure |
|---|---|---|
| 204 | 1060 | 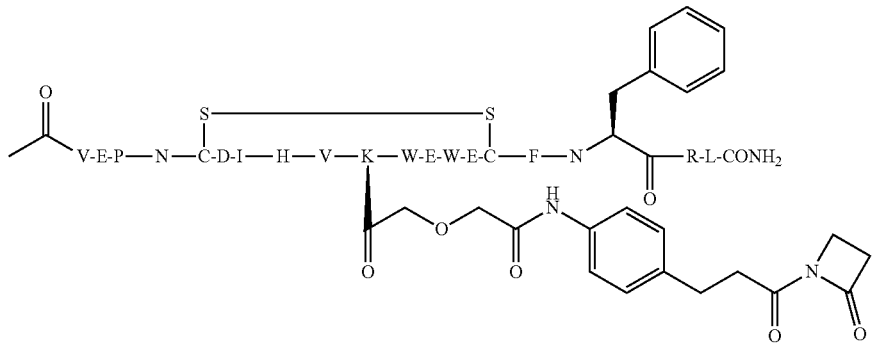 |
| 205 | 1061 | 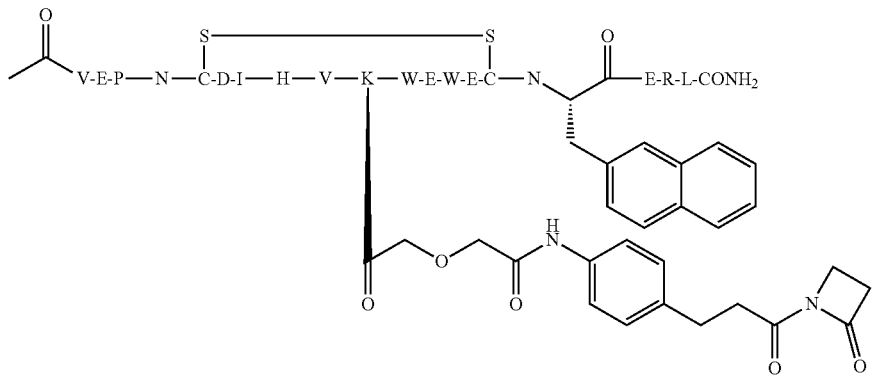 |
| 34 | 1062 | 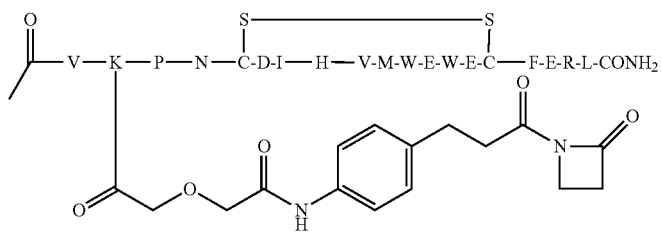 |
| 34 | 1063 | 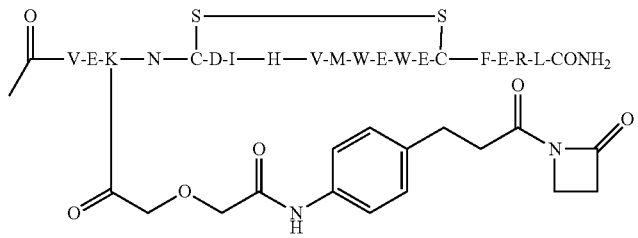 |
| 34 | 1064 | 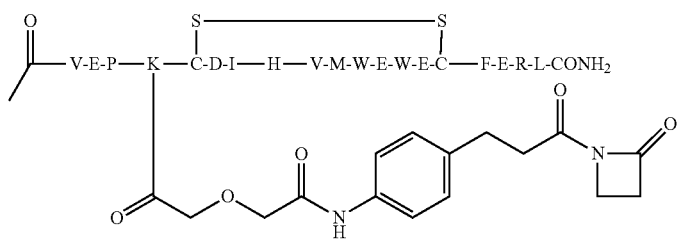 |

TABLE 9-continued
[VEGF-Peptide]-Linker Compounds
| SEQ ID | Compound # | Structure |
|---|---|---|
| 34 | 1065 | 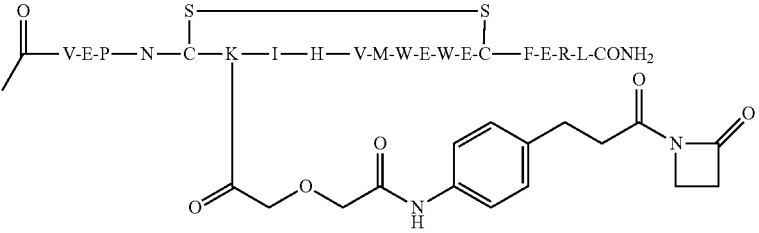 |
| 34 | 1066 | 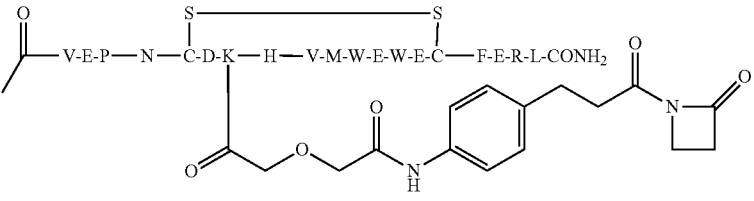 |
| 34 | 1067 | 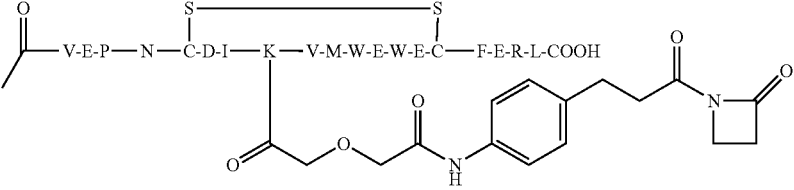 |
| 34 | 1068 | 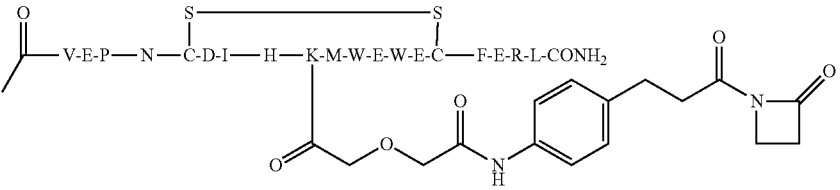 |
| 34 | 1069 | 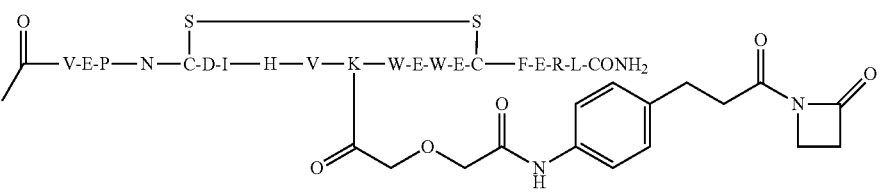 |
| 34 | 1070 | 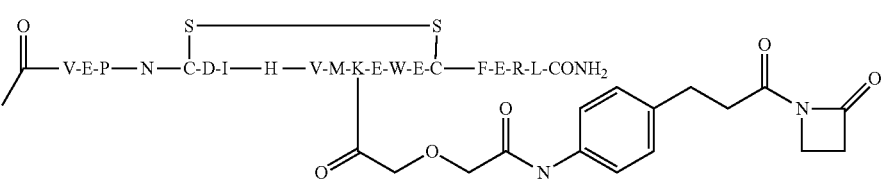 |
| 34 | 1071 | 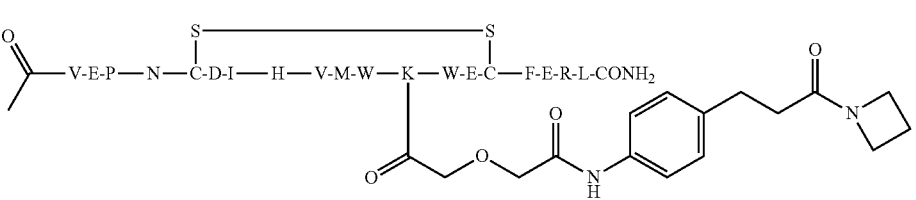 |

TABLE 9-continued

[VEGF-Peptide]-Linker Compounds

| SEQ ID | Compound # | Structure |
|---|---|---|
| 34 | 1072 | Ac-V-E-P-N-C-D-I-H-V-M-W-E-W-E-C-K-E-R-L-CONH₂ (disulfide C–C); linker on K: –CO–CH₂–O–CH₂–CO–NH–C₆H₄–CH₂CH₂–CO–N(azetidin-2-one) |
| 34 | 1073 | Ac-VEPNCDIHVMWEWECFKRL-CONH₂ (disulfide); linker on K: –CO–CH₂–O–CH₂–CO–NH–C₆H₄–CH₂CH₂–CO–N(azetidin-2-one) |
| 34 | 1074 | Ac-V-E-P-N-C-D-I-H-V-M-W-E-K-E-C-F-E-R-L-CONH₂ (disulfide C–C); linker on K: –CO–CH₂–O–CH₂–CO–NH–C₆H₄–CH₂CH₂–CO–N(azetidin-2-one) |
| 34 | 1075 | Ac-V-E-P-N-C-D-I-H-V-M-W-E-W-K-C-F-E-R-L-CONH₂ (disulfide C–C); linker on K: –CO–CH₂–O–CH₂–CO–NH–C₆H₄–CH₂CH₂–CO–N(azetidin-2-one) |
| 34 | 1076 | Ac-V-E-P-N-C-D-I-H-V-M-W-E-W-E-C-F-E-K-L-CONH₂ (disulfide C–C); linker on K: –CO–CH₂–O–CH₂–CO–NH–C₆H₄–CH₂CH₂–CO–N(azetidin-2-one) |
| 34 | 1077 | Ac-V-E-P-N-C-D-I-H-V-M-W-E-W-E-C-F-E-R-K-CONH₂ (disulfide C–C); linker on K: –CO–CH₂–O–CH₂–CO–NH–C₆H₄–CH₂CH₂–CO–N(azetidin-2-one) |
| 34 | 1078 | V-E-P-N-C-D-I-H-V-M-W-E-W-E-C-F-E-R-I-CONH₂ (disulfide C–C); N-terminal linker: –CO–CH₂–O–CH₂–CO–NH–C₆H₄–CH₂CH₂–CO–N(azetidin-2-one) |
| 206 | 1079 | Ac-V-E-P-N-C-D-I-H-V-M-W-V-W-E-C-F-K-R-L-Y-G-L-T-CONH₂ (disulfide C–C); linker on K: –CO–CH₂–O–CH₂–CO–NH–C₆H₄–CH₂CH₂–CO–N(azetidin-2-one) |

TABLE 9-continued
[VEGF-Peptide]-Linker Compounds
| SEQ ID | Compound # | Structure |
|---|---|---|
| 207 | 1080 | 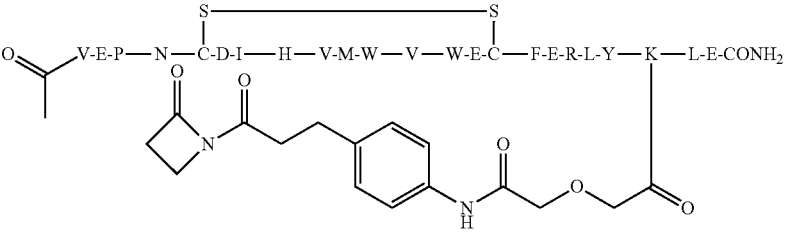 |
TABLE 10
[VEGF-Peptide]-[Linker]-Antibody compounds
| Incorporates SEQ ID # | Compound # | Structure |
|---|---|---|
| 74 | 2001 | 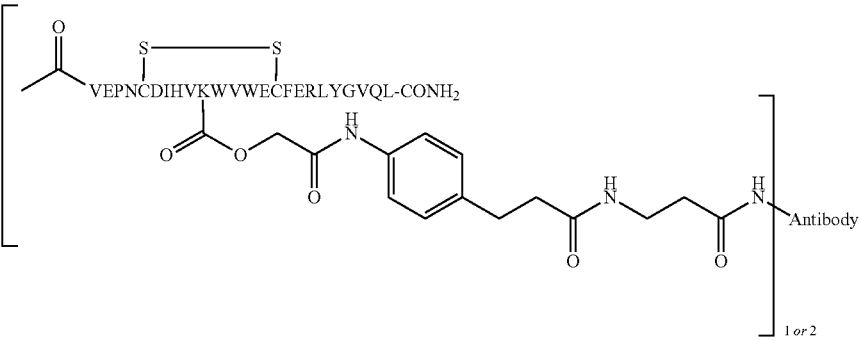 |
| 74 | 2002 | 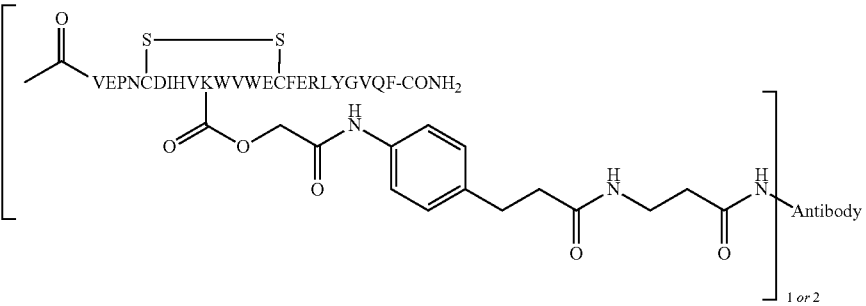 |
| 74 | 2003 | 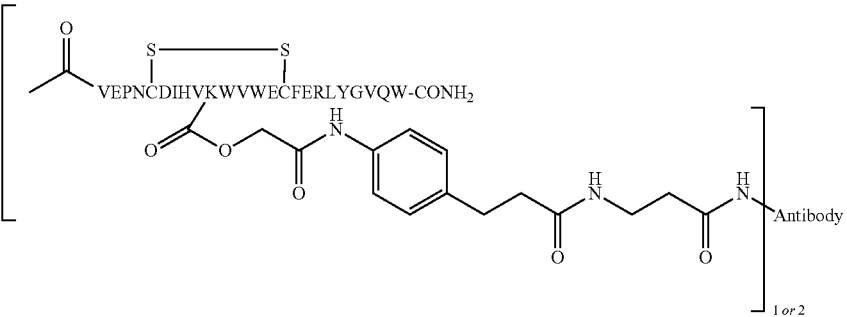 |

TABLE 10-continued
[VEGF-Peptide]-[Linker]-Antibody compounds
| Incorporates SEQ ID # | Compound # | Structure |
|---|---|---|
| 74 | 2004 | 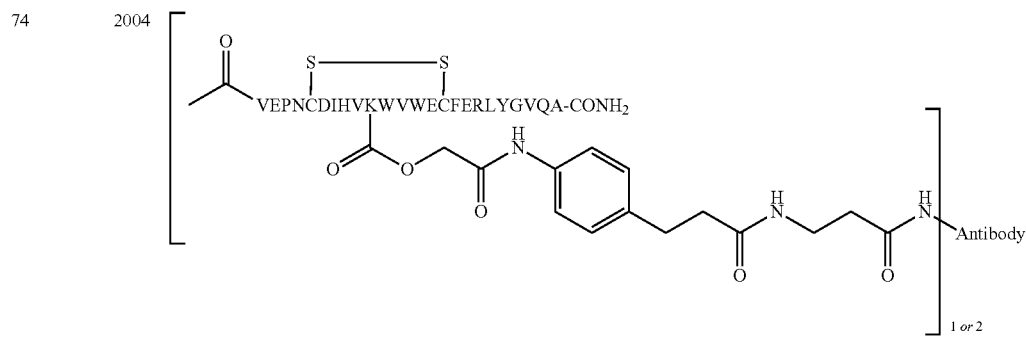 |
| 74 | 2005 | 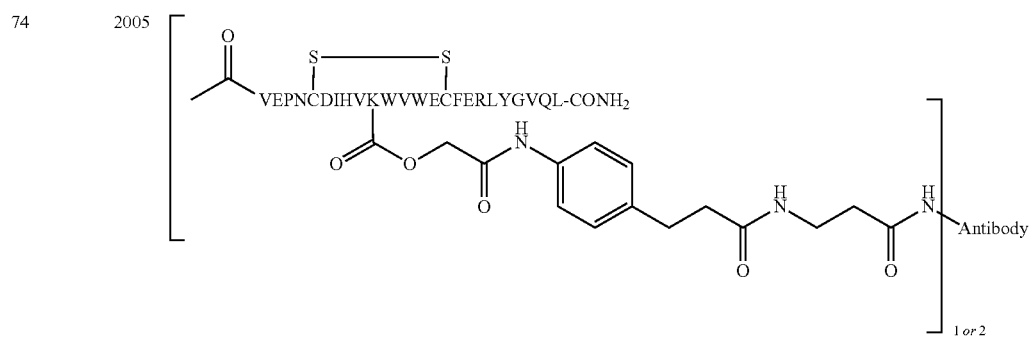 |
| 90 | 2006 | 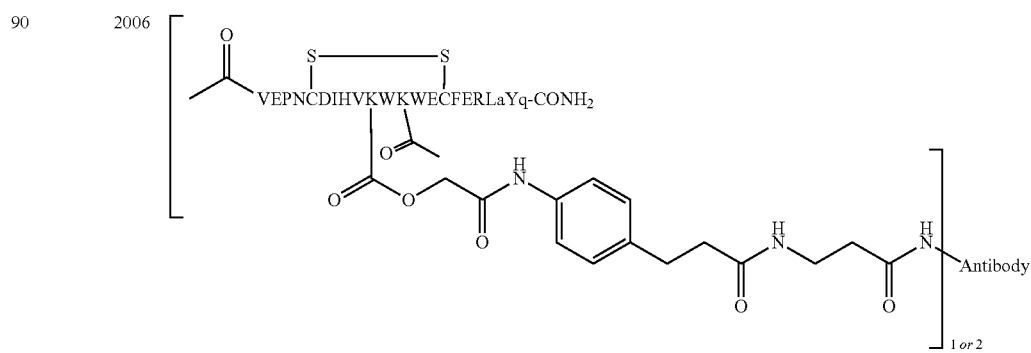 |
| 84 | 2007 | 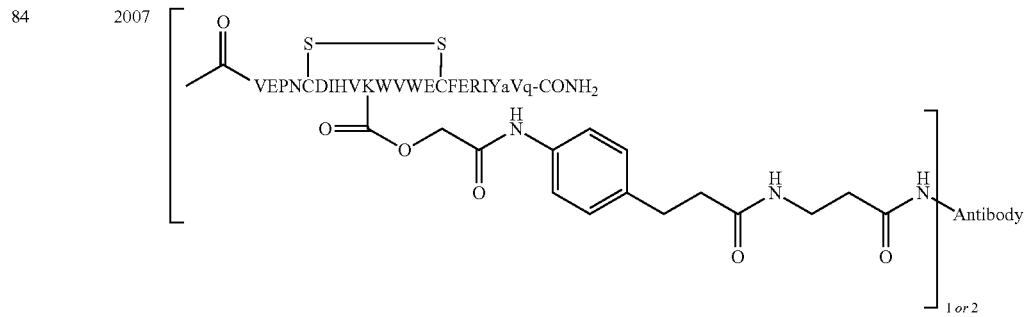 |

TABLE 10-continued
[VEGF-Peptide]-[Linker]-Antibody compounds
| Incorporates SEQ ID # | Compound # | Structure |
|---|---|---|
| 90 | 2008 | 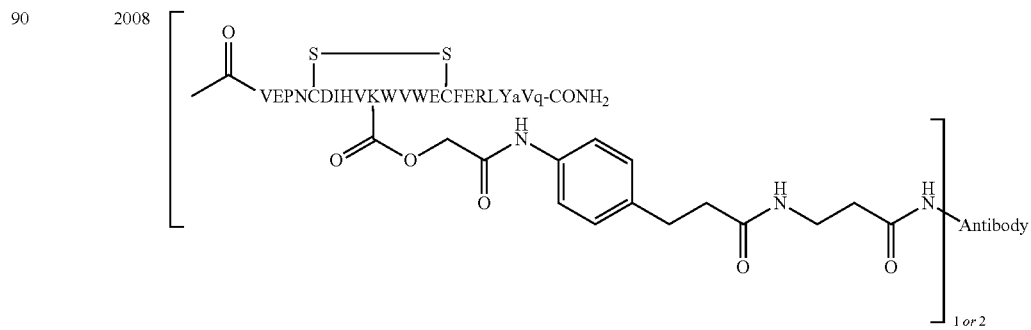 |
| 88 | 2009 | 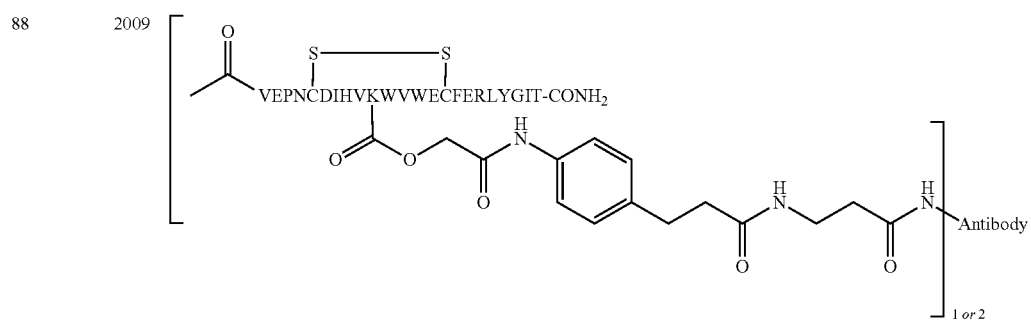 |
| 85 | 2010 | 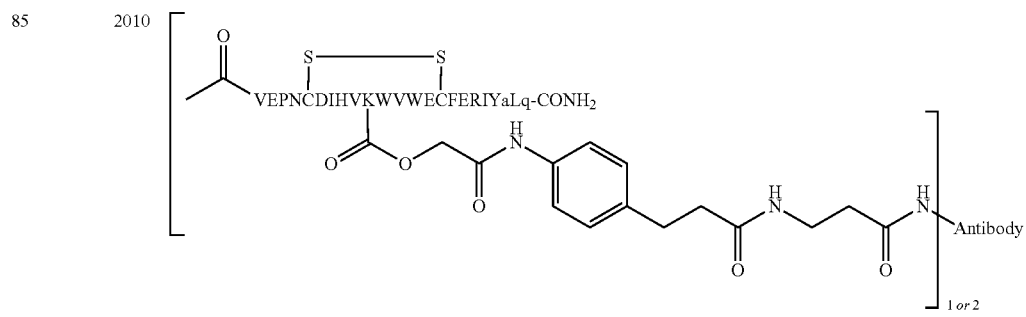 |
| 82 | 2011 | 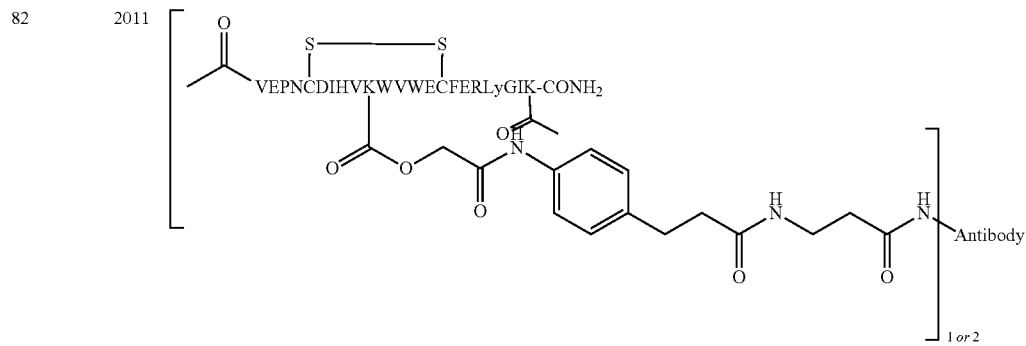 |

TABLE 10-continued
[VEGF-Peptide]-[Linker]-Antibody compounds
| Incorporates SEQ ID # | Compound # | Structure |
|---|---|---|
| 81 | 2012 | 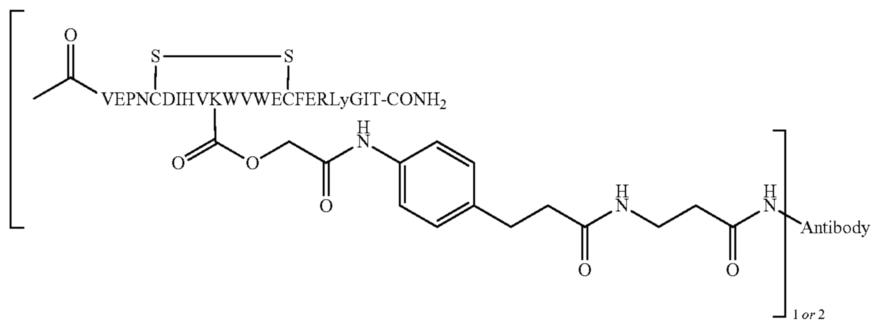 |
| 80 | 2013 | 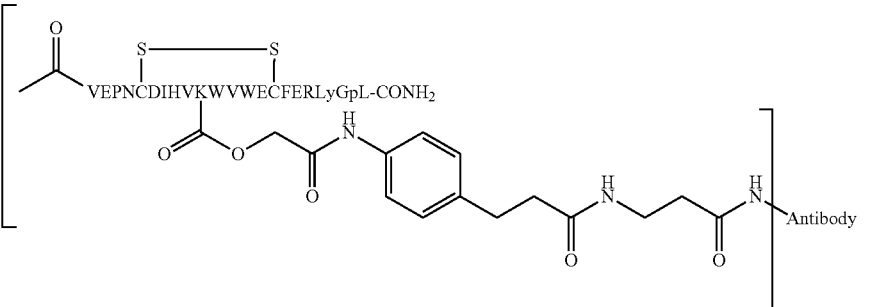 |
| 89 | 2014 | 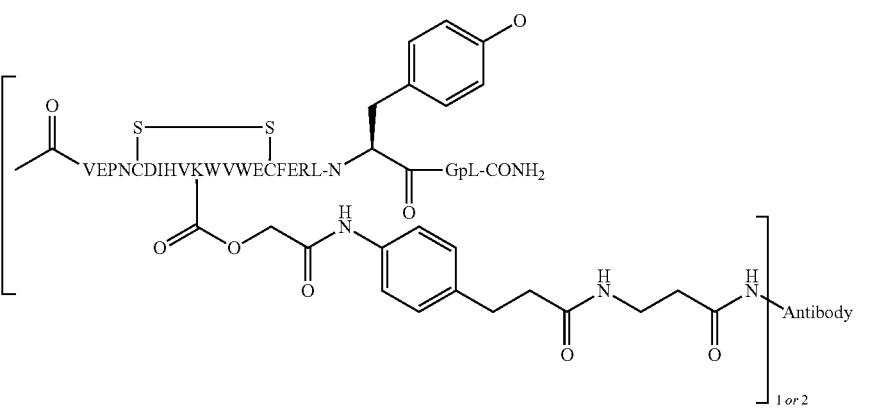 |
| 73 | 2015 | 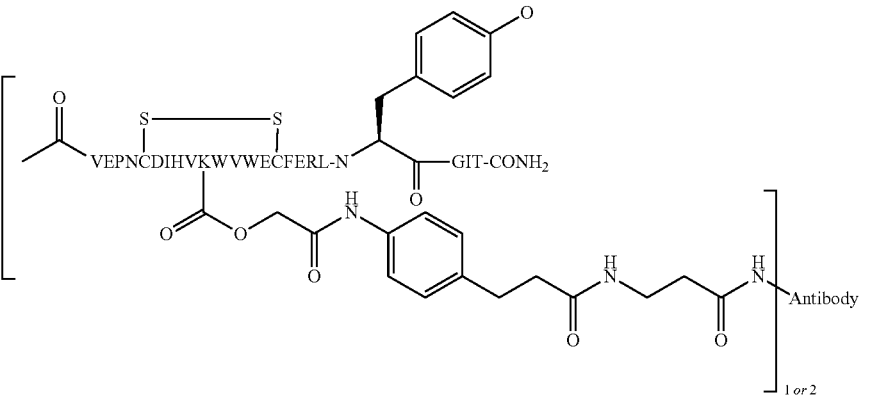 |

TABLE 10-continued
[VEGF-Peptide]-[Linker]-Antibody compounds
| Incorporates SEQ ID # | Compound # | Structure |
|---|---|---|
| 86 | 2016 | 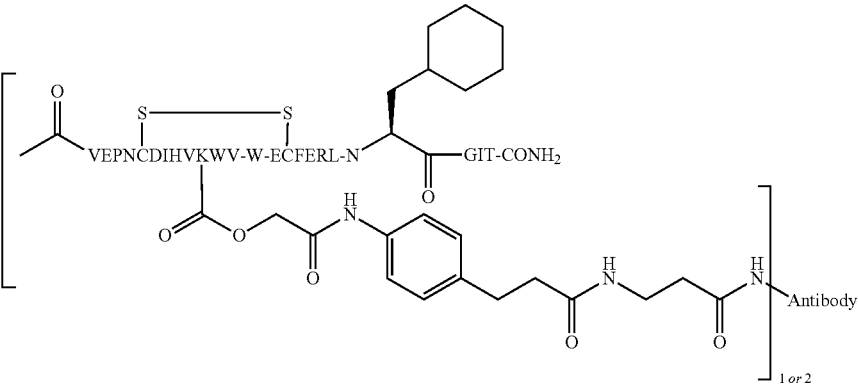 |
| 60 | 2017 | 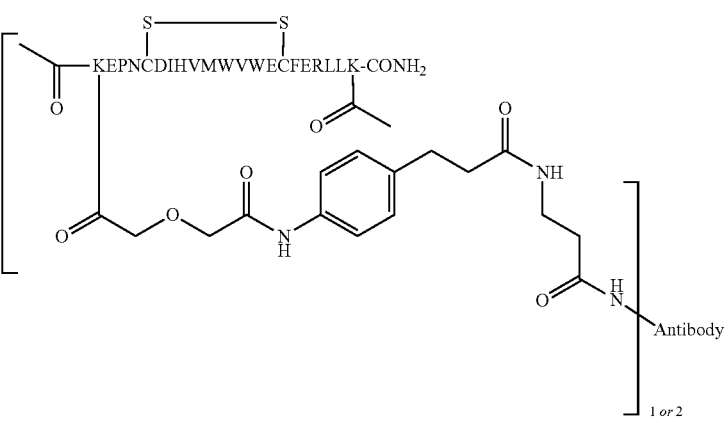 |
| 78 195 (specifying K[10] as linking residue) | 2018 | 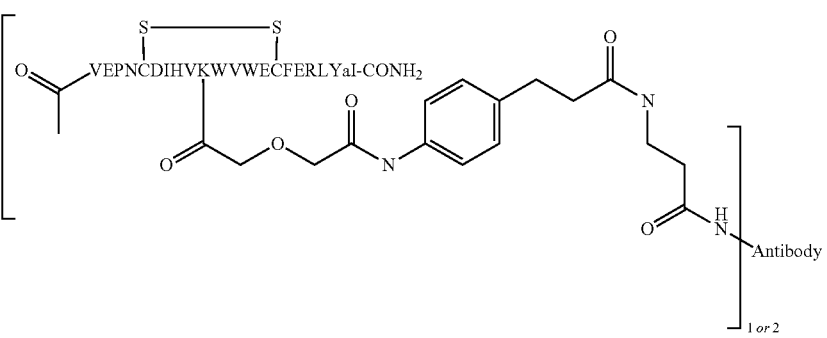 |
| 97 | 2019 | 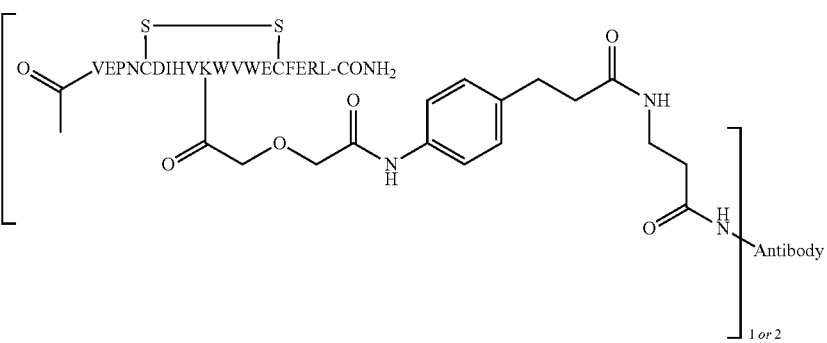 |

TABLE 10-continued
[VEGF-Peptide]-[Linker]-Antibody compounds
| Incorporates SEQ ID # | Compound # | Structure |
|---|---|---|
| 79 | 2020 | 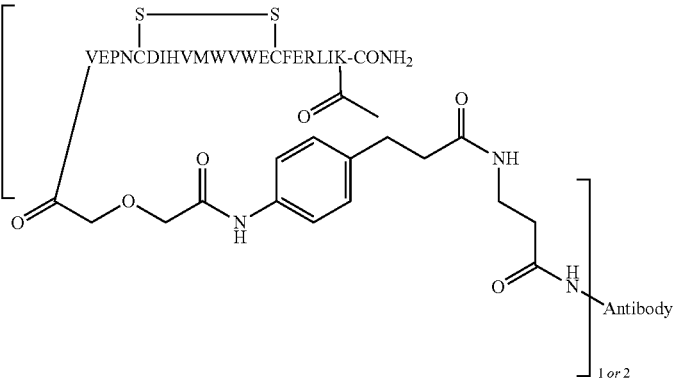 |
| 196 | 2021 | 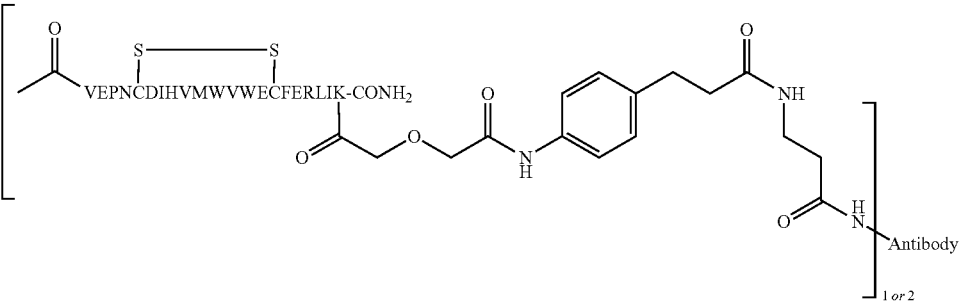 |
| 84 | 2022 | 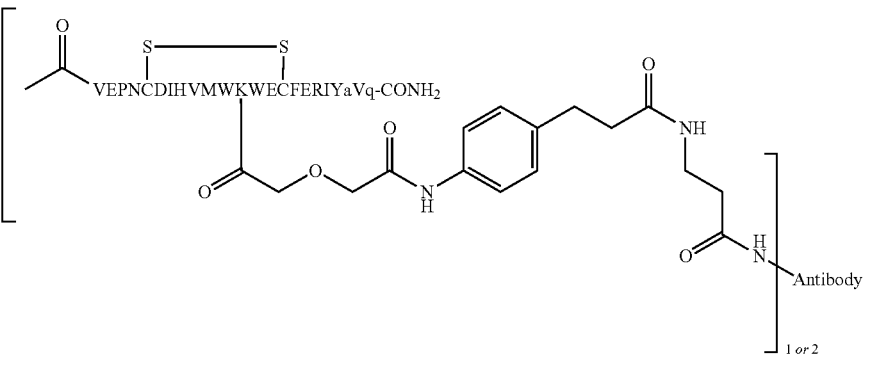 |
| 90 | 2023 | 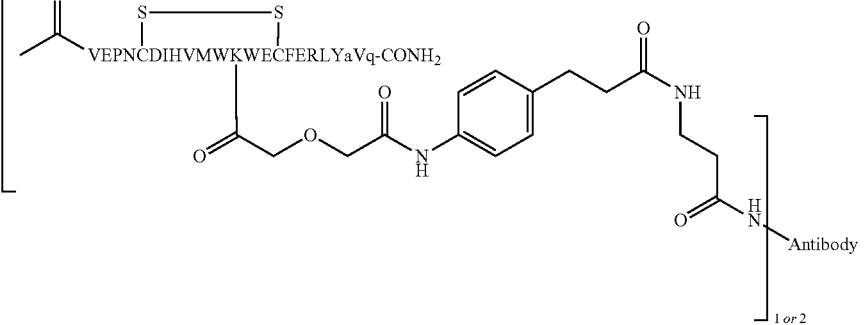 |

TABLE 10-continued
[VEGF-Peptide]-[Linker]-Antibody compounds
| Incorporates SEQ ID # | Compound # | Structure |
|---|---|---|
| 74 | 2024 | 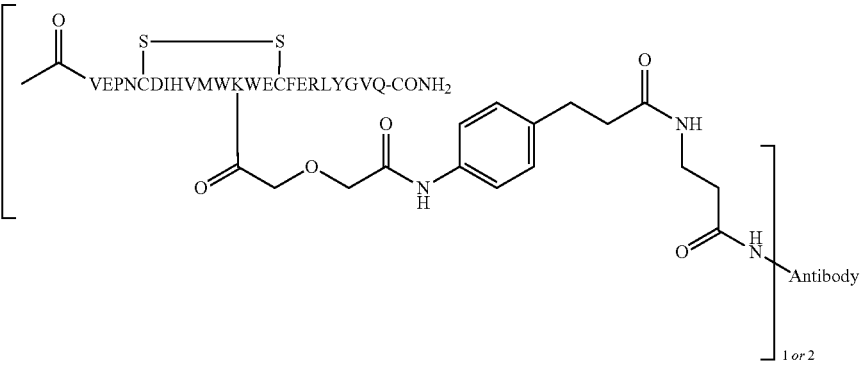 |
| 60 | 2025 | 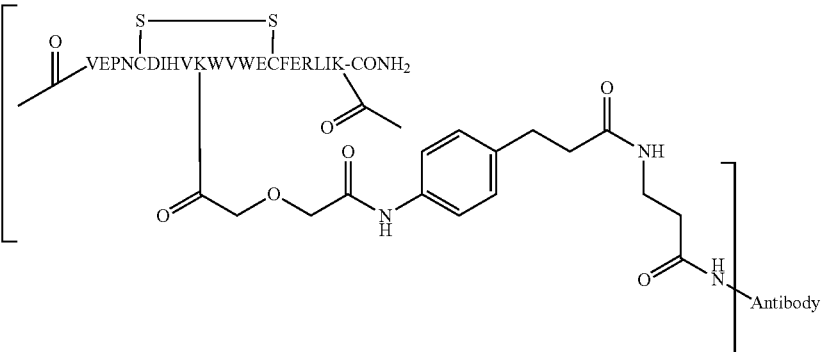 |
| 83 | 2026 | 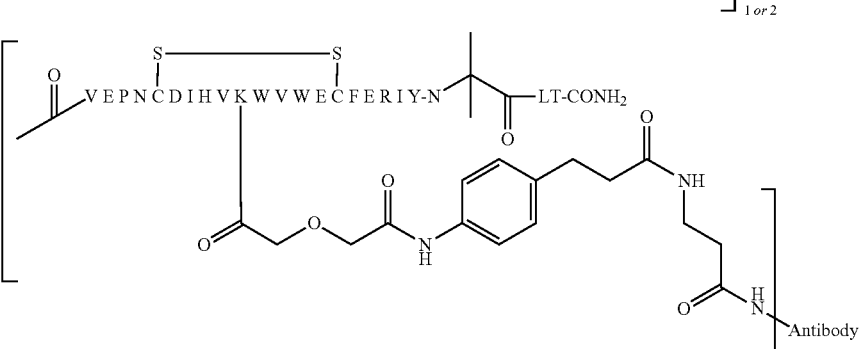 |
| 87 | 2027 | 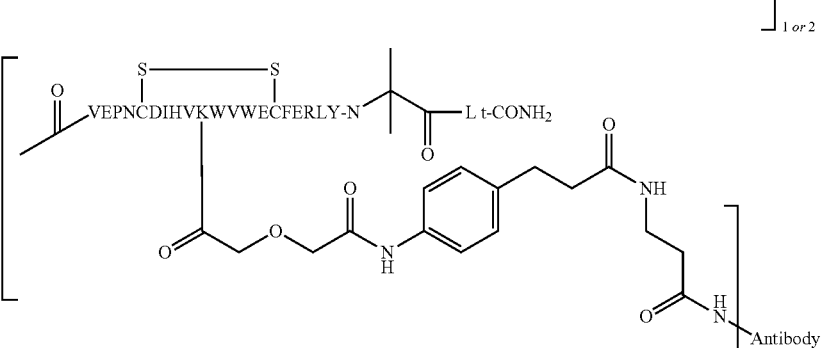 |

TABLE 10-continued
[VEGF-Peptide]-[Linker]-Antibody compounds
| Incorporates SEQ ID # | Compound # | Structure |
|---|---|---|
| 83 | 2028 | 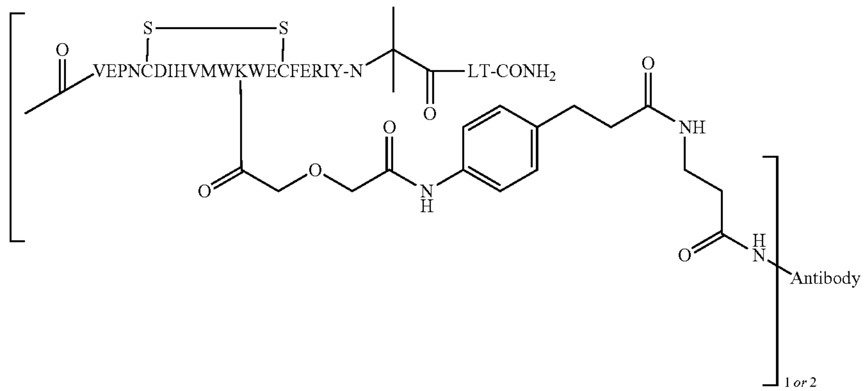 |
| 87 | 2029 | 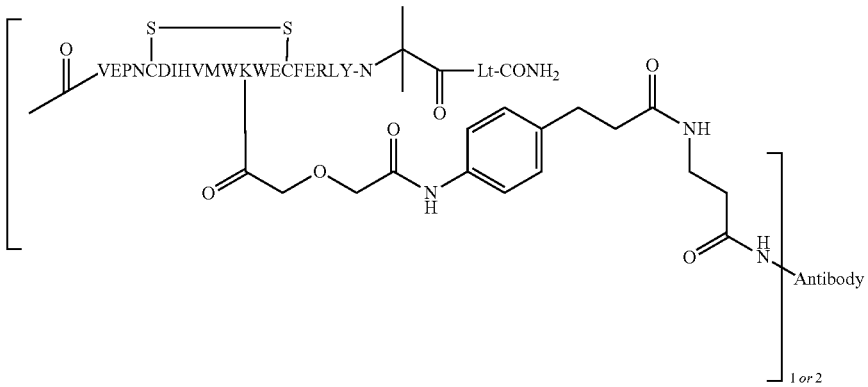 |
| 91 | 2030 | 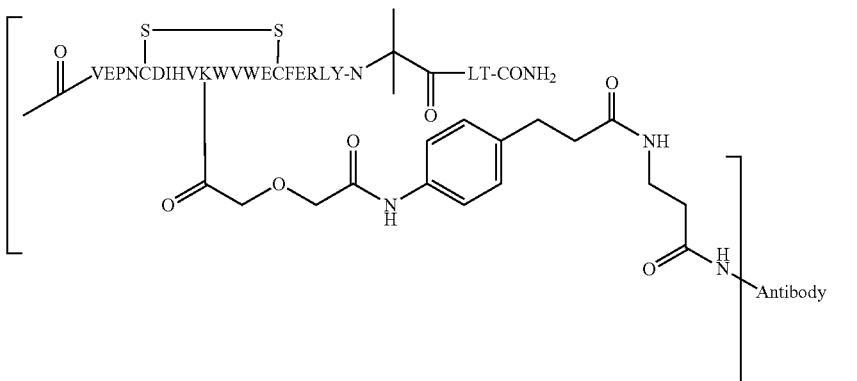 |
| 91 | 2031 | 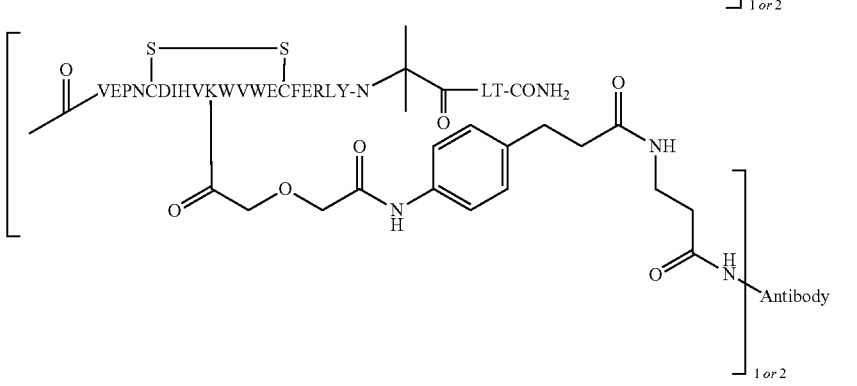 |

TABLE 10-continued
[VEGF-Peptide]-[Linker]-Antibody compounds
| Incorporates SEQ ID # | Compound # | Structure |
|---|---|---|
| 197 | 2032 | 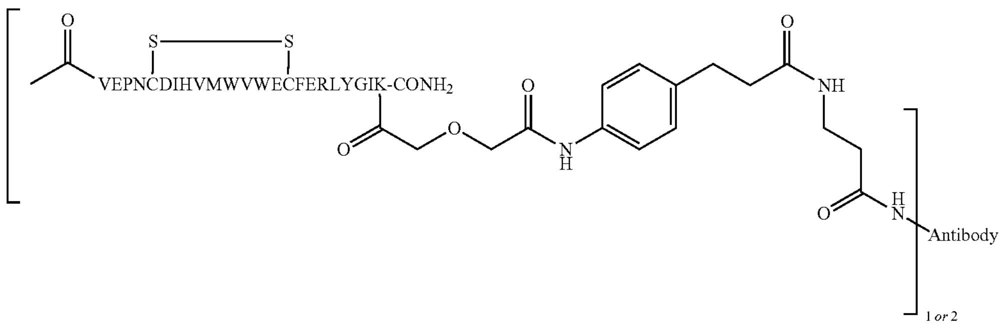 |
| 92 | 2033 | 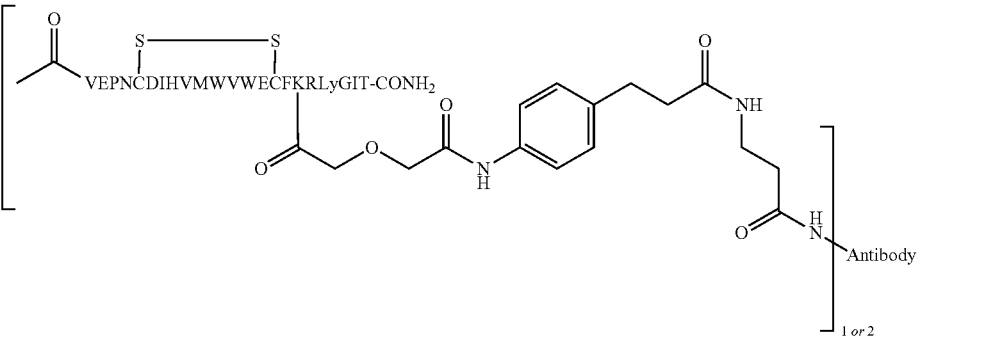 |
| 95 | 2034 | 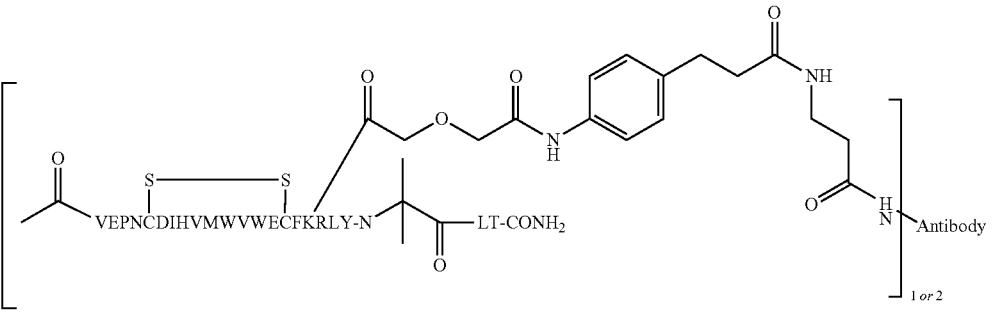 |
| 60 | 2035 | 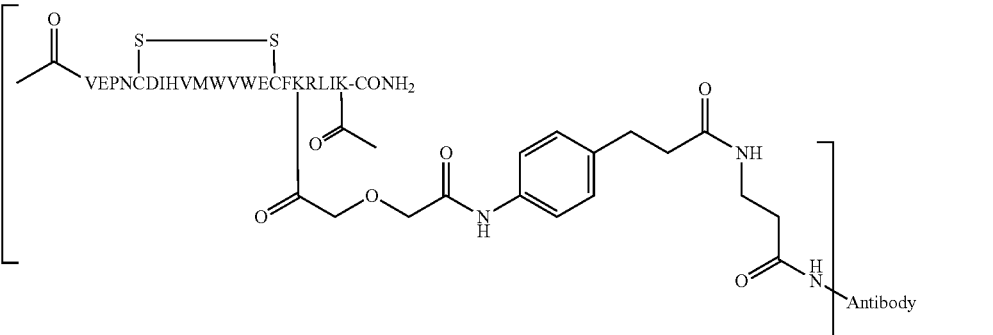 |

TABLE 10-continued
[VEGF-Peptide]-[Linker]-Antibody compounds
| Incorporates SEQ ID # | Compound # | Structure |
|---|---|---|
| 60 192 (specifying K[12] as linking residue) | 2036 | 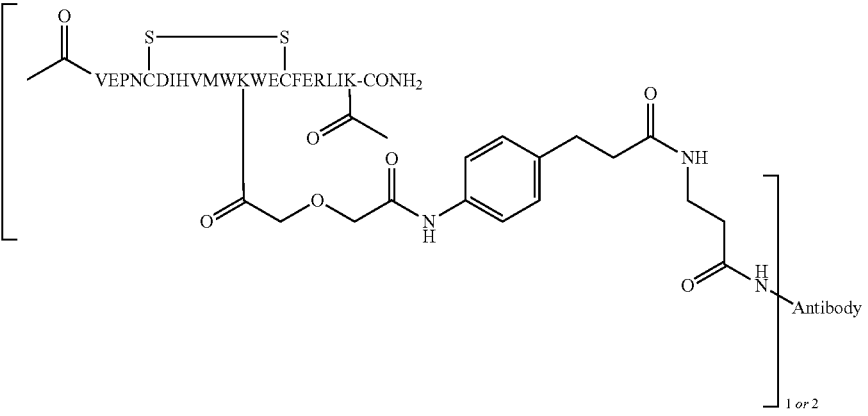 |
| 94 | 2037 | 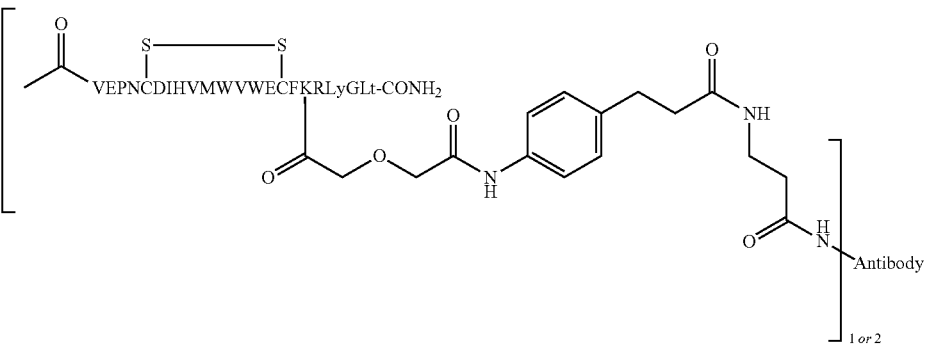 |
| 96 | 2038 | 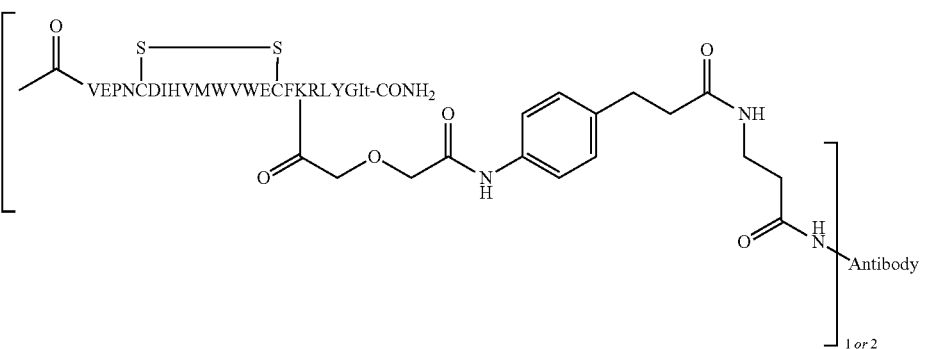 |
| 55 | 2039 | 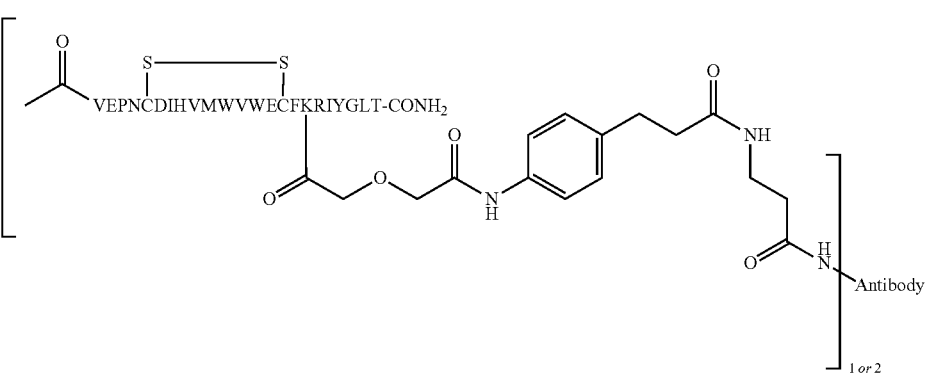 |

TABLE 10-continued
[VEGF-Peptide]-[Linker]-Antibody compounds
| Incorporates SEQ ID # | Compound # | Structure |
|---|---|---|
| 93 | 2040 | 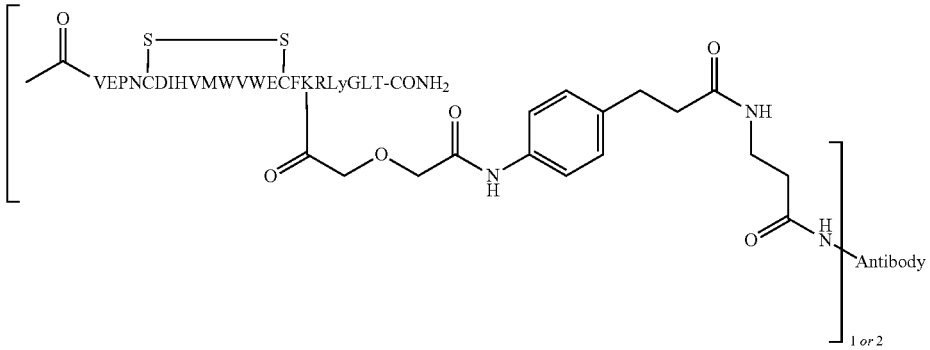 |
| 77 | 2041 | 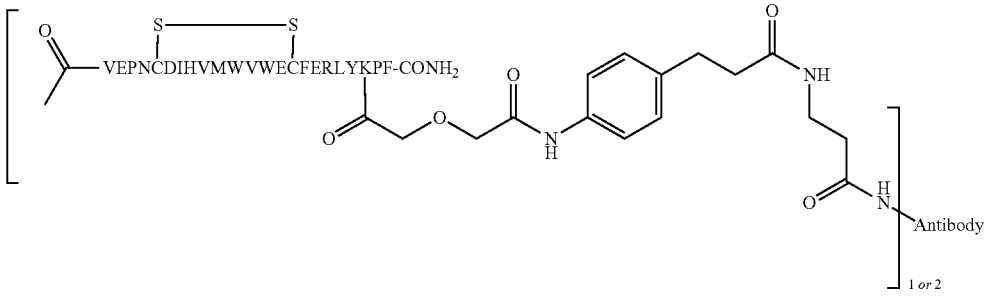 |
| 75 | 2042 | 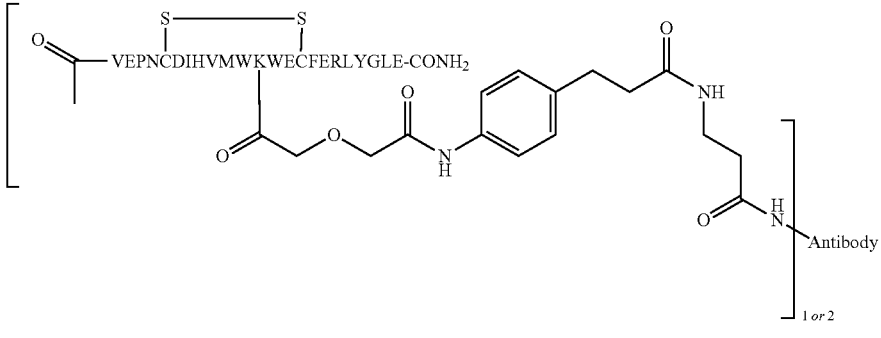 |
| 76 | 2043 | 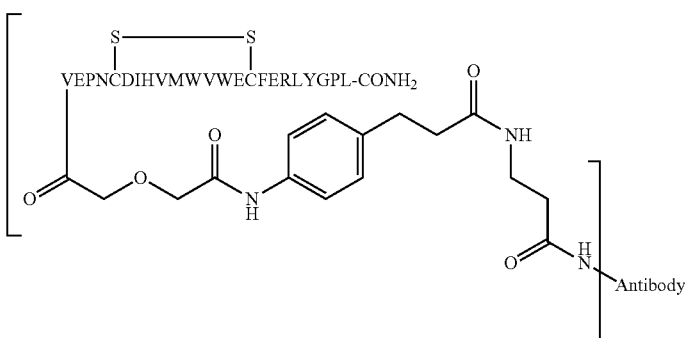 |

TABLE 10-continued

[VEGF-Peptide]-[Linker]-Antibody compounds

| Incorporates SEQ ID # | Compound # | Structure |
|---|---|---|
| 76 | 2044 | [VEPNCDIHVMWVWECFERLYKPL-CONH$_2$, disulfide bridge between the two C residues, N-acetyl, linker to Antibody]$_{1\ or\ 2}$ |
| 76<br>194 (specifying K$^{17}$ as linking residue) | 2045 | [VEPNCDIHVMWVWECFKRLYGPL-CONH$_2$, disulfide bridge between the two C residues, N-acetyl, linker to Antibody]$_{1\ or\ 2}$ |
| 76 | 2046 | [VEPNCDIHVKWVWECFERLYGPL-CONH$_2$, disulfide bridge between the two C residues, N-acetyl, linker to Antibody]$_{1\ or\ 2}$ |
| 77 | 2047 | [VEPNCDIHVMWVWECFKRLYGPF-CONH$_2$, disulfide bridge between the two C residues, N-acetyl, linker to Antibody]$_{1\ or\ 2}$ |

TABLE 10-continued
[VEGF-Peptide]-[Linker]-Antibody compounds
| Incorporates SEQ ID # | Compound # | Structure |
|---|---|---|
| 77 | 2048 | 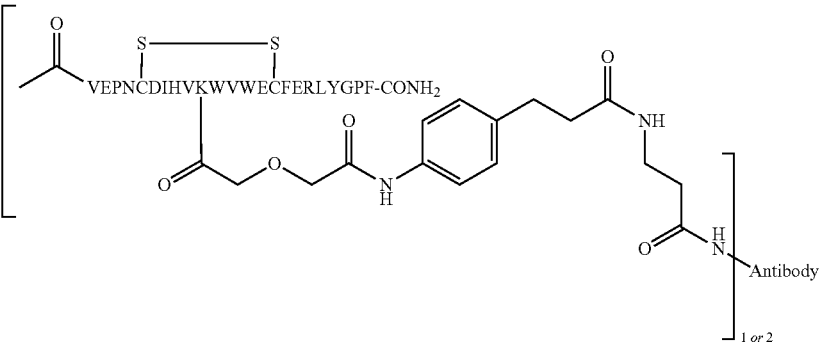 |
| 73 | 2049 | 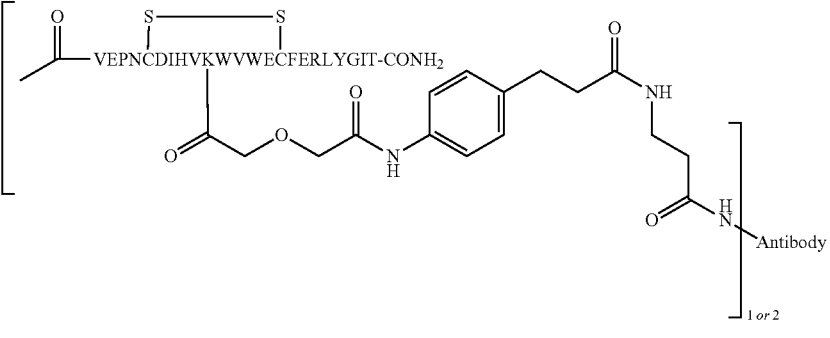 |
| 73 193 (specifying $K^{17}$ as linking residue) | 2050 | 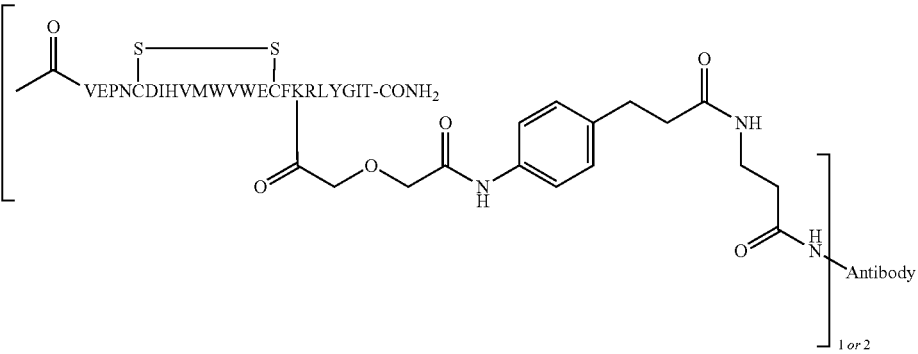 |
| 73 | 2051 | 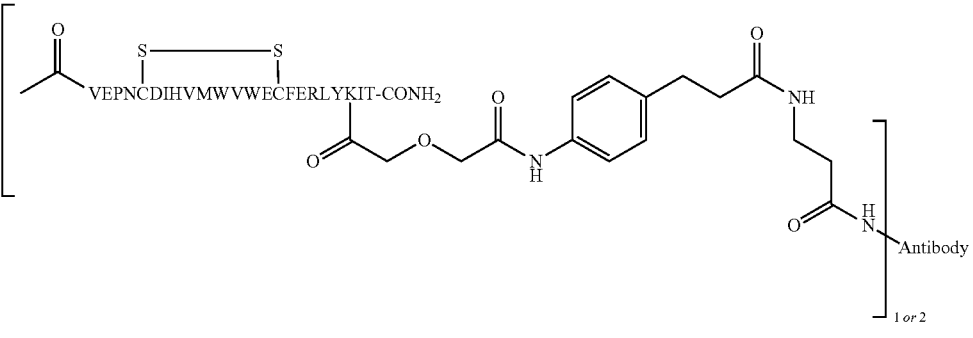 |

TABLE 10-continued
[VEGF-Peptide]-[Linker]-Antibody compounds
| Incorporates SEQ ID # | Compound # | Structure |
|---|---|---|
| 75 | 2052 | 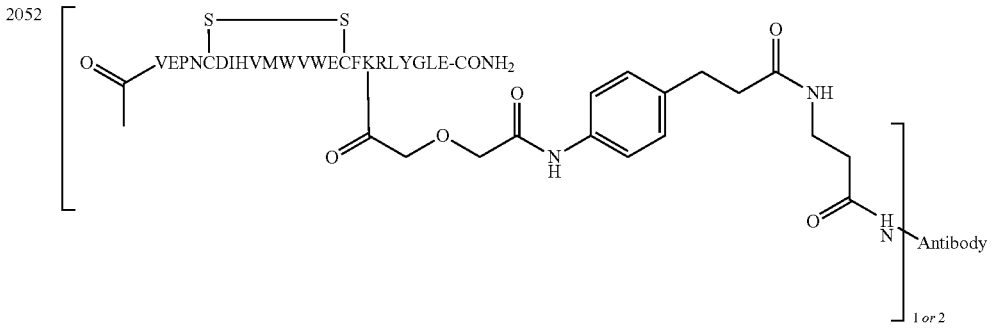 |
| 75 | 2053 | 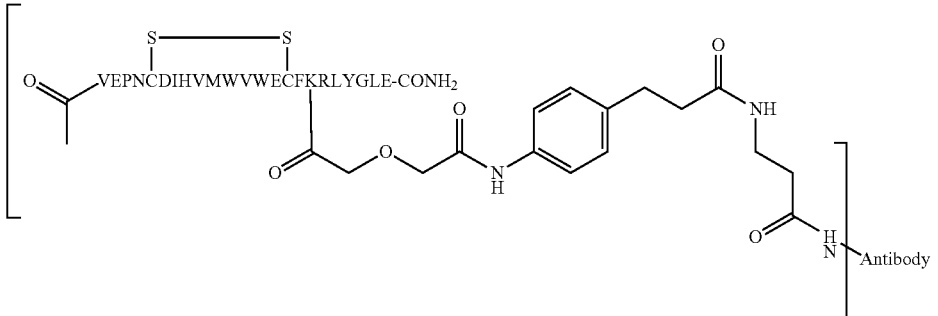 |
| 198 | 2054 | 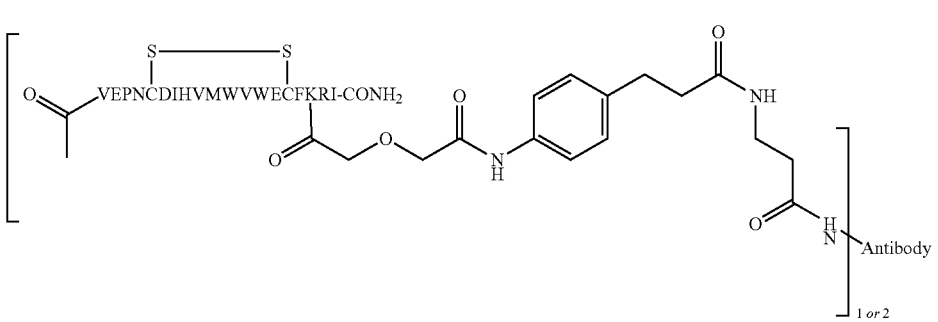 |
| 199 | 2055 | 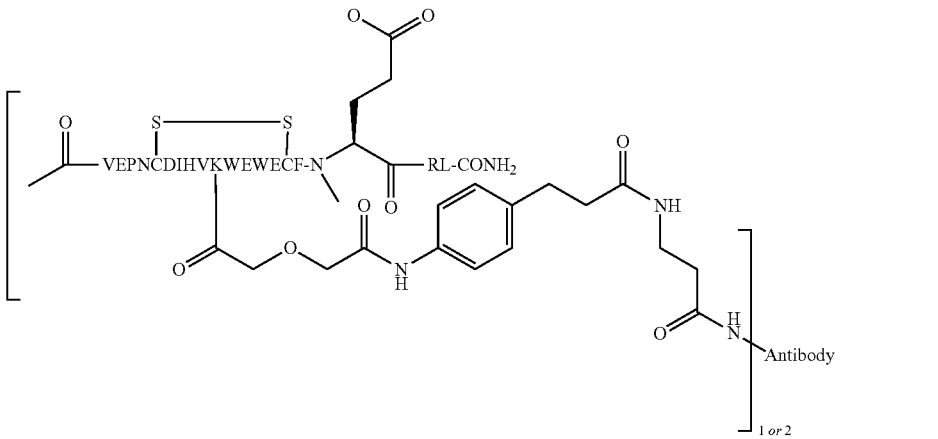 |

TABLE 10-continued

[VEGF-Peptide]-[Linker]-Antibody compounds

| Incorporates SEQ ID # | Compound # | Structure |
|---|---|---|
| 200 | 2056 | VEPNCDIHVKWEWECFeRL-CONH₂ linked via disulfide-containing cyclic peptide through phenyl-propanamide-β-alanyl-Antibody (1 or 2) |
| 201 | 2057 | VEPNCDIHVKWEWECFE-N(Me)-Arg-L-CONH₂ linked through phenyl-propanamide-β-alanyl-Antibody (1 or 2) |
| 202 | 2058 | VEPNCDIHVKWEWECFER-N(Me)-Leu linked through phenyl-propanamide-β-alanyl-Antibody (1 or 2) |
| 203 | 2059 | VEPNCDIHVKWEWECFER-N-Aib linked through phenyl-propanamide-β-alanyl-Antibody (1 or 2) |

141 142
TABLE 10-continued
[VEGF-Peptide]-[Linker]-Antibody compounds
| Incorporates SEQ ID # | Compound # | Structure |
|---|---|---|
| 204 | 2060 | 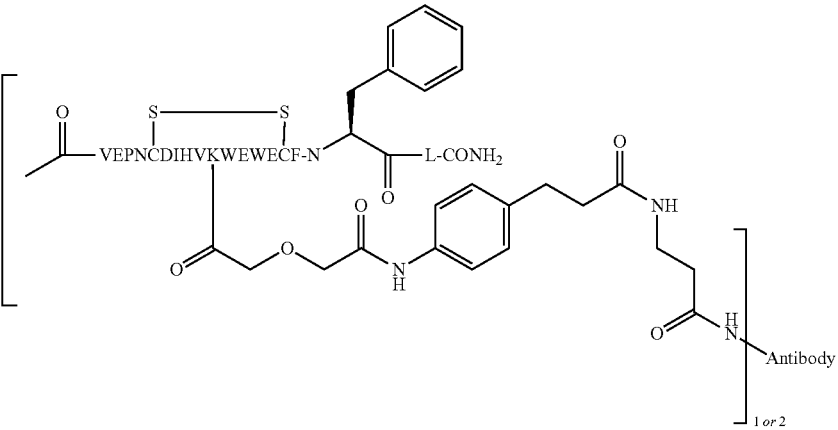 |
| 205 | 2061 | 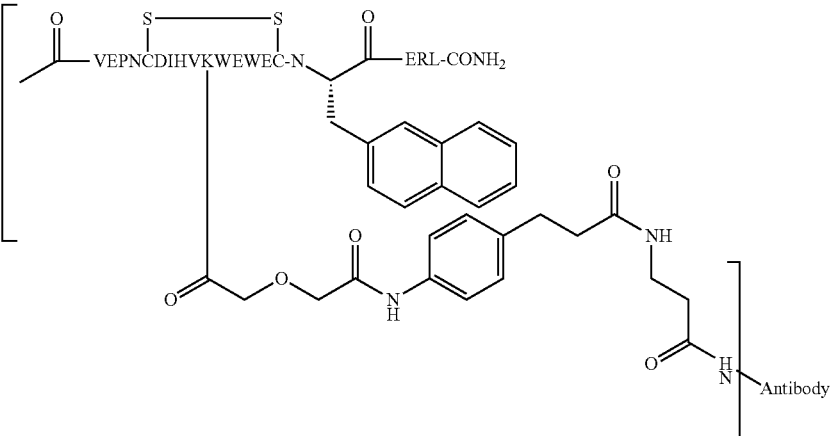 |
| 34 | 2062 | 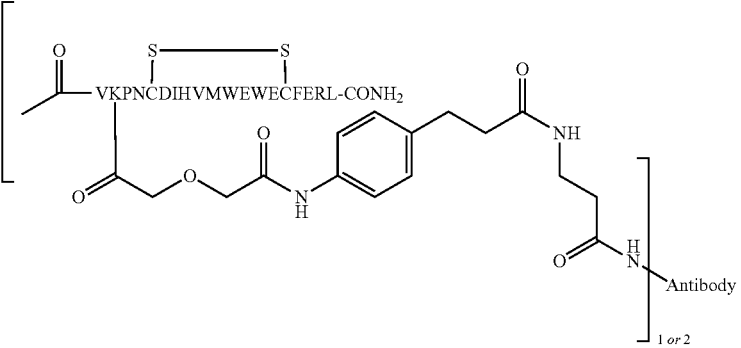 |

TABLE 10-continued
[VEGF-Peptide]-[Linker]-Antibody compounds
| Incorporates SEQ ID # | Compound # | Structure |
|---|---|---|
| 34 | 2063 | 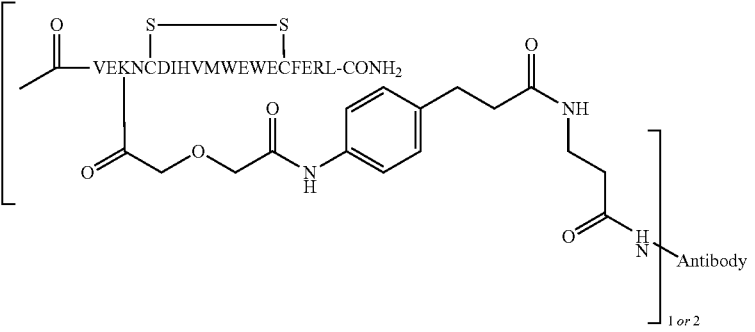 |
| 34 | 2064 | 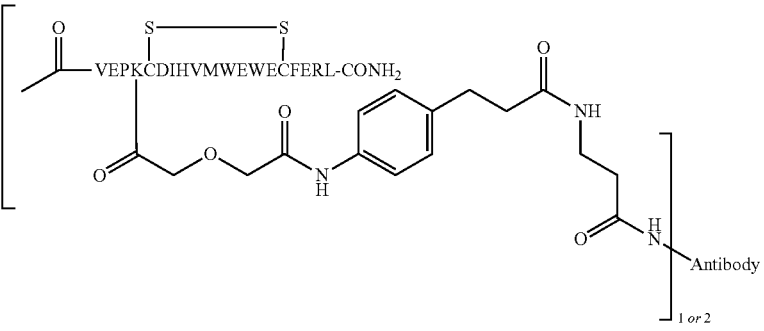 |
| 34 | 2065 | 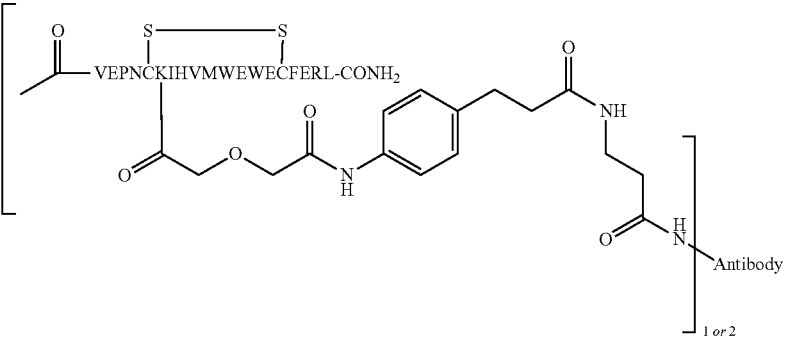 |
| 34 | 2066 | 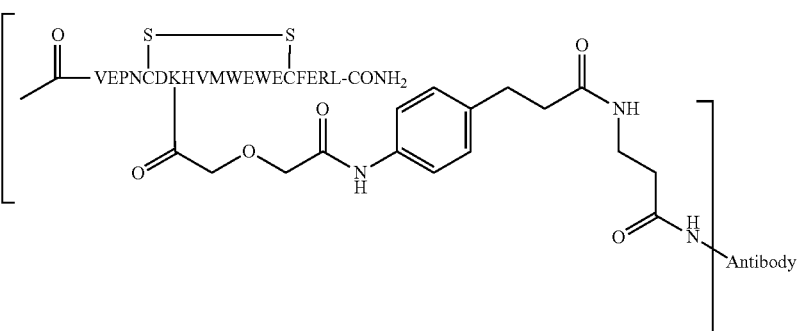 |

TABLE 10-continued
[VEGF-Peptide]-[Linker]-Antibody compounds
| Incorporates SEQ ID # | Compound # | Structure |
|---|---|---|
| 34 | 2067 | 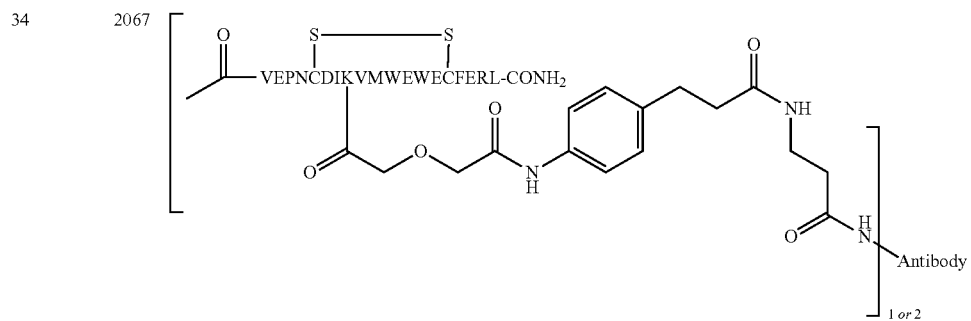 |
| 34 | 2068 | 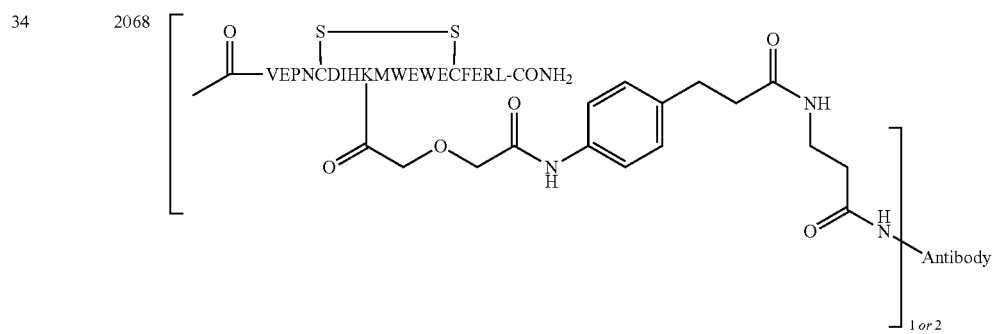 |
| 34 | 2069 | 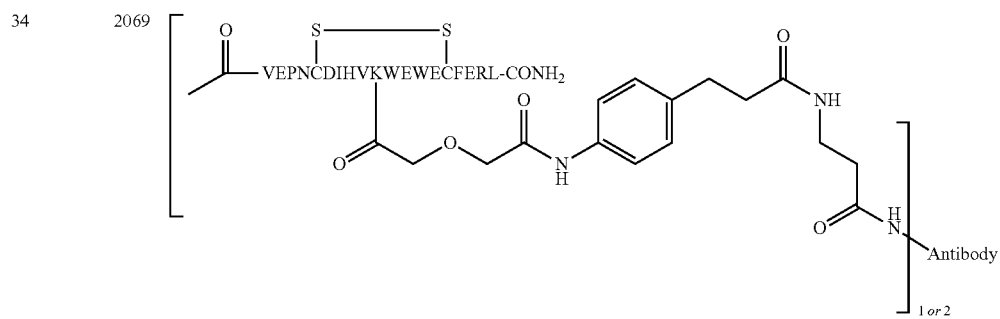 |
| 34 | 2070 | 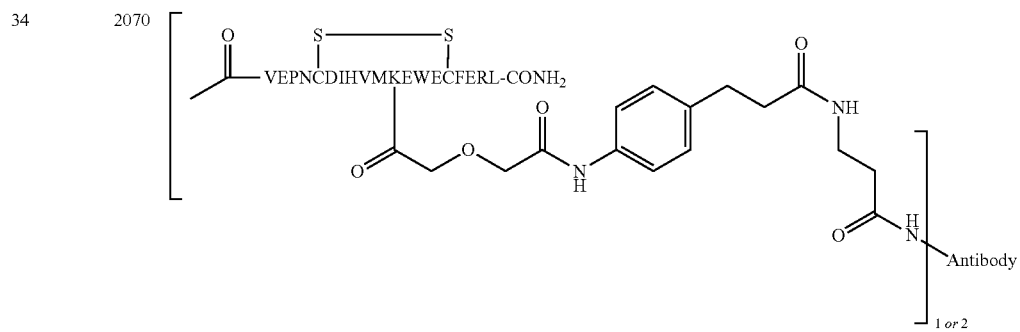 |

TABLE 10-continued
[VEGF-Peptide]-[Linker]-Antibody compounds
| Incorporates SEQ ID # | Compound # | Structure |
|---|---|---|
| 34 | 2071 | 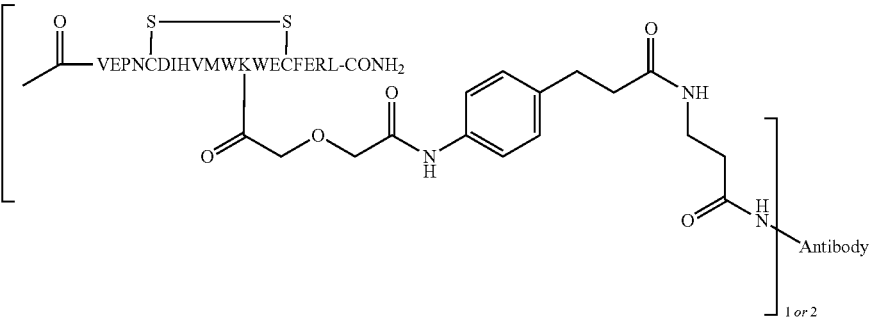 |
| 34 | 2072 | 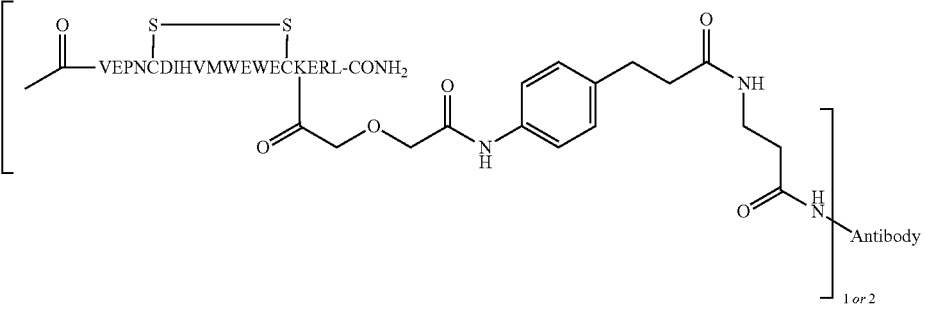 |
| 34 | 2073 | 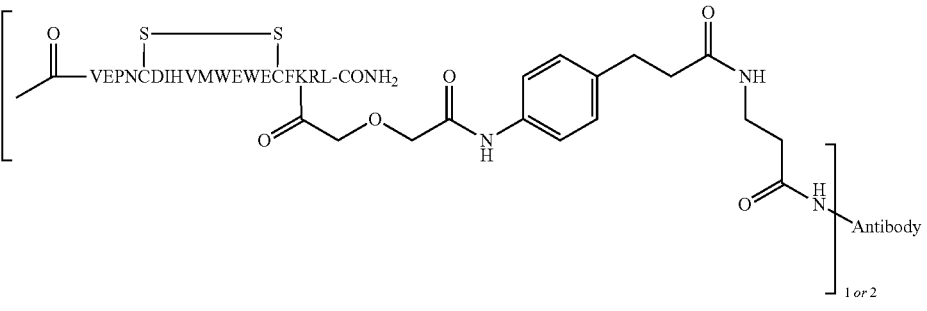 |
| 34 | 2074 | 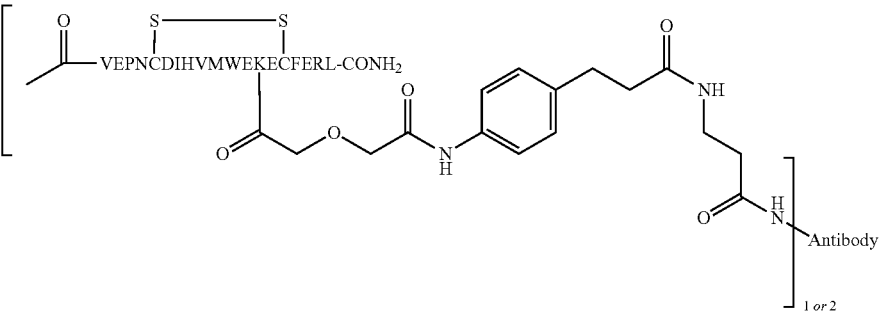 |

TABLE 10-continued
[VEGF-Peptide]-[Linker]-Antibody compounds
| Incorporates SEQ ID # | Compound # | Structure |
|---|---|---|
| 34 | 2075 | 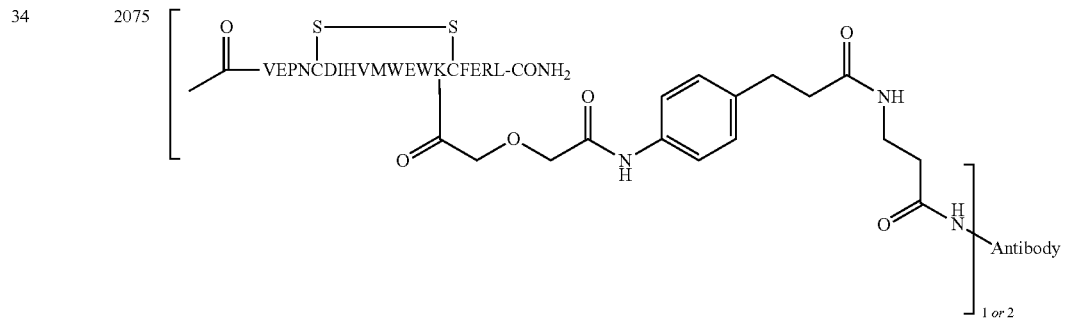 |
| 34 | 2076 | 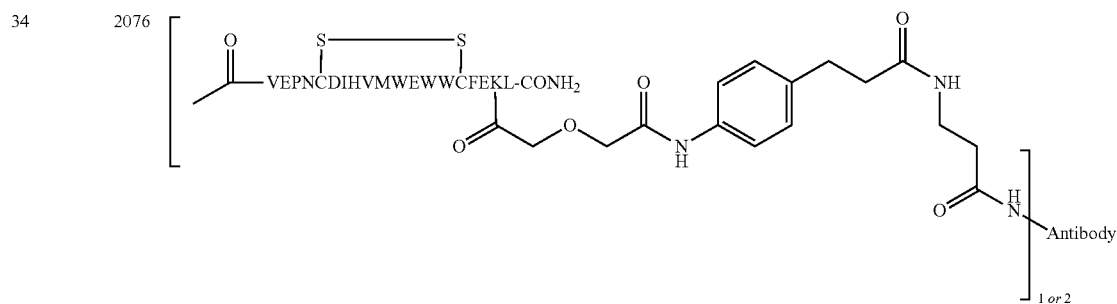 |
| 34 | 2077 | 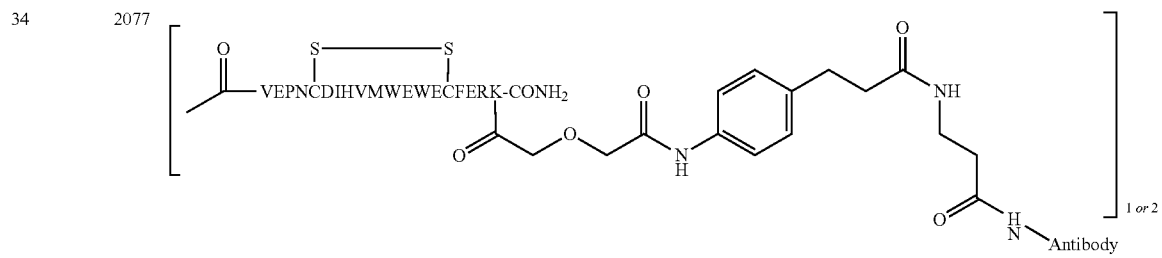 |

TABLE 10-continued
[VEGF-Peptide]-[Linker]-Antibody compounds
| Incorporates SEQ ID # | Compound # | Structure |
|---|---|---|
| 34 | 2078 | 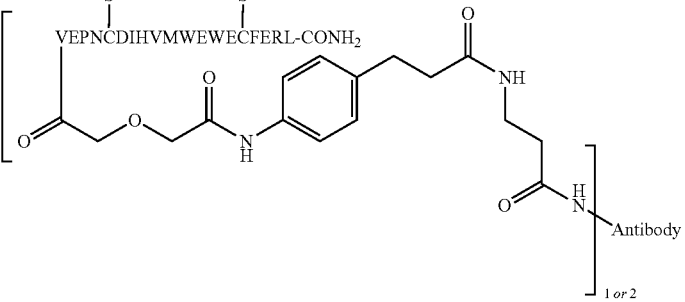 |
| 206 | 2079 | 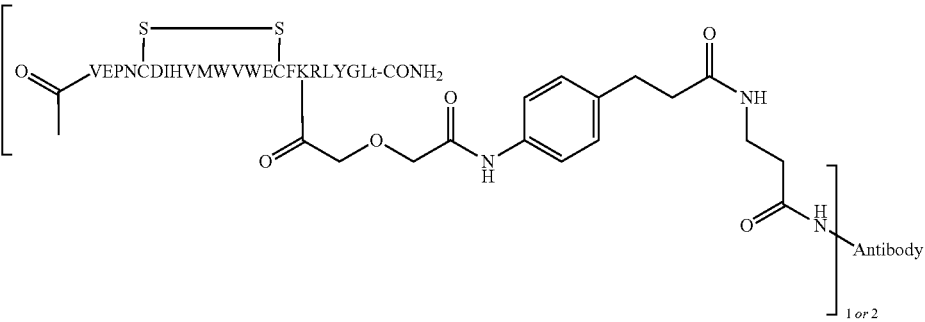 |
| 207 | 2080 | 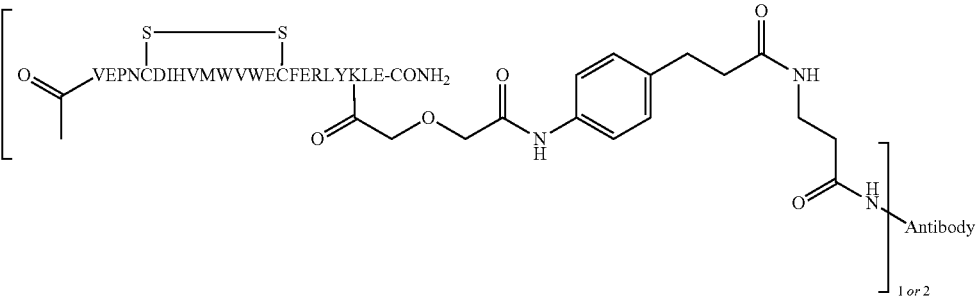 |

TABLE 11

Compounds of the invention of the formula: [Ang2-Peptide]-[Connector]-[VEGF-Peptide]

| Cmpd # | Chemical Structure |
|---|---|
| 5001 VEGF SEQ:34 | V-E-P-N-C-D-I-H-V-M-W-E-C-F-E-R-L-CONH₂ (disulfide bridge between the two C residues); linked via thioether-maleimide-PEG-amide connector to H₂NOC-G-Q-L-I-F-Q-E-Y-L-R-Q-E-L-D-D-M-P-M-F-N-T, terminated with 2-oxoazetidine-phenylpropanoyl group |
| 5002 VEGF SEQ:34 | V-E-P-N-C-D-I-H-V-M-W-E-C-F-E-R-L-CONH₂ (disulfide bridge between the two C residues); linked via thioether-maleimide-PEG-amide connector to H₂NOC-G-Q-L-I-F-Q-E-Y-L-R-Q-E-L-D-D-M-P-M-F-N-T, terminated with 2-oxoazetidine-phenylpropanoyl group |

TABLE 11-continued

Compounds of the invention of the formula: [Ang2-Peptide]-[Connector]-[VEGF-Peptide]

| Cmpd # | Chemical Structure |
|---|---|
| 5003 VEGF SEQ:34 P3, N4 are wrongly shown as N3, P4 | (structure shown) H₂NOC-L-R-EF-CE-W-E-W-M-V-H-I-DCPNE-V ... N-F-M-P-M-D-D-L-E-Q-R-L-Y-E-Q-F-I-L-Q-Q-G-CONH₂ |
| 5004 VEGF SEQ:34 | (structure shown) H₂NOC-L-R-EF-CE-W-E-W-M-V-H-I-DCN-P-EV ... T-N-F-M-P-M-D-D-L-E-Q-R-L-Y-E-Q-F-I-L-Q-Q-G-N-H |
| 5005 VEGF SEQ:34 | (structure shown) V-E-P-N-C-D-I-H-V-M-W-E-W-E-C-F-E-R-L-CONH₂ ... T-N-F-M-P-M-D-D-L-E-Q-R-L-Y-E-Q-F-I-L-L-Q-Q-G-G-G-G-K-G-G-G |

TABLE 11-continued

Compounds of the invention of the formula: [Ang2-Peptide]-[Connector]-[VEGF-Peptide]

| Cmpd # | Chemical Structure |
|---|---|
| 5006 VEGF SEQ:34 M¹⁰ subs with K as linking residue | (structure) |
| 5007 VEGF SEQ:34 M¹⁰ subs with K as linking residue | (structure) |

TABLE 11-continued

Compounds of the invention of the formula: [Ang2-Peptide]-[Connector]-[VEGF-Peptide]

| Cmpd # | Chemical Structure |
|---|---|
| 5008 VEGF SEQ:34 M¹⁰ subs with K as linking residue | V-E-P-N-C-D-I-H-V-K-W-E-W-E-C-F-E-R-L-CONH₂ ... Q-K-Y-Q-P-L-D-E-K-D-K-T-L-Y-D-Q-F-M-L-Q-Q-G-CONH₂ |
| 5009 VEGF SEQ:34 M¹⁰ subs with K as linking residue | V-E-P-N-C-D-I-H-V-K-W-E-W-E-C-F-E-R-L-CONH₂ ... Q-K-Y-Q-P-L-D-E-K-D-K-T-L-Y-D-Q-F-M-L-Q-Q-G-CONH₂ |

TABLE 11-continued

Compounds of the invention of the formula: [Ang2-Peptide]-[Connector]-[VEGF-Peptide]

| Cmpd # | Chemical Structure |
|---|---|
| 5010 VEGF SEQ:34 M$^{10}$ subs with K as linking residue | 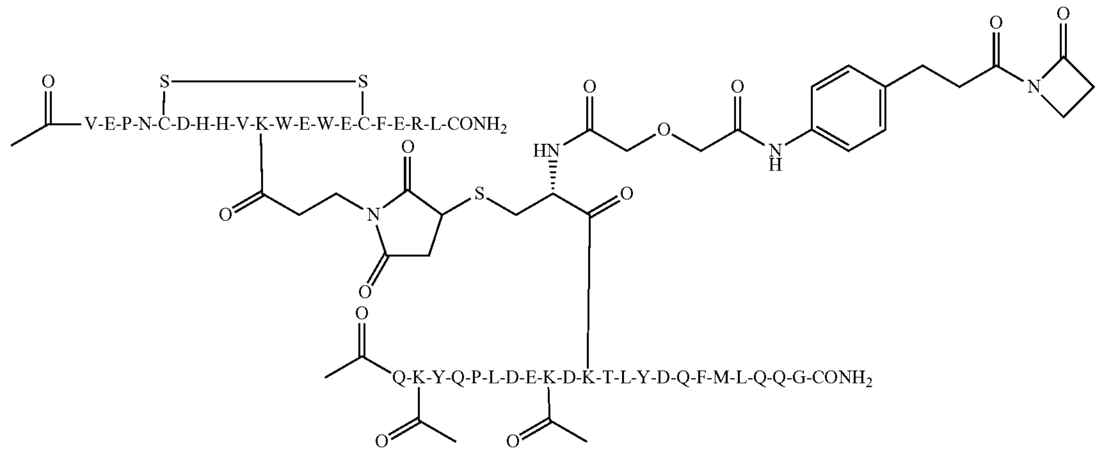 |
| 5011 VEGF SEQ:34 E$^{12}$ subs with K as linking residue | 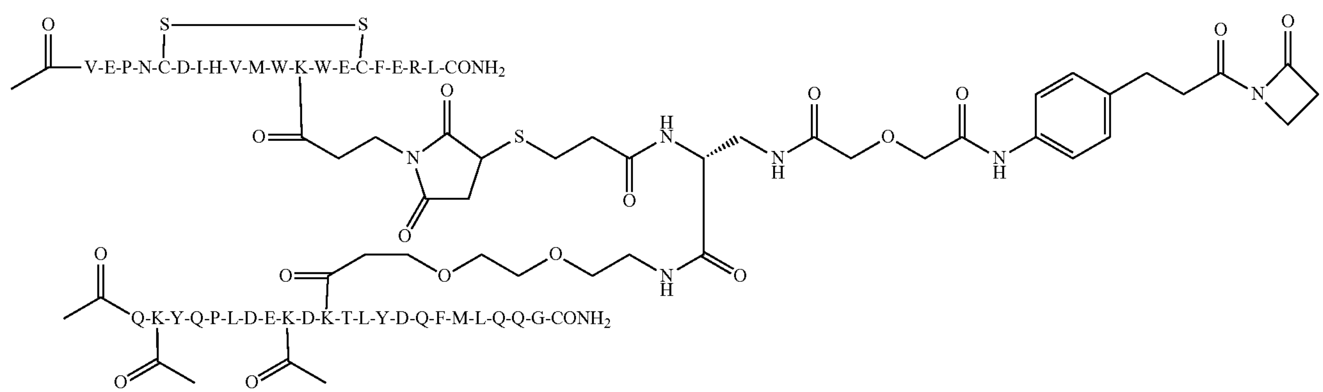 |

TABLE 11-continued

Compounds of the invention of the formula: [Ang2-Peptide]-[Connector]-[VEGF-Peptide]

| Cmpd # | Chemical Structure |
|---|---|
| 5012 VEGF SEQ:34 M[10] subs with K as linking residue | [Ang2-Peptide]: V-E-P-N-C-D-I-H-V-K-W-E-W-E-C-F-E-R-L-CONH$_2$ <br> [VEGF-Peptide]: Q-K-Y-Q-P-L-D-E-K-D-K-T-L-Y-D-Q-F-M-L-Q-Q-G-CONH$_2$ |

TABLE 11-continued
Compounds of the invention of the formula: [Ang2-Peptide]-[Connector]-[VEGF-Peptide]
| Cmpd # | Chemical Structure |
|---|---|
| 5013 VEGF SEQ:34 E$^{17}$ subs with K as linking residue | 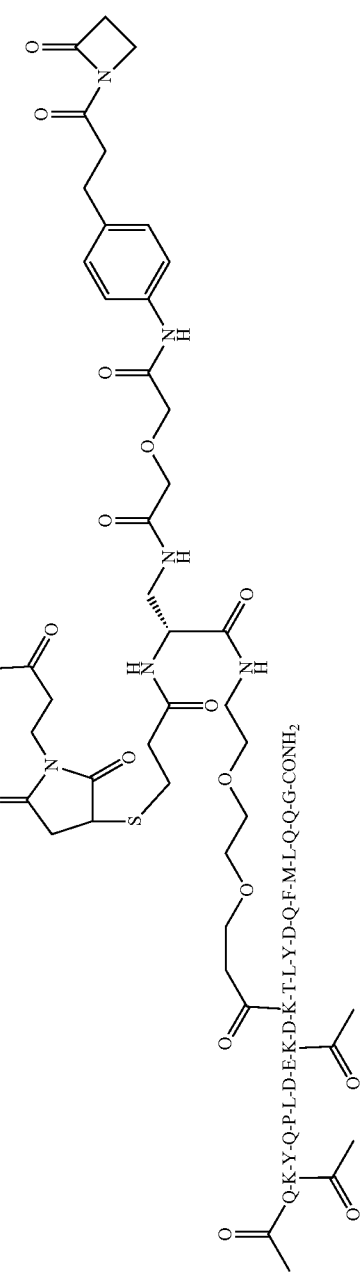 |
| 5014 VEGF SEQ:34 M$^{10}$ subs with K as linking residue | 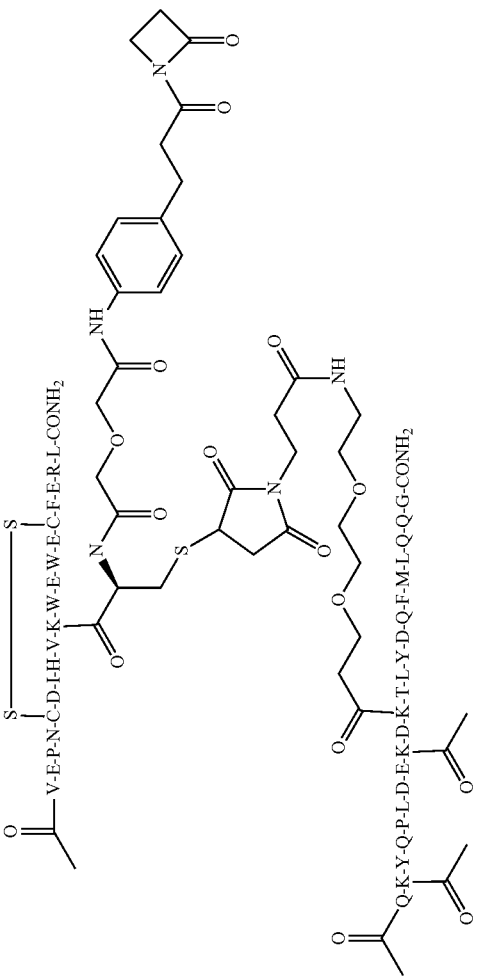 |

TABLE 11-continued

Compounds of the invention of the formula: [Ang2-Peptide]-[Connector]-[VEGF-Peptide]

| Cmpd # | Chemical Structure |
|---|---|
| 5015 VEGF SEQ:34 | (structure with Ang2 peptide H₂NOC-L-R-E-F-C-E-W-E-W-M-V-H-I-D-C-N-P-E-V linked via connector containing 2-oxoazetidine, phenyl, glycine-ether-glycine, and 2,5-dioxocyclopentyl-thioether to VEGF peptide T-N-F-M-P-M-D-D-L-E-Q-R-L-Y-E-Q-F-I-L-Q-Q-CONH₂) |
| 5016 VEGF SEQ:34 | (structure with Ang2 peptide H₂NOC-L-R-E-F-C-E-W-E-W-M-V-H-I-D-C-N-P-E-V linked via connector containing 2-oxoazetidine, phenyl, glycine amide, and succinimide-thioether to VEGF peptide T-N-F-M-P-M-D-D-L-E-Q-R-L-Y-E-Q-F-I-L-Q-Q-CONH₂) |

TABLE 11-continued

Compounds of the invention of the formula: [Ang2-Peptide]-[Connector]-[VEGF-Peptide]

| Cmpd # | Chemical Structure |
|---|---|
| 5017 VEGF SEQ:34 M¹⁰ subs with K as linking residue | Ac-V-E-P-N-C-D-I-H-V-K-W-E-W-E-C-F-E-R-L-CONH₂ (disulfide bridged), linked via PEG-maleimide-PEG to Ac,Ac-Q-K-Y-Q-P-L-D-E-K-D-K-T-L-Y-D-Q-F-M-L-Q-Q-G-CONH₂, with aryl-azetidinone conn TABLE 11-continued Compounds of the invention of the formula: [Ang2-Peptide]-[Connector]-[VEGF-Peptide]

| Cmpd # | Chemical Structure |
|---|---|
| 5018 VEGF SEQ:34 E$^{12}$ subs with K as linking residue | Ac-V-E-P-N-C-D-I-H-V-M-W-K-W-E-C-F-E-R-L-CONH$_2$ (disulfide); Ac-Q-K-Y-Q-P-L-D-E-K-D-K-T-L-Y-D-Q-F-M-L-Q-Q-CONH$_2$ with connector containing PEG linkers, succinimide/thioether, and terminal 2-oxoazetidine group |

TABLE 11-continued

Compounds of the invention of the formula: [Ang2-Peptide]-[Connector]-[VEGF-Peptide]

| Cmpd # | Chemical Structure |
|---|---|
| 5019 VEGF SEQ:34 E[17] subs with K as linking residue | V-E-P-N-C-D-I-H-V-M-W-E-W-E-C-F-K-R-L-CONH$_2$ (with disulfide bridge; connector bearing PEG, biotin-like bicyclic moiety, phenyl, and β-lactam); Ang2 peptide: Q-K-Y-Q-P-L-D-E-K-D-K-T-L-Y-D-Q-F-M-L-Q-Q-G-CONH$_2$ |
| 5020 VEGF SEQ:34 | V-E-P-N-C-D-I-H-V-M-W-E-W-E-C-F-E-R-L-COOH (with disulfide bridge); H$_2$NOC-G-Q-L-M-F-Q-D-Y-L-T-K-D-K-E-D-L-P-Q-Y-K-Q |

TABLE 11-continued

Compounds of the invention of the formula: [Ang2-Peptide]-[Connector]-[VEGF-Peptide]

| Cmpd # | Chemical Structure |
|---|---|
| 5021 VEGF SEQ:34 M[10] subs with K as linking residue | |
| 5022 VEGF SEQ:34 E[12] subs with K as linking residue | |

TABLE 11-continued

Compounds of the invention of the formula: [Ang2-Peptide]-[Connector]-[VEGF-Peptide]

| Cmpd # | Chemical Structure |
|---|---|
| 5023 VEGF SEQ:34 M[10] subs with K as linking residue | V-E-P-N-C-D-I-H-V-K-W-E-W-E-C-F-E-R-L-CONH$_2$ (disulfide bridged, N-acetyl); linked via PEG-maleimide-thioether-PEG connector to Dap-branched VEGF peptide Q-K-Y-Q-P-L-D-E-L-D-K-T-L-Y-D-Q-F-K-L-Q-Q-G-CONH$_2$ (bis-acetylated) with p-aminophenylpropanoyl-β-lactam cap |

TABLE 11-continued

Compounds of the invention of the formula: [Ang2-Peptide]-[Connector]-[VEGF-Peptide]

| Cmpd # | Chemical Structure |
|---|---|
| 5024 VEGF SEQ:34 M¹⁰ subs with K as linking residue | Ac-V-E-P-N-C-D-I-H-V-K-W-E-W-E-C-F-E-R-L-CONH₂ (with disulfide bridge between the two C residues)<br><br>Ac-Q-K-Y-Q-P-L-D-E-K-D-K-T-L-Y-D-Q-F-M-L-Q-Q-G-CONH₂ |

TABLE 11-continued

Compounds of the invention of the formula: [Ang2-Peptide]-[Connector]-[VEGF-Peptide]

| Cmpd # | Chemical Structure |
|---|---|
| 5025 VEGF SEQ:34 M¹⁰ subs with K as linking residue | Ac-V-E-P-N-C-D-I-H-V-K-W-E-W-E-C-F-E-R-L-CONH₂ (disulfide bridge between the two C residues), linked via PEG/azetidinone connector to H₂NOC-G-Q-Q-L-M-F-Q-D-Y-L-T-K-D-K-E-D-L-P-Q-Y-K-Q (with acetyl groups) |

TABLE 11-continued
Compounds of the invention of the formula: [Ang2-Peptide]-[Connector]-[VEGF-Peptide]
| Cmpd # | Chemical Structure |
|---|---|
| 5026 VEGF SEQ:208 | 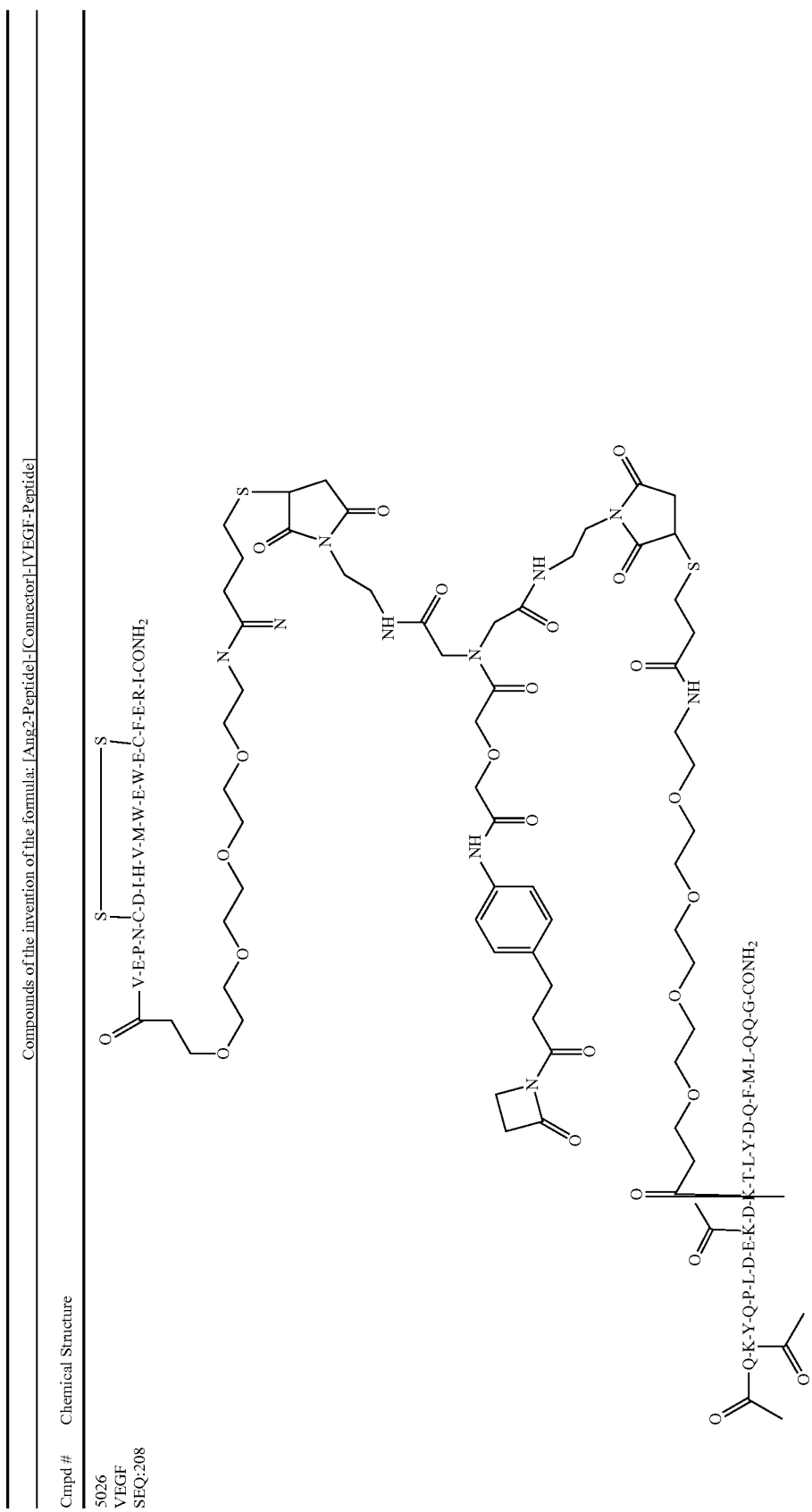 |

TABLE 11-continued

Compounds of the invention of the formula: [Ang2-Peptide]-[Connector]-[VEGF-Peptide]

| Cmpd # | Chemical Structure |
|---|---|
| 5027 VEGF SEQ:34 E[17] subs with K as linking residue | 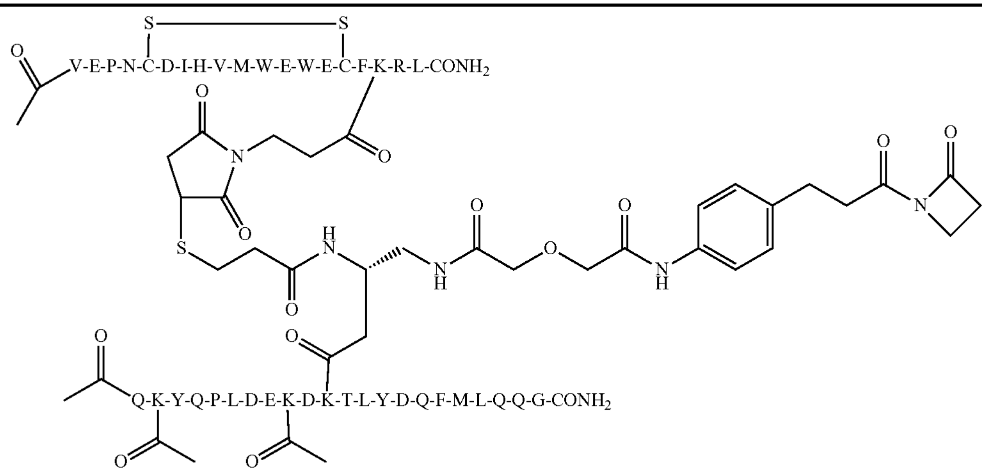 |
| 5028 VEGF SEQ:34 E[17] subs with K as linking residue | 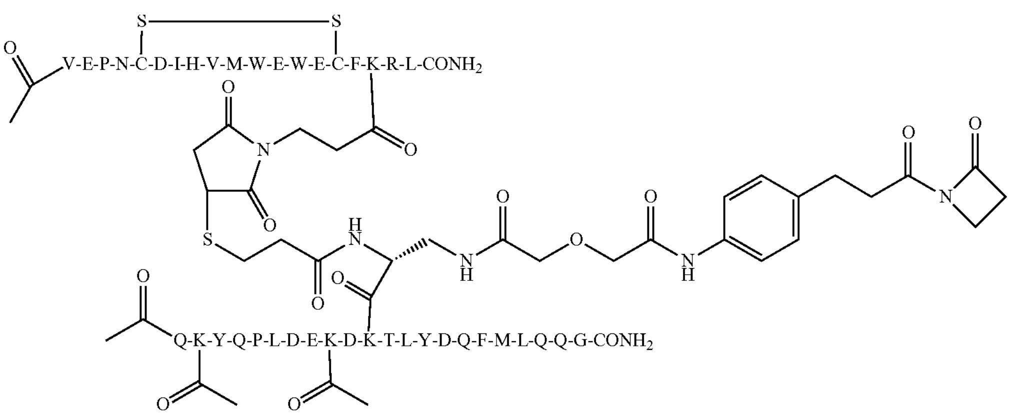 |

TABLE 11-continued

Compounds of the invention of the formula: [Ang2-Peptide]-[Connector]-[VEGF-Peptide]

| Cmpd # | Chemical Structure |
|---|---|
| 5031 VEGF SEQ:209 | |
| 5032 VEGF SEQ:78 | |

TABLE 11-continued
Compounds of the invention of the formula: [Ang2-Peptide]-[Connector]-[VEGF-Peptide]
| Cmpd # | Chemical Structure |
|---|---|
| 5033 VEGF SEQ:76 | 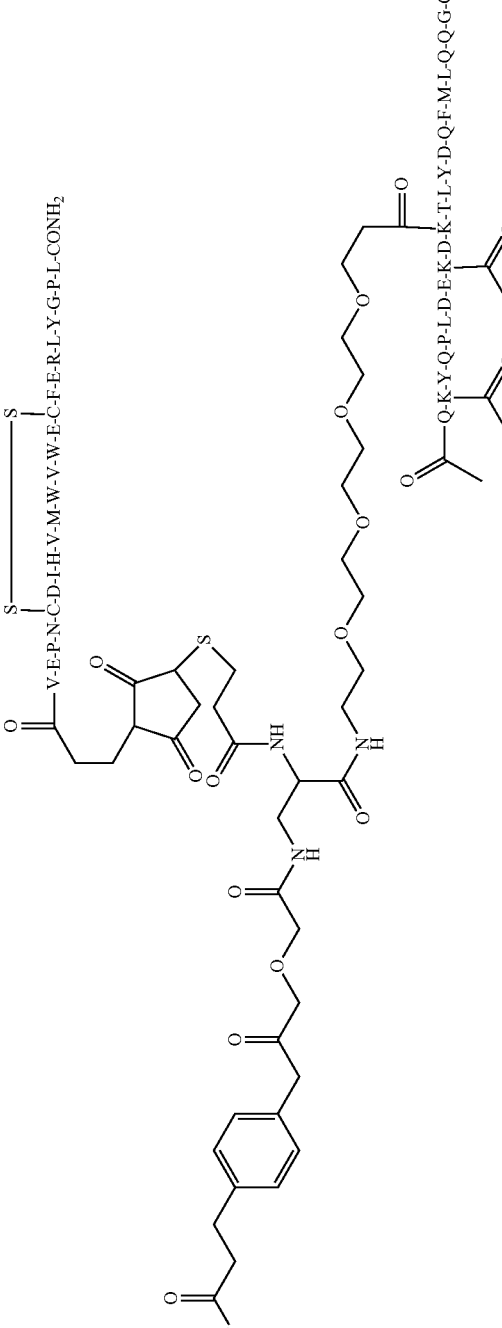 |
| 5034 VEGF SEQ:73 E$^{17}$ subs with K as linking residue | 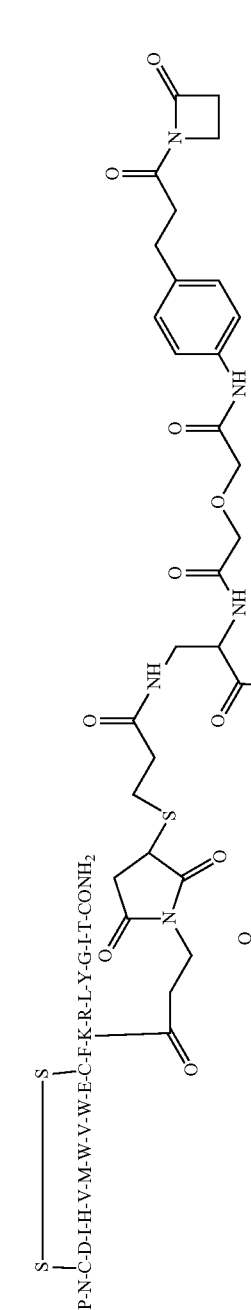 |

TABLE 11-continued
Compounds of the invention of the formula: [Ang2-Peptide]-[Connector]-[VEGF-Peptide]
| Cmpd # | Chemical Structure |
|---|---|
| 5035 VEGF SEQ:76 | 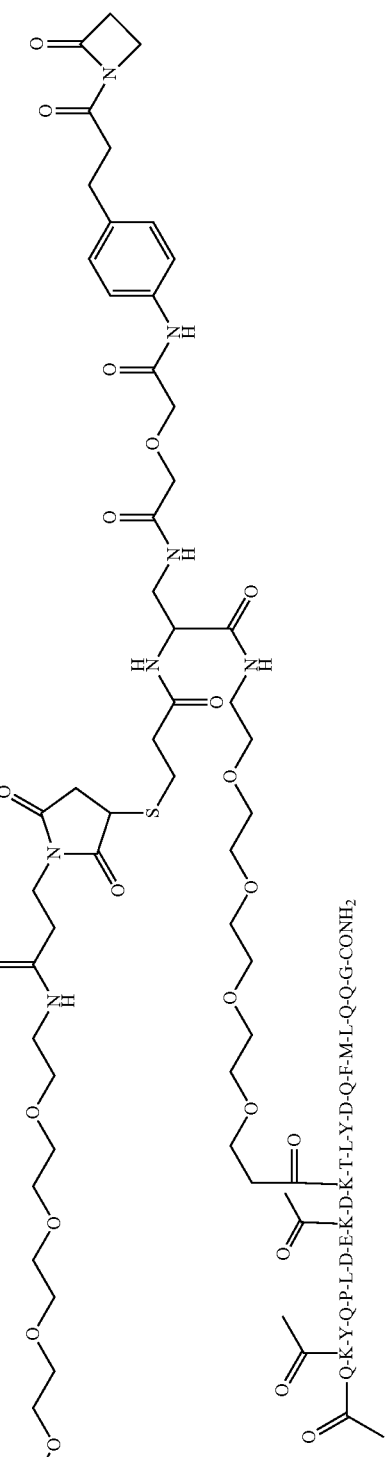 |
| 5036 VEGF SEQ:73 E[17] subs with K as linking residue | 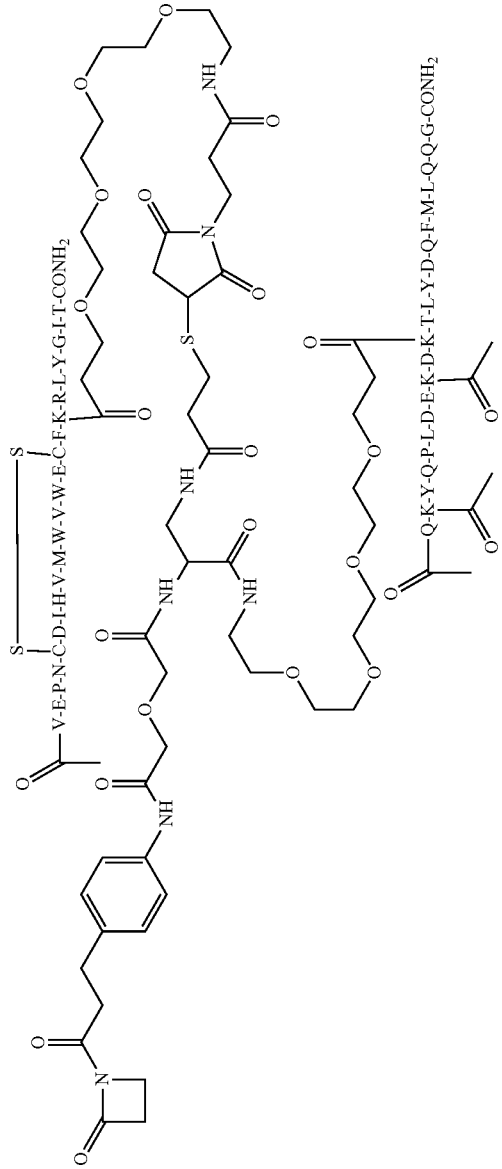 |

TABLE 11-continued

Compounds of the invention of the formula: [Ang2-Peptide]-[Connector]-[VEGF-Peptide]

| Cmpd # | Chemical Structure |
|---|---|
| 5037 VEGF SEQ:75 M[10] subs with K as linking residue | Ac-V-E-P-N-C-D-I-H-V-K-W-V-W-E-C-F-E-R-L-Y-G-L-E-CONH$_2$ (with disulfide bridge between the two C residues); linked via PEG-maleimide-PEG connector to Ac-Q-K-Y-Q-P-L-D-E-K-D-K-T-L-Y-D-Q-F-M-L-Q-Q-G-CONH$_2$ (with acetyl group), terminating in a 4-oxoazetidin-1-yl group attached via phenyl-amide-PEG linker. |
| 5038 VEGF SEQ:75 E[17] subs with K as linking residue | Ac-V-E-P-N-C-D-I-H-V-M-W-V-W-E-C-F-K-R-L-Y-G-L-E-CONH$_2$ (with disulfide bridge between the two C residues); linked via maleimide-PEG connector to Ac-Q-K-Y-Q-P-L-D-E-K-D-K-T-L-Y-D-Q-F-M-L-Q-Q-G-CONH$_2$ (with acetyl group), terminating in a 2-oxocyclobutyl group attached via phenyl-amide-PEG linker. |

TABLE 11-continued

Compounds of the invention of the formula: [Ang2-Peptide]-[Connector]-[VEGF-Peptide]

| Cmpd # | Chemical Structure |
|---|---|
| 5039 VEGF SEQ:75 E[17] subs with K as linking residue | |
| 5040 VEGF SEQ:96 E[17] subs with K as linking residue | |

TABLE 11-continued
Compounds of the invention of the formula: [Ang2-Peptide]-[Connector]-[VEGF-Peptide]
| Cmpd # | Chemical Structure |
|---|---|
| 5041 VEGF SEQ:211 | 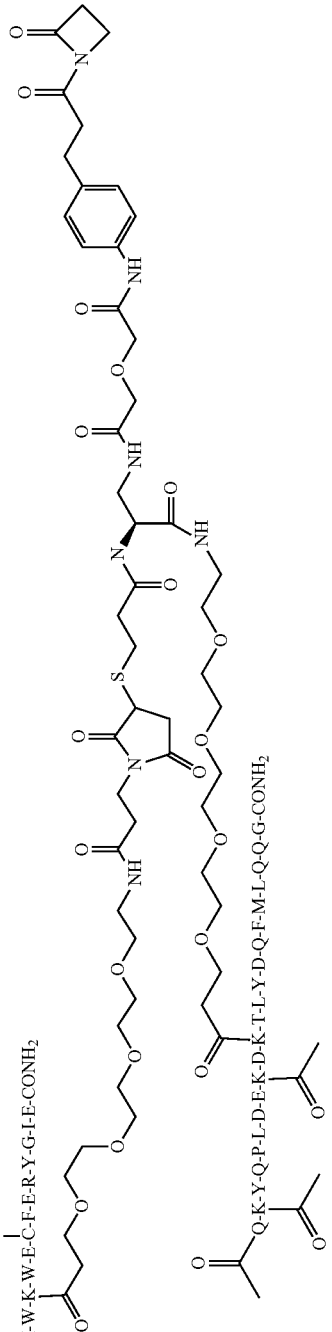 |
| 5042 VEGF SEQ:73 V$^{12}$ subs with K as linking residue | 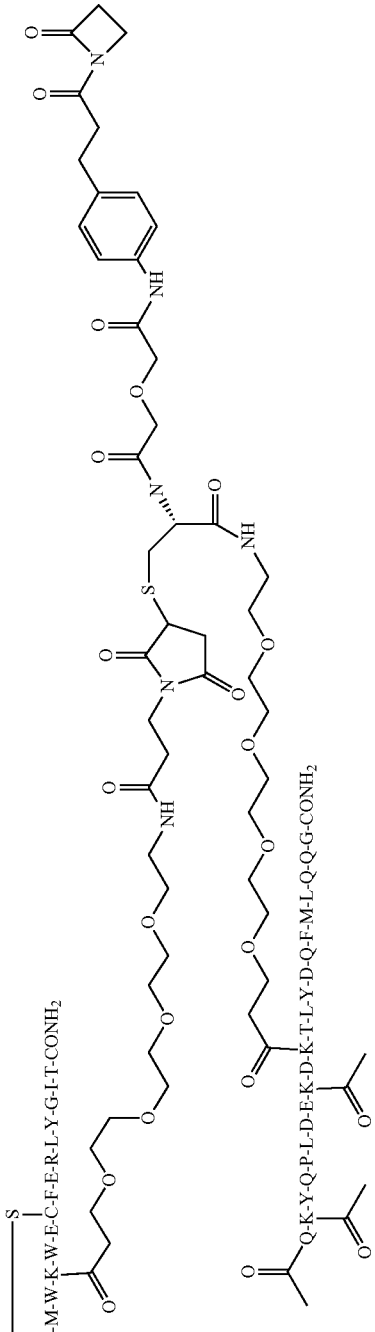 |

TABLE 11-continued

Compounds of the invention of the formula: [Ang2-Peptide]-[Connector]-[VEGF-Peptide]

| Cmpd # | Chemical Structure |
|---|---|
| 5043 VEGF SEQ:212 | V-E-P-N-C-D-I-H-V-K-W-V-W-E-C-F-E-R-L-Y-G-I-E-CONH$_2$ (disulfide); Q-K-Y-Q-P-L-D-E-K-D-K-T-L-Y-D-Q-F-M-L-Q-Q-G-CONH$_2$ |
| 5044 VEGF SEQ:212 | V-E-P-N-C-D-I-H-V-K-W-V-W-E-C-F-E-R-L-Y-G-I-E-CONH$_2$ (disulfide); Q-K-Y-Q-P-L-D-E-K-D-K-T-L-Y-D-Q-F-M-L-Q-Q-G-CONH$_2$ |

TABLE 11-continued
Compounds of the invention of the formula: [Ang2-Peptide]-[Connector]-[VEGF-Peptide]
| Cmpd # | Chemical Structure |
|---|---|
| 5045 VEGF SEQ:73 $M^{10}$ subs with K as linking residue | 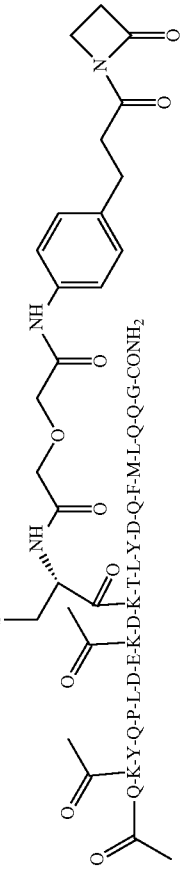 |
| 5046 VEGF SEQ:73 $V^{12}$ subs with K as linking residue | 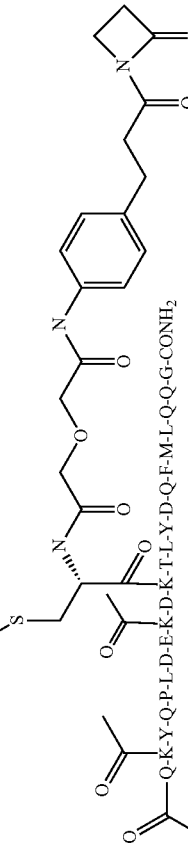 |

TABLE 11-continued

Compounds of the invention of the formula: [Ang2-Peptide]-[Connector]-[VEGF-Peptide]

| Cmpd # | Chemical Structure |
|---|---|
| 5047 VEGF SEQ:213 | V-E-P-N-C-D-I-H-V-K-W-V-W-E-C-F-E-R-L-Y-N / L-E-CONH$_2$ ... Q-K-Y-Q-P-L-D-E-K-D-K-T-L-Y-D-Q-F-M-L-Q-Q-G-CONH$_2$ |
| 5048 VEGF SEQ:214 | V-E-P-N-C-D-I-H-V-M-W-K-W-E-C-F-E-R-L-Y-N / L-E-CONH$_2$ ... Q-K-Y-Q-P-L-D-E-K-D-K-T-L-Y-D-Q-F-M-L-Q-Q-G-CONH$_2$ |

TABLE 11-continued

Compounds of the invention of the formula: [Ang2-Peptide]-[Connector]-[VEGF-Peptide]

| Cmpd # | Chemical Structure |
|---|---|
| 5049 VEGF SEQ:215 | Q-K-Y-Q-P-L-D-E-K-D-K-T-L-Y-D-Q-F-M-L-Q-Q-G-CONH₂<br>V-E-P-N-C-D-I-H-V-M-W-K-W-E-C-F-E-R-LIK-CONH₂ |

TABLE 11-continued

Compounds of the invention of the formula: [Ang2-Peptide]-[Connector]-[VEGF-Peptide]

| Cmpd # | Chemical Structure |
|---|---|
| 5050 VEGF SEQ:79 V$^{12}$ subs with K as linking residue | Ac-V-E-P-N-C-D-I-H-V-M-W-K-W-E-C-F-E-R-L-I-K-CONH$_2$ (disulfide C-C); linker via K to maleimide-PEG-amide cysteine thioether core, branched to Ac-Q-K-Y-Q-P-L-D-E-K-D-K-T-L-Y-D-Q-F-M-L-Q-Q-G-CONH$_2$ via PEG linker and to 4-aminophenyl-propanoyl-azetidinone cap |

TABLE 11-continued

Compounds of the invention of the formula: [Ang2-Peptide]-[Connector]-[VEGF-Peptide]

| Cmpd # | Chemical Structure |
|---|---|
| 5051 VEGF SEQ:79 V$_{12}$ subs with K as linking residue | |

Ac-V-E-P-N-C-D-I-H-V-M-W-K-W-E-C-F-E-R-LIK-CONH$_2$ (with disulfide bridge between the two C residues, and the K side chain linked via amide to a PEG-maleimide-Cys connector)

Ac-Q-K-Y-Q-P-L-D-E-K-D-K-T-L-Y-D-Q-F-M-L-Q-Q-G-CONH$_2$ (linked via side chain to the connector terminating in an azetidinone via a phenyl-glycolamide linker)

TABLE 11-continued

Compounds of the invention of the formula: [Ang2-Peptide]-[Connector]-[VEGF-Peptide]

| Cmpd # | Chemical Structure |
|---|---|
| 5052 VEGF SEQ:79 V¹² subs with K as linking residue | Ang2-Peptide: Ac-V-E-P-N-C-D-I-H-V-K-W-V-W-E-C-F-E-R-LIK-CONH₂ (disulfide bridge between the two C residues); VEGF-Peptide: Ac-Q-K-Y-Q-P-L-D-E-K-D-K-T-L-Y-D-Q-F-M-L-Q-Q-G-CONH₂; connected via PEG-maleimide-Cys linker bearing a 4-aminophenyl-propionyl-azetidinone group |

TABLE 11-continued
Compounds of the invention of the formula: [Ang2-Peptide]-[Connector]-[VEGF-Peptide]
| Cmpd # | Chemical Structure |
|---|---|
| 5053 VEGF SEQ:78 M¹⁰ subs with K as linking residue | 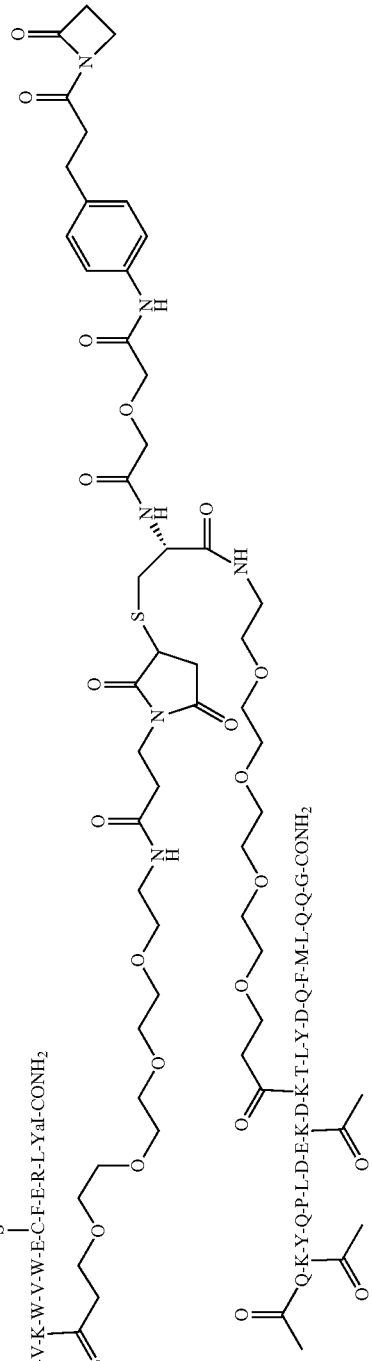 |

TABLE 11-continued
Compounds of the invention of the formula: [Ang2-Peptide]-[Connector]-[VEGF-Peptide]
| Cmpd # | Chemical Structure |
|---|---|
| 5054 VEGF SEQ:79 $V^1$ subs with K as linking residue | 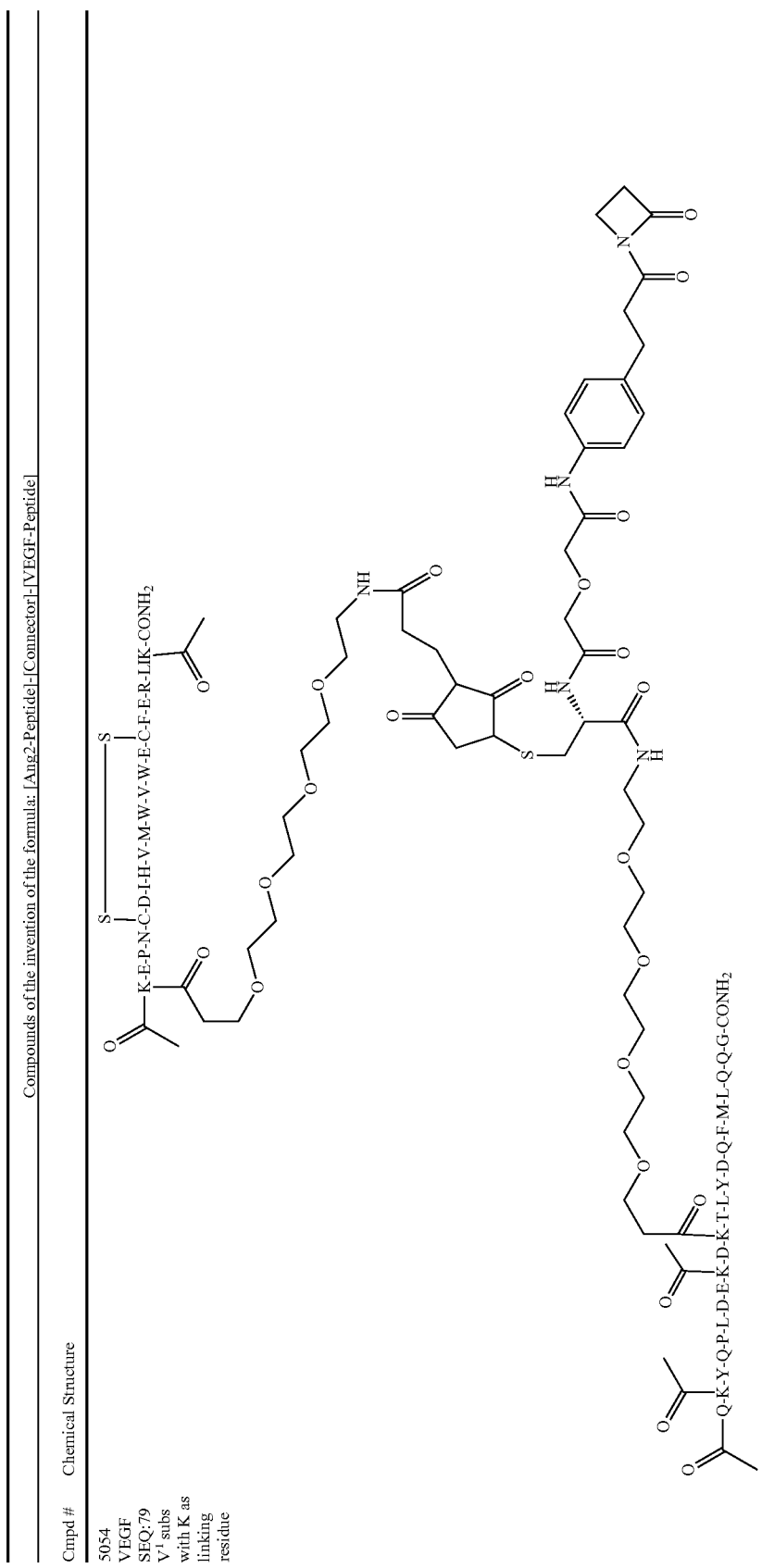 |

TABLE 11-continued

Compounds of the invention of the formula: [Ang2-Peptide]-[Connector]-[VEGF-Peptide]

| Cmpd # | Chemical Structure |
|---|---|
| 5055 VEGF SEQ:79 $V^1$ subs with K as linking residue | V-E-P-N-C-D-I-H-V-M-W-V-W-E-C-F-E-R-LIK-CONH$_2$ (disulfide bridge); Q-K-Y-Q-P-L-D-E-K-D-K-T-L-Y-D-Q-F-M-L-Q-Q-G-CONH$_2$ |

TABLE 11-continued

Compounds of the invention of the formula: [Ang2-Peptide]-[Connector]-[VEGF-Peptide]

| Cmpd # | Chemical Structure |
|---|---|
| 5056 VEGF SEQ:79 $V^{12}$ subs with K as linking residue | V-E-P-N-C-D-I-H-V-M-W-K-W-E-C-F-E-R-LIK-CONH$_2$ (disulfide bridged); linked via PEG-maleimide-Cys connector with azetidinone aryl group to Q-K-Y-Q-P-L-D-E-L-D-K-T-L-Y-D-Q-F-K-L-Q-Q-G-CONH$_2$ |

TABLE 11-continued

Compounds of the invention of the formula: [Ang2-Peptide]-[Connector]-[VEGF-Peptide]

| Cmpd # | Chemical Structure |
|---|---|
| 5057 VEGF SEQ:79 $V^{12}$ subs with K as linking residue | 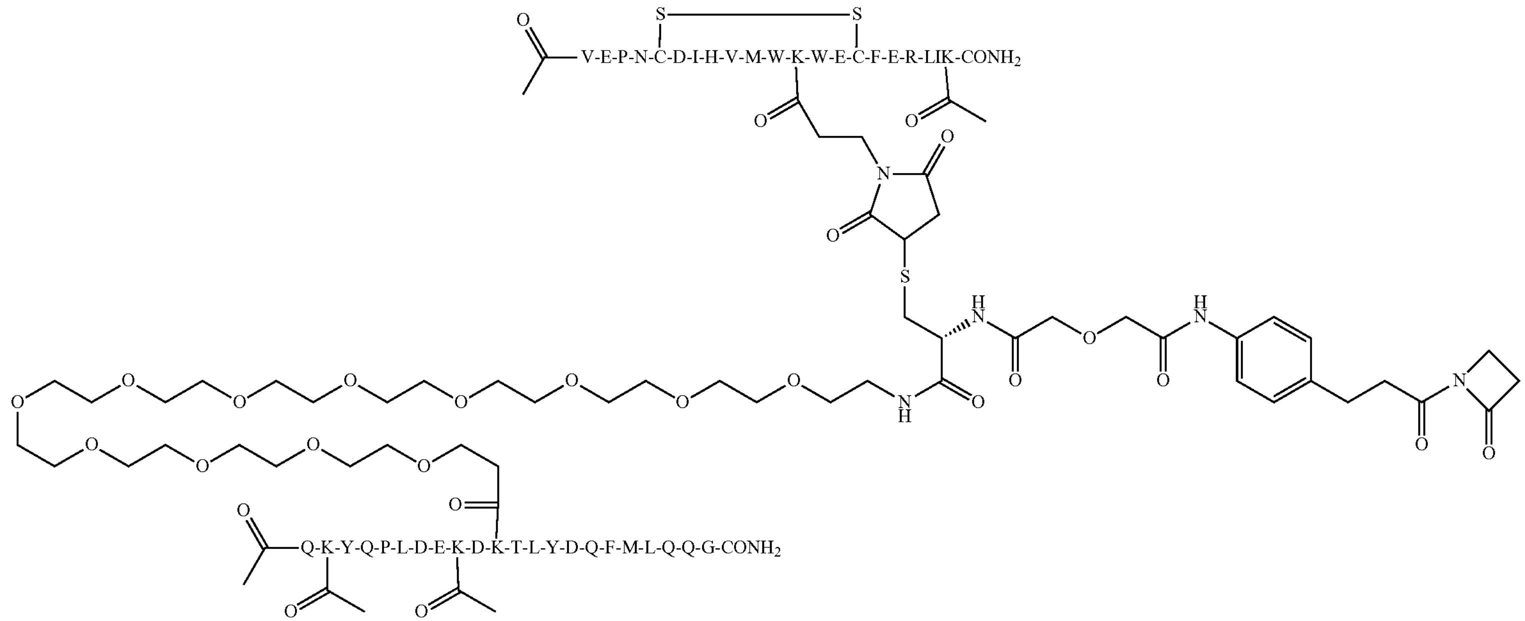 |

TABLE 11-continued

Compounds of the invention of the formula: [Ang2-Peptide]-[Connector]-[VEGF-Peptide]

| Cmpd # | Chemical Structure |
|---|---|
| 5058 VEGF SEQ:79 $V^{12}$ subs with K as linking residue | Ac-V-E-P-N-C-D-I-H-V-M-W-K-W-E-C-F-E-R-LIK-CONH$_2$ (disulfide), linked via PEG-maleimide-Cys to Ac-Q-K-Y-Q-P-L-D-E-K-D-K-T-L-Y-D-Q-F-M-L-Q-Q-G-CONH$_2$ with azetidinone-phenyl terminus |

TABLE 11-continued
Compounds of the invention of the formula: [Ang2-Peptide]-[Connector]-[VEGF-Peptide]
| Cmpd # | Chemical Structure |
|---|---|
| 5059 VEGF SEQ:79 $V^{12}$ subs with K as linking residue | 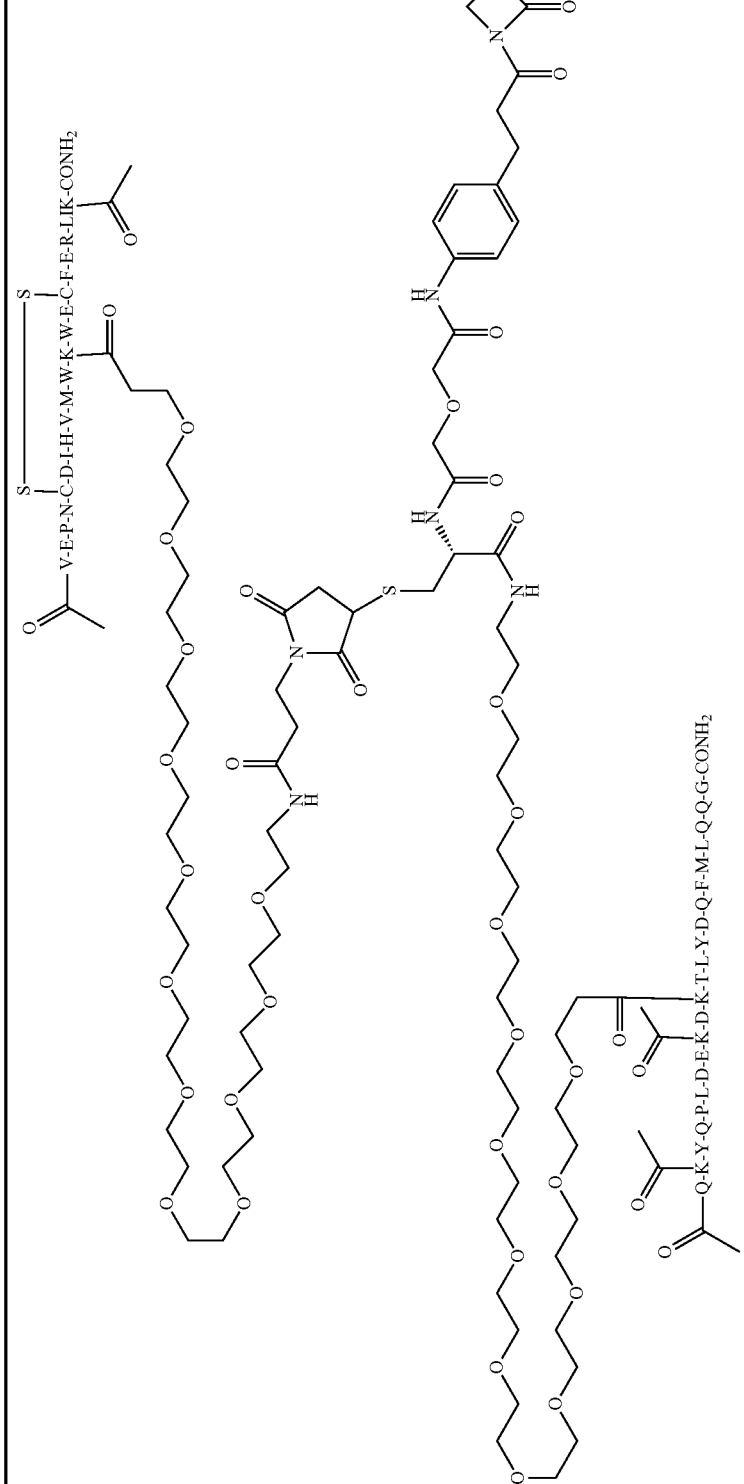 |

TABLE 11-continued

Compounds of the invention of the formula: [Ang2-Peptide]-[Connector]-[VEGF-Peptide]

| Cmpd # | Chemical Structure |
|---|---|
| 5060 VEGF SEQ:78 M¹⁰ subs with K as linking residue | |
| 5061 VEGF SEQ:78 M¹⁰ subs with K as linking residue | |

TABLE 11-continued

Compounds of the invention of the formula: [Ang2-Peptide]-[Connector]-[VEGF-Peptide]

| Cmpd # | Chemical Structure |
|---|---|
| 5062 VEGF SEQ:78 M¹⁰ subs with K as linking residue | V-E-P-N-C-D-I-H-V-K-W-V-W-E-C-F-E-R-L-YaI-CONH₂ (Ang2 peptide) linked via maleimide-PEG-connector to Q-K-Y-Q-P-L-D-E-K-D-K-T-L-Y-D-Q-F-M-L-Q-Q-G-CONH₂ (VEGF peptide) with 2-oxoazetidine terminated aryl cap |
| 5063 VEGF SEQ:89 M¹⁰ subs with K as linking residue | V-E-P-N-C-D-I-H-V-K-W-V-W-E-C-F-E-R-L-YGpL-CONH₂ (Ang2 peptide) linked via maleimide-PEG-connector to Q-K-Y-Q-P-L-D-E-K-D-K-T-L-Y-D-Q-F-M-L-Q-Q-G-CONH₂ (VEGF peptide) with 2-oxoazetidine terminated aryl cap |

TABLE 11-continued

Compounds of the invention of the formula: [Ang2-Peptide]-[Connector]-[VEGF-Peptide]

| Cmpd # | Chemical Structure |
|---|---|
| 5064 VEGF SEQ:90 M¹⁰ subs with K as linking residue | Ac-Q-K-Y-Q-P-L-D-E-K-D-K-T-L-Y-D-Q-F-M-L-Q-Q-G-CONH₂ / Ac-V-E-P-N-C-D-I-H-V-K-W-V-W-E-C-F-E-R-L-YaVq-CONH₂ |
| 5070 VEGF SEQ:216 | Ac-Q-K-Y-Q-P-L-D-E-K-D-K-T-L-Y-D-Q-F-M-L-Q-Q-G-CONH₂ / Ac-V-E-P-N-C-D-I-H-V-K-W-V-W-E-C-F-E-K-L-Y-a-I-CONH₂ |

TABLE 11-continued

Compounds of the invention of the formula: [Ang2-Peptide]-[Connector]-[VEGF-Peptide]

| Cmpd # | Chemical Structure |
|---|---|
| 5071 VEGF SEQ:217 | |
| 5072 VEGF SEQ:218 | |

TABLE 11-continued
Compounds of the invention of the formula: [Ang2-Peptide]-[Connector]-[VEGF-Peptide]
| Cmpd # | Chemical Structure |
|---|---|
| 5073 VEGF SEQ:210 | 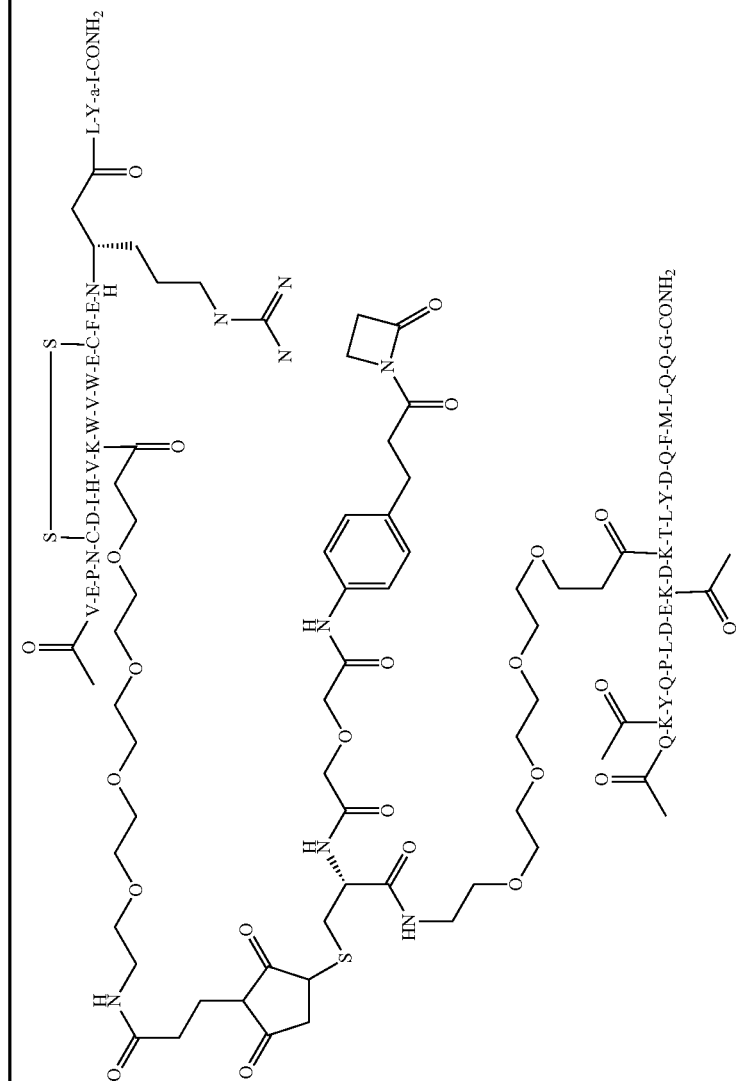 |

TABLE 11-continued

Compounds of the invention of the formula: [Ang2-Peptide]-[Connector]-[VEGF-Peptide]

| Cmpd # | Chemical Structure |
|---|---|
| 5074 VEGF SEQ:73 | Q-K-Y-Q-P-L-D-E-K-D-K-T-L-Y-D-Q-F-M-L-Q-Q-G-CONH$_2$ <br> V-E-P-N-C-D-I-H-V-M-W-M-W-E-C-F-E-R-L-I-K-CONH$_2$ |

TABLE 12
{[(Ang2-Peptide]-[Connector]-[VEGF-Peptide])$_{1 or 2}$}-[Antibody]
| Cmpd # | Chemical Structure |
|---|---|
| 6001 VEGF SEQ: 34 | 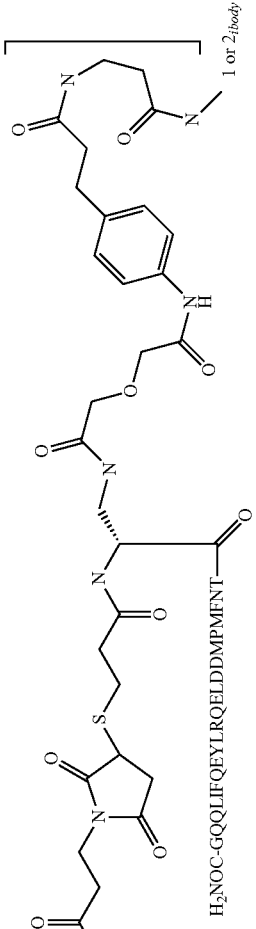 |
| 6002 VEGF SEQ: 34 | 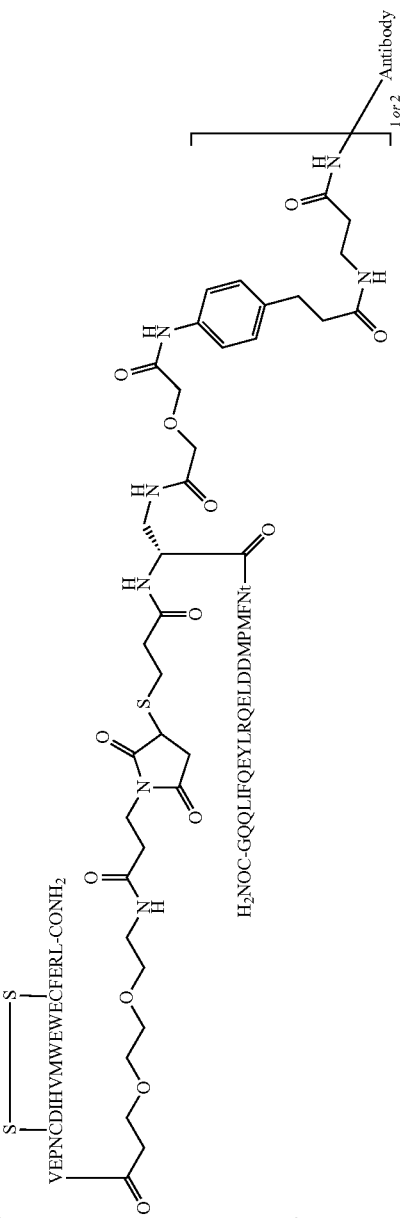 |

TABLE 12-continued
{([Ang2-Peptide]-[Connector]-[VEGF-Peptide])₁ ₒᵣ ₂}-[Antibody]
| Cmpd # | Chemical Structure |
|---|---|
| 6003 VEGF SEQ: 34 | 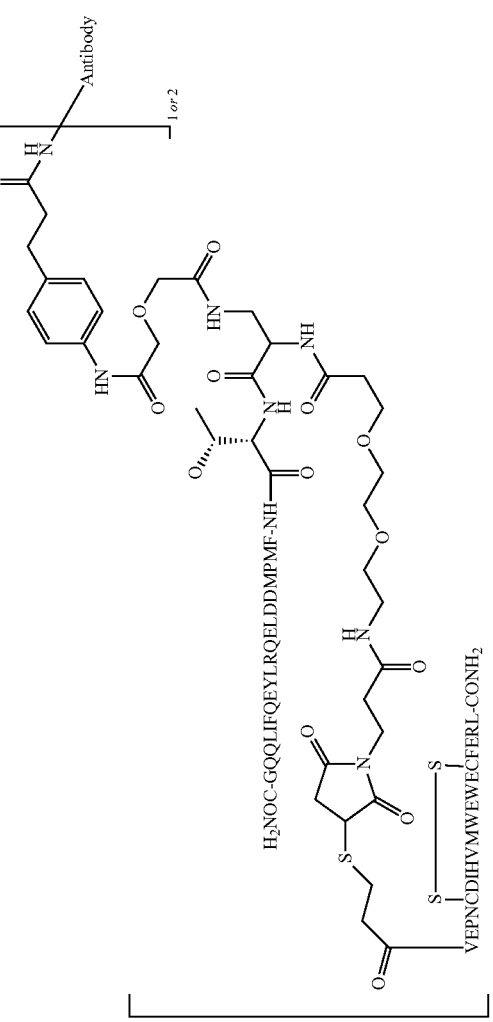 |
| 6004 VEGF SEQ: 34 | 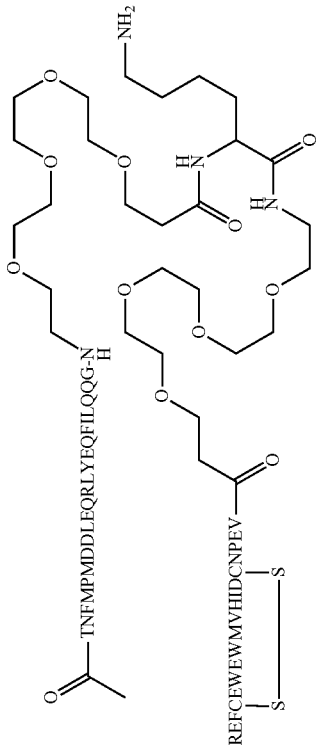 |
| 6005 VEGF SEQ: 34 | 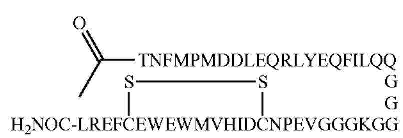 |

TABLE 12-continued

{[[Ang2-Peptide]-[Connector]-[VEGF-Peptide])₁ₒᵣ₂}-[Antibody]

| Cmpd # | Chemical Structure |
|---|---|
| 6006 VEGF SEQ: 34 M¹⁰ subs with K as linking residue | |
| 6007 VEGF SEQ: 34 M¹⁰ subs with K as linking residue | |

TABLE 12-continued

{([Ang2-Peptide]-[Connector]-[VEGF-Peptide])$_{1 or 2}$}-[Antibody]

| Cmpd # | Chemical Structure |
|---|---|
| 6008 VEGF SEQ: 34 M$^{1o}$ subs with K as linking residue | |
| 6009 VEGF SEQ: 34 M$^{1o}$ subs with K as linking residue | |

TABLE 12-continued
{[[Ang2-Peptide]-[Connector]-[VEGF-Peptide]]₁ or ₂}-[Antibody]
| Cmpd # | Chemical Structure |
|---|---|
| 6010 VEGF SEQ: 34 M¹⁰ subs with K as linking residue | 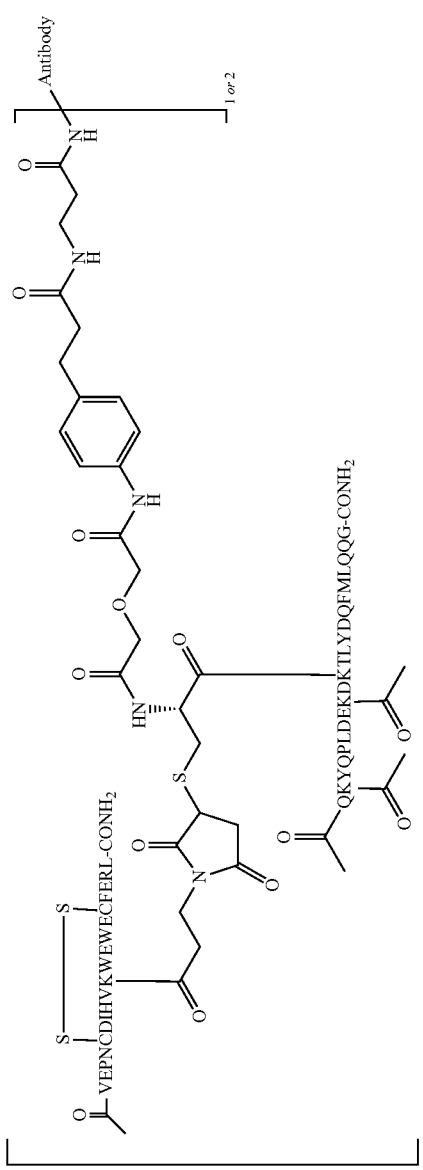 |
| 6011 VEGF SEQ: 34 E¹² subs with K as linking residue | 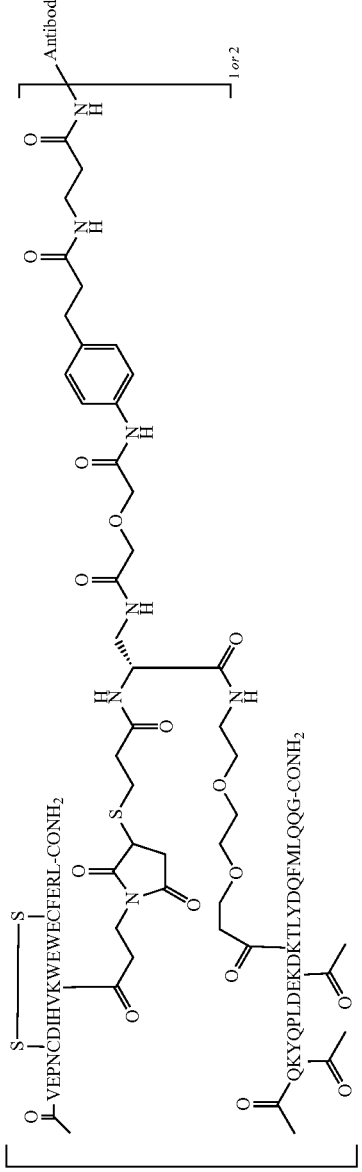 |

TABLE 12-continued
{[[Ang2-Peptide]-[Connector]-[VEGF-Peptide]]$_{1 or 2}$}-[Antibody]
| Cmpd # | Chemical Structure |
|---|---|
| 6012 VEGF SEQ: 34 M$^{10}$ subs with K as linking residue | 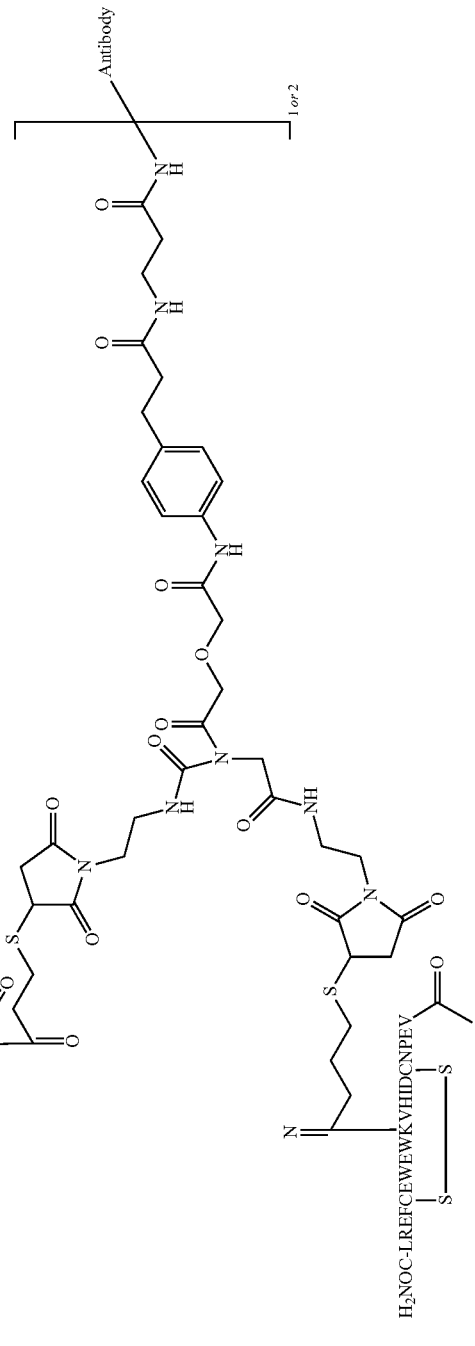 |

TABLE 12-continued

{[[Ang2-Peptide]-[Connector]-[VEGF-Peptide]]₁ₒᵣ₂}-[Antibody]

| Cmpd # | Chemical Structure |
|---|---|
| 6013 VEGF SEQ: 34 E¹⁷ subs with K as linking residue | |
| 6014 VEGF SEQ: 34 M¹⁰ subs with K as linking residue | |

TABLE 12-continued
{([Ang2-Peptide]-[Connector]-[VEGF-Peptide])₁ₒᵣ₂}-[Antibody]
| Cmpd # | Chemical Structure |
|---|---|
| 6015 VEGF SEQ: 34 | 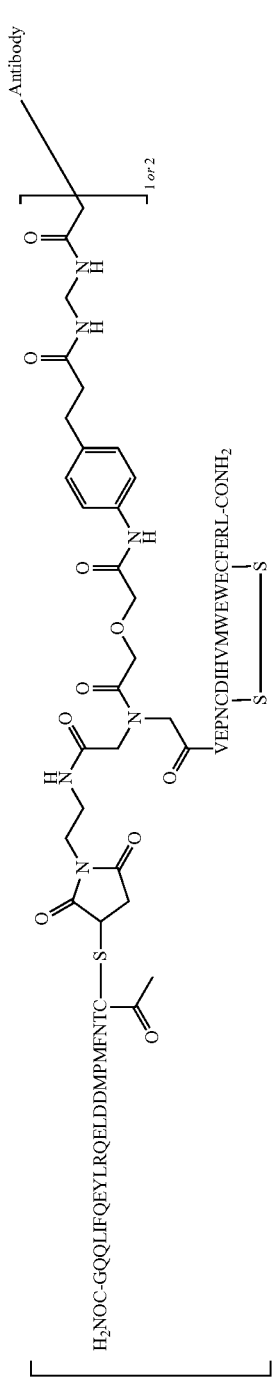 |
| 6016 VEGF SEQ: 34 | 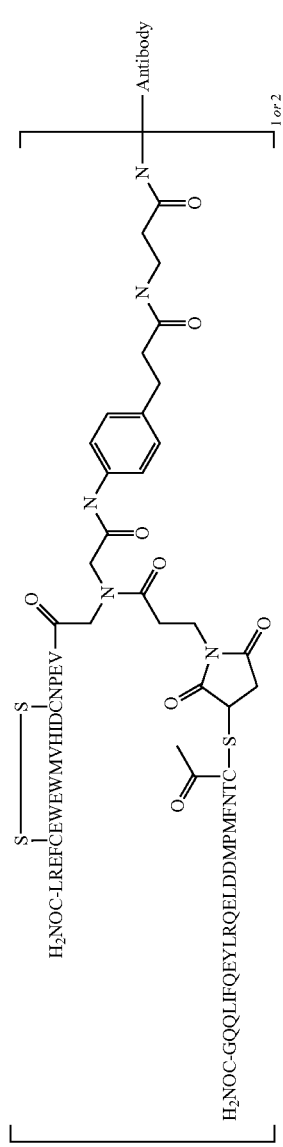 |

TABLE 12-continued

{([Ang2-Peptide]-[Connector]-[VEGF-Peptide])₁ₒᵣ₂}-[Antibody]

| Cmpd # | Chemical Structure |
|---|---|
| 6017 VEGF SEQ: 34 M¹⁰ subs with K as linking residue | (structure shown) |

VEPNCDIHVKWEWECFERL-CONH₂

QKYQPLDEKDKTLYDQFMLQQG-CONH₂

TABLE 12-continued
{[[Ang2-Peptide]-[Connector]-[VEGF-Peptide]]$_{1 or 2}$}-[Antibody]
| Cmpd # | Chemical Structure |
|---|---|
| 6018 VEGF SEQ: 34 $E^{12}$ subs with K as linking residue | 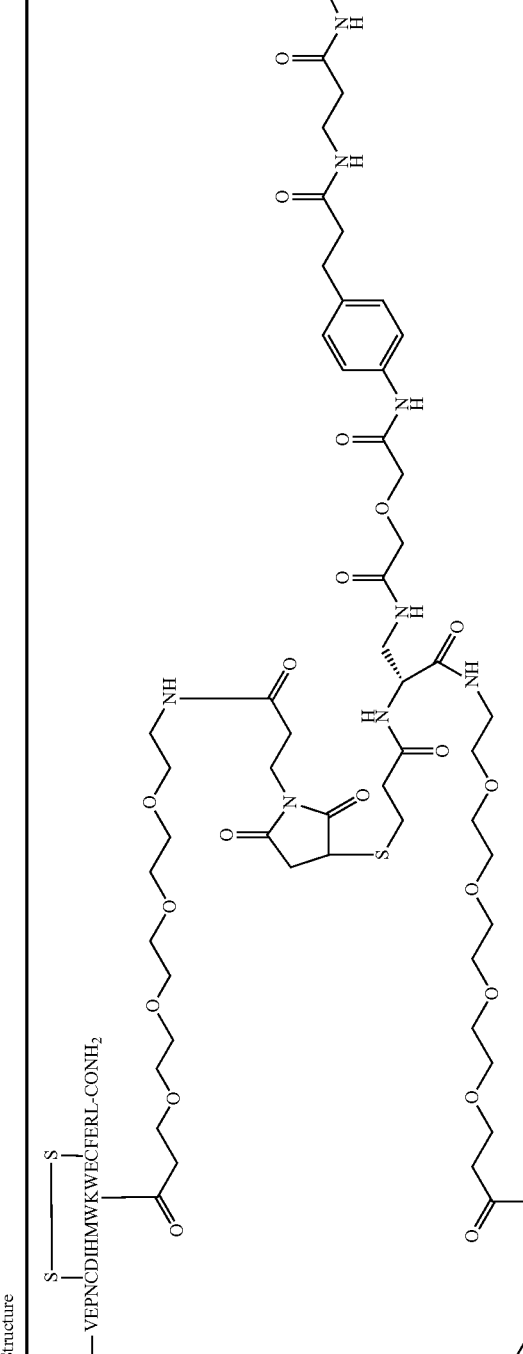 |

TABLE 12-continued

{[[Ang2-Peptide]-[Connector]-[VEGF-Peptide]]$_{1 or 2}$}-[Antibody]

| Cmpd # | Chemical Structure |
|---|---|
| 6019 VEGF SEQ: 34 E$^{17}$ subs with K as linking residue | 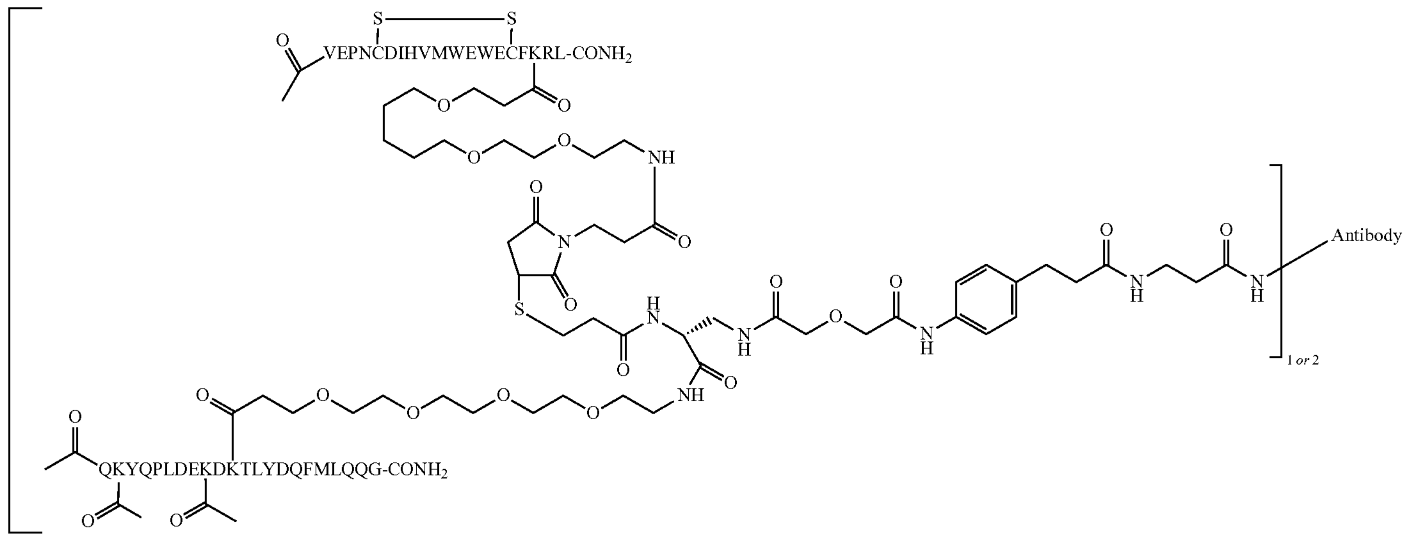 |
| 6020 VEGF SEQ: 34 | 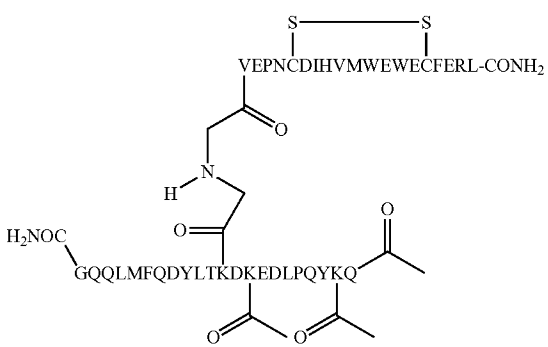 |

TABLE 12-continued

{[[Ang2-Peptide]-[Connector]-[VEGF-Peptide]]$_{1 or 2}$}-[Antibody]

| Cmpd # | Chemical Structure |
|---|---|
| 6021 VEGF SEQ: 34 M$^{10}$ subs with K as linking residue | 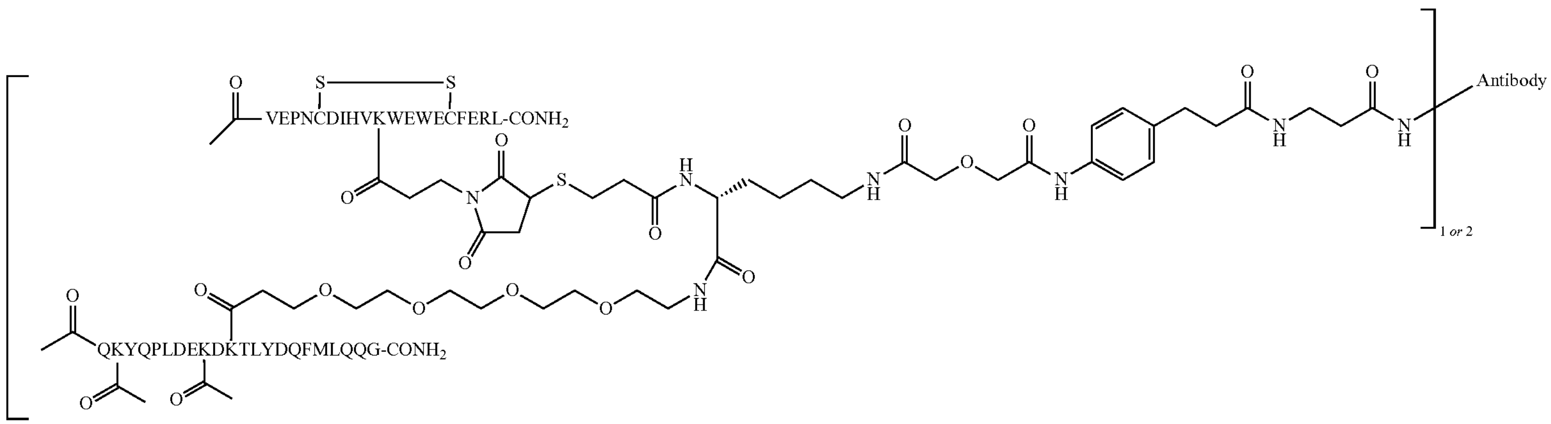 |
| 6022 VEGF SEQ: 34 E$^{12}$ subs with K as linking residue | 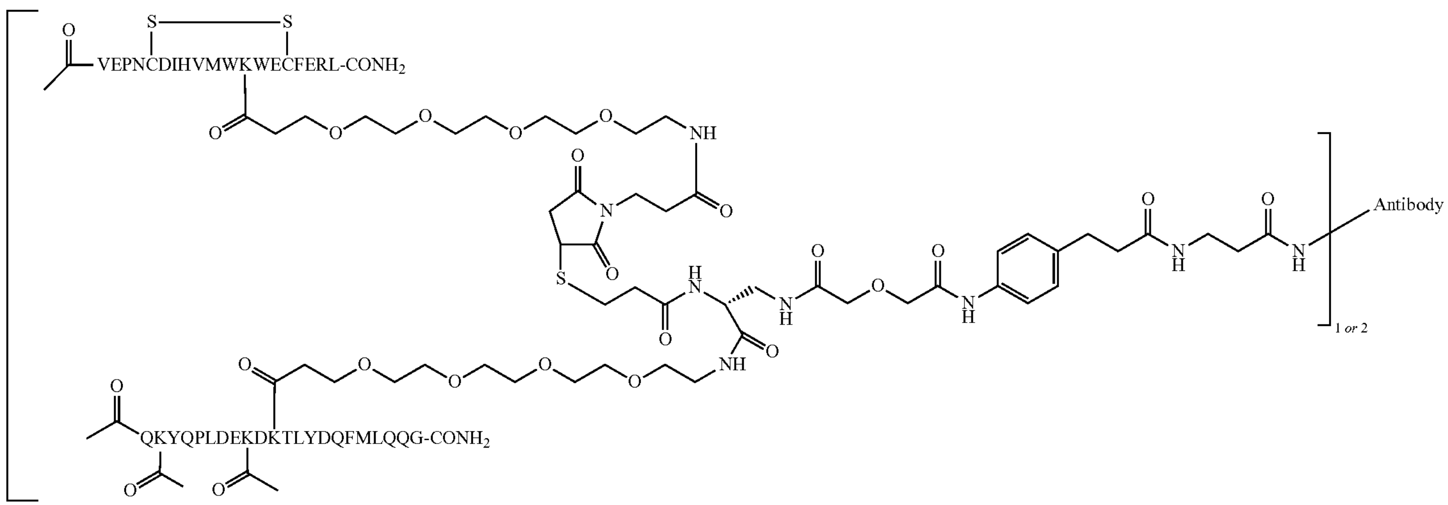 |

TABLE 12-continued
{([Ang2-Peptide]-[Connector]-[VEGF-Peptide])$_{1 or 2}$}-[Antibody]
| Cmpd # | Chemical Structure |
|---|---|
| 6023 VEGF SEQ: 34 M$^{10}$ subs with K as linking residue | 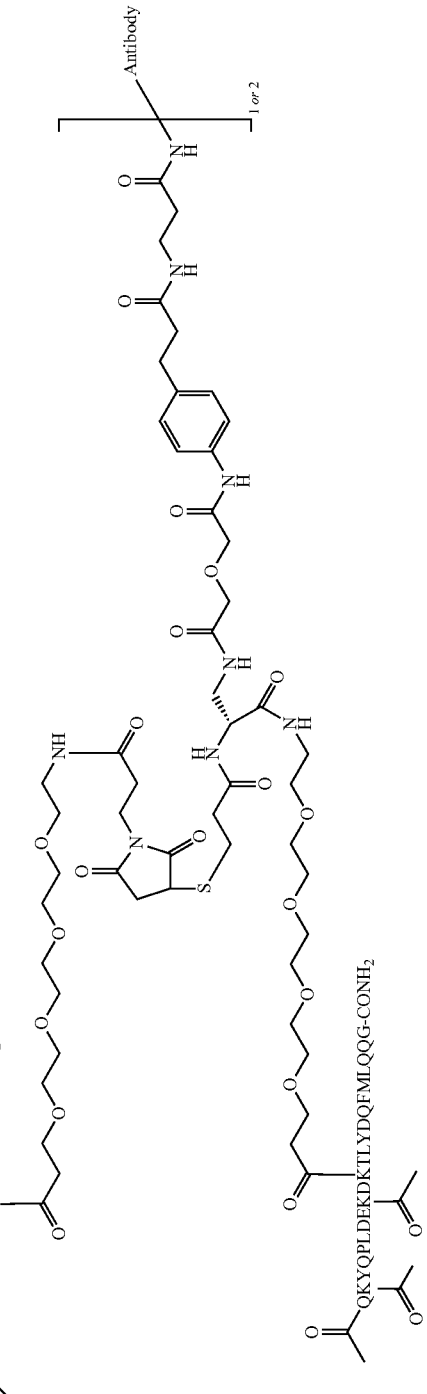 |

TABLE 12-continued
{[[Ang2-Peptide]-[Connector]-[VEGF-Peptide]]₁ ₒᵣ ₂}-[Antibody]
| Cmpd # | Chemical Structure |
|---|---|
| 6024 VEGF SEQ: 34 M¹⁰ subs with K as linking residue | 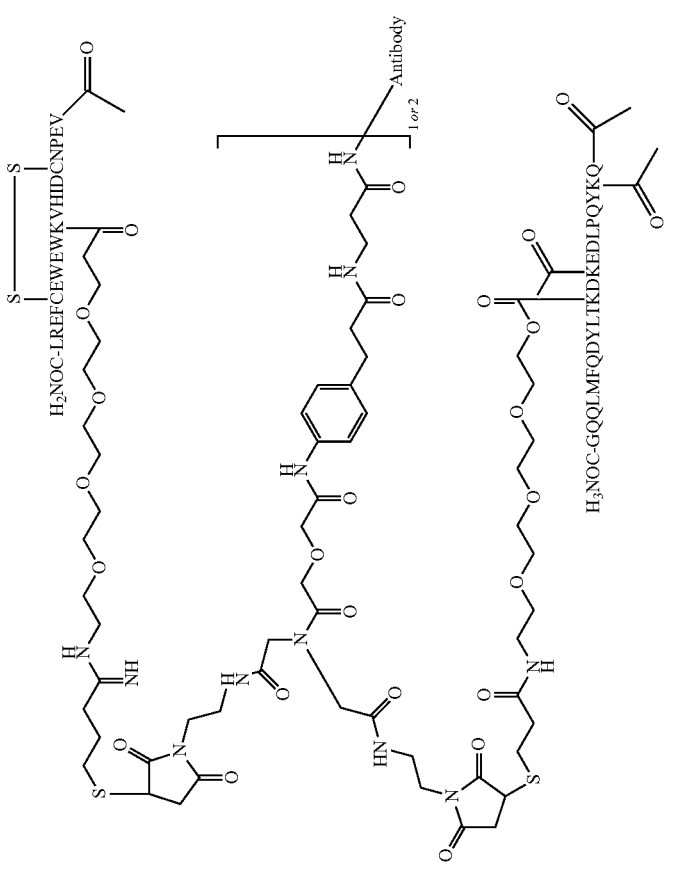 |

TABLE 12-continued

{([Ang2-Peptide]-[Connector]-[VEGF-Peptide])$_{1 or 2}$}-[Antibody]

| Cmpd # | Chemical Structure |
|---|---|
| 6025 VEGF SEQ: 34 M$^{1o}$ subs with K as linking residue | Ang2-Peptide: Q-K-Y-Q-P-L-D-E-K-D-K-T-L-Y-D-Q-F-M-L-Q-Q-G-CONH$_2$ (with two acetyl groups); VEGF-Peptide: H$_2$NOC-L-R-E-F-C-E-W-E-W-K-V-H-I-D-C-P-E-V- (with disulfide bridge between the two C residues) |

TABLE 12-continued

{([Ang2-Peptide]-[Connector]-[VEGF-Peptide])$_{1 or 2}$}-[Antibody]

| Cmpd # | Chemical Structure |
|---|---|
| 6026 VEGF SEQ: 208 | H$_2$NOC-IR-E-F-C-E-W-E-W-M-V-H-I-D-C-N-P-E-V- ... -G-Q-L-M-F-Q-D-Y-L-T-K-D-K-E-D-L-P-Q-Y-K-Q-CONH$_2$ |

TABLE 12-continued

{([Ang2-Peptide]-[Connector]-[VEGF-Peptide])$_{1 or 2}$}-[Antibody]

| Cmpd # | Chemical Structure |
|---|---|
| 6029 VEGF SEQ: 34 E$^{17}$ subs with K as linking residue (analogous to 5027) | |
| 6028 VEGF SEQ: 34 E$^{17}$ subs with K as linking residue | 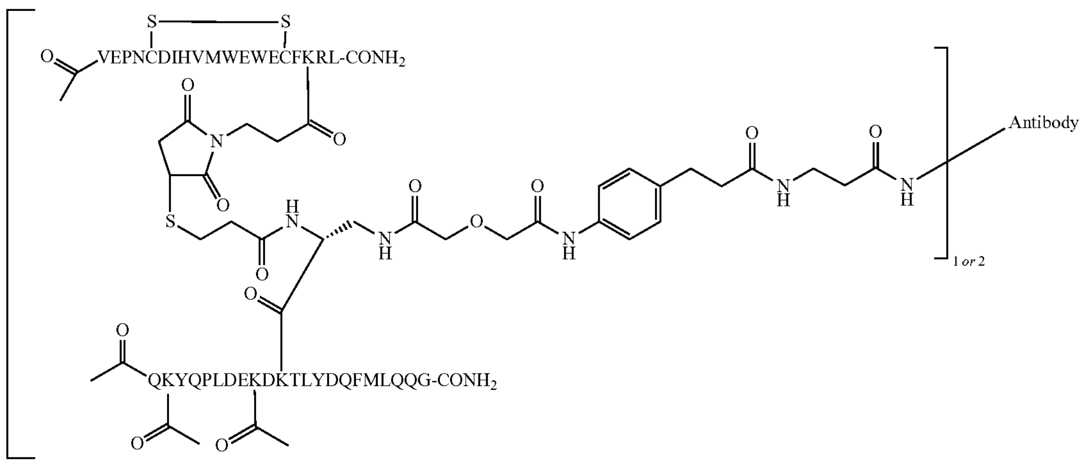 |

TABLE 12-continued
{[[Ang2-Peptide]-[Connector]-[VEGF-Peptide]]$_{1 or 2}$}-[Antibody]
| Cmpd # | Chemical Structure |
|---|---|
| 6031 VEGF SEQ: 209 | 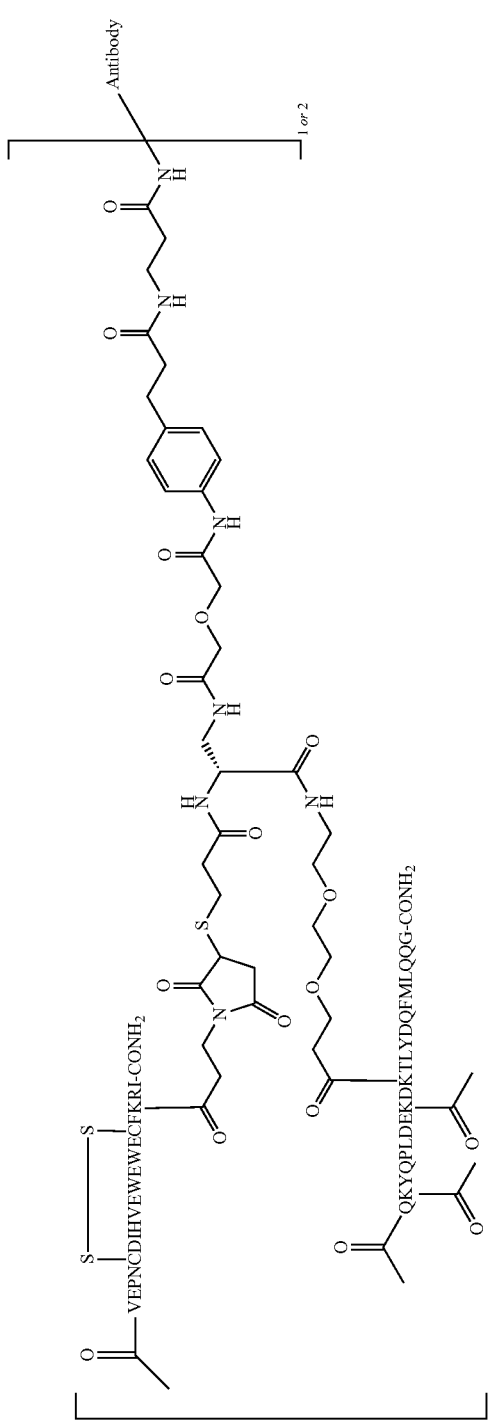 |
| 6032 VEGF SEQ: 76 | 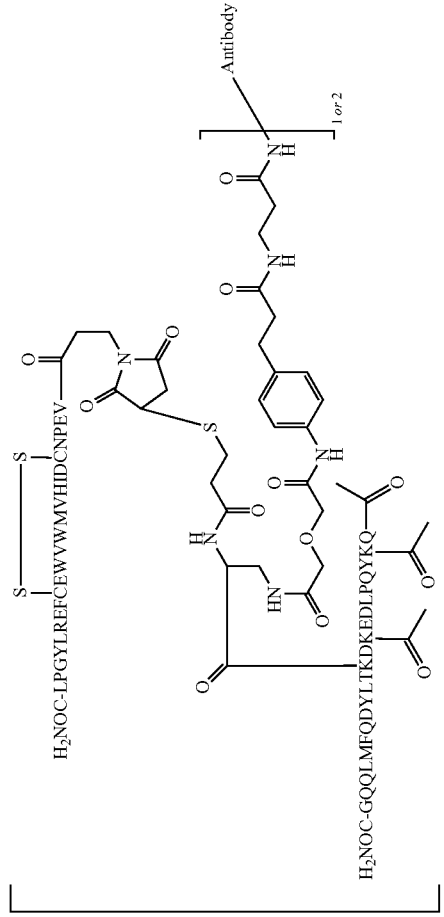 |

TABLE 12-continued
{([Ang2-Peptide]-[Connector]-[VEGF-Peptide])₁ₒᵣ₂}-[Antibody]
| Cmpd # | Chemical Structure |
|---|---|
| 6033 VEGF SEQ: 76 | 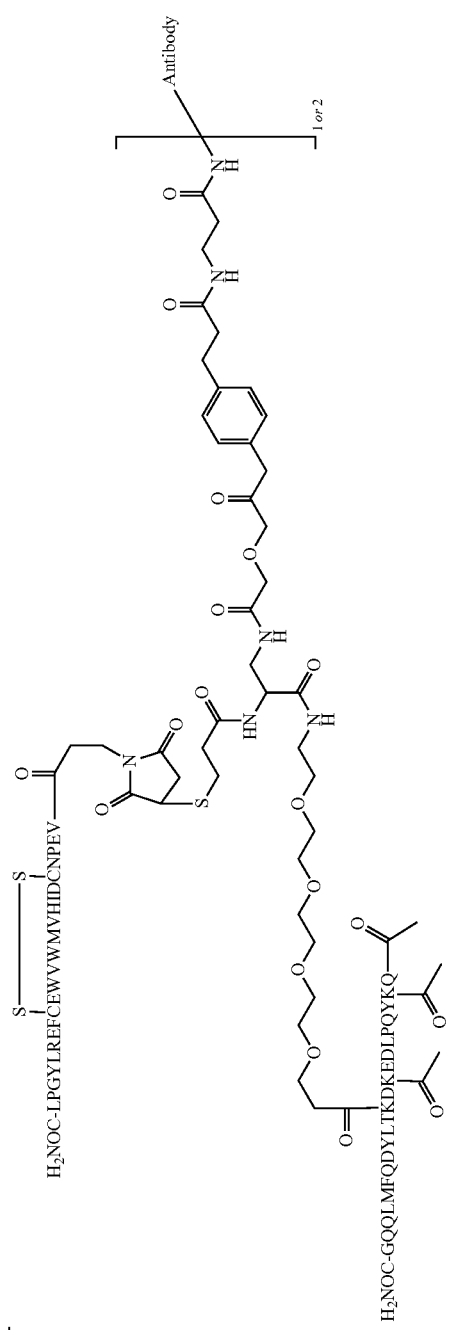 |
| 6034 VEGF SEQ: 73 E¹⁷ subs with K as linking residue | 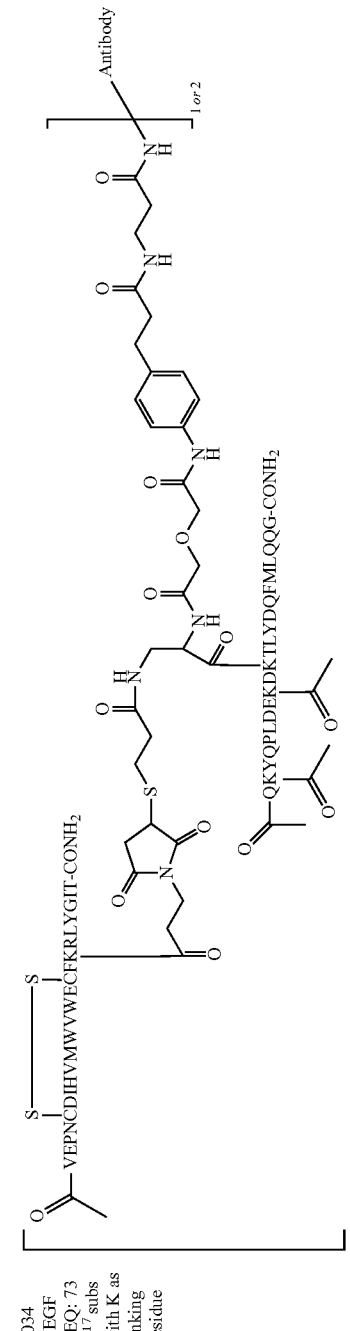 |

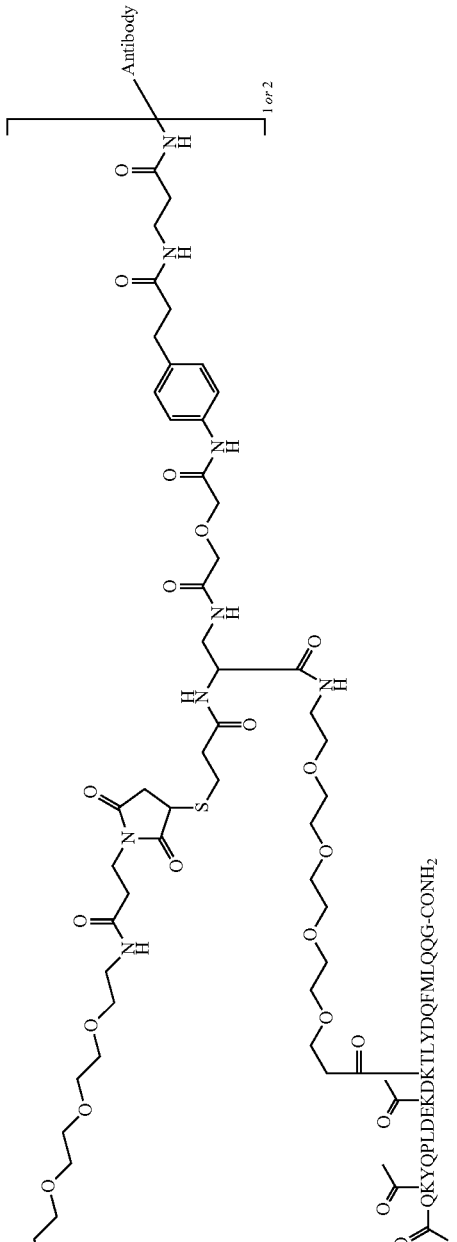

TABLE 12-continued

{([Ang2-Peptide]-[Connector]-[VEGF-Peptide])$_{1 or 2}$}-[Antibody]

| Cmpd # | Chemical Structure |
|---|---|
| 6037 VEGF SEQ: 75 M$^{10}$ subs with K as linking residue | 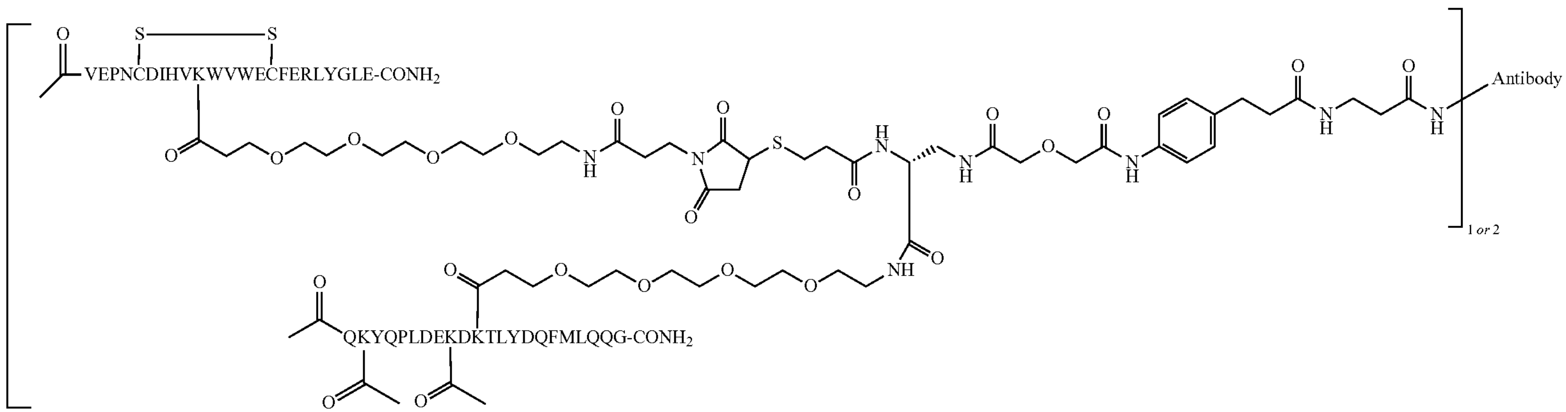 |
| 6038 VEGF SEQ: 75 E$^{17}$ subs with K as linking residue | 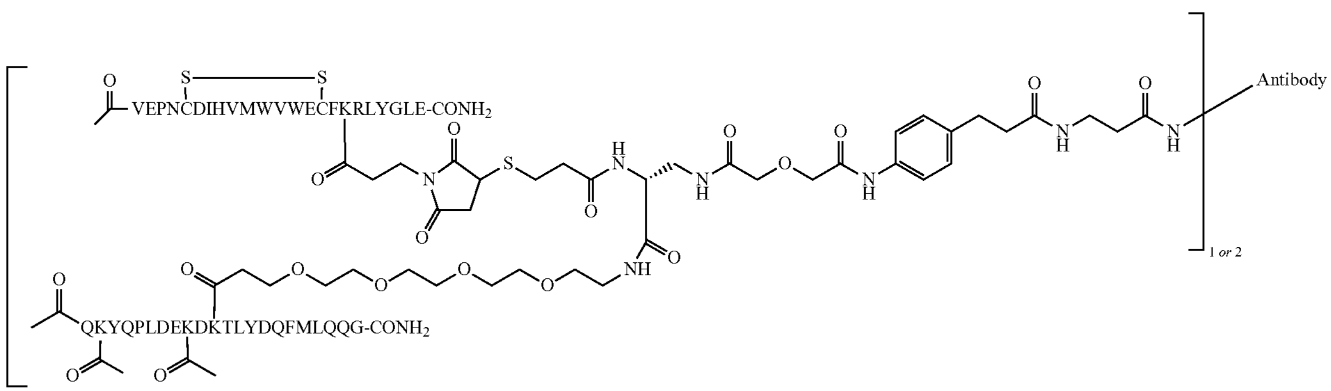 |

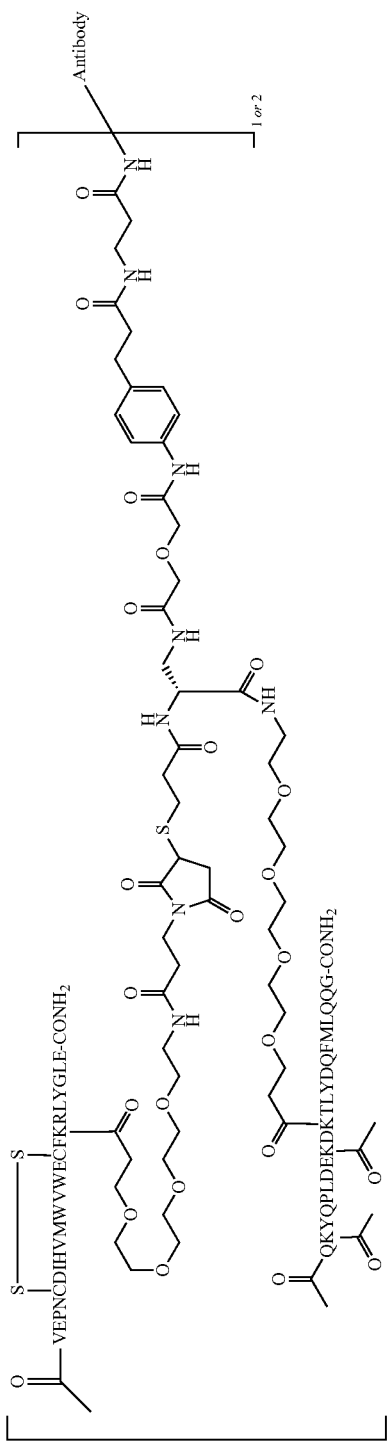

TABLE 12-continued
{[[Ang2-Peptide]-[Connector]-[VEGF-Peptide])$_{1 or 2}$]-[Antibody]}
| Cmpd # | Chemical Structure |
|---|---|
| 6041<br>SEQ: 211 | 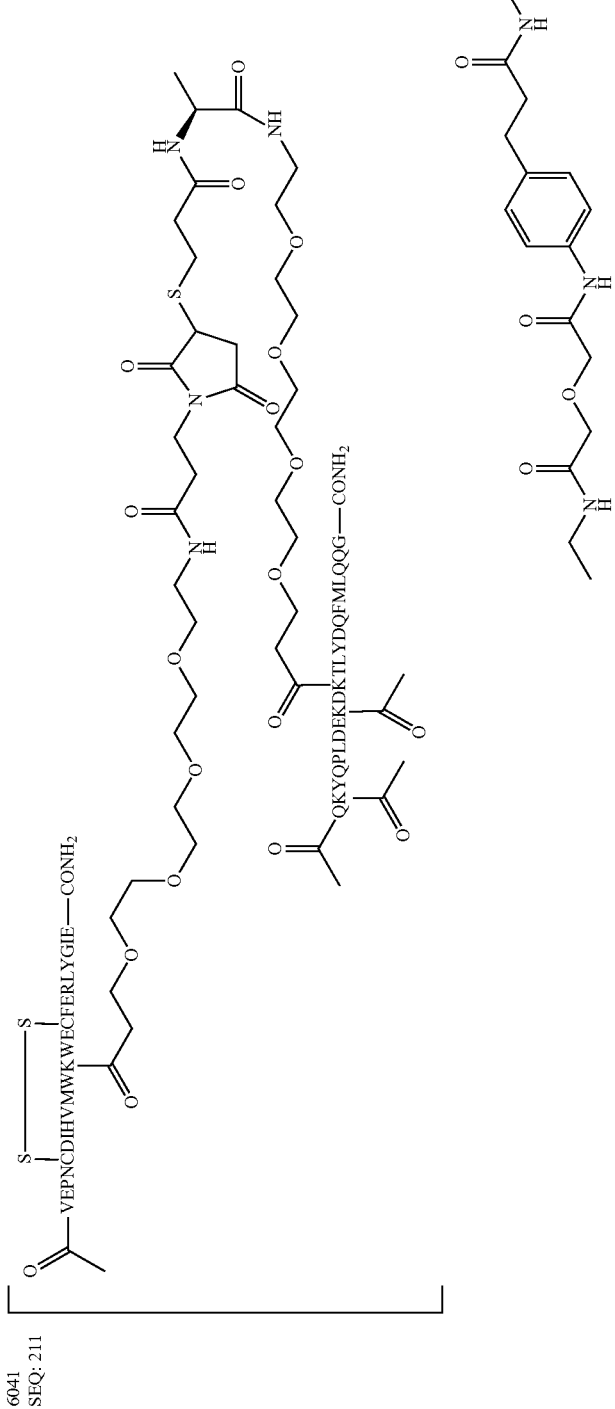 |

TABLE 12-continued

{[[Ang2-Peptide]-[Connector]-[VEGF-Peptide]]$_{1 or 2}$}-[Antibody]

| Cmpd # | Chemical Structure |
|---|---|
| 6042 SEQ: 73 V$^{12}$ subs with K as linking residue | Ac-V-E-P-N-C-D-I-H-V-M-W-K-W-E-C-F-E-R-L-Y-G-I-T-CONH$_2$ (disulfide bridge between the two C residues); connector with maleimide, PEG linkers, and p-ethylphenyl amide; Ac-Q-K-Y-Q-P-L-D-E-K-D-K-T-L-Y-D-Q-F-M-L-Q-G-CONH$_2$; linked via β-alanine amide to Antibody (1 or 2) |

TABLE 12-continued
{[[Ang2-Peptide]-[Connector]-[VEGF-Peptide]]$_{1 or 2}$]-[Antibody]
| Cmpd # | Chemical Structure |
|---|---|
| 6043<br>SEQ: 212 | 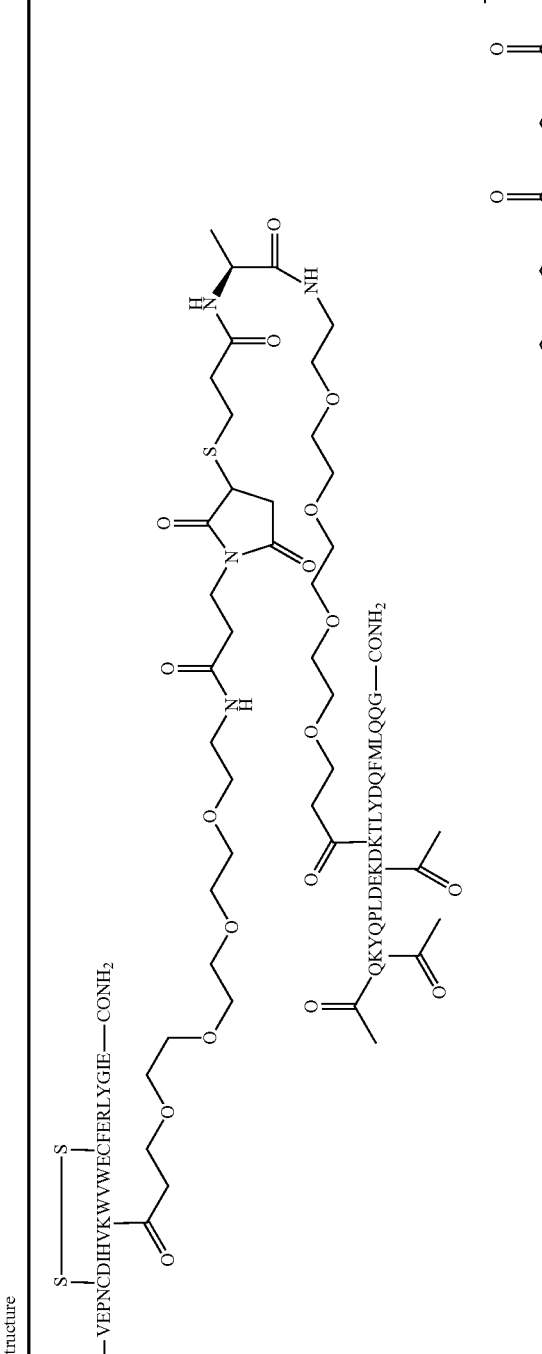 |

TABLE 12-continued

{[[Ang2-Peptide]-[Connector]-[VEGF-Peptide]]$_{1 or 2}$}-[Antibody]

| Cmpd # | Chemical Structure |
|---|---|
| 6044
SEQ: 212 | |

TABLE 12-continued
{[[Ang2-Peptide]-[Connector]-[VEGF-Peptide]]$_{1 or 2}$}-[Antibody]
| Cmpd # | Chemical Structure |
|---|---|
| 6045 SEQ: 73 M$^{10}$ subs with K as linking residue | 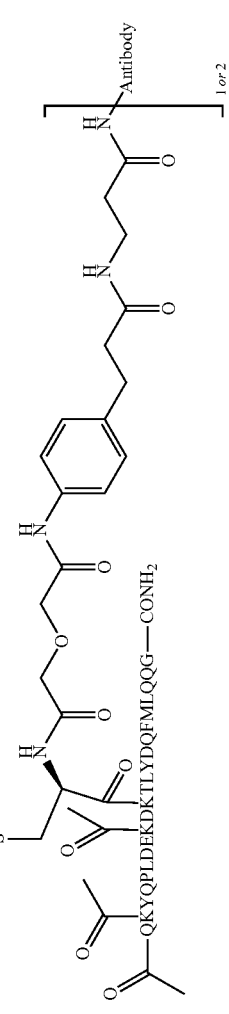 |
| 6046 SEQ: 73 V$^{12}$ subs with K as linking residue | 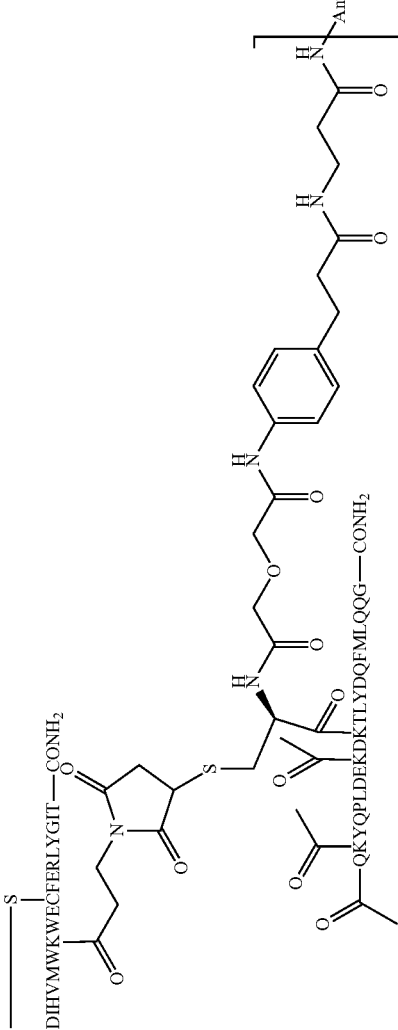 |

TABLE 12-continued

{[[Ang2-Peptide]-[Connector]-[VEGF-Peptide]]$_{1 or 2}$]-[Antibody]

| Cmpd # | Chemical Structure |
|---|---|
| 6047<br>SEQ: 213 | 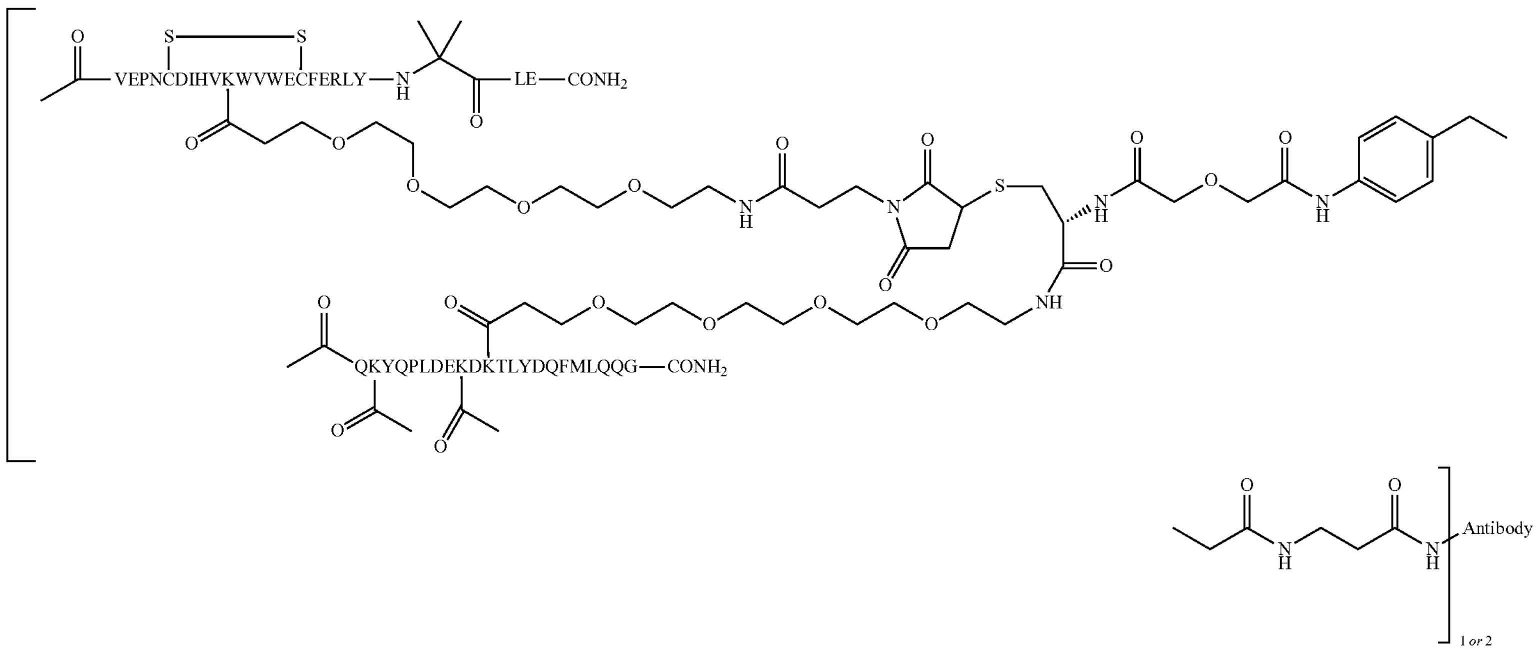 |

TABLE 12-continued
{[[Ang2-Peptide]-[Connector]-[VEGF-Peptide])$_{1 or 2}$]-[Antibody]}
| Cmpd # | Chemical Structure |
|---|---|
| 6048<br>SEQ: 214 | 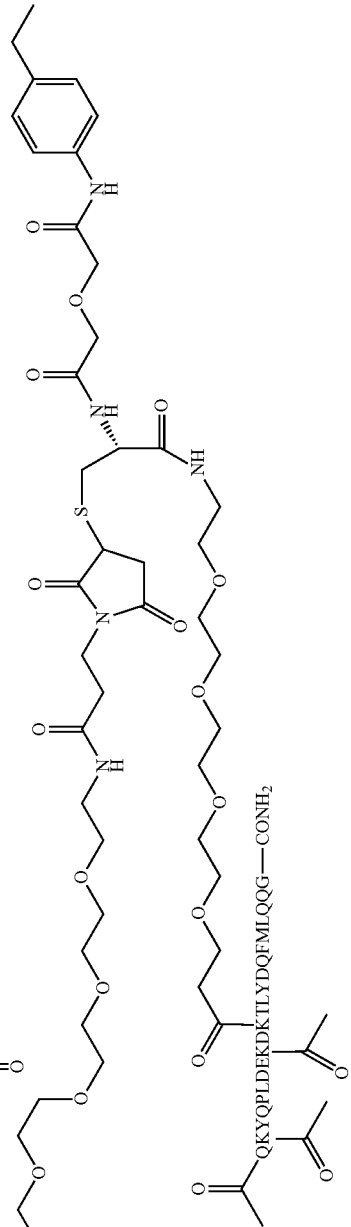 |

TABLE 12-continued
{[[Ang2-Peptide]-[Connector]-[VEGF-Peptide]]₁ₒᵣ₂}-[Antibody]
| Cmpd # | Chemical Structure |
|---|---|
| 6049 SEQ: 215 | 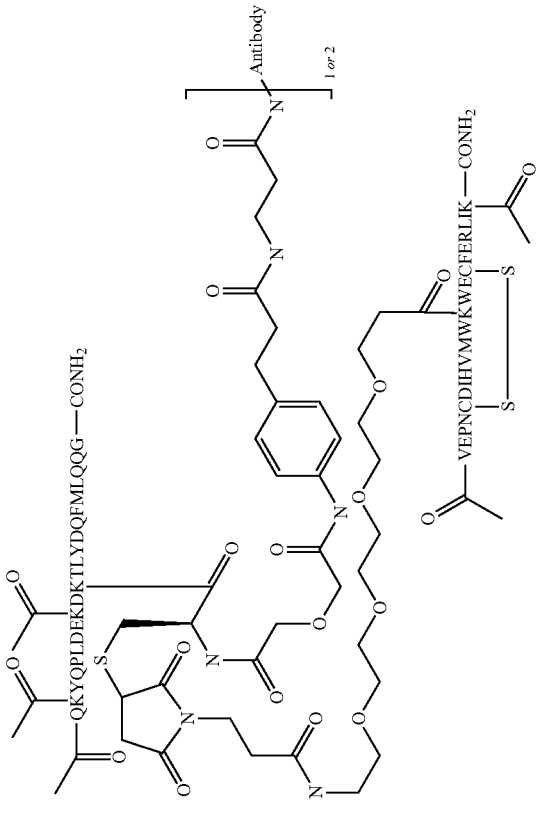 |

TABLE 12-continued

{[[Ang2-Peptide]-[Connector]-[VEGF-Peptide]]$_{1 or 2}$}-[Antibody]

| Cmpd # | Chemical Structure |
|---|---|
| 6050 SEQ: 79 V$^{12}$ subs with K as linking residue | |

TABLE 12-continued

{[[Ang2-Peptide]-[Connector]-[VEGF-Peptide]]$_{1 or 2}$}-[Antibody]

| Cmpd # | Chemical Structure |
|---|---|
| 6051 SEQ: 79 V$^{12}$ subs with K as linking residue | 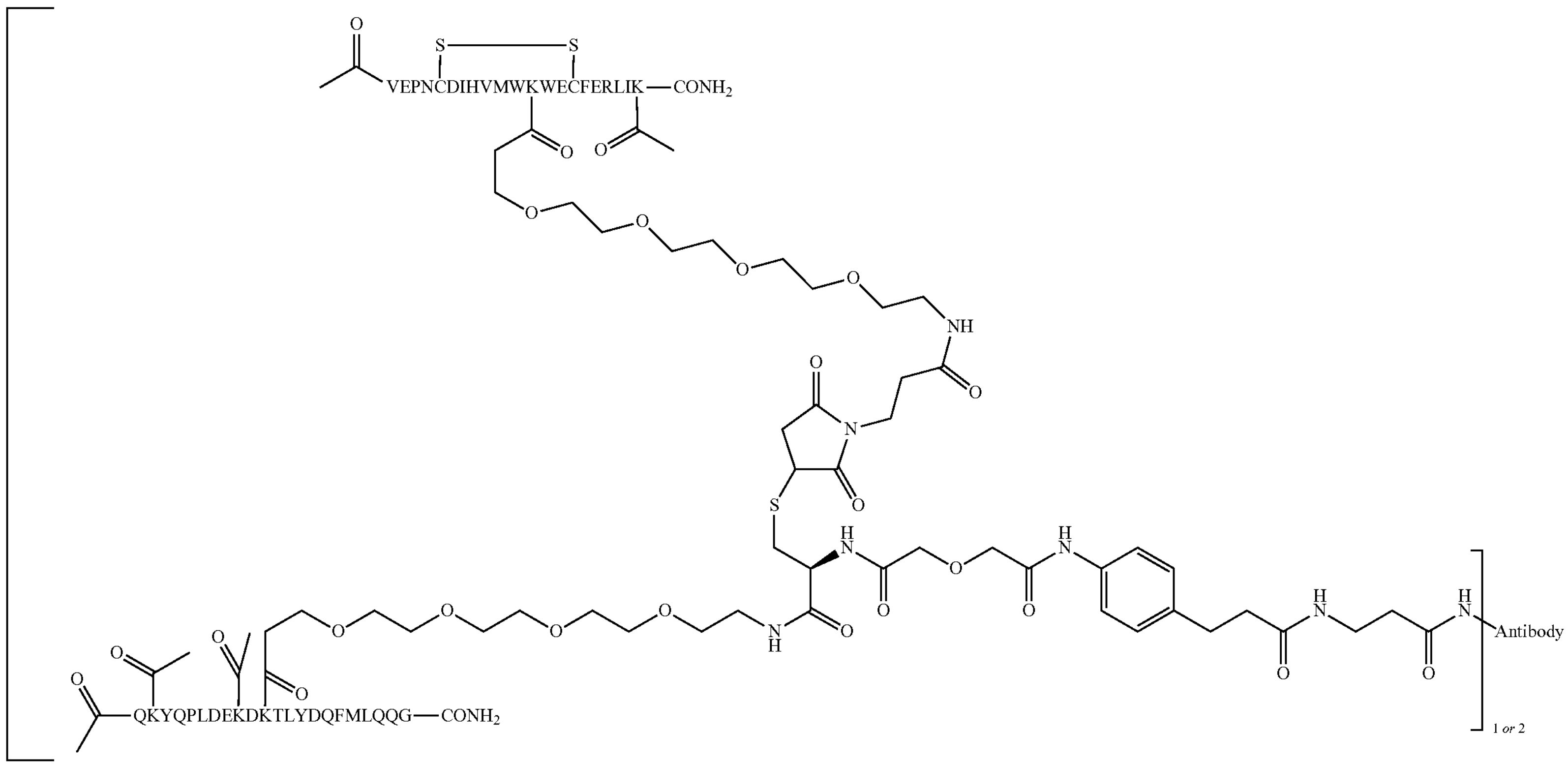 |

Ang2-Peptide: Ac-VEPNCDIHVMWKWECFERLIK-CONH$_2$ (disulfide)

VEGF-Peptide: Ac-QKYQPLDEKDKTLYDQFMLQQG-CONH$_2$

TABLE 12-continued
{([Ang2-Peptide]-[Connector]-[VEGF-Peptide])$_{1 or 2}$}-[Antibody]
| Cmpd # | Chemical Structure |
|---|---|
| 6052 SEQ: 79 V$^{12}$ subs with K as linking residue | 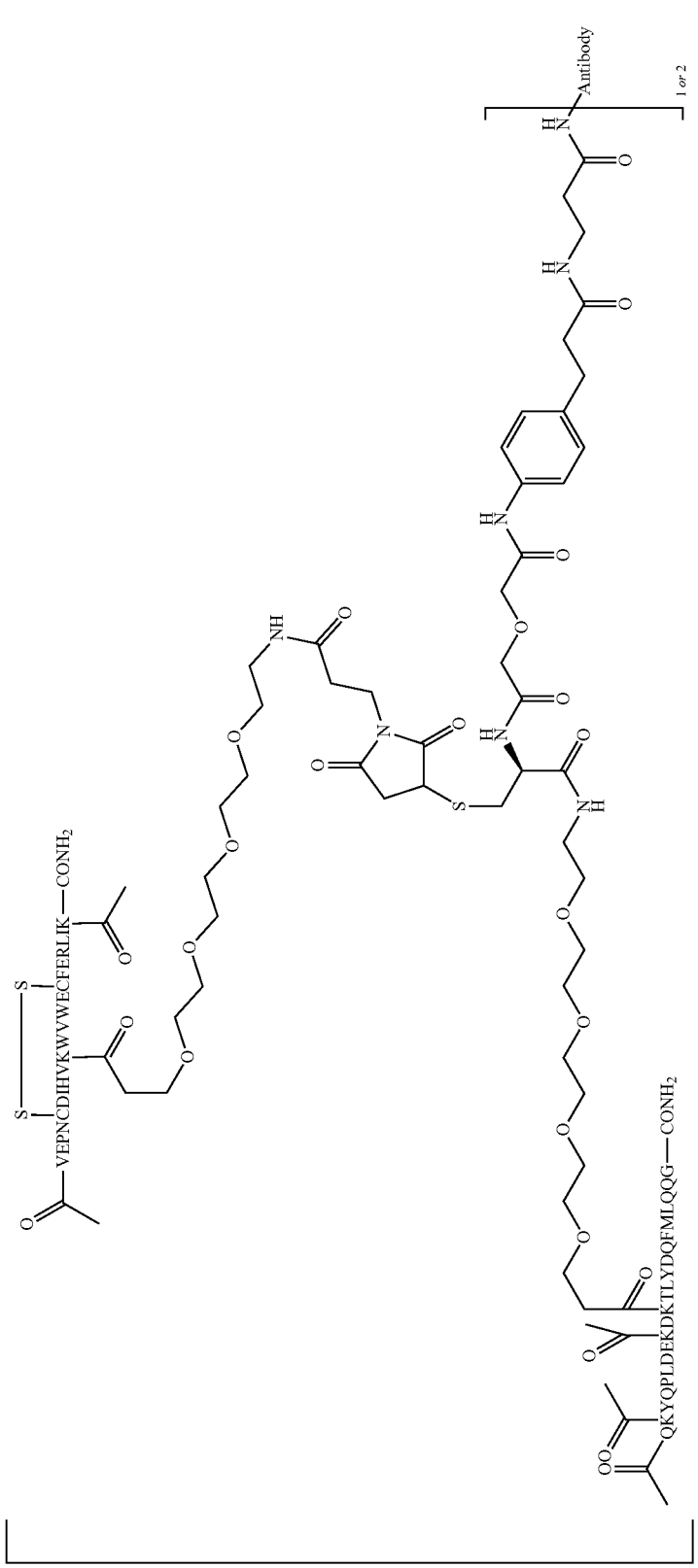 |

TABLE 12-continued

{[[Ang2-Peptide]-[Connector]-[VEGF-Peptide]]$_{1 or 2}$}-[Antibody]

| Cmpd # | Chemical Structure |
|---|---|
| 6053 SEQ: 78 M$^{10}$ subs with K as linking residue | 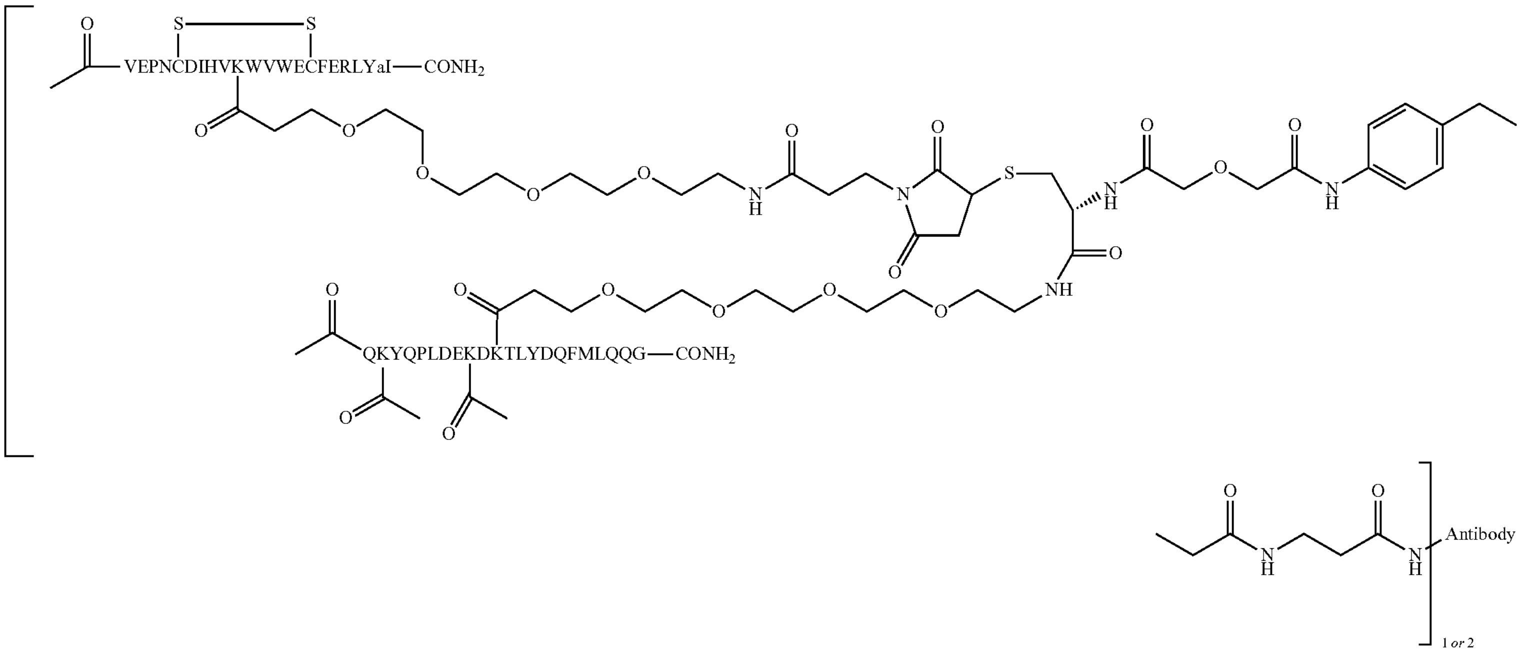 |

TABLE 12-continued
{[[Ang2-Peptide]-[Connector]-[VEGF-Peptide]]_{1 or 2}}-[Antibody]
| Cmpd # | Chemical Structure |
|---|---|
| 6054 SEQ: 79 V¹ subs with K as linking residue | 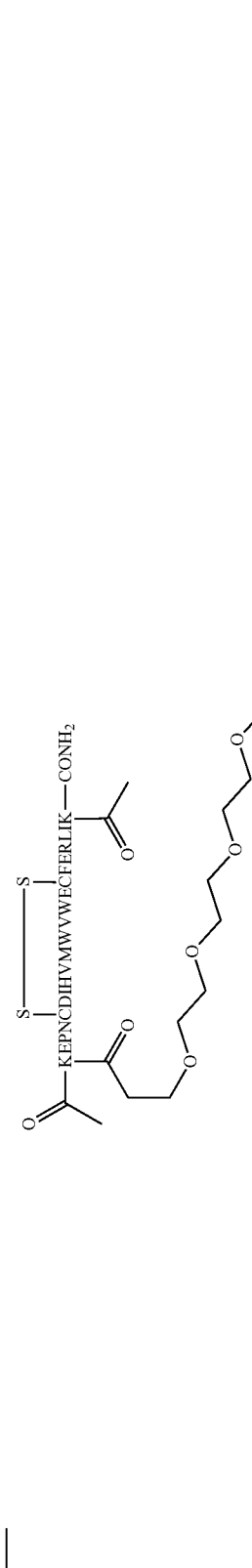 |

TABLE 12-continued
{([Ang2-Peptide]-[Connector]-[VEGF-Peptide])₁ₒᵣ₂}-[Antibody]
| Cmpd # | Chemical Structure |
|---|---|
| 6055 SEQ: 79 V¹ subs with K as linking residue | 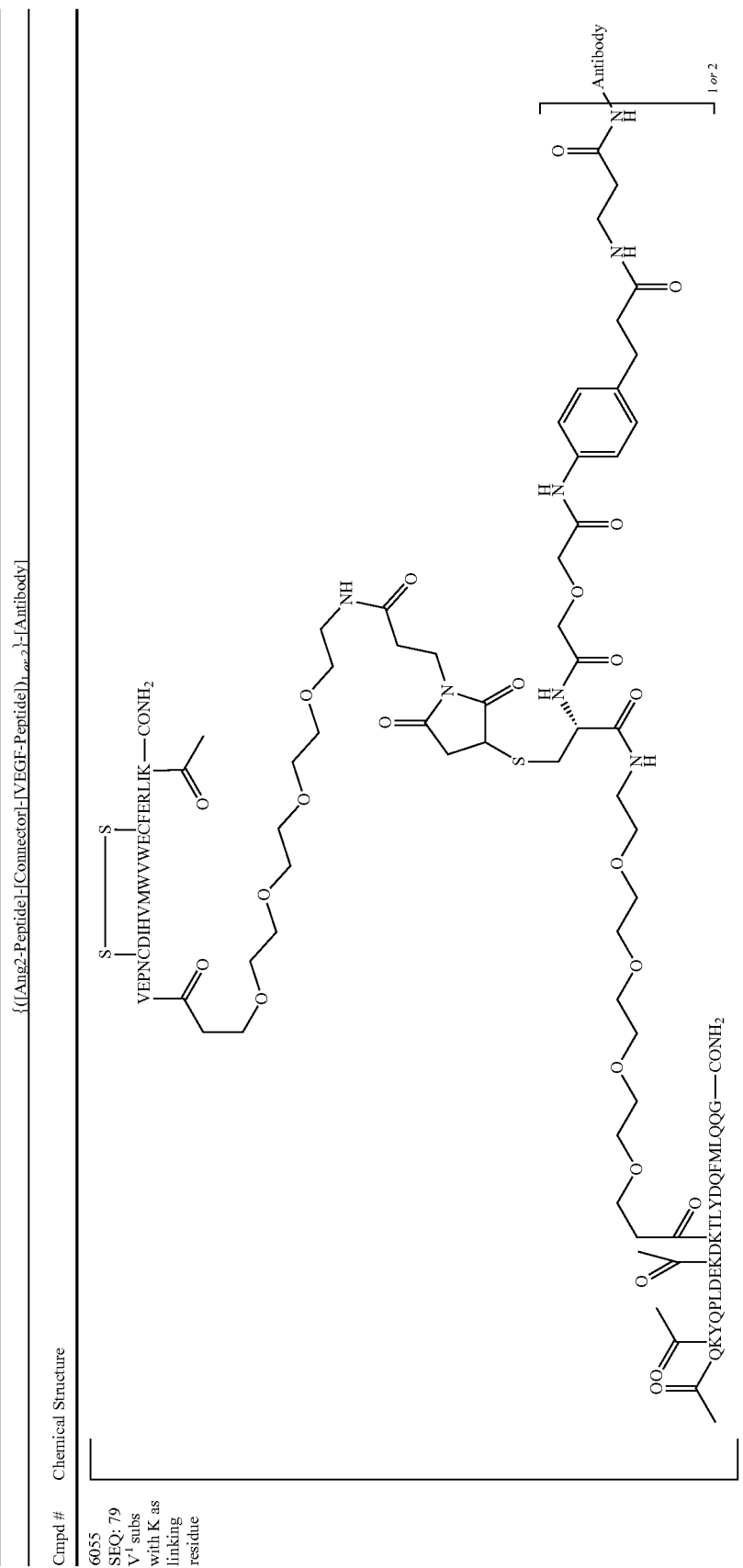 |

TABLE 12-continued

{[[Ang2-Peptide]-[Connector]-[VEGF-Peptide]]$_{1 or 2}$}-[Antibody]

| Cmpd # | Chemical Structure |
|---|---|
| 6056 SEQ: 79 V$^{12}$ subs with K as linking residue | VEPNCDIHVMWKWECFERLIK-CONH$_2$ ... QKYQPLDELDKTLYDQFKLQQG-CONH$_2$ |

TABLE 12-continued
{[[Ang2-Peptide]-[Connector]-[VEGF-Peptide]]$_{1 or 2}$}-[Antibody]
| Cmpd # | Chemical Structure |
|---|---|
| 6057<br>SEQ: 79<br>V$^{12}$ subs with K as linking residue | 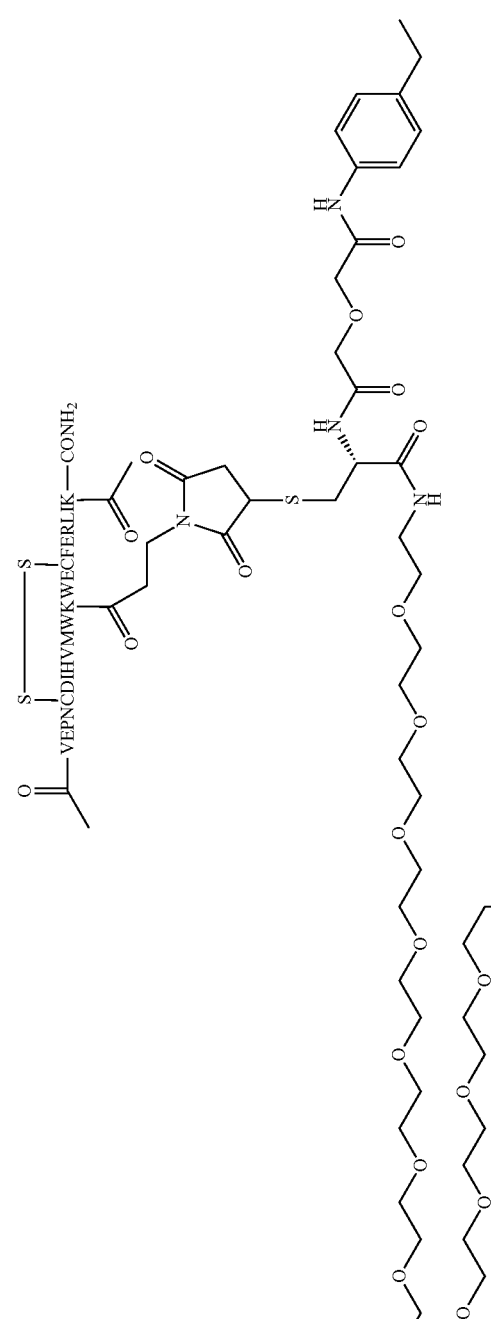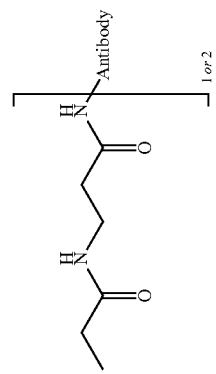 |

TABLE 12-continued
{[(Ang2-Peptide]-[Connector]-[VEGF-Peptide])$_{1 or 2}$]-[Antibody]
| Cmpd # | Chemical Structure |
|---|---|
| 6058 SEQ: 79 V$^{12}$ subs with K as linking residue | 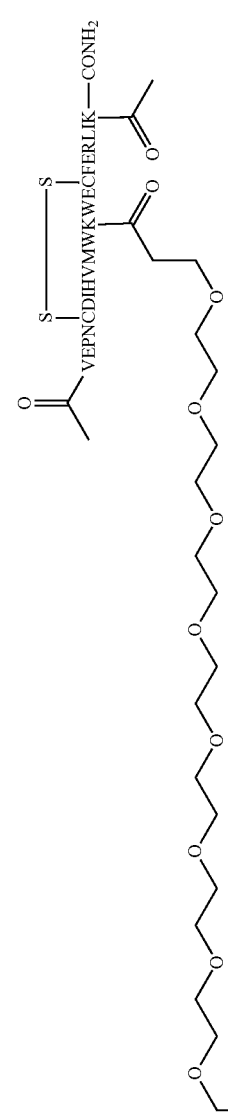 |

TABLE 12-continued
{[[Ang2-Peptide]-[Connector]-[VEGF-Peptide]]$_{1 or 2}$}-[Antibody]
| Cmpd # | Chemical Structure |
|---|---|
| 6059 SEQ: 73 $V^{12}$ subs with K as linking residue | 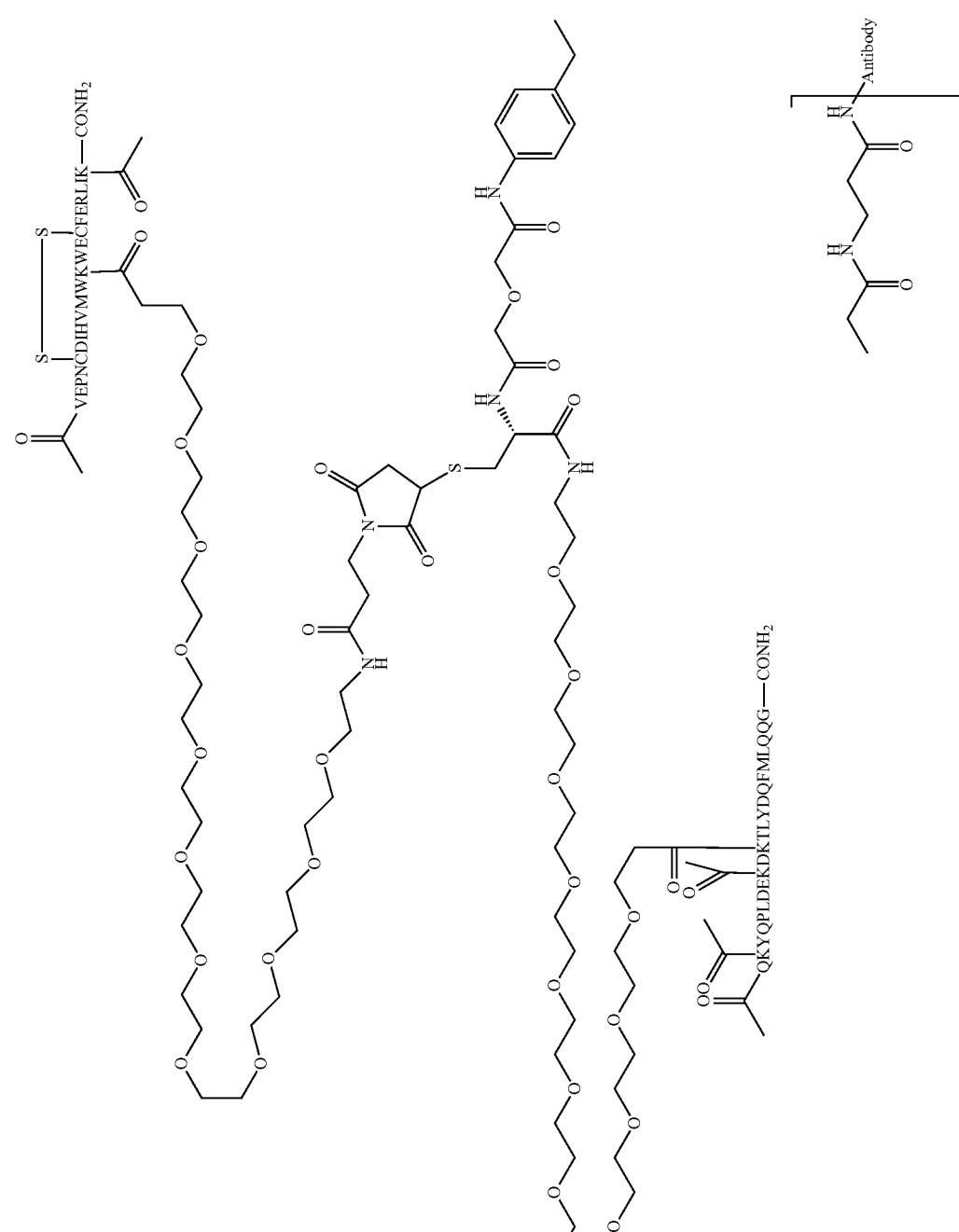 |

TABLE 12-continued
{[[Ang2-Peptide]-[Connector]-[VEGF-Peptide]]$_{1 or 2}$}-[Antibody]
| Cmpd # | Chemical Structure |
|---|---|
| 6060 SEQ: 78 M[10] subs with K as linking residue | 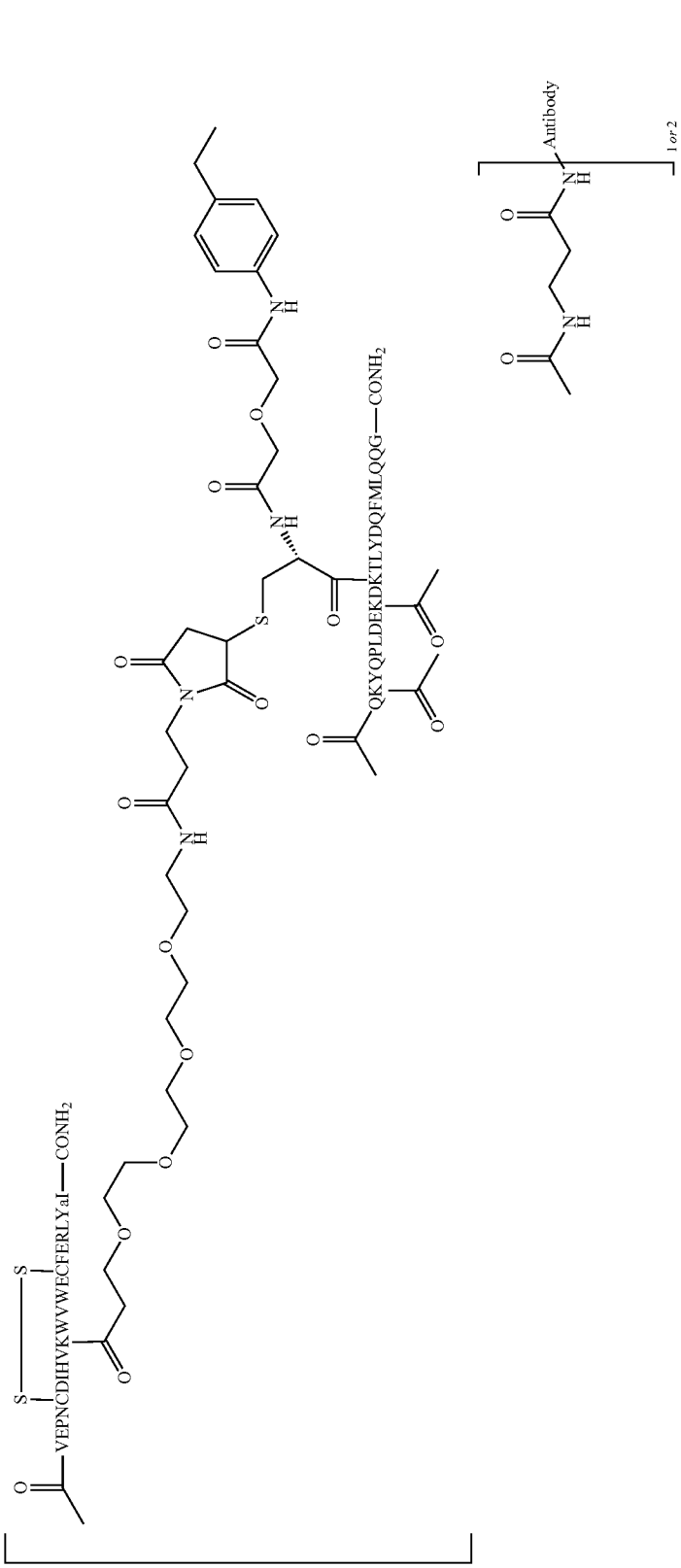 |

TABLE 12-continued
{[[Ang2-Peptide]-[Connector]-[VEGF-Peptide]]$_{1 or 2}$]-[Antibody]
| Cmpd # | Chemical Structure |
|---|---|
| 6061 SEQ: 78 M$^{10}$ subs with K as linking residue | 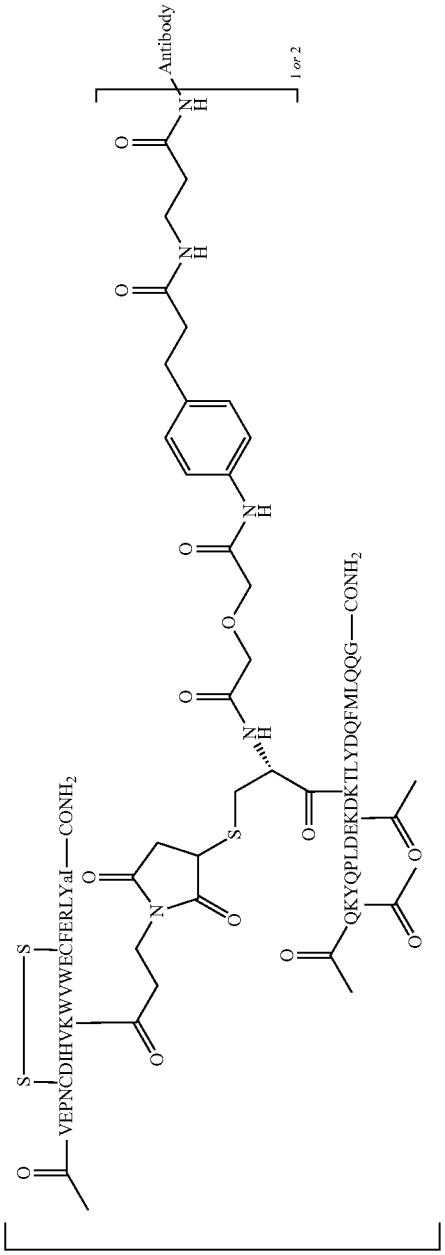 |
| 6062 SEQ: 78 M$^{10}$ subs with K as linking residue | 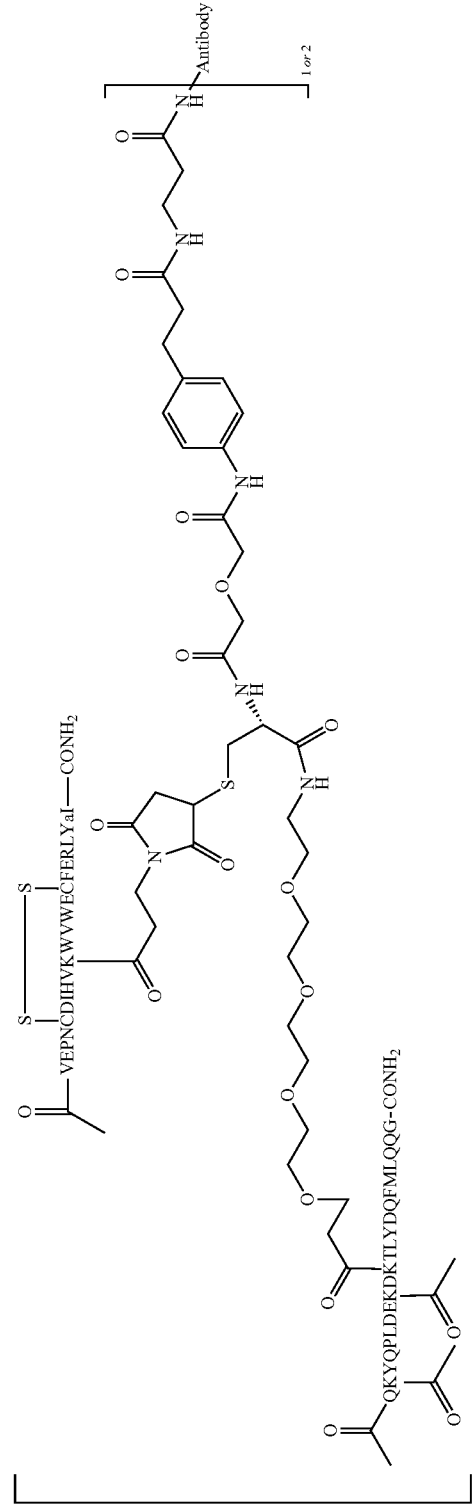 |

TABLE 12-continued

{[[Ang2-Peptide]-[Connector]-[VEGF-Peptide])$_{1\,or\,2}$]-[Antibody]

| Cmpd # | Chemical Structure |
|---|---|
| 6063<br>SEQ: 89<br>M$^{10}$ subs with K as linking residue | VEPNCDIHVKWVWECFERLYGpL—CONH$_2$ ... QKYQPLDEKDKTLYDQFMLQQG—CONH$_2$ |

TABLE 12-continued
{([Ang2-Peptide]-[Connector]-[VEGF-Peptide])$_{1 or 2}$]-[Antibody]
| Cmpd # | Chemical Structure |
|---|---|
| 6064<br>SEQ: 90<br>M$^{10}$ subs<br>with K as<br>linking<br>residue | 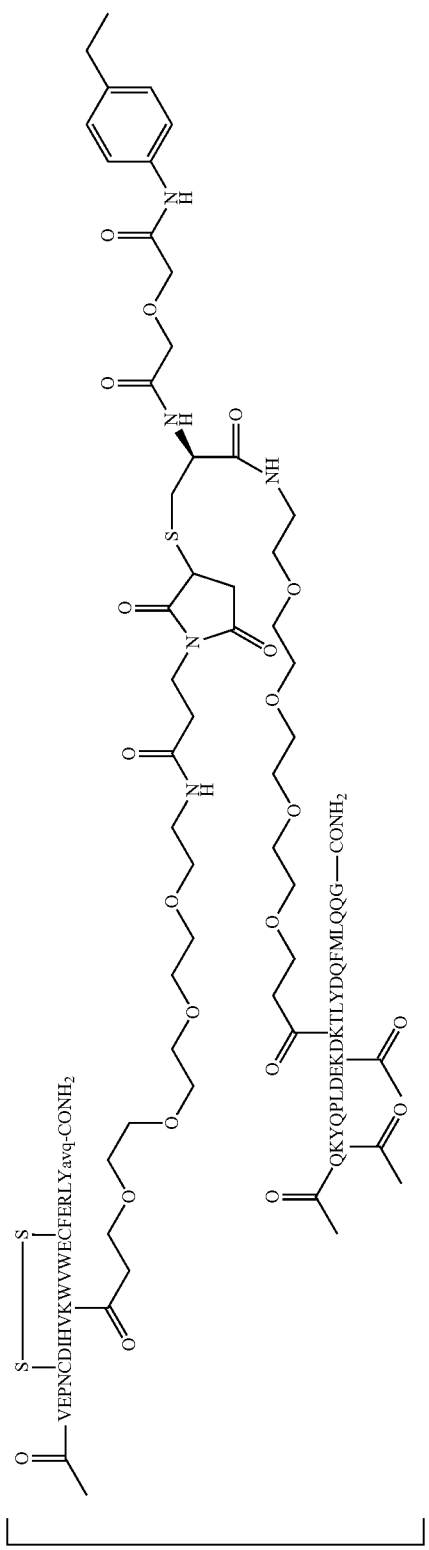 |

TABLE 12-continued
{[[Ang2-Peptide]-[Connector]-[VEGF-Peptide]]₁ₒᵣ₂}-[Antibody]
| Cmpd # | Chemical Structure |
|---|---|
| 6065 SEQ: 79 V¹² subs with K as linking residue | 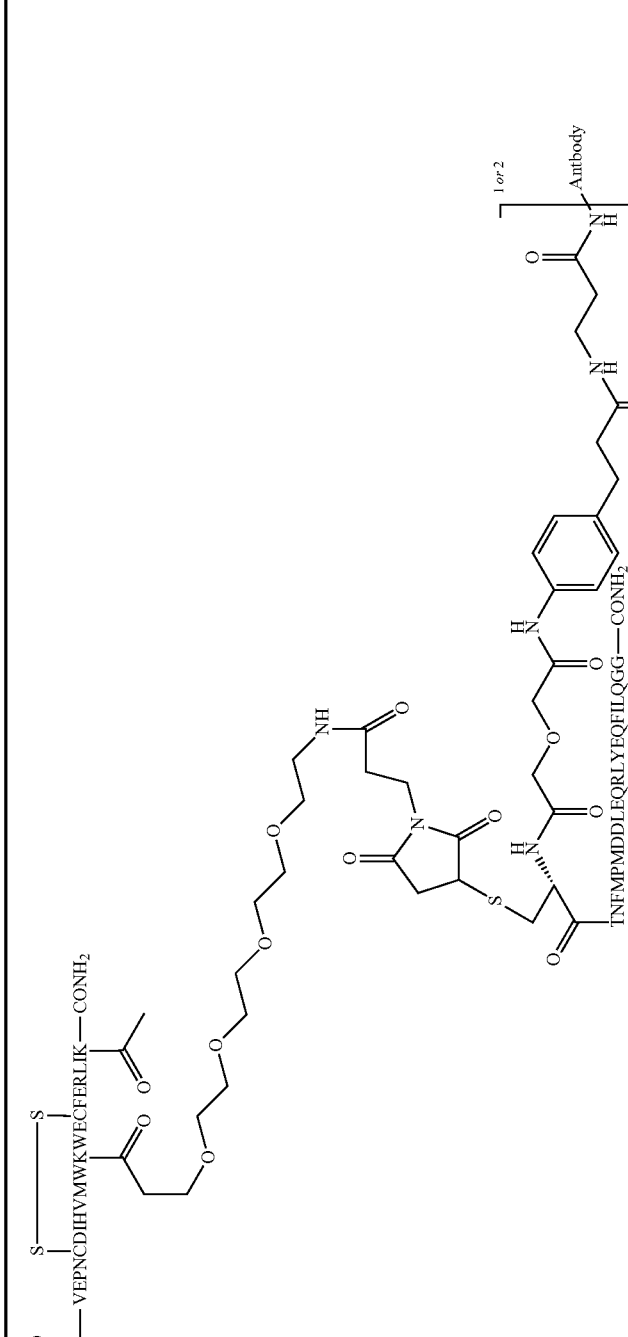 |

TABLE 12-continued
{[[Ang2-Peptide]-[Connector]-[VEGF-Peptide]]$_{1 or 2}$}-[Antibody]
| Cmpd # | Chemical Structure |
|---|---|
| 6066 SEQ: 79 N[4] subs with K as linking residue | 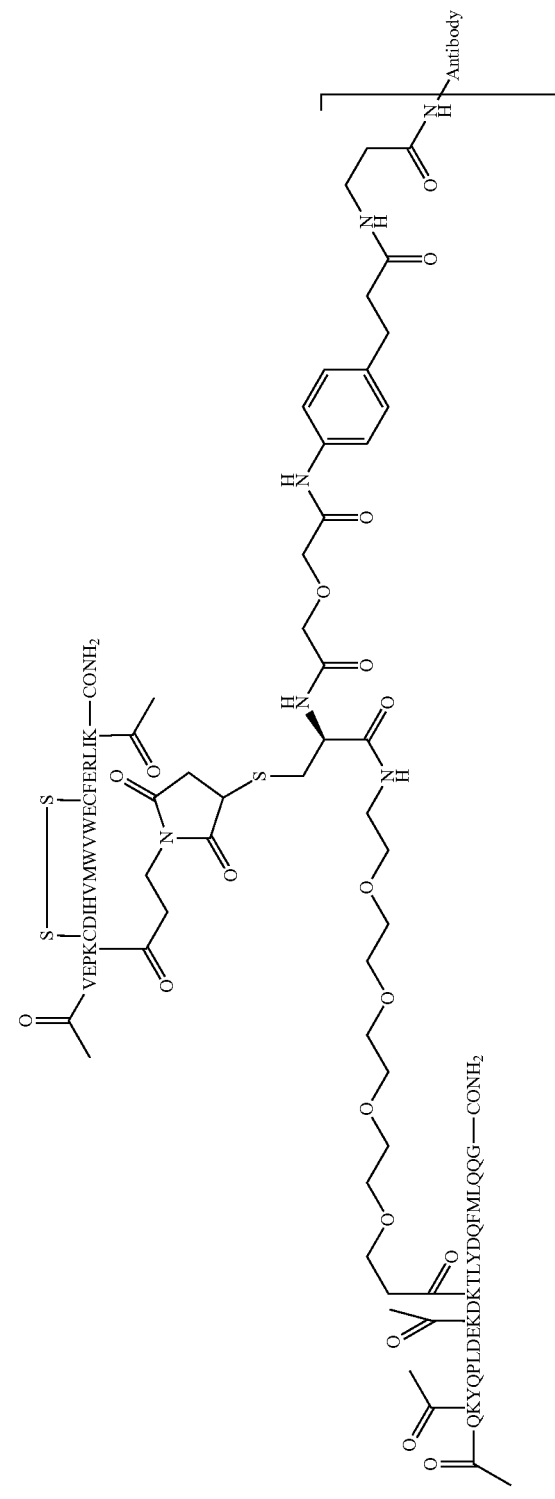 |

TABLE 12-continued
{([Ang2-Peptide]-[Connector]-[VEGF-Peptide])₁ₒᵣ₂}-[Antibody]
| Cmpd # | Chemical Structure |
|---|---|
| 6067<br>SEQ: 79<br>V¹ subs<br>with K as<br>linking<br>residue | 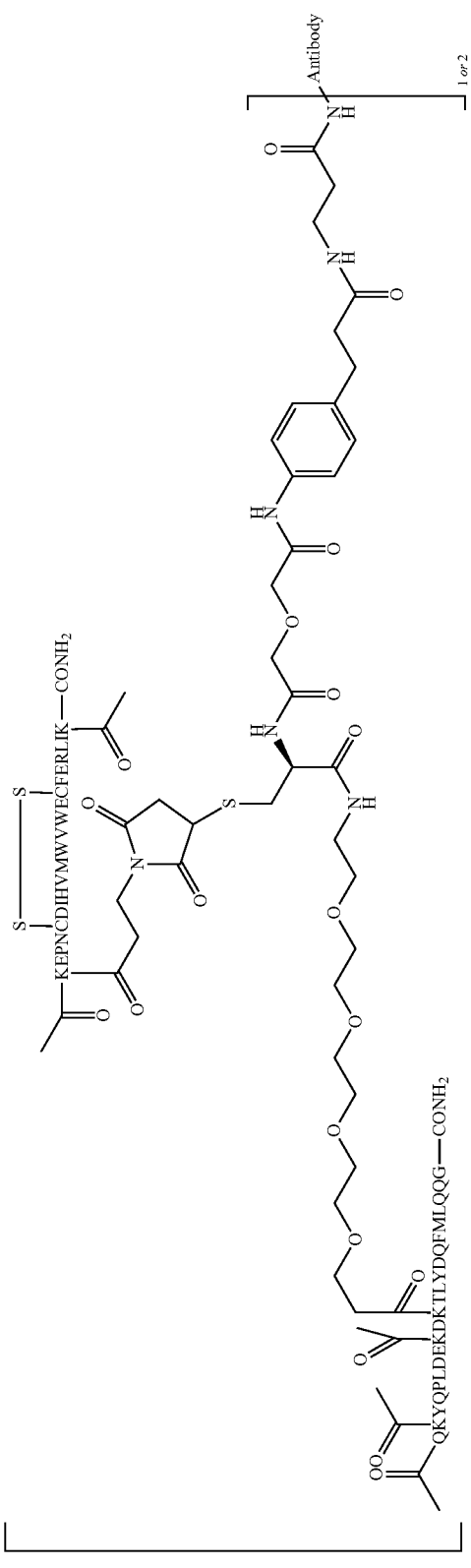 |

TABLE 12-continued
{([Ang2-Peptide]-[Connector]-[VEGF-Peptide])$_{1 or 2}$}-[Antibody]
| Cmpd # | Chemical Structure |
|---|---|
| 6068 SEQ: 79 V$^9$ subs with K as linking residue | 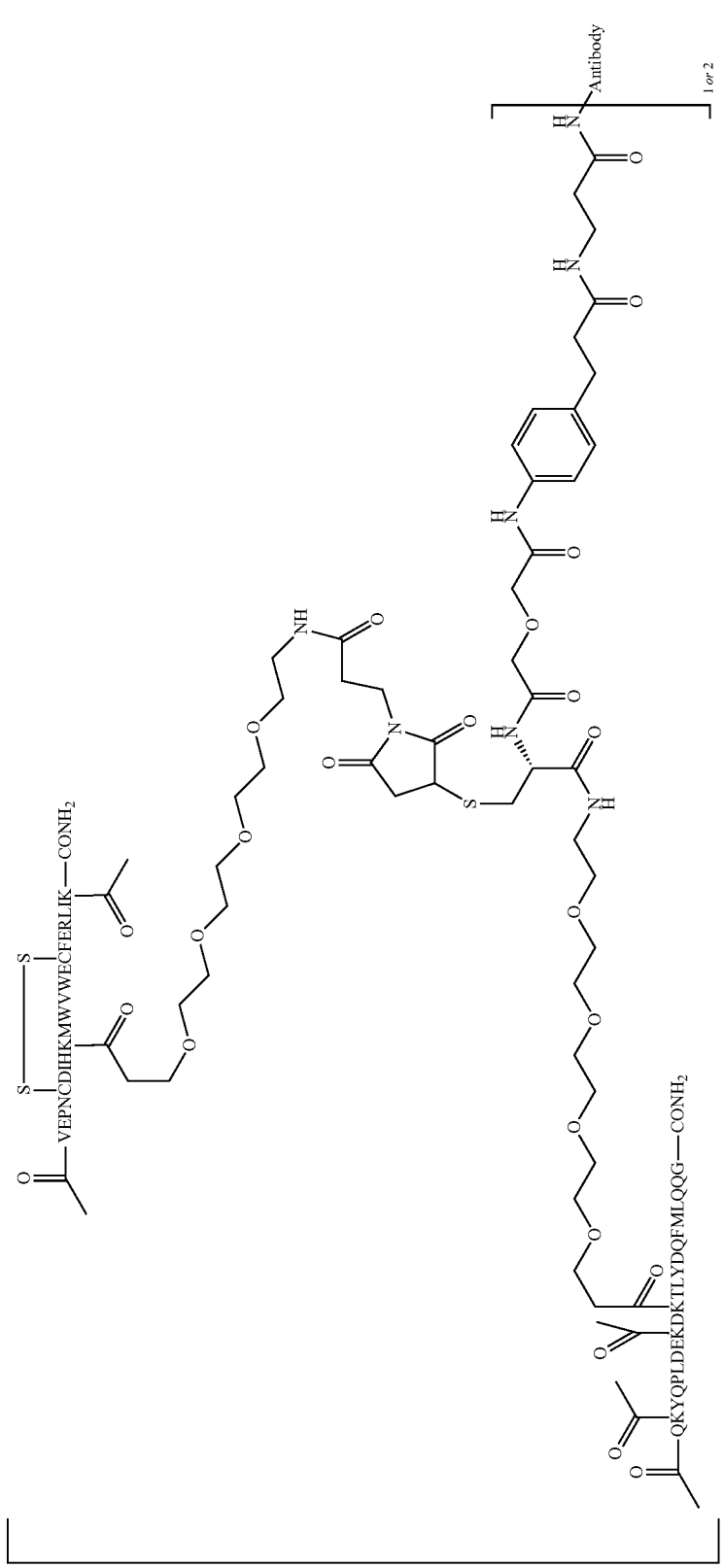 |

TABLE 12-continued

{[[Ang2-Peptide]-[Connector]-[VEGF-Peptide]]$_{1 or 2}$}-[Antibody]

| Cmpd # | Chemical Structure |
|---|---|
| 6069 SEQ: 60 V$^{12}$ subs with K as linking residue | (structure shown) |

TABLE 12-continued
{[[Ang2-Peptide]-[Connector]-[VEGF-Peptide]]$_{1 or 2}$}-[Antibody]
| Cmpd # | Chemical Structure |
|---|---|
| 6070 SEQ: 216 | 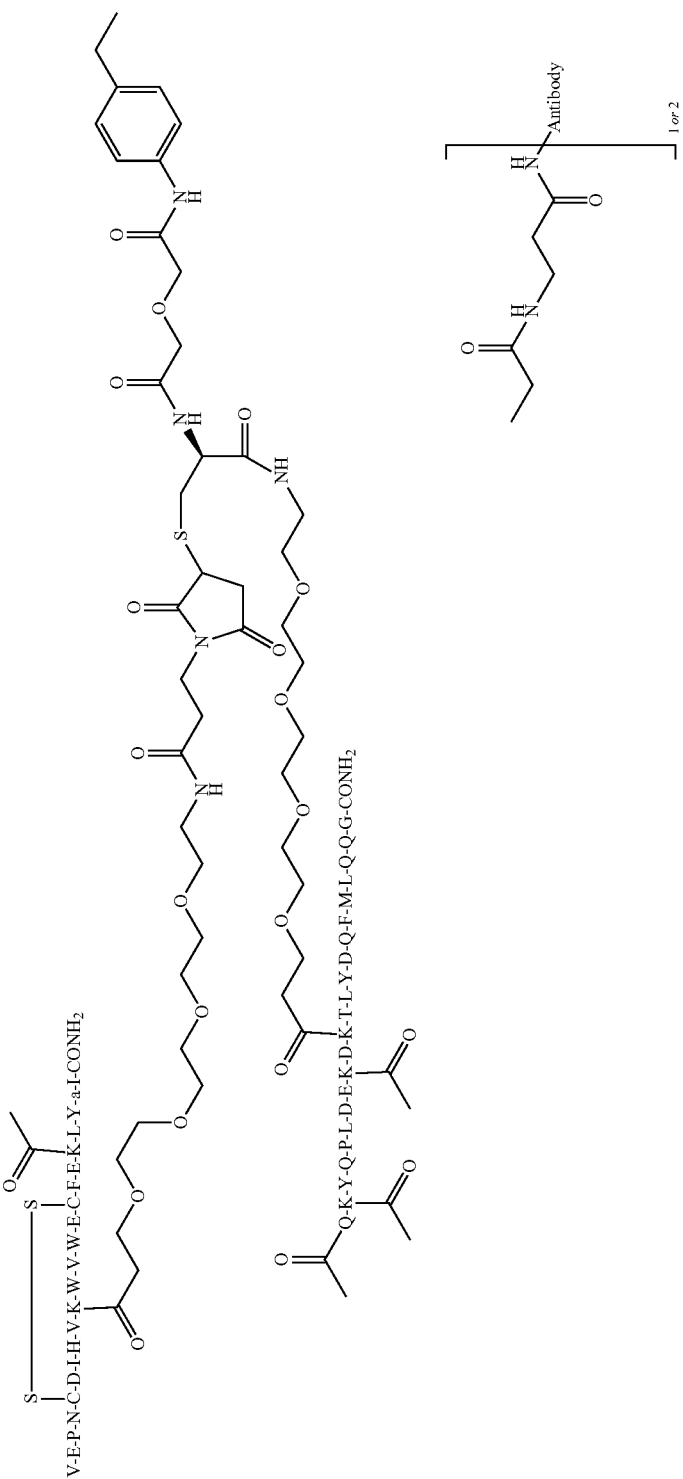 |

TABLE 12-continued

{[[Ang2-Peptide]-[Connector]-[VEGF-Peptide]]₁ₒᵣ₂}-[Antibody]

| Cmpd # | Chemical Structure |
|---|---|
| 6071 SEQ: 217 | Ac-V-E-P-N-C-D-I-H-V-K-W-V-W-E-C-F-E-K-N—[cyclobutane]—C(O)-Y-a-I-CONH₂ (disulfide bridge between the two C residues); connected via PEG linker through maleimide-cysteine to VEGF peptide Ac-Q-K-Y-Q-P-L-D-E-K-D-K-T-L-Y-D-Q-F-M-L-Q-Q-G-CONH₂ with 4-ethylaniline c TABLE 12-continued
{([Ang2-Peptide]-[Connector]-[VEGF-Peptide])$_{1 or 2}$}-[Antibody]
| Cmpd # | Chemical Structure |
|---|---|
| 6072 SEQ: 218 | 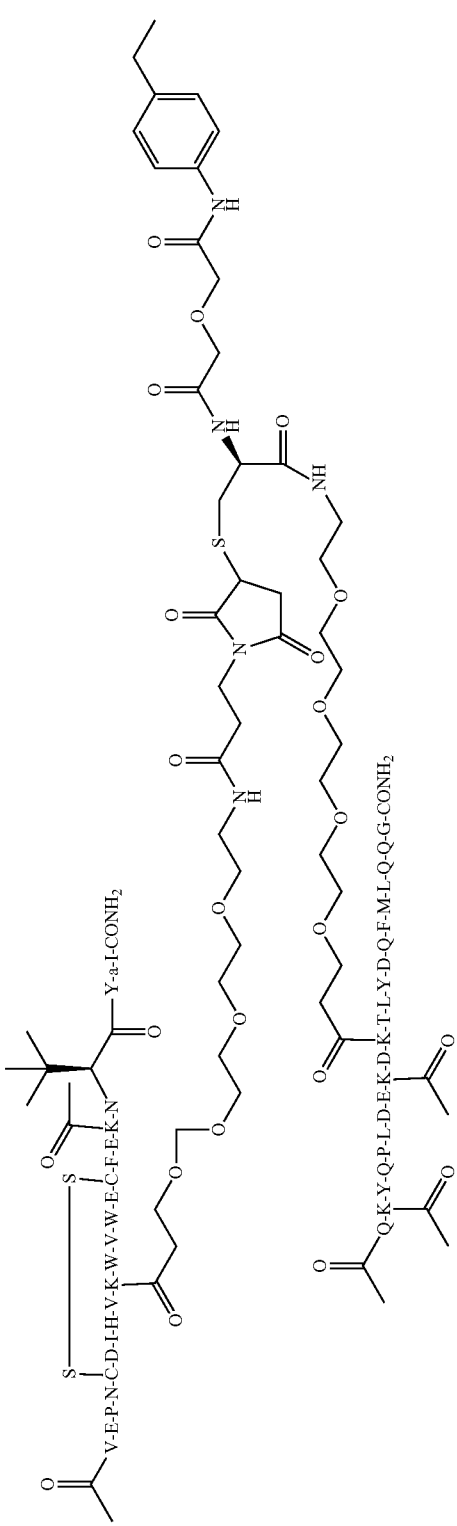 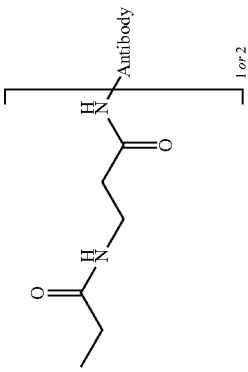 |

TABLE 12-continued
{[[Ang2-Peptide]-[Connector]-[VEGF-Peptide]]$_{1 or 2}$}-[Antibody]
| Cmpd # | Chemical Structure |
|---|---|
| 6073<br>SEQ: 210 | 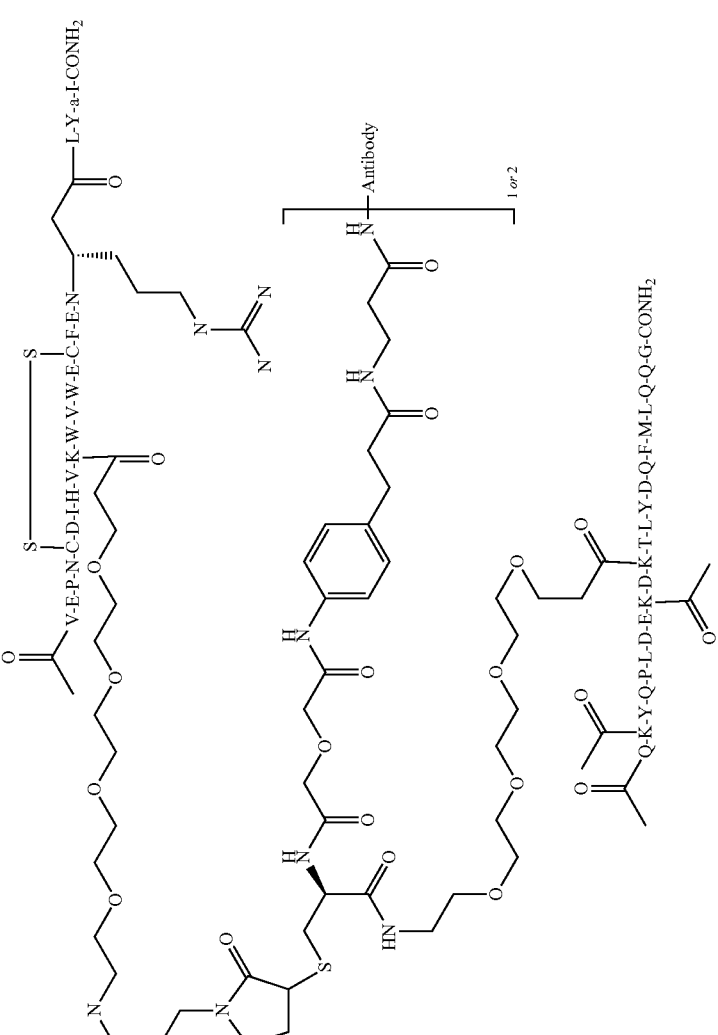 |

TABLE 12-continued
{[[Ang2-Peptide]-[Connector]-[VEGF-Peptide]]$_{1 or 2}$}-[Antibody]
| Cmpd # | Chemical Structure |
|---|---|
| 6074 SEQ: 73 | 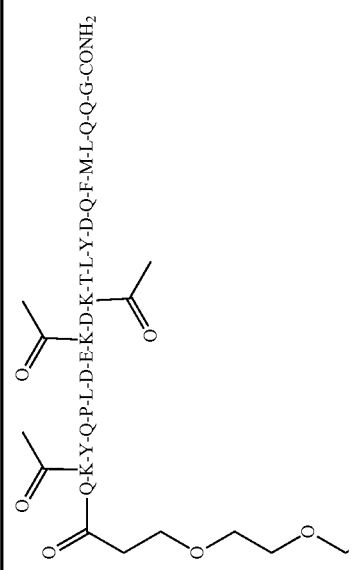 Q-K-Y-Q-P-L-D-E-K-D-K-T-L-Y-D-Q-F-M-L-Q-Q-G-CONH$_2$ |

TABLE 12-continued
{([Ang2-Peptide]-[Connector]-[VEGF-Peptide])_{1 or 2}}-[Antibody]
| Cmpd # | Chemical Structure |
|---|---|
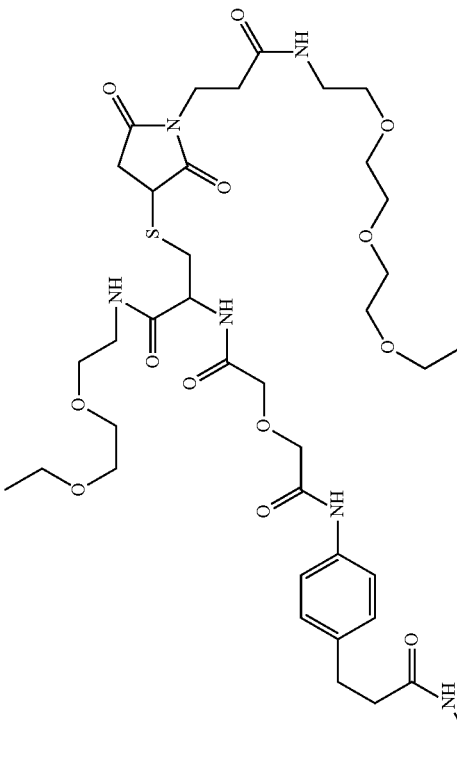

TABLE 13

Comparison of Compounds 2018, 4043, and 6053

|  | IC50 (nM) | | Mouse T½ (hr) | | Rat T½ (hr) | |
| --- | --- | --- | --- | --- | --- | --- |
|  | VEGF | Ang2 | VEGF | Ang2 | VEGF | Ang2 |
| Cmpd 2018 | 0.7 |  | 109 |  | 72 |  |
| Cmpd 4043 |  | 0.6 |  | ~90 |  | 95 |
| Cmpd 6053 | 0.7 | 0.6 | 92 | 92 | 97 | 111 |

TABLE 14

Comparison of Compounds 2018, 4043, and 6053

|  | IC50 (nM) | | Mouse T½ (hr) | |
| --- | --- | --- | --- | --- |
|  | VEGF | Ang2 | VEGF | Ang2 |
| Cmpd 6054 | 0.3 | 0.4 | 18 |  |
| Cmpd 6037 | 0.6 | 1.6 | [~36] |  |
| Cmpd 6044 | 0.7 | 0.9 | 43 | 82 |

The invention claimed is:

1. A compound of the formula: $R^1$-[VEGF-Peptide]-$R^2$ wherein [VEGF-Peptide] is a peptide having the sequence:

$V^1$-$E^2$-$P^3$—$N^4$—$C^5$-$D^6$-$I^7$—$H^8$—$V^9$-$M^{10}$-$W^{11}$—$V^{12}$—$W^{13}$—$X^{14}$—$C^{15}$—$F^{16}$-$E^{17}$-$R^{18}$—$X^{19}$—$X^{20}$—$X^{21}$—$X^{22}$—$X^{23}$ (SEQ ID NO:126) wherein $R^1$ is absent, $CH_3$, $C(O)CH_3$, $C(O)CH_2CH_3$, $C(O)CH_2CH_2CH_3$, $C(O)CH(CH_3)CH_3$, $C(O)CH_2CH_2CH_2CH_3$, $C(O)CH(CH_3)CH_2CH_3$, $C(O)C_6H_5$, $C(O)CH_2CH_2(CH_2CH_2O)_{1-5}Me$, amido-2-PEG, or an N-acyl or N-alkyl amino protecting group, a lipid fatty acid group or a carbohydrate;

$R^2$ is absent, OH, $NH_2$, $NH(CH_3)$, $NHCH_2CH_3$, $NHCH_2CH_2CH_3$, $NHCH(CH_3)CH_3$, $NHCH_2CH_2CH_2CH_3$, $NHCH(CH_3)CH_2CH_3$, $NHC_6H_5$, $NHCH_2CH_2OCH_3$, $NHOCH_3$, $NHOCH_2CH_3$, a carboxy protecting group, a lipid fatty acid group or a carbohydrate;

$X^{14}$ is E or V;

$X^{19}$ may be any hydrophobic amino acid residue, or D-isomer thereof;

$X^{20}$ may be absent, or may be any neutral, hydrophobic or aromatic amino acid or D-isomer thereof;

$X^{21}$ may be absent, or may be any positively charged residue or any aliphatic non-polar residue or D-isoform thereof;

$X^{22}$ may be absent, or may be selected from the group consisting of G, V, L, I, P, S, T, W, F, E, Kac, or D-isomers thereof;

$X^{23}$ may be absent, or is selected from the group consisting of G, A, I, L, Q, E, F, T, S, Y, and Kac and D-isomers thereof; and the peptide may be covalently linked to an antibody directly or via an intermediate linker connected to an N-terminus amino group or C-terminus carboxyl group of the peptide or the side chain of a linking residue selected from the group consisting of K, R, Y, C, T, S, homocysteine, homoserine, Dap, and Dab; where the linking residue is at one of residue positions 1, 2, 3, 4, 9, 10, 12, 14, 17 or the C-terminus residue; or a pharmaceutically acceptable salt thereof.

2. The compound or salt thereof according to claim 1, wherein the [VEGF-Peptide] comprises a sequence selected from the group consisting of SEQ ID NOs: 35-106, 192-197, and 211-215.

3. The compound or salt thereof according to claim 1, wherein the $R^1$-[VEGF-Peptide]-$R^2$ comprises the formula (SEQ ID NO:195):

V-E-P—N—C-D-I—H—V—K—W—V—W-E-C—F-E-R-L-Y-(D-Ala)-(D-Leu), and wherein K at position 10 is the linking residue.

4. The compound or salt thereof according to claim 1, wherein a linking residue is present, and wherein a linear or branched linker is covalently linked to the side chain of the linking residue.

5. The compound or salt thereof according to claim 4, wherein the linker comprises the formula Linker or Linker', and Linker is of the formula: -[Connector]-X-(Recognition Group Y)—Z, or —X-(Recognition Group Y)—Z—, and Linker' is of the formula: -[Connector]-X-(Recognition group Y)—Z', or —X-(Recognition Group Y)—Z'—, wherein:

[Connector] is present where the linker is branched, and where present is covalently linked to the linking residue, and one or more additional Active Molecules, X is a biologically compatible connecting chain including any atom selected from the group consisting of C, H, N, O, P, S, F, Cl, Br, and I, and may comprise a polymer or block co-polymer, and is covalently linked to the linking residue where the linker is linear, (Recognition Group Y) is an optionally present recognition group comprising the optionally substituted structure:

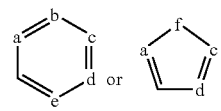

wherein a, b, c, d, and e are independently carbon or nitrogen; f is carbon, nitrogen, oxygen, or sulfur; (Recognition Group is attached to X and Z independently at any two ring positions of sufficient valence; and no more than four of a, b, c, d, e, or f are simultaneously nitrogen and preferably a, b, c, d, and e in the ring structure are each carbon;
and wherein Z if present has the structure:

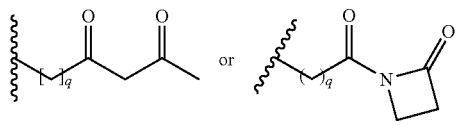

and wherein Z' if present has the structure:

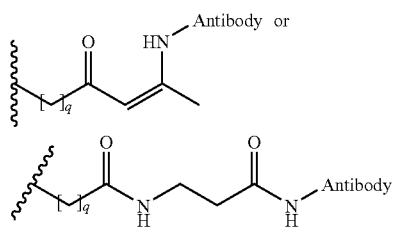

wherein q=0–5 and Antibody-N— if present is a covalent bond to a side chain in a combining site of an antibody.

6. The compound or salt thereof according to claim 5, wherein X-(Recognition Group Y) is

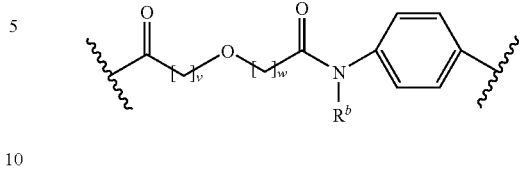

wherein v and w are selected such that the backbone length of X is 6-12 atoms, and Rb is hydrogen, substituted or unsubstituted $C_{1-10}$ alkyl, substituted or unsubstituted $C_{3-7}$ cycloalkyl $C_{1-6}$ alkyl, or substituted or unsubstituted aryl $C_{1-6}$ alkyl, v=1 or 2; w=1 or 2; and Rb is preferably hydrogen.

7. The compound or salt thereof according to claim 5, wherein the linker is linear and the [Connector] is absent, wherein the compound is selected from the group consisting of Compounds 1001-1040, 1042-1043, 1045-1050, 1052-1053, 1071, and 1079; where Z is present,
and selected from the group consisting of Compounds 2001-2040, 2042-2043, 2045-2050, 2052-2054, 2071, and 2079; where Z' is present.

8. A compound according to claim 1, comprising the formula of Compound 2018:

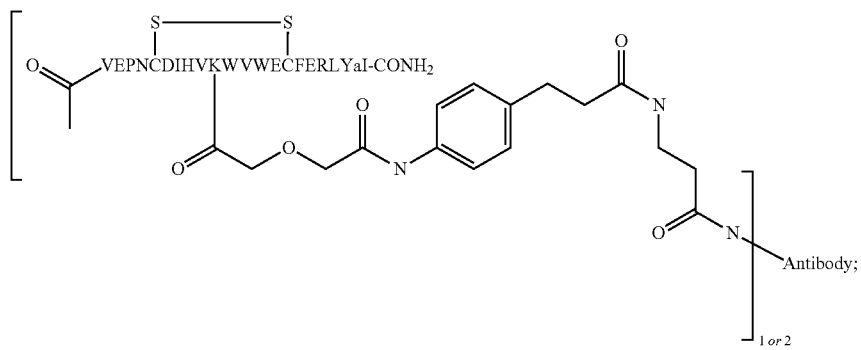

or a pharmaceutically acceptable salt thereof.

9. A compound comprising the formula:

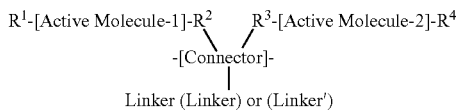

wherein [Active Molecule-1] is a [VEGF-Peptide] according to claim 1, and [Connector] is covalently bonded to both [VEGF-Peptide] and [Active Molecule-2] and [Connector] is also covalently linked to the Linker or Linker'; or a pharmaceutically acceptable salt thereof.

10. The compound or salt thereof according to claim 9, wherein [Connector] comprises the formula: -[Active Molecule-1-Spacer]-[Branch]-[Active Molecule-2-Spacer]-, and wherein [Active Molecule-1-Spacer] and [Active Molecule-2-Spacer] are each independently a biologically compatible polymer, block copolymer C, H, N, O, P, S, halogen or a salt thereof, alkyl, alkenyl, alkynyl, oxoalkyl, oxoalkenyl, oxoalkynyl, aminoalkyl, aminoalkenyl, aminoalkynyl, sulfoalkyl, sulfoalkenyl, sulfoalkynyl, phosphoalkyl, phosphoalkenyl, or phosphoalkynyl group, covalently bonded to [Branch], and [Branch] is molecule with at least three reactive groups, and [Active Molecule-1-Spacer] is covalently linked to [Branch] and to the [Active Molecule-1], and [Active Molecule-2-Spacer] is covalently linked to [Branch] and to the [Active Molecule-2].

11. The compound or salt thereof according to claim 10, wherein [Branch] is a chemical moiety comprising three orthogonal reactive groups, and is selected from the group consisting of: a cysteine branch, diaminopropionic acid based branch, diaminobutanoic acid based branch, ornithine based branch, lysine based branch, homocysteine branch, bismaleimide branch, and maleimide-acid branch, and derivitaves and homologs thereof, and the following structures:
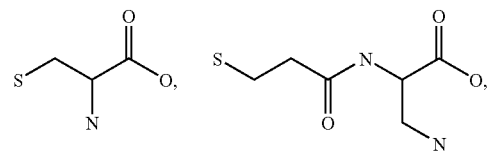
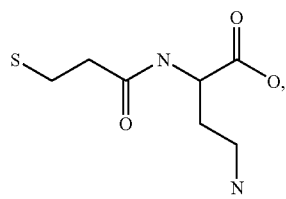
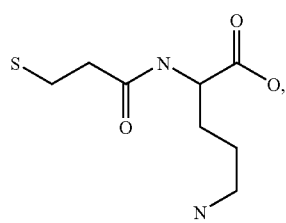
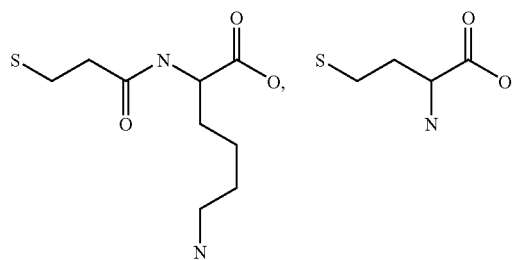
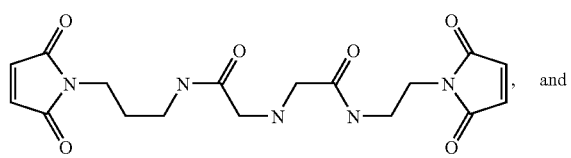
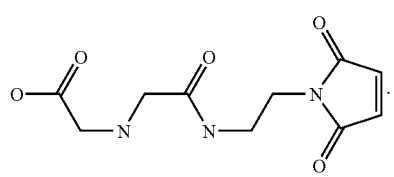
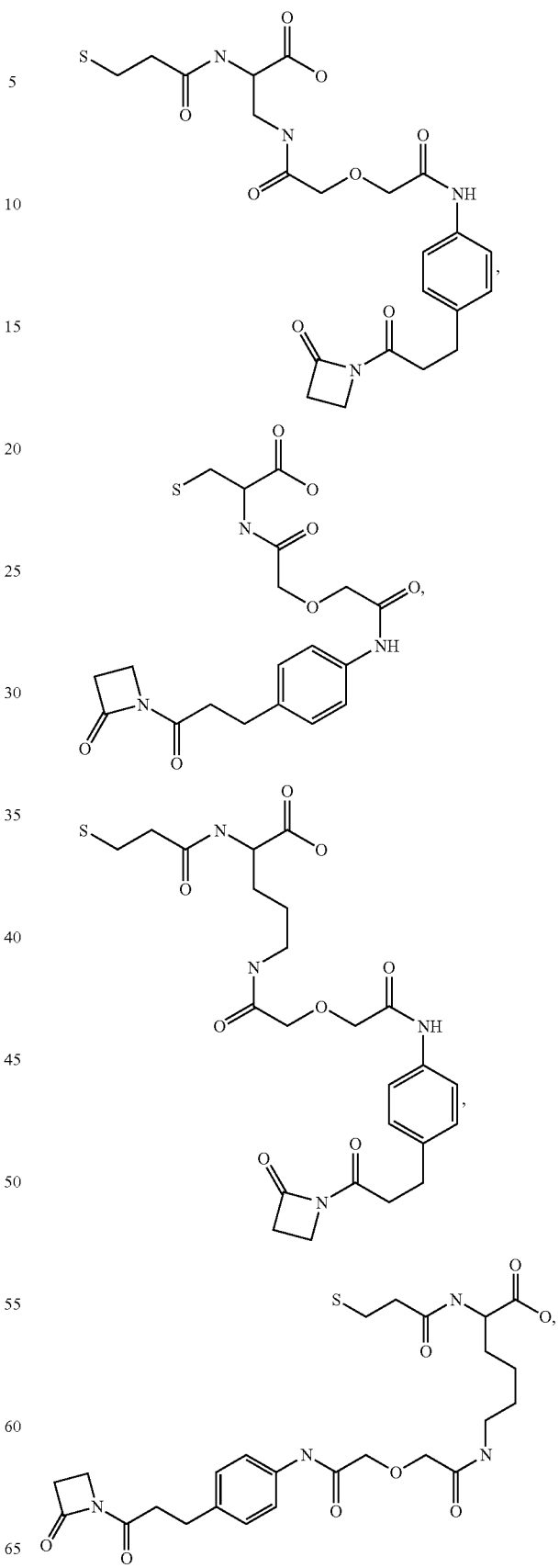
12. The compound or salt thereof according to claim 11, wherein [Branch]-Linker is selected from the group consisting of:

-continued

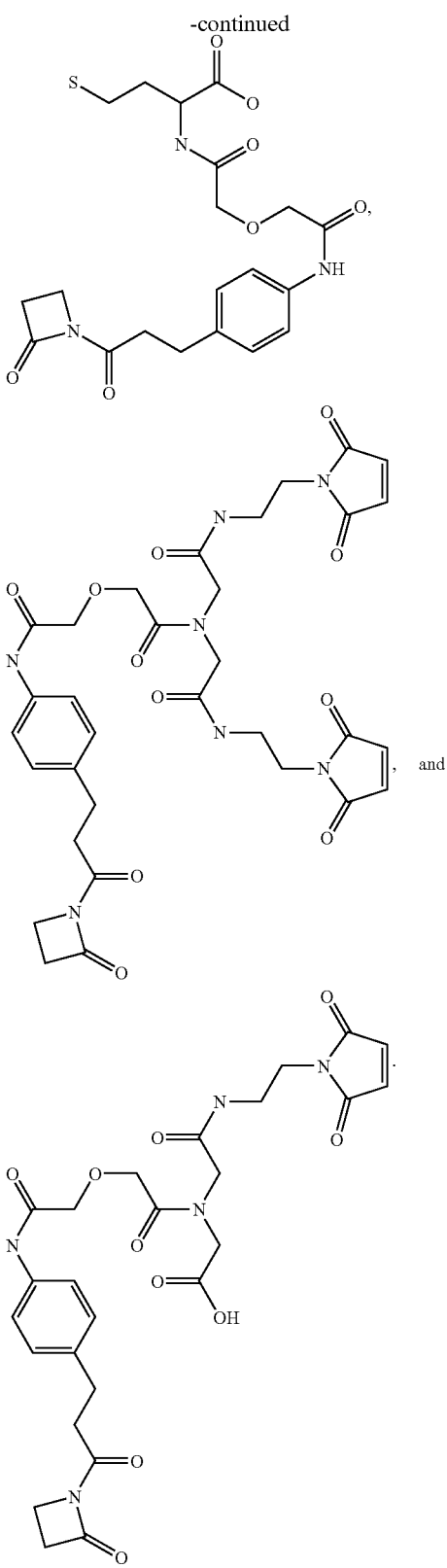

13. The compound or salt thereof according to claim 9, wherein [Active Molecule 2] is an Ang-2 binding peptide of the formula:

R³-[Ang2-peptide]-R⁴ wherein R³ is absent, CH₃, C(O) CH₃, C(O)CH₂CH₃, C(O)CH₂CH₂CH₃, C(O)CH(CH₃) CH₃, C(O)CH₂CH₂CH₂CH₃, C(O)CH(CH₃)CH₂CH₃, C(O)C₆H₅, C(O)CH₂CH₂(CH₂CH₂O)₁₋₅Me, amido-2-PEG, an N-acyl or N-alkyl amino protecting group, a lipid fatty acid group or a carbohydrate; and R⁴ is absent, OH, NH₂, NH(CH₃), NHCH₂CH₃, NHCH₂CH₂CH₃, NHCH(CH₃)CH₃, NHCH₂CH₂CH₂CH₃, NHCH(CH₃)CH₂CH₃, NHC₆H₅, NHCH₂CH₂OCH₃, NHOCH₃, NHOCH₂CH₃, a carboxy protecting group, a lipid fatty acid group or a carbohydrate, and wherein [Ang2-Peptide] comprises a sequence: Q¹X²Y³Q⁴X⁵L⁶D⁷E⁸X⁹D¹⁰X¹¹X¹²X¹³X¹⁴D¹⁵X¹⁶F¹⁷M¹⁸X¹⁹Q²⁰Q²¹G²² (SEQ ID NO:107), wherein X² is selected from the group consisting of K, N, R, H, Kac, Nick, and CbcK, and X⁵ is selected from the group consisting of P, hP, dhP, and BnHP, and X⁹ is selected from the group consisting of L, I, ThA, and Kac, and X¹¹ is selected from the group consisting of Q, N, C, K, Kac, Dab, and Dap, and X¹² is selected from the group consisting of L, HL, Nva, I, HchA, HF, and ThA, and X¹³ is selected from the group consisting of L, HL, Nva, I, HchA, HF, and ThA, and X¹⁴ is selected from the group consisting of aromatic residues, and X¹⁶ is selected from the group consisting of Q and N, and X¹⁹ is selected from the group consisting of L, and I, and [Ang-2-Peptide] is covalently linked to [Connector] through a nucleophilic side chain or N-terminus amino group or C-terminus carboxyl group of an Ang2-linking residue, the Ang2-linking residue being selected from the group consisting of K, R, Y, C, T, S, homologs of lysine, homocysteine, homoserine, Dap, Dab, the N-terminus residue and the C-terminus residue, and wherein one of Q¹, E⁸, X⁹, X¹¹, X¹², D¹⁵, X¹⁶, M¹⁸, X¹⁹ and G²² is substituted with the Ang2-linking residue.

14. The compound or salt thereof according to claim 13, wherein the [Ang2-peptide] comprises a sequence selected from the group consisting of: SEQ ID NOs:137-191.

15. The compound or salt thereof according to claim 14, wherein R¹-[Ang-peptide]-R² is (SEQ ID NO:153):

{C(O)CH₃}-Q-(Kac)-Y-Q-P-L-D-E-(Kac)-D-K-T-L-Y-D-Q-F-M-L-Q-Q-G-{NH₂} and K at position 11 is the Ang2-linking residue covalently linked to the [Connector].

16. The compound or salt thereof according to claim 9, wherein [VEGF-Peptide] is covalently linked to [Connector] through a nucleophilic side chain or the N-terminus amino group or C-terminus carboxyl group of an VEGF-linking residue, the VEGF-linking residue being selected from the group consisting of K, R, Y, C, T, S, homologs of lysine, homocysteine, homoserine, Dap, Dab, the N-terminus residue or C-terminus residue.

17. The compound or salt thereof according to claim 9, wherein the compound is selected from the group consisting of: Compound 5011, 5018, 5022, 5032 to 5064 and 5074 or a pharmaceutically acceptable salt thereof.

18. The compound or salt thereof according to claim 16, wherein the linking residue is covalently linked to the combining site of an antibody, and the compound is selected from the group consisting of: compounds 6011, 6022, 6032-6069, and 6074.

19. The compound according to claim 1, comprising the formula of Compound 6053 (including SEQ ID NO:78 and SEQ ID NO:153):

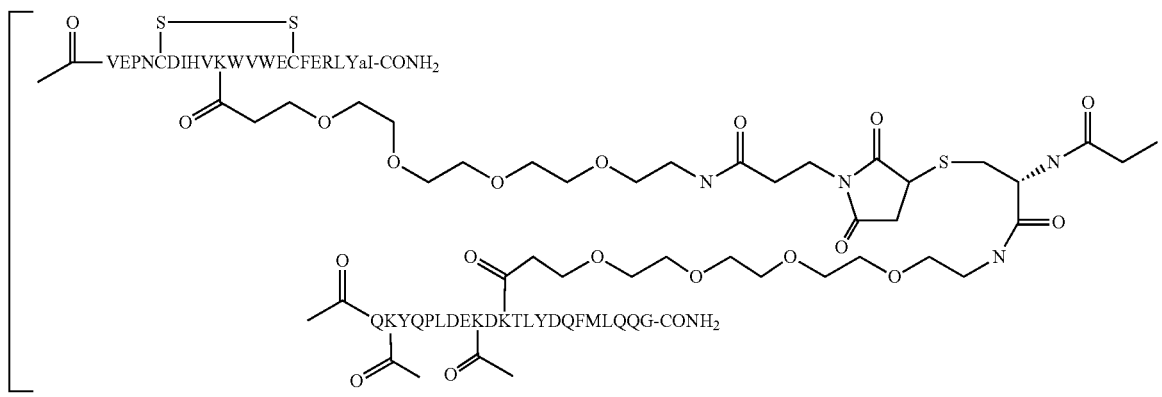

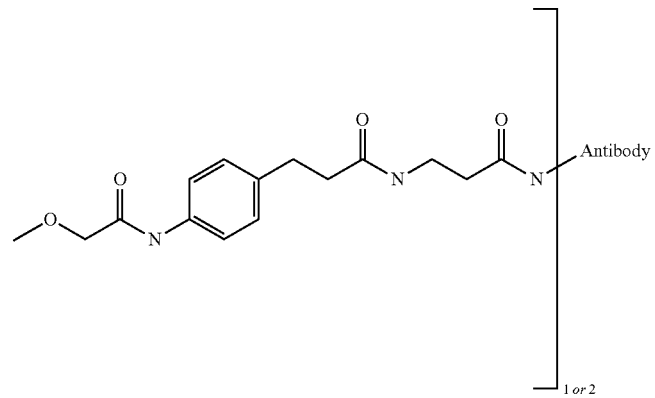

and pharmaceutically acceptable salts thereof.

20. The compound or salt thereof according to claim 19, wherein the Antibody is a full-length antibody, Fab, Fab', F(ab')$_2$, F$_v$, dsF$_v$, scF$_v$, V$_H$, V$_L$, diabody, minibody comprising V$_H$ and V$_L$ domains from h38c2, or full length antibody comprising the V$_H$ and V$_L$ domains from h38c2 and a constant domain selected from the group consisting of IgG1, IgG2, IgG3, and IgG4.

21. A pharmaceutical composition comprising a therapeutically effective amount of the compound or salt according to claim 19, and a pharmaceutically acceptable carrier.

22. The compound or salt thereof according to claim 1 wherein the [VEGF-Peptide] includes a sequence homologous to: V-E-P—N—C-D-I—H—V-M-W—V—W-E-C—F-E-R-L-Y-(D-Ala)-(D-Leu) (SEQ ID NO:78).

23. The compound or salt thereof according to claim 1, wherein R$^1$ is C(O)CH$_3$.

24. The compound or salt thereof according to claim 1, wherein R$^2$ is NH$_2$.

25. A compound of the formula: R$^1$-[VEGF-Peptide]-R$^2$ wherein [VEGF-Peptide] is a peptide having the sequence:
V$^1$-E$^2$-P$^3$—N$^4$—C$^5$-D$^6$-I$^7$—H$^8$—V$^9$—K$^{10}$—W$^{11}$—V$^{12}$—W$^{13}$—X$^{14}$—C$^{15}$—F$^{16}$-E$^{17}$-R$^{18}$—X$^{19}$—X$^{20}$—X$^{21}$—X$^{22}$—X$^{23}$ (SEQ ID NO:126) wherein R$^1$ is absent, CH$_3$, C(O)CH$_3$, C(O)CH$_2$CH$_3$, C(O)CH$_2$CH$_2$CH$_3$, C(O)CH(CH$_3$)CH$_3$, C(O)CH$_2$CH$_2$CH$_2$CH$_3$, C(O)CH(CH$_3$)CH$_2$CH$_3$, C(O)C$_6$H$_5$, C(O)CH$_2$CH$_2$(CH$_2$CH$_2$O)$_{1-5}$Me, amido-2-PEG, or an N-acyl or N-alkyl amino protecting group, a lipid fatty acid group or a carbohydrate;

R$^2$ is absent, OH, NH$_2$, NH(CH$_3$), NHCH$_2$CH$_3$, NHCH$_2$CH$_2$CH$_3$, NHCH(CH$_3$)CH$_3$, NHCH$_2$CH$_2$CH$_2$CH$_3$, NHCH(CH$_3$)CH$_2$CH$_3$, NHC$_6$H$_5$, NHCH$_2$CH$_2$OCH$_3$, NHOCH$_3$, NHOCH$_2$CH$_3$, a carboxy protecting group, a lipid fatty acid group or a carbohydrate;

X$^{14}$ is E or V;

X$^{19}$ may be any hydrophobic amino acid residue, or D-isomer thereof;

X$^{20}$ may be absent, or may be any neutral, hydrophobic or aromatic amino acid or D-isomer thereof;

X$^{21}$ may be absent, or may be any positively charged residue or any aliphatic non-polar residue or D-isoform thereof;

X$^{22}$ may be absent, or may be selected from the group consisting of G, V, L, I, P, S, T, W, F, E, Kac, or D-isomers thereof;

X$^{23}$ may be absent, or is selected from the group consisting of G, A, I, L, Q, E, F, T, S, Y, and Kac and D-isomers thereof; and the peptide may be covalently linked to an antibody directly or via an intermediate linker connected to the side chain of a linking residue located at position 10, selected from the group consisting of K, R, Y, C, T, S, homocysteine, homoserine, Dap, and Dab; or a pharmaceutically acceptable salt thereof.

26. A compound of the formula: $R^1$-[VEGF-Peptide]-$R^2$ wherein [VEGF-Peptide] is a peptide having the sequence:

V-E-P—N—C-D-I—H—V-M-W—V—W-E-C—F-E-R-L-Y-(D-Ala)-(D-Leu) (SEQ ID NO:78) wherein $R^1$ is absent, $CH_3$, $C(O)CH_3$, $C(O)CH_2CH_3$, $C(O)CH_2CH_2CH_3$, $C(O)CH(CH_3)CH_3$, $C(O)CH_2CH_2CH_2CH_3$, $C(O)CH(CH_3)CH_2CH_3$, $C(O)C_6H_5$, $C(O)CH_2CH_2(CH_2CH_2O)_{1-5}Me$, amido-2-PEG, or an N-acyl or N-alkyl amino protecting group, a lipid fatty acid group or a carbohydrate;

$R^2$ is absent, OH, $NH_2$, $NH(CH_3)$, $NHCH_2CH_3$, $NHCH_2CH_2CH_3$, $NHCH(CH_3)CH_3$, $NHCH_2CH_2CH_2CH_3$, $NHCH(CH_3)CH_2CH_3$, $NHC_6H_5$, $NHCH_2CH_2OCH_3$, $NHOCH_3$, $NHOCH_2CH_3$, a carboxy protecting group, a lipid fatty acid group or a carbohydrate; and the peptide may be covalently linked to an antibody directly or via an intermediate linker connected to an N-terminus amino group or C-terminus carboxyl group of the peptide or the side chain of a linking residue selected from the group consisting of K, R, Y, C, T, S, homocysteine, homoserine, Dap, and Dab; where the linking residue is at one of residue positions 1, 2, 3, 4, 9, 10, 12, 14, 17 or the C-terminus residue; or a pharmaceutically acceptable salt thereof.

27. A compound comprising the formula of Compound 6053 (SEQ ID NO:78 and SEQ ID NO:153) or a pharmaceutically acceptable salt thereof.

28. A compound comprising the formula of Compound 6053 (including SEQ ID NO:78 and SEQ ID NO:153):

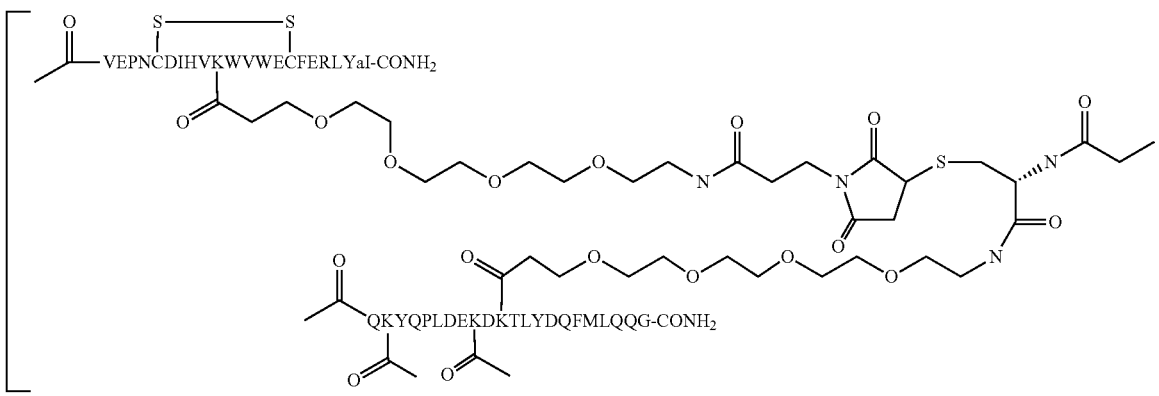

wherein the antibody comprises SEQ ID NO:1 and SEQ ID NO:2; and pharmaceutically acceptable salts thereof.

29. The compound or salt thereof according to claim 8, wherein the antibody comprises SEQ ID NO:1 and SEQ ID NO:2.

30. The compound or salt thereof according to claim 18, wherein the antibody comprises SEQ ID NO:1 and SEQ ID NO:2.

31. The compound or salt thereof according to claim 19, wherein the antibody comprises SEQ ID NO:1 and SEQ ID NO:2.

32. The compound or salt thereof according to claim 17, wherein the compound is selected from the group consisting of Compounds 5053, 5060, 5061 and 5062; or a pharmaceutically acceptable salt thereof.

33. The compound or salt thereof according to claim 18, wherein the compound is selected from the group consisting of Compounds 6053, 6060, 6061 and 6062; or a pharmaceutically acceptable salt thereof.

* * * * *

SEQUENCE LISTING

<160> NUMBER OF SEQ ID NOS: 218

<210> SEQ ID NO 1
<211> LENGTH: 219
<212> TYPE: PRT
<213> ORGANISM: Homo sapiens

<400> SEQUENCE: 1

```
Glu Leu Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu His Thr
            20                  25                  30

Tyr Gly Ser Pro Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Val Tyr Phe Cys Ser Gln Gly
                85                  90                  95

Thr His Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 2
<211> LENGTH: 448
<212> TYPE: PRT
<213> ORGANISM: Homo sapiens

<400> SEQUENCE: 2

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asn Tyr
            20                  25                  30

Trp Met Ser Trp Val Arg Gln Ser Pro Glu Lys Gly Leu Glu Trp Val
        35                  40                  45

Ser Glu Ile Arg Leu Arg Ser Asp Asn Tyr Ala Thr His Tyr Ala Glu
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Gly Ile Tyr
                85                  90                  95

Tyr Cys Lys Thr Tyr Phe Tyr Ser Phe Ser Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 3
<211> LENGTH: 165
<212> TYPE: PRT
<213> ORGANISM: Homo sapiens

<400> SEQUENCE: 3

Ala Pro Met Ala Glu Gly Gly Gln Asn His His Glu Val Val Lys
1               5                   10                  15

Phe Met Asp Val Tyr Gln Arg Ser Tyr Cys His Pro Ile Glu Thr Leu
                20                  25                  30

Val Asp Ile Phe Gln Glu Tyr Pro Asp Glu Ile Glu Tyr Ile Phe Lys
            35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Asn Pro Cys Gly Pro Cys Ser Glu Arg Arg Lys His Leu Phe
        115                 120                 125

Val Gln Asp Pro Gln Thr Cys Lys Cys Ser Cys Lys Asn Thr Asp Ser
130                 135                 140

Arg Cys Lys Ala Arg Gln Leu Glu Leu Asn Glu Arg Thr Cys Arg Cys
145                 150                 155                 160

Asp Lys Pro Arg Arg
                165

<210> SEQ ID NO 4
<211> LENGTH: 336
<212> TYPE: DNA
<213> ORGANISM: Mouse

<400> SEQUENCE: 4
gacgttgtga tgacccagac tccactctcc ctgcctgtcc gtcttggaga tcaagcctcc      60
atctcttgca gatctagtca gagccttcta cacacttatg gaagcccta tttaaattgg     120 tacctgcaga agccaggcca gtcgccaaag ctcctgatct acaaagtttc caaccgcttt     180
tctggggtcc cagacaggtt cagtggcagt ggatcaggga cagatttcac actcaggatc     240
agcagagtgg aggctgagga tctgggagtt tatttctgct ctcaaggtac acatcttccg     300
tacacgttcg gaggggggac caaactggaa atcaaa                              336

<210> SEQ ID NO 5
<211> LENGTH: 351
<212> TYPE: DNA
<213> ORGANISM: Mouse

<400> SEQUENCE: 5
gaggtgaaac tggtggagtc tggaggaggc ttggtgcaac tggaggaac catgaaactc      60 tcctgtgaaa tttctggatt aactttcaga aattattgga tgtcttgggt ccgccagtct    120
ccagagaagg ggcttgagtg ggttgctgaa attagattga gatctgataa ttatgcaaca    180
cattatgcgg agtctgtgaa agggaagttc accatctcaa gagatgattc caaaagtcgt    240
ctctacctgc aaatgaacag cttaagaact gaagacactg gaatttatta ctgtaaaacc    300

```
tattttttact cattttctta ctggggccaa gggactctgg tcactgtctc t           351
```

<210> SEQ ID NO 6
<211> LENGTH: 287
<212> TYPE: DNA
<213> ORGANISM: Human

<400> SEQUENCE: 6

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctcc                 287
```

<210> SEQ ID NO 7
<211> LENGTH: 38
<212> TYPE: DNA
<213> ORGANISM: Homo sapiens

<400> SEQUENCE: 7

```
gctcactttc ggcggaggga ccaaggtgga gatcaaac                            38
```

<210> SEQ ID NO 8
<211> LENGTH: 296
<212> TYPE: DNA
<213> ORGANISM: Homo sapiens

<400> SEQUENCE: 8

```
gaggtgcagc tgttggagtc tgggggaggc ttggtacagc ctggggggtc cctgagactc    60
tcctgtgcag cctctggatt cacctttagc agctatgcca tgagctgggt ccgccaggct   120
ccagggaagg ggctgagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtat attactgtgc gaaaga       296
```

<210> SEQ ID NO 9
<211> LENGTH: 48
<212> TYPE: DNA
<213> ORGANISM: Homo sapiens

<400> SEQUENCE: 9

```
actactttga ctactggggc caaggaaccc tggtcaccgt ctcctcag                 48
```

<210> SEQ ID NO 10
<211> LENGTH: 48
<212> TYPE: DNA
<213> ORGANISM: Homo sapiens

<400> SEQUENCE: 10

```
actactttga ctactggggc cagggaaccc tggtcaccgt ctcctcag                 48
```

<210> SEQ ID NO 11
<211> LENGTH: 48
<212> TYPE: DNA
<213> ORGANISM: Homo sapiens

<400> SEQUENCE: 11

```
gctactttga ctactggggc caagggaccc tggtcaccgt ctcctcag                 48
```

<210> SEQ ID NO 12

```
<211> LENGTH: 54
<212> TYPE: DNA
<213> ORGANISM: Artificial Sequence
<220> FEATURE:
<223> OTHER INFORMATION: Synthetic

<400> SEQUENCE: 12
gaggaggagg aggagggccc aggcggccga gctccagatg acccagtctc tcca            54

<210> SEQ ID NO 13
<211> LENGTH: 68
<212> TYPE: DNA
<213> ORGANISM: Artificial Sequence
<220> FEATURE:
<223> OTHER INFORMATION: Synthetic

<400> SEQUENCE: 13
gagctccaga tgacccagtc tccatcctcc ctgtctgcat ctgtaggtga ccgcgtcacc      60
atcacttg                                                              68

<210> SEQ ID NO 14
<211> LENGTH: 69
<212> TYPE: DNA
<213> ORGANISM: Artificial Sequence
<220> FEATURE:
<223> OTHER INFORMATION: Synthetic

<400> SEQUENCE: 14
attcagatat gggctgccat aagtgtgcag gaggctctga ctggagcggc aagtgatggt      60
gacgcggtc                                                             69

<210> SEQ ID NO 15
<211> LENGTH: 66
<212> TYPE: DNA
<213> ORGANISM: Artificial Sequence
<220> FEATURE:
<223> OTHER INFORMATION: Synthetic

<400> SEQUENCE: 15
tatggcagcc catatctgaa ttggtatctc cagaaaccag gccagtctcc taagctcctg      60
atctat                                                                66

<210> SEQ ID NO 16
<211> LENGTH: 65
<212> TYPE: DNA
<213> ORGANISM: Artificial Sequence
<220> FEATURE:
<223> OTHER INFORMATION: Synthetic

<400> SEQUENCE: 16
ctgaaacgtg atgggacacc actgaaacga ttggacactt tatagatcag gagcttagga     60
gactg                                                                 65

<210> SEQ ID NO 17
<211> LENGTH: 90
<212> TYPE: DNA
<213> ORGANISM: Artificial Sequence
<220> FEATURE:
<223> OTHER INFORMATION: Synthetic

<400> SEQUENCE: 17
agtggtgtcc catcacgttt cagtggcagt ggttctggca cagatttcac tctcaccatc     60
agcagtctgc aacctgaaga ttttgcagtg                                      90
```

```
<210> SEQ ID NO 18
<211> LENGTH: 87
<212> TYPE: DNA
<213> ORGANISM: Artificial Sequence
<220> FEATURE:
<223> OTHER INFORMATION: Synthetic

<400> SEQUENCE: 18
gatctccacc ttggtccctc cgccgaaagt ataagggagg tgggtgccct gactacagaa      60
gtacactgca aaatcttcag gttgcag                                         87

<210> SEQ ID NO 19
<211> LENGTH: 48
<212> TYPE: DNA
<213> ORGANISM: Artificial Sequence
<220> FEATURE:
<223> OTHER INFORMATION: Synthetic

<400> SEQUENCE: 19
gacagatggt gcagccacag ttcgtttgat ctccaccttg gtccctcc                   48

<210> SEQ ID NO 20
<211> LENGTH: 48
<212> TYPE: DNA
<213> ORGANISM: Artificial Sequence
<220> FEATURE:
<223> OTHER INFORMATION: Synthetic

<400> SEQUENCE: 20
gctgcccaac cagccatggc cgaggtgcag ctggtggagt ctggggga                   48

<210> SEQ ID NO 21
<211> LENGTH: 79
<212> TYPE: DNA
<213> ORGANISM: Artificial Sequence
<220> FEATURE:
<223> OTHER INFORMATION: Synthetic

<400> SEQUENCE: 21
gaggtgcagc tggtggagtc tggcggtggc ttggtacagc ctggcggttc cctgcgcctc      60
tcctgtgcag cctctggct                                                  79

<210> SEQ ID NO 22
<211> LENGTH: 81
<212> TYPE: DNA
<213> ORGANISM: Artificial Sequence
<220> FEATURE:
<223> OTHER INFORMATION: Synthetic

<400> SEQUENCE: 22
ctccaggccc ttctctggag actggcggac ccagctcatc caatagttgc taaaggtgaa      60
gccagaggct gcacaggaga g                                               81

<210> SEQ ID NO 23
<211> LENGTH: 81
<212> TYPE: DNA
<213> ORGANISM: Artificial Sequence
<220> FEATURE:
<223> OTHER INFORMATION: Synthetic

<400> SEQUENCE: 23
tctccagaga agggcctgga gtgggtctca gagattcgtc tgcgcagtga caactacgcc      60
acgcactatg cagagtctgt c                                               81
```

```
<210> SEQ ID NO 24
<211> LENGTH: 73
<212> TYPE: DNA
<213> ORGANISM: Artificial Sequence
<220> FEATURE:
<223> OTHER INFORMATION: Synthetic

<400> SEQUENCE: 24
cagatacagc gtgttcttgg aattgtcacg ggagatggtg aagcggccct tgacagactc      60
tgcatagtgc gtg                                                         73

<210> SEQ ID NO 25
<211> LENGTH: 76
<212> TYPE: DNA
<213> ORGANISM: Artificial Sequence
<220> FEATURE:
<223> OTHER INFORMATION: Synthetic

<400> SEQUENCE: 25
caattccaag aacacgctgt atctgcaaat gaacagcctg cgcgccgagg acacgggcat      60
ttattactgt aaaacg                                                      76

<210> SEQ ID NO 26
<211> LENGTH: 79
<212> TYPE: DNA
<213> ORGANISM: Artificial Sequence
<220> FEATURE:
<223> OTHER INFORMATION: Synthetic

<400> SEQUENCE: 26
tgaggagacg gtgaccaggg tgccctggcc ccagtagctg aaactgtaga agtacgtttt      60
acagtaataa atgcccgtg                                                   79

<210> SEQ ID NO 27
<211> LENGTH: 48
<212> TYPE: DNA
<213> ORGANISM: Artificial Sequence
<220> FEATURE:
<223> OTHER INFORMATION: Synthetic

<400> SEQUENCE: 27
gaccgatggg cccttggtgg aggctgagga gacggtgacc agggtgcc                   48

<210> SEQ ID NO 28
<211> LENGTH: 22
<212> TYPE: DNA
<213> ORGANISM: Artificial Sequence
<220> FEATURE:
<223> OTHER INFORMATION: Synthetic

<400> SEQUENCE: 28
aagacagcta tcgcgattgc ag                                               22

<210> SEQ ID NO 29
<211> LENGTH: 22
<212> TYPE: DNA
<213> ORGANISM: Artificial Sequence
<220> FEATURE:
<223> OTHER INFORMATION: Synthetic

<400> SEQUENCE: 29
ctattgccta cggcagccgc tg                                               22

<210> SEQ ID NO 30
```

```
<211> LENGTH: 48
<212> TYPE: DNA
<213> ORGANISM: Artificial Sequence
<220> FEATURE:
<223> OTHER INFORMATION: Synthetic

<400> SEQUENCE: 30
gaggaggagg aggaggagct cactccgagg tgcagctggt ggagtctg            48

<210> SEQ ID NO 31
<211> LENGTH: 24
<212> TYPE: DNA
<213> ORGANISM: Artificial Sequence
<220> FEATURE:
<223> OTHER INFORMATION: Synthetic

<400> SEQUENCE: 31
gcccccttat tagcgtttgc catc                                       24

<210> SEQ ID NO 32
<211> LENGTH: 72
<212> TYPE: DNA
<213> ORGANISM: Artificial Sequence
<220> FEATURE:
<223> OTHER INFORMATION: Synthetic

<400> SEQUENCE: 32
gaggaggagg aggagaagct tgttgctctg gatctctggt gcctacgggg agctccagat   60
gacccagtct cc                                                       72

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
gccatggctg gttgggcagc                                            20

<210> SEQ ID NO 34
<211> LENGTH: 19
<212> TYPE: PRT
<213> ORGANISM: Artificial Sequence
<220> FEATURE:
<223> OTHER INFORMATION: Synthetic

<400> SEQUENCE: 34

Val Glu Pro Asn Cys Asp Ile His Val Met Trp Glu Trp Glu Cys Phe
1               5                   10                  15

Glu Arg Leu

<210> SEQ ID NO 35
<211> LENGTH: 23
<212> TYPE: PRT
<213> ORGANISM: Artificial Sequence
<220> FEATURE:
<223> OTHER INFORMATION: Synthetic

<400> SEQUENCE: 35

Val Glu Pro Asn Cys Asp Ile His Val Met Trp Val Trp Glu Cys Phe
1               5                   10                  15

Glu Arg Leu Tyr Gly Gly Trp
            20
```

```
<210> SEQ ID NO 36
<211> LENGTH: 23
<212> TYPE: PRT
<213> ORGANISM: Artificial Sequence
<220> FEATURE:
<223> OTHER INFORMATION: Synthetic

<400> SEQUENCE: 36

Val Glu Pro Asn Cys Asp Ile His Val Met Trp Val Trp Val Cys Phe
1               5                   10                  15

Glu Arg Leu Phe Arg Glu Ala
            20

<210> SEQ ID NO 37
<211> LENGTH: 23
<212> TYPE: PRT
<213> ORGANISM: Artificial Sequence
<220> FEATURE:
<223> OTHER INFORMATION: Synthetic

<400> SEQUENCE: 37

Val Glu Pro Asn Cys Asp Ile His Val Met Trp Val Trp Val Cys Phe
1               5                   10                  15

Glu Arg Leu Phe Lys Glu Ala
            20

<210> SEQ ID NO 38
<211> LENGTH: 21
<212> TYPE: PRT
<213> ORGANISM: Artificial Sequence
<220> FEATURE:
<223> OTHER INFORMATION: Synthetic

<400> SEQUENCE: 38

Val Glu Pro Asn Cys Asp Ile His Val Met Trp Val Trp Val Cys Phe
1               5                   10                  15

Glu Arg Leu Met Lys
            20

<210> SEQ ID NO 39
<211> LENGTH: 23
<212> TYPE: PRT
<213> ORGANISM: Artificial Sequence
<220> FEATURE:
<223> OTHER INFORMATION: Synthetic

<400> SEQUENCE: 39

Val Glu Pro Asn Cys Asp Ile His Val Met Trp Val Trp Glu Cys Phe
1               5                   10                  15

Glu Arg Leu Tyr Arg Glu Leu
            20

<210> SEQ ID NO 40
<211> LENGTH: 23
<212> TYPE: PRT
<213> ORGANISM: Artificial Sequence
<220> FEATURE:
<223> OTHER INFORMATION: Synthetic

<400> SEQUENCE: 40

Val Glu Pro Asn Cys Asp Ile His Val Met Trp Val Trp Glu Cys Phe
1               5                   10                  15

Glu Arg Leu Tyr Gly Ile Phe
            20
```

```
<210> SEQ ID NO 41
<211> LENGTH: 20
<212> TYPE: PRT
<213> ORGANISM: Artificial Sequence
<220> FEATURE:
<223> OTHER INFORMATION: Synthetic

<400> SEQUENCE: 41

Val Glu Pro Asn Cys Asp Ile His Val Met Trp Val Trp Glu Cys Phe
1               5                   10                  15

Glu Arg Leu Tyr
            20

<210> SEQ ID NO 42
<211> LENGTH: 23
<212> TYPE: PRT
<213> ORGANISM: Artificial Sequence
<220> FEATURE:
<223> OTHER INFORMATION: Synthetic

<400> SEQUENCE: 42

Val Glu Pro Asn Cys Asp Ile His Val Met Trp Val Trp Glu Cys Phe
1               5                   10                  15

Glu Arg Leu Tyr Gly Trp Gly
            20

<210> SEQ ID NO 43
<211> LENGTH: 23
<212> TYPE: PRT
<213> ORGANISM: Artificial Sequence
<220> FEATURE:
<223> OTHER INFORMATION: Synthetic

<400> SEQUENCE: 43

Val Glu Pro Asn Cys Asp Ile His Val Met Trp Val Trp Val Cys Phe
1               5                   10                  15

Glu Arg Leu Tyr Gly Gly Gly
            20

<210> SEQ ID NO 44
<211> LENGTH: 23
<212> TYPE: PRT
<213> ORGANISM: Artificial Sequence
<220> FEATURE:
<223> OTHER INFORMATION: Synthetic

<400> SEQUENCE: 44

Val Glu Pro Asn Cys Asp Ile His Val Met Trp Val Trp Glu Cys Phe
1               5                   10                  15

Glu Arg Leu Tyr Gly Leu Tyr
            20

<210> SEQ ID NO 45
<211> LENGTH: 23
<212> TYPE: PRT
<213> ORGANISM: Artificial Sequence
<220> FEATURE:
<223> OTHER INFORMATION: Synthetic

<400> SEQUENCE: 45

Val Glu Pro Asn Cys Asp Ile His Val Met Trp Val Trp Glu Cys Phe
1               5                   10                  15

Glu Arg Leu Ser Gly Gly Gly
            20
```

```
<210> SEQ ID NO 46
<211> LENGTH: 23
<212> TYPE: PRT
<213> ORGANISM: Artificial Sequence
<220> FEATURE:
<223> OTHER INFORMATION: Synthetic

<400> SEQUENCE: 46

Val Glu Pro Asn Cys Asp Ile His Val Met Trp Val Trp Glu Cys Phe
1               5                   10                  15

Glu Arg Leu Met Arg Leu Thr
            20

<210> SEQ ID NO 47
<211> LENGTH: 21
<212> TYPE: PRT
<213> ORGANISM: Artificial Sequence
<220> FEATURE:
<223> OTHER INFORMATION: Synthetic

<400> SEQUENCE: 47

Val Glu Pro Asn Cys Asp Ile His Val Met Trp Val Trp Glu Cys Phe
1               5                   10                  15

Glu Arg Leu Tyr Gly
            20

<210> SEQ ID NO 48
<211> LENGTH: 21
<212> TYPE: PRT
<213> ORGANISM: Artificial Sequence
<220> FEATURE:
<223> OTHER INFORMATION: Synthetic

<400> SEQUENCE: 48

Val Glu Pro Asn Cys Asp Ile His Val Met Trp Val Trp Glu Cys Phe
1               5                   10                  15

Glu Arg Leu Val Lys
            20

<210> SEQ ID NO 49
<211> LENGTH: 21
<212> TYPE: PRT
<213> ORGANISM: Artificial Sequence
<220> FEATURE:
<223> OTHER INFORMATION: Synthetic

<400> SEQUENCE: 49

Val Glu Pro Asn Cys Asp Ile His Val Met Trp Val Trp Glu Cys Phe
1               5                   10                  15

Glu Arg Leu Met Arg
            20

<210> SEQ ID NO 50
<211> LENGTH: 23
<212> TYPE: PRT
<213> ORGANISM: Artificial Sequence
<220> FEATURE:
<223> OTHER INFORMATION: Synthetic

<400> SEQUENCE: 50

Val Glu Pro Asn Cys Asp Ile His Val Met Trp Val Trp Glu Cys Phe
1               5                   10                  15

Glu Arg Leu Tyr Gly Ile Leu
            20
```

```
<210> SEQ ID NO 51
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (20)
<223> OTHER INFORMATION: Xaa is L-tyrosine methyl ester

<400> SEQUENCE: 51

Val Glu Pro Asn Cys Asp Ile His Val Met Trp Val Trp Glu Cys Phe
1               5                   10                  15

Glu Arg Leu Xaa Gly Leu Thr
            20

<210> SEQ ID NO 52
<211> LENGTH: 22
<212> TYPE: PRT
<213> ORGANISM: Artificial Sequence
<220> FEATURE:
<223> OTHER INFORMATION: Synthetic

<400> SEQUENCE: 52

Val Glu Pro Asn Cys Asp Ile His Val Met Trp Val Trp Glu Cys Phe
1               5                   10                  15

Glu Arg Leu Tyr Gly Gly
            20

<210> SEQ ID NO 53
<211> LENGTH: 23
<212> TYPE: PRT
<213> ORGANISM: Artificial Sequence
<220> FEATURE:
<223> OTHER INFORMATION: Synthetic

<400> SEQUENCE: 53

Val Glu Pro Asn Cys Asp Ile His Val Met Trp Val Trp Glu Cys Phe
1               5                   10                  15

Glu Arg Leu Phe Lys Glu Ala
            20

<210> SEQ ID NO 54
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (20)
<223> OTHER INFORMATION: Xaa is norleucine

<400> SEQUENCE: 54

Val Glu Pro Asn Cys Asp Ile His Val Met Trp Val Trp Glu Cys Phe
1               5                   10                  15

Glu Arg Leu Xaa Lys
            20

<210> SEQ ID NO 55
<211> LENGTH: 23
<212> TYPE: PRT
<213> ORGANISM: Artificial Sequence
<220> FEATURE:
<223> OTHER INFORMATION: Synthetic

<400> SEQUENCE: 55
```

```
Val Glu Pro Asn Cys Asp Ile His Val Met Trp Val Trp Glu Cys Phe
1               5                   10                  15

Glu Arg Leu Tyr Gly Leu Thr
            20

<210> SEQ ID NO 56
<211> LENGTH: 23
<212> TYPE: PRT
<213> ORGANISM: Artificial Sequence
<220> FEATURE:
<223> OTHER INFORMATION: Synthetic

<400> SEQUENCE: 56

Val Glu Pro Asn Cys Asp Ile His Val Met Trp Val Trp Glu Cys Phe
1               5                   10                  15

Glu Arg Leu Tyr Gly Gly Phe
            20

<210> SEQ ID NO 57
<211> LENGTH: 21
<212> TYPE: PRT
<213> ORGANISM: Artificial Sequence
<220> FEATURE:
<223> OTHER INFORMATION: Synthetic

<400> SEQUENCE: 57

Val Glu Pro Asn Cys Asp Ile His Val Met Trp Val Trp Glu Cys Phe
1               5                   10                  15

Glu Arg Leu Ile Lys
            20

<210> SEQ ID NO 58
<211> LENGTH: 21
<212> TYPE: PRT
<213> ORGANISM: Artificial Sequence
<220> FEATURE:
<223> OTHER INFORMATION: Synthetic

<400> SEQUENCE: 58

Val Glu Pro Asn Cys Asp Ile His Val Met Trp Val Trp Glu Cys Phe
1               5                   10                  15

Glu Arg Leu Tyr Lys
            20

<210> SEQ ID NO 59
<211> LENGTH: 23
<212> TYPE: PRT
<213> ORGANISM: Artificial Sequence
<220> FEATURE:
<223> OTHER INFORMATION: Synthetic

<400> SEQUENCE: 59

Val Glu Pro Asn Cys Asp Ile His Val Met Trp Val Trp Glu Cys Phe
1               5                   10                  15

Glu Arg Leu Met Gly Leu Thr
            20

<210> SEQ ID NO 60
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (20)
<223> OTHER INFORMATION: Xaa is D-Leu
<220> FEATURE:
<221> NAME/KEY: misc_feature
<222> LOCATION: (21)
<223> OTHER INFORMATION: Xaa is acyl-Lysine

<400> SEQUENCE: 60

Val Glu Pro Asn Cys Asp Ile His Val Met Trp Val Trp Glu Cys Phe
1               5                   10                  15

Glu Arg Leu Xaa Xaa
            20

<210> SEQ ID NO 61
<211> LENGTH: 23
<212> TYPE: PRT
<213> ORGANISM: Artificial Sequence
<220> FEATURE:
<223> OTHER INFORMATION: Synthetic

<400> SEQUENCE: 61

Val Glu Pro Asn Cys Asp Ile His Val Met Trp Val Trp Glu Cys Phe
1               5                   10                  15

Glu Arg Leu Tyr Gly Gly Gly
            20

<210> SEQ ID NO 62
<211> LENGTH: 21
<212> TYPE: PRT
<213> ORGANISM: Artificial Sequence
<220> FEATURE:
<223> OTHER INFORMATION: Synthetic

<400> SEQUENCE: 62

Val Glu Pro Asn Cys Asp Ile His Val Met Trp Val Trp Glu Cys Phe
1               5                   10                  15

Glu Arg Leu Met Lys
            20

<210> SEQ ID NO 63
<211> LENGTH: 23
<212> TYPE: PRT
<213> ORGANISM: Artificial Sequence
<220> FEATURE:
<223> OTHER INFORMATION: Synthetic

<400> SEQUENCE: 63

Val Glu Pro Asn Cys Asp Ile His Val Met Trp Val Trp Glu Cys Phe
1               5                   10                  15

Glu Arg Leu Met Arg Glu Leu
            20

<210> SEQ ID NO 64
<211> LENGTH: 19
<212> TYPE: PRT
<213> ORGANISM: Artificial Sequence
<220> FEATURE:
<223> OTHER INFORMATION: Synthetic

<400> SEQUENCE: 64

Val Glu Pro Asn Cys Asp Ile His Val Met Trp Val Trp Glu Cys Phe
1               5                   10                  15

Glu Arg Leu

<210> SEQ ID NO 65
```

```
<211> LENGTH: 23
<212> TYPE: PRT
<213> ORGANISM: Artificial Sequence
<220> FEATURE:
<223> OTHER INFORMATION: Synthetic

<400> SEQUENCE: 65

Val Glu Pro Asn Cys Asp Ile His Val Met Trp Val Trp Glu Cys Phe
1               5                   10                  15

Glu Arg Leu Met Lys Glu Leu
            20

<210> SEQ ID NO 66
<211> LENGTH: 23
<212> TYPE: PRT
<213> ORGANISM: Artificial Sequence
<220> FEATURE:
<223> OTHER INFORMATION: Synthetic

<400> SEQUENCE: 66

Val Glu Pro Asn Cys Asp Ile His Val Met Trp Val Trp Glu Cys Phe
1               5                   10                  15

Glu Arg Leu Tyr Gly Pro Trp
            20

<210> SEQ ID NO 67
<211> LENGTH: 21
<212> TYPE: PRT
<213> ORGANISM: Artificial Sequence
<220> FEATURE:
<223> OTHER INFORMATION: Synthetic

<400> SEQUENCE: 67

Val Glu Pro Asn Cys Asp Ile His Val Met Trp Val Trp Glu Cys Phe
1               5                   10                  15

Glu Arg Leu Leu Lys
            20

<210> SEQ ID NO 68
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (21)
<223> OTHER INFORMATION: Xaa is acyl-Lysine

<400> SEQUENCE: 68

Val Glu Pro Asn Cys Asp Ile His Val Met Trp Val Trp Glu Cys Phe
1               5                   10                  15

Glu Arg Leu Leu Xaa
            20

<210> SEQ ID NO 69
<211> LENGTH: 23
<212> TYPE: PRT
<213> ORGANISM: Artificial Sequence
<220> FEATURE:
<223> OTHER INFORMATION: Synthetic

<400> SEQUENCE: 69

Val Glu Pro Asn Cys Asp Ile His Val Met Trp Val Trp Glu Cys Phe
1               5                   10                  15

Glu Arg Leu Tyr Gly Leu Thr
```

-continued

```
            20

<210> SEQ ID NO 70
<211> LENGTH: 23
<212> TYPE: PRT
<213> ORGANISM: Artificial Sequence
<220> FEATURE:
<223> OTHER INFORMATION: Synthetic

<400> SEQUENCE: 70

Val Glu Pro Asn Cys Asp Ile His Val Met Trp Val Trp Glu Cys Phe
1               5                   10                  15

Glu Arg Leu Tyr Gly Glu Phe
            20

<210> SEQ ID NO 71
<211> LENGTH: 23
<212> TYPE: PRT
<213> ORGANISM: Artificial Sequence
<220> FEATURE:
<223> OTHER INFORMATION: Synthetic

<400> SEQUENCE: 71

Val Glu Pro Asn Cys Asp Ile His Val Met Trp Val Trp Glu Cys Phe
1               5                   10                  15

Glu Arg Leu Tyr Gly Leu Ser
            20

<210> SEQ ID NO 72
<211> LENGTH: 22
<212> TYPE: PRT
<213> ORGANISM: Artificial Sequence
<220> FEATURE:
<223> OTHER INFORMATION: Synthetic

<400> SEQUENCE: 72

Val Glu Pro Asn Cys Asp Ile His Val Met Trp Val Trp Glu Cys Phe
1               5                   10                  15

Glu Arg Leu Tyr Gly Leu
            20

<210> SEQ ID NO 73
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (22)
<223> OTHER INFORMATION: Xaa is D-Leu

<400> SEQUENCE: 73

Val Glu Pro Asn Cys Asp Ile His Val Met Trp Val Trp Glu Cys Phe
1               5                   10                  15

Glu Arg Leu Tyr Gly Xaa Thr
            20

<210> SEQ ID NO 74
<211> LENGTH: 23
<212> TYPE: PRT
<213> ORGANISM: Artificial Sequence
<220> FEATURE:
<223> OTHER INFORMATION: Synthetic

<400> SEQUENCE: 74
```

Val Glu Pro Asn Cys Asp Ile His Val Met Trp Val Trp Glu Cys Phe
1               5                   10                  15

Glu Arg Leu Tyr Gly Val Gln
            20

<210> SEQ ID NO 75
<211> LENGTH: 23
<212> TYPE: PRT
<213> ORGANISM: Artificial Sequence
<220> FEATURE:
<223> OTHER INFORMATION: Synthetic

<400> SEQUENCE: 75

Val Glu Pro Asn Cys Asp Ile His Val Met Trp Val Trp Glu Cys Phe
1               5                   10                  15

Glu Arg Leu Tyr Gly Leu Glu
            20

<210> SEQ ID NO 76
<211> LENGTH: 23
<212> TYPE: PRT
<213> ORGANISM: Artificial Sequence
<220> FEATURE:
<223> OTHER INFORMATION: Synthetic

<400> SEQUENCE: 76

Val Glu Pro Asn Cys Asp Ile His Val Met Trp Val Trp Glu Cys Phe
1               5                   10                  15

Glu Arg Leu Tyr Gly Pro Leu
            20

<210> SEQ ID NO 77
<211> LENGTH: 23
<212> TYPE: PRT
<213> ORGANISM: Artificial Sequence
<220> FEATURE:
<223> OTHER INFORMATION: Synthetic

<400> SEQUENCE: 77

Val Glu Pro Asn Cys Asp Ile His Val Met Trp Val Trp Glu Cys Phe
1               5                   10                  15

Glu Arg Leu Tyr Gly Pro Phe
            20

<210> SEQ ID NO 78
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (21)
<223> OTHER INFORMATION: Xaa is D-Ala
<220> FEATURE:
<221> NAME/KEY: misc_feature
<222> LOCATION: (22)
<223> OTHER INFORMATION: Xaa is D-Leu

<400> SEQUENCE: 78

Val Glu Pro Asn Cys Asp Ile His Val Met Trp Val Trp Glu Cys Phe
1               5                   10                  15

Glu Arg Leu Tyr Xaa Xaa
            20

<210> SEQ ID NO 79

```
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (21)
<223> OTHER INFORMATION: Xaa is D-Leu
<220> FEATURE:
<221> NAME/KEY: misc_feature
<222> LOCATION: (22)
<223> OTHER INFORMATION: Xaa is acyl-Lysine

<400> SEQUENCE: 79

Val Glu Pro Asn Cys Asp Ile His Val Met Trp Val Trp Glu Cys Phe
1               5                   10                  15

Glu Arg Leu Arg Xaa Xaa
            20

<210> SEQ ID NO 80
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (20)
<223> OTHER INFORMATION: Xaa is D-Tyr
<220> FEATURE:
<221> NAME/KEY: misc_feature
<222> LOCATION: (22)
<223> OTHER INFORMATION: Xaa is D-Pro

<400> SEQUENCE: 80

Val Glu Pro Asn Cys Asp Ile His Val Met Trp Val Trp Glu Cys Phe
1               5                   10                  15

Glu Arg Leu Xaa Gly Xaa Leu
            20

<210> SEQ ID NO 81
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (20)
<223> OTHER INFORMATION: Xaa is D-Tyr
<220> FEATURE:
<221> NAME/KEY: misc_feature
<222> LOCATION: (22)
<223> OTHER INFORMATION: Xaa is D-Pro
<220> FEATURE:
<221> NAME/KEY: misc_feature
<222> LOCATION: (23)
<223> OTHER INFORMATION: Xaa is D-Leu

<400> SEQUENCE: 81

Val Glu Pro Asn Cys Asp Ile His Val Met Trp Val Trp Glu Cys Phe
1               5                   10                  15

Glu Arg Leu Xaa Gly Xaa Xaa
            20

<210> SEQ ID NO 82
<211> LENGTH: 23
<212> TYPE: PRT
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (20)
<223> OTHER INFORMATION: Xaa is D-Tyr
<220> FEATURE:
<221> NAME/KEY: misc_feature
<222> LOCATION: (22)
<223> OTHER INFORMATION: Xaa is D-Leu
<220> FEATURE:
<221> NAME/KEY: misc_feature
<222> LOCATION: (23)
<223> OTHER INFORMATION: Xaa is acyl-Lysine

<400> SEQUENCE: 82

Val Glu Pro Asn Cys Asp Ile His Val Met Trp Val Trp Glu Cys Phe
1               5                   10                  15

Glu Arg Leu Xaa Gly Xaa Xaa
            20

<210> SEQ ID NO 83
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (19)
<223> OTHER INFORMATION: Xaa is D-Leu
<220> FEATURE:
<221> NAME/KEY: misc_feature
<222> LOCATION: (21)
<223> OTHER INFORMATION: Xaa is 2-aminoisobutyric acid

<400> SEQUENCE: 83

Val Glu Pro Asn Cys Asp Ile His Val Met Trp Val Trp Glu Cys Phe
1               5                   10                  15

Glu Arg Xaa Tyr Xaa Leu Thr
            20

<210> SEQ ID NO 84
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (19)
<223> OTHER INFORMATION: Xaa is D-Leu
<220> FEATURE:
<221> NAME/KEY: misc_feature
<222> LOCATION: (21)
<223> OTHER INFORMATION: Xaa is D-Ala
<220> FEATURE:
<221> NAME/KEY: misc_feature
<222> LOCATION: (23)
<223> OTHER INFORMATION: Xaa is D-Gln

<400> SEQUENCE: 84

Val Glu Pro Asn Cys Asp Ile His Val Met Trp Val Trp Glu Cys Phe
1               5                   10                  15

Glu Arg Xaa Tyr Xaa Val Xaa
            20

<210> SEQ ID NO 85
<211> LENGTH: 23
<212> TYPE: PRT
<213> ORGANISM: Artificial Sequence
<220> FEATURE:
```

```
-continued

<223> OTHER INFORMATION: Synthetic
<220> FEATURE:
<221> NAME/KEY: misc_feature
<222> LOCATION: (19)
<223> OTHER INFORMATION: Xaa is D-Leu
<220> FEATURE:
<221> NAME/KEY: misc_feature
<222> LOCATION: (21)
<223> OTHER INFORMATION: Xaa is D-Ala
<220> FEATURE:
<221> NAME/KEY: misc_feature
<222> LOCATION: (23)
<223> OTHER INFORMATION: Xaa is D-Thr

<400> SEQUENCE: 85

Val Glu Pro Asn Cys Asp Ile His Val Met Trp Val Trp Glu Cys Phe
1               5                   10                  15

Glu Arg Xaa Tyr Xaa Leu Xaa
            20

<210> SEQ ID NO 86
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (20)
<223> OTHER INFORMATION: Xaa is beta cyclohexyl-L-alanine
<220> FEATURE:
<221> NAME/KEY: misc_feature
<222> LOCATION: (22)
<223> OTHER INFORMATION: Xaa is D-Leu

<400> SEQUENCE: 86

Val Glu Pro Asn Cys Asp Ile His Val Met Trp Val Trp Glu Cys Phe
1               5                   10                  15

Glu Arg Leu Xaa Gly Xaa Thr
            20

<210> SEQ ID NO 87
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (21)
<223> OTHER INFORMATION: Xaa is 2-aminosobutyric acid
<220> FEATURE:
<221> NAME/KEY: misc_feature
<222> LOCATION: (23)
<223> OTHER INFORMATION: Xaa is D-Thr

<400> SEQUENCE: 87

Val Glu Pro Asn Cys Asp Ile His Val Met Trp Val Trp Glu Cys Phe
1               5                   10                  15

Glu Arg Leu Tyr Xaa Leu Xaa
            20

<210> SEQ ID NO 88
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (21)
```

```
<223> OTHER INFORMATION: Xaa is  sarcosine
<220> FEATURE:
<221> NAME/KEY: misc_feature
<222> LOCATION: (22)
<223> OTHER INFORMATION: Xaa is D-Leu

<400> SEQUENCE: 88

Val Glu Pro Asn Cys Asp Ile His Val Met Trp Val Trp Glu Cys Phe
1               5                   10                  15

Glu Arg Leu Tyr Xaa Xaa Thr
            20

<210> SEQ ID NO 89
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (22)
<223> OTHER INFORMATION: Xaa is D-Pro

<400> SEQUENCE: 89

Val Glu Pro Asn Cys Asp Ile His Val Met Trp Val Trp Glu Cys Phe
1               5                   10                  15

Glu Arg Leu Tyr Gly Xaa Leu
            20

<210> SEQ ID NO 90
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (21)
<223> OTHER INFORMATION: Xaa is D-Ala
<220> FEATURE:
<221> NAME/KEY: misc_feature
<222> LOCATION: (23)
<223> OTHER INFORMATION: Xaa is D-Gln

<400> SEQUENCE: 90

Val Glu Pro Asn Cys Asp Ile His Val Met Trp Val Trp Glu Cys Phe
1               5                   10                  15

Glu Arg Leu Tyr Xaa Val Xaa
            20

<210> SEQ ID NO 91
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (21)
<223> OTHER INFORMATION: Xaa is 2-aminosobutyric acid

<400> SEQUENCE: 91

Val Glu Pro Asn Cys Asp Ile His Val Met Trp Val Trp Glu Cys Phe
1               5                   10                  15

Glu Arg Leu Tyr Xaa Leu Thr
            20

<210> SEQ ID NO 92
```

<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (20)
<223> OTHER INFORMATION: Xaa is D-Tyr
<220> FEATURE:
<221> NAME/KEY: misc_feature
<222> LOCATION: (22)
<223> OTHER INFORMATION: Xaa is D-Leu

<400> SEQUENCE: 92

Val Glu Pro Asn Cys Asp Ile His Val Met Trp Val Trp Glu Cys Phe
1               5                   10                  15

Glu Arg Leu Xaa Gly Xaa Thr
            20

<210> SEQ ID NO 93
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (20)
<223> OTHER INFORMATION: Xaa is D-Tyr

<400> SEQUENCE: 93

Val Glu Pro Asn Cys Asp Ile His Val Met Trp Val Trp Glu Cys Phe
1               5                   10                  15

Glu Arg Leu Xaa Gly Leu Thr
            20

<210> SEQ ID NO 94
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (20)
<223> OTHER INFORMATION: Xaa is D-Tyr
<220> FEATURE:
<221> NAME/KEY: misc_feature
<222> LOCATION: (23)
<223> OTHER INFORMATION: Xaa is D-Thr

<400> SEQUENCE: 94

Val Glu Pro Asn Cys Asp Ile His Val Met Trp Val Trp Glu Cys Phe
1               5                   10                  15

Glu Arg Leu Xaa Asp Leu Xaa
            20

<210> SEQ ID NO 95
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (20)
<223> OTHER INFORMATION: Xaa is D-Leu
<220> FEATURE:
<221> NAME/KEY: misc_feature
<222> LOCATION: (21)

<223> OTHER INFORMATION: Xaa is aminoisobutyric acid

<400> SEQUENCE: 95

Val Glu Pro Asn Cys Asp Ile His Val Met Trp Val Trp Glu Cys Phe
1               5                   10                  15

Glu Arg Leu Xaa Xaa
            20

<210> SEQ ID NO 96
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (22)
<223> OTHER INFORMATION: Xaa is D-Leu
<220> FEATURE:
<221> NAME/KEY: misc_feature
<222> LOCATION: (23)
<223> OTHER INFORMATION: Xaa is D-Thr

<400> SEQUENCE: 96

Val Glu Pro Asn Cys Asp Ile His Val Met Trp Val Trp Glu Cys Phe
1               5                   10                  15

Glu Arg Leu Tyr Gly Xaa Xaa
            20

<210> SEQ ID NO 97
<211> LENGTH: 19
<212> TYPE: PRT
<213> ORGANISM: Artificial Sequence
<220> FEATURE:
<223> OTHER INFORMATION: Synthetic

<400> SEQUENCE: 97

Val Glu Pro Asn Cys Asp Ile His Val Met Trp Val Trp Val Cys Phe
1               5                   10                  15

Glu Arg Leu

<210> SEQ ID NO 98
<211> LENGTH: 23
<212> TYPE: PRT
<213> ORGANISM: Artificial Sequence
<220> FEATURE:
<223> OTHER INFORMATION: Synthetic

<400> SEQUENCE: 98

Val Glu Pro Asn Cys Asp Ile His Val Met Trp Val Trp Val Cys Phe
1               5                   10                  15

Glu Arg Leu Tyr Gly Pro Phe
            20

<210> SEQ ID NO 99
<211> LENGTH: 22
<212> TYPE: PRT
<213> ORGANISM: Artificial Sequence
<220> FEATURE:
<223> OTHER INFORMATION: Synthetic

<400> SEQUENCE: 99

Val Glu Pro Asn Cys Asp Ile His Val Met Trp Val Trp Val Cys Phe
1               5                   10                  15

Glu Arg Leu Tyr Gly Pro
            20

<210> SEQ ID NO 100
<211> LENGTH: 23
<212> TYPE: PRT
<213> ORGANISM: Artificial Sequence
<220> FEATURE:
<223> OTHER INFORMATION: Synthetic

<400> SEQUENCE: 100

Val Glu Pro Asn Cys Asp Ile His Val Met Trp Val Trp Val Cys Phe
1               5                   10                  15

Glu Arg Leu Tyr Gly Pro Glu
            20

<210> SEQ ID NO 101
<211> LENGTH: 23
<212> TYPE: PRT
<213> ORGANISM: Artificial Sequence
<220> FEATURE:
<223> OTHER INFORMATION: Synthetic

<400> SEQUENCE: 101

Val Glu Pro Asn Cys Asp Ile His Val Met Trp Val Trp Val Cys Phe
1               5                   10                  15

Glu Arg Leu Tyr Gly Pro Gln
            20

<210> SEQ ID NO 102
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (22)
<223> OTHER INFORMATION: Xaa is D-Leu

<400> SEQUENCE: 102

Val Glu Pro Asn Cys Asp Ile His Val Met Trp Val Trp Val Cys Phe
1               5                   10                  15

Glu Arg Leu Tyr Gly Xaa Thr
            20

<210> SEQ ID NO 103
<211> LENGTH: 22
<212> TYPE: PRT
<213> ORGANISM: Artificial Sequence
<220> FEATURE:
<223> OTHER INFORMATION: Synthetic

<400> SEQUENCE: 103

Val Glu Pro Asn Cys Asp Ile His Val Met Trp Val Trp Val Cys Phe
1               5                   10                  15

Glu Arg Leu Tyr Gly Leu
            20

<210> SEQ ID NO 104
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (20)
<223> OTHER INFORMATION: Xaa is D-Leu

```
<220> FEATURE:
<221> NAME/KEY: misc_feature
<222> LOCATION: (21)
<223> OTHER INFORMATION: Xaa is Epsilon acyl lysine

<400> SEQUENCE: 104

Val Glu Pro Asn Cys Asp Ile His Val Met Trp Val Trp Val Cys Phe
1               5                   10                  15

Glu Arg Leu Xaa Xaa
            20

<210> SEQ ID NO 105
<211> LENGTH: 23
<212> TYPE: PRT
<213> ORGANISM: Artificial Sequence
<220> FEATURE:
<223> OTHER INFORMATION: Synthetic

<400> SEQUENCE: 105

Val Glu Pro Asn Cys Asp Ile His Val Met Trp Val Trp Val Cys Phe
1               5                   10                  15

Glu Arg Leu Tyr Gly Leu Thr
            20

<210> SEQ ID NO 106
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (21)
<223> OTHER INFORMATION: Xaa is D-Ala
<220> FEATURE:
<221> NAME/KEY: misc_feature
<222> LOCATION: (22)
<223> OTHER INFORMATION: Xaa is D-Leu

<400> SEQUENCE: 106

Val Glu Pro Asn Cys Asp Ile His Val Met Trp Val Trp Val Cys Phe
1               5                   10                  15

Glu Arg Leu Tyr Xaa Xaa
            20

<210> SEQ ID NO 107
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa at position 2 may be substituted with any
      residue selected from the group consisting of K, N, R, H, epsilon
      acyl lysine, nicotinyl lysine, and epsilon chloro benzyl carbamate
      lysine in no particular order
<220> FEATURE:
<221> NAME/KEY: misc_feature
<222> LOCATION: (5)
<223> OTHER INFORMATION: Xaa at position 5 may be substituted with any
      residue selected from the group consisting of P, hydroxyproline,
      dehydroxyproline, and (2S,4R)-4-Hydroxyproline in no
      particular order
<220> FEATURE:
<221> NAME/KEY: misc_feature
<222> LOCATION: (9)
<223> OTHER INFORMATION: Xaa at position 9 may be substituted with any
      residue selected from the group consisting of L, I, thiazolyl
      alanine,and epsilon acyl lysine in no particular order
```

```
<220> FEATURE:
<221> NAME/KEY: misc_feature
<222> LOCATION: (11)
<223> OTHER INFORMATION: Xaa at position 11 may be substituted with any
      residue selected from the group consisting of Q, N, C, K, epsilon
      acyl lysine, diaminobutyric acid, and diaminopropionic acid in no
      particular order
<220> FEATURE:
<221> NAME/KEY: misc_feature
<222> LOCATION: (12)
<223> OTHER INFORMATION: Xaa at position 12 may be substituted with any
      residue selected from the group consisting of L, homoleucine,
      norvaline, I, homocyclohexyl alanine, homophenyl alanine,
      and thiazolyl alanine in no particular order
<220> FEATURE:
<221> NAME/KEY: misc_feature
<222> LOCATION: (13)
<223> OTHER INFORMATION: Xaa at position 13 may be substituted with any
      residue selected from the group consisting of L, homoleucine,
      norvaline, I, homocyclohexyl alanine, homophenyl alanine, and
      thiazolyl alanine in no particular order
<220> FEATURE:
<221> NAME/KEY: misc_feature
<222> LOCATION: (14)
<223> OTHER INFORMATION: Xaa at position 14 may be substituted with any
      aromatic residue in no particular order
<220> FEATURE:
<221> NAME/KEY: misc_feature
<222> LOCATION: (16)
<223> OTHER INFORMATION: Xqq at position 16 may be substituted with Q or
      N in no particular order
<220> FEATURE:
<221> NAME/KEY: misc_feature
<222> LOCATION: (19)
<223> OTHER INFORMATION: Xaa at position 19 may be substituted with L or
      I in no particular order

<400> SEQUENCE: 107

Gln Xaa Tyr Gln Xaa Leu Asp Glu Xaa Asp Xaa Xaa Xaa Xaa Asp Xaa
1               5                   10                  15

Phe Met Xaa Gln Gln Gly
            20

<210> SEQ ID NO 108
<211> LENGTH: 22
<212> TYPE: PRT
<213> ORGANISM: Artificial Sequence
<220> FEATURE:
<223> OTHER INFORMATION: Synthetic

<400> SEQUENCE: 108

Val Glu Pro Asn Cys Asp Ile His Val Met Trp Glu Trp Glu Cys Phe
1               5                   10                  15

Glu Arg Leu Tyr Ala Lys
            20

<210> SEQ ID NO 109
<211> LENGTH: 24
<212> TYPE: PRT
<213> ORGANISM: Artificial Sequence
<220> FEATURE:
<223> OTHER INFORMATION: Synthetic

<400> SEQUENCE: 109

Val Glu Pro Asn Cys Asp Ile His Val Met Trp Glu Trp Glu Cys Phe
1               5                   10                  15

Glu Arg Leu Tyr Phe Lys Glu Trp
            20

<210> SEQ ID NO 110
<211> LENGTH: 22
```

```
<212> TYPE: PRT
<213> ORGANISM: Artificial Sequence
<220> FEATURE:
<223> OTHER INFORMATION: Synthetic

<400> SEQUENCE: 110

Val Glu Pro Asn Cys Asp Ile His Val Met Trp Glu Trp Glu Cys Phe
1               5                   10                  15

Glu Arg Leu Tyr Ala Arg
            20

<210> SEQ ID NO 111
<211> LENGTH: 22
<212> TYPE: PRT
<213> ORGANISM: Artificial Sequence
<220> FEATURE:
<223> OTHER INFORMATION: Synthetic

<400> SEQUENCE: 111

Val Glu Pro Asn Cys Asp Ile His Val Met Trp Glu Trp Glu Cys Phe
1               5                   10                  15

Glu Arg Leu Tyr Phe Lys
            20

<210> SEQ ID NO 112
<211> LENGTH: 24
<212> TYPE: PRT
<213> ORGANISM: Artificial Sequence
<220> FEATURE:
<223> OTHER INFORMATION: Synthetic

<400> SEQUENCE: 112

Val Glu Pro Asn Cys Asp Ile His Val Met Trp Glu Trp Glu Cys Phe
1               5                   10                  15

Glu Arg Leu Tyr Ala Lys Glu Phe
            20

<210> SEQ ID NO 113
<211> LENGTH: 24
<212> TYPE: PRT
<213> ORGANISM: Artificial Sequence
<220> FEATURE:
<223> OTHER INFORMATION: Synthetic

<400> SEQUENCE: 113

Val Glu Pro Asn Cys Asp Ile His Val Met Trp Glu Trp Glu Cys Phe
1               5                   10                  15

Glu Arg Leu Tyr Ser Gly Trp Gly
            20

<210> SEQ ID NO 114
<211> LENGTH: 24
<212> TYPE: PRT
<213> ORGANISM: Artificial Sequence
<220> FEATURE:
<223> OTHER INFORMATION: Synthetic

<400> SEQUENCE: 114

Val Glu Pro Asn Cys Asp Ile His Val Met Trp Glu Trp Glu Cys Phe
1               5                   10                  15

Glu Arg Leu Tyr Ser Gly Trp Phe
            20

<210> SEQ ID NO 115
<211> LENGTH: 24
```

```
<212> TYPE: PRT
<213> ORGANISM: Artificial Sequence
<220> FEATURE:
<223> OTHER INFORMATION: Synthetic

<400> SEQUENCE: 115

Val Glu Pro Asn Cys Asp Ile His Val Met Trp Glu Trp Glu Cys Phe
1               5                   10                  15

Glu Arg Leu Tyr Ala Lys Glu Ala
            20

<210> SEQ ID NO 116
<211> LENGTH: 24
<212> TYPE: PRT
<213> ORGANISM: Artificial Sequence
<220> FEATURE:
<223> OTHER INFORMATION: Synthetic

<400> SEQUENCE: 116

Val Glu Pro Asn Cys Asp Ile His Val Met Trp Glu Trp Glu Cys Phe
1               5                   10                  15

Glu Arg Leu Tyr Ala Lys Glu Met
            20

<210> SEQ ID NO 117
<211> LENGTH: 24
<212> TYPE: PRT
<213> ORGANISM: Artificial Sequence
<220> FEATURE:
<223> OTHER INFORMATION: Synthetic

<400> SEQUENCE: 117

Val Glu Pro Asn Cys Asp Ile His Val Met Trp Glu Trp Glu Cys Phe
1               5                   10                  15

Glu Arg Leu Tyr Ala Lys Glu Leu
            20

<210> SEQ ID NO 118
<211> LENGTH: 24
<212> TYPE: PRT
<213> ORGANISM: Artificial Sequence
<220> FEATURE:
<223> OTHER INFORMATION: Synthetic

<400> SEQUENCE: 118

Val Glu Pro Asn Cys Asp Ile His Val Met Trp Glu Trp Glu Cys Phe
1               5                   10                  15

Glu Arg Leu Tyr Phe Lys Glu Leu
            20

<210> SEQ ID NO 119
<211> LENGTH: 24
<212> TYPE: PRT
<213> ORGANISM: Artificial Sequence
<220> FEATURE:
<223> OTHER INFORMATION: Synthetic

<400> SEQUENCE: 119

Val Glu Pro Asn Cys Asp Ile His Val Met Trp Glu Trp Glu Cys Phe
1               5                   10                  15

Glu Arg Leu Tyr Phe Lys Glu Ala
            20

<210> SEQ ID NO 120
<211> LENGTH: 24
```

```
<212> TYPE: PRT
<213> ORGANISM: Artificial Sequence
<220> FEATURE:
<223> OTHER INFORMATION: Synthetic

<400> SEQUENCE: 120

Val Glu Pro Asn Cys Asp Ile His Val Met Trp Glu Trp Glu Cys Phe
1               5                   10                  15

Glu Arg Leu Tyr Tyr Gly Gly Gly
            20

<210> SEQ ID NO 121
<211> LENGTH: 22
<212> TYPE: PRT
<213> ORGANISM: Artificial Sequence
<220> FEATURE:
<223> OTHER INFORMATION: Synthetic

<400> SEQUENCE: 121

Val Glu Pro Asn Cys Asp Ile His Val Met Trp Glu Trp Glu Cys Phe
1               5                   10                  15

Glu Arg Leu Tyr Met Lys
            20

<210> SEQ ID NO 122
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (14)
<223> OTHER INFORMATION: Xaa at position 14 may be substituted E or V in
      no particular order
<220> FEATURE:
<221> NAME/KEY: misc_feature
<222> LOCATION: (19)
<223> OTHER INFORMATION: Xaa at position 19 may be substituted with any
      natural or unnatural hydrophobic amino acid or D-isomer thereof,
      in no particular order

<400> SEQUENCE: 122

Val Glu Pro Asn Cys Asp Ile His Val Met Trp Val Trp Xaa Cys Phe
1               5                   10                  15

Glu Arg Xaa

<210> SEQ ID NO 123
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (14)
<223> OTHER INFORMATION: Xaa at position 14 may be substituted with E or
      V in no particular order
<220> FEATURE:
<221> NAME/KEY: misc_feature
<222> LOCATION: (19)
<223> OTHER INFORMATION: Xaa at position 19 may be substituted with any
      natural or unnatural hydrophobic amino acid or D-isomer thereof,
      in no particular order
<220> FEATURE:
<221> NAME/KEY: misc_feature
<222> LOCATION: (20)
<223> OTHER INFORMATION: Xaa at position 20 may be substituted with any
      neutral, hydrophobic or aromatic amino acid, or D-isoforms
      thereof, in no particular order
```

```
<400> SEQUENCE: 123

Val Glu Pro Asn Cys Asp Ile His Val Met Trp Val Trp Xaa Cys Phe
1               5                   10                  15

Glu Arg Xaa Xaa
            20

<210> SEQ ID NO 124
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (14)
<223> OTHER INFORMATION: Xaa at position 14 may be substituted with E or
      V in no particular order
<220> FEATURE:
<221> NAME/KEY: misc_feature
<222> LOCATION: (19)
<223> OTHER INFORMATION: Xaa at position 19 may be substituted with any
      natural or unnatural hydrophobic amino acid or D-isomer thereof,
      in no particular order
<220> FEATURE:
<221> NAME/KEY: misc_feature
<222> LOCATION: (20)
<223> OTHER INFORMATION: Xaa at position 20 may be substituted with any
      neutral, hydrophobic or aromatic amino acid or D-isoforms thereof,
      in no particular order
<220> FEATURE:
<221> NAME/KEY: misc_feature
<222> LOCATION: (21)
<223> OTHER INFORMATION: Xaa at position 21 may be substituted with any
      neutral or positively charged amino acid or D-isoforms thereof, in
      no particular order

<400> SEQUENCE: 124

Val Glu Pro Asn Cys Asp Ile His Val Met Trp Val Trp Xaa Cys Phe
1               5                   10                  15

Glu Arg Xaa Xaa Xaa
            20

<210> SEQ ID NO 125
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (14)
<223> OTHER INFORMATION: Xaa at position 14 may be substituted with E or
      V in no particular order
<220> FEATURE:
<221> NAME/KEY: misc_feature
<222> LOCATION: (19)
<223> OTHER INFORMATION: Xaa at position 19 may be substituted with any
      natural or unnatural hydrophobic amino acid or D-isomer thereof,
      in no particular order
<220> FEATURE:
<221> NAME/KEY: misc_feature
<222> LOCATION: (20)
<223> OTHER INFORMATION: Xaa at position 20 may be substituted with any
      neutral, hydrophobic or aromatic amino acid or D-isoforms thereof,
      in no particular order
<220> FEATURE:
<221> NAME/KEY: misc_feature
<222> LOCATION: (21)
<223> OTHER INFORMATION: Xaa at position 21 may be substituted with any
      neutral or positively charged amino acid or D-isoforms thereof, in
      no particular order
<220> FEATURE:
<221> NAME/KEY: misc_feature
<222> LOCATION: (22)
```

```
<223> OTHER INFORMATION: Xaa at position 22 may be substituted with any
      aliphatic, polar, or negatively charged amino acid or D-isoforms
      thereof, in no particular order

<400> SEQUENCE: 125

Val Glu Pro Asn Cys Asp Ile His Val Met Trp Val Trp Xaa Cys Phe
1               5                   10                  15

Glu Arg Xaa Xaa Xaa Xaa
            20

<210> SEQ ID NO 126
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (14)
<223> OTHER INFORMATION: Xaa at position 14 may be substituted with E or
      V in no particular order
<220> FEATURE:
<221> NAME/KEY: misc_feature
<222> LOCATION: (19)
<223> OTHER INFORMATION: Xaa at position 19 may be substituted with any
      natural or unnatural hydrophobic amino acid or D-isomer thereof,
      in no particular order
<220> FEATURE:
<221> NAME/KEY: misc_feature
<222> LOCATION: (20)
<223> OTHER INFORMATION: Xaa at position 20 may be substituted with any
      neutral, hydrophobic or aromatic amino acid or D-isoforms thereof,
      in no particular order
<220> FEATURE:
<221> NAME/KEY: misc_feature
<222> LOCATION: (21)
<223> OTHER INFORMATION: Xaa at position 21 may be substituted with any
      neutral or positively charged amino acid or D-isoforms thereof, in
      no particular order
<220> FEATURE:
<221> NAME/KEY: misc_feature
<222> LOCATION: (22)
<223> OTHER INFORMATION: Xaa at position 22 may be substituted with any
      aliphatic, polar, or negatively charged amino acid or D-isoforms
      thereof, in no particular order
<220> FEATURE:
<221> NAME/KEY: misc_feature
<222> LOCATION: (23)
<223> OTHER INFORMATION: Xaa at position 23 may be substituted with any
      amino acid or D-isoforms thereof, in no particular order

<400> SEQUENCE: 126

Val Glu Pro Asn Cys Asp Ile His Val Met Trp Val Trp Xaa Cys Phe
1               5                   10                  15

Glu Arg Xaa Xaa Xaa Xaa Xaa
            20

<210> SEQ ID NO 127
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (14)
<223> OTHER INFORMATION: Xaa at position 14 may be substituted with E or
      V in no particular order
<220> FEATURE:
<221> NAME/KEY: misc_feature
<222> LOCATION: (19)
<223> OTHER INFORMATION: Xaa at position 19 may be substituted with any
      natural or unnatural hydrophobic amino acid or D-isomer thereof,
      in no particular order
```

```
<220> FEATURE:
<221> NAME/KEY: misc_feature
<222> LOCATION: (20)
<223> OTHER INFORMATION: Xaa at position 20 may be substituted with any
      neutral, hydrophobic or aromatic amino acid or D-isoforms thereof,
      in no particular order
<220> FEATURE:
<221> NAME/KEY: misc_feature
<222> LOCATION: (21)
<223> OTHER INFORMATION: Xaa at position 21 may be substituted with any
      neutral or positively charged amino acid or D-isoforms thereof, in
      no particular order
<220> FEATURE:
<221> NAME/KEY: misc_feature
<222> LOCATION: (22)
<223> OTHER INFORMATION: Xaa at position 22 may be absent, or
      substituted with any aliphatic, polar, or negatively charged amino
      acid or D-isoforms thereof, in no particular order
<220> FEATURE:
<221> NAME/KEY: misc_feature
<222> LOCATION: (23)
<223> OTHER INFORMATION: Xaa at position 23 may be absent, or
      substituted with any amino acid or D-isoforms thereof, in no
      particular order

<400> SEQUENCE: 127

Val Glu Pro Asn Cys Asp Ile His Val Met Trp Glu Trp Xaa Cys Phe
1               5                   10                  15

Glu Arg Xaa Xaa Xaa Xaa Xaa
            20

<210> SEQ ID NO 128
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: Xaa is Norleucine
<220> FEATURE:
<221> NAME/KEY: misc_feature
<222> LOCATION: (21)
<223> OTHER INFORMATION: Xaa is 2-aminoisobutyric acid

<400> SEQUENCE: 128

Val Glu Pro Asn Cys Asp Ile His Val Xaa Trp Val Trp Glu Cys Phe
1               5                   10                  15

Glu Arg Leu Tyr Xaa Leu Thr
            20

<210> SEQ ID NO 129
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (21)
<223> OTHER INFORMATION: Xaa is 2-aminoisobutyric acid

<400> SEQUENCE: 129

Val Glu Pro Asn Cys Asp Ile His Val Leu Trp Val Trp Glu Cys Phe
1               5                   10                  15

Glu Arg Leu Tyr Xaa Leu Thr
            20

<210> SEQ ID NO 130
<211> LENGTH: 23
```

```
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (21)
<223> OTHER INFORMATION: Xaa is 2-aminoisobutyric acid

<400> SEQUENCE: 130

Val Glu Pro Asn Cys Asp Ile His Val Val Trp Val Trp Glu Cys Phe
1               5                   10                  15

Glu Arg Leu Tyr Xaa Leu Thr
            20

<210> SEQ ID NO 131
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)
<223> OTHER INFORMATION: Xaa at position 1 may be substituted with any
      hydrophobic amino acid in no particular order
<220> FEATURE:
<221> NAME/KEY: misc_feature
<222> LOCATION: (2)
<223> OTHER INFORMATION: Xaa at position 2 may be substituted with any
      negatively charged residue in no particular order
<220> FEATURE:
<221> NAME/KEY: misc_feature
<222> LOCATION: (6)
<223> OTHER INFORMATION: Xaa at position 6 may be substituted with any
      negatively charged residue in no particular order
<220> FEATURE:
<221> NAME/KEY: misc_feature
<222> LOCATION: (7)
<223> OTHER INFORMATION: Xaa at position 7 may be substituted with any
      hydrophobic amino acid particular order
<220> FEATURE:
<221> NAME/KEY: misc_feature
<222> LOCATION: (8)
<223> OTHER INFORMATION: Xaa at position 8 may be substituted with any
      residue comprising a ring structure in no particular order
<220> FEATURE:
<221> NAME/KEY: misc_feature
<222> LOCATION: (10)
<223> OTHER INFORMATION: Xaa at position 10 may be substituted with Met
      or any hydrophobic amino acid in no particular order
<220> FEATURE:
<221> NAME/KEY: misc_feature
<222> LOCATION: (11)
<223> OTHER INFORMATION: Xaa at position 11 may be substituted with any
      aromatic amino acid in no particular order
<220> FEATURE:
<221> NAME/KEY: misc_feature
<222> LOCATION: (12)
<223> OTHER INFORMATION: Xaa at position 12 may be substituted with V, E
      and epsilon acyl lysine in no particular order
<220> FEATURE:
<221> NAME/KEY: misc_feature
<222> LOCATION: (14)
<223> OTHER INFORMATION: Xaa at position 14 may be substituted with E or
      V in no particular order
<220> FEATURE:
<221> NAME/KEY: misc_feature
<222> LOCATION: (19)
<223> OTHER INFORMATION: Xaa at position 19 may be substituted with any
      natural or unnatural hydrophobic amino acid or D-isomer thereof,
      in no particular order
<220> FEATURE:
<221> NAME/KEY: misc_feature
<222> LOCATION: (20)
<223> OTHER INFORMATION: Xaa at position 20 may be substituted with any
      neutral, hydrophobic or aromatic amino acid or D-isoforms thereof,
```

```
      in no particular order
<220> FEATURE:
<221> NAME/KEY: misc_feature
<222> LOCATION: (21)
<223> OTHER INFORMATION

```
<222> LOCATION: (23)
<223> OTHER INFORMATION: Xaa at position 23 may be absent or may be
      substituted with a residue selected from the group consisting of
      G, A, I, L, Q, E, F, T, W, S, Y, and epsilon acyl lysine and
      D-isoforms thereof, in no particular order

<400> SEQUENCE: 132

Val Glu Pro Asn Cys Asp Ile His Val Xaa Trp Xaa Trp Xaa Cys Phe
1               5                   10                  15

Glu Arg Xaa Xaa Xaa Xaa Xaa
            20

<210> SEQ ID NO 133
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (12)
<223> OTHER INFORMATION: Xaa at position 12 may be substituted with V, E
      and epsilon acyl lysine in no particular order
<220> FEATURE:
<221> NAME/KEY: misc_feature
<222> LOCATION: (14)
<223> OTHER INFORMATION: Xaa at position 14 may be substituted with E or
      V in no particular order
<220> FEATURE:
<221> NAME/KEY: misc_feature
<222> LOCATION: (19)
<223> OTHER INFORMATION: Xaa at position 19 may be substituted with any
      natural or unnatural hydrophobic amino acid or D-isomer thereof,
      in no particular order
<220> FEATURE:
<221> NAME/KEY: misc_feature
<222> LOCATION: (20)
<223> OTHER INFORMATION: Xaa at position 20 may be substituted with any
      neutral, hydrophobic or aromatic amino acid or D-isoforms thereof,
      in no particular order
<220> FEATURE:
<221> NAME/KEY: misc_feature
<222> LOCATION: (21)
<223> OTHER INFORMATION: Xaa at position 21 may be substituted with any
      neutral or positively charged amino acid or D-isoforms thereof, in
      no particular order
<220> FEATURE:
<221> NAME/KEY: misc_feature
<222> LOCATION: (22)
<223> OTHER INFORMATION: Xaa at position 22 may be absent, or may be
      substituted with a residue selected from the group consisting of
      G, V, L, I, P, S, T, W, F, E, epsilon acyl lysine, or D-isomers
      thereof and D-isoforms thereof, in no particular order
<220> FEATURE:
<221> NAME/KEY: misc_feature
<222> LOCATION: (23)
<223> OTHER INFORMATION: Xaa at position 23 may be absent or may be
      substituted with a residue selected from the group consisting of
      G, A, I, L, Q, E, F, T, W, S, Y, and Kac and D-isoforms thereof,
      in no particular order

<400> SEQUENCE: 133

Val Glu Pro Asn Cys Asp Ile His Val Met Trp Xaa Trp Xaa Cys Phe
1               5                   10                  15

Glu Arg Xaa Xaa Xaa Xaa Xaa
            20

<210> SEQ ID NO 134
<211> LENGTH: 23
<212> TYPE: PRT
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (14)
<223> OTHER INFORMATION: Xaa at position 14 may be substituted with E or
      V in no particular order
<220> FEATURE:
<221> NAME/KEY: misc_feature
<222> LOCATION: (19)
<223> OTHER INFORMATION: Xaa at position 19 may be substituted with any
      natural or unnatural hydrophobic amino acid or D-isomer thereof,
      in no particular order
<220> FEATURE:
<221> NAME/KEY: misc_feature
<222> LOCATION: (20)
<223> OTHER INFORMATION: Xaa at position 20 may be substituted with any
      neutral, hydrophobic or aromatic amino acid or D-isoforms thereof,
      in no particular order
<220> FEATURE:
<221> NAME/KEY: misc_feature
<222> LOCATION: (21)
<223> OTHER INFORMATION: Xaa at position 21 may be substituted with any
      neutral or positively charged amino acid or D-isoforms thereof, in
      no particular order
<220> FEATURE:
<221> NAME/KEY: misc_feature
<222> LOCATION: (22)
<223> OTHER INFORMATION: Xaa at position 22 may be absent, or may be
      substituted with a residue selected from the group consisting of
      G, V, L, I, P, S, T, W, F, E, Kac, or D-isomers thereof and
      D-isoforms thereof, in no particular order
<220> FEATURE:
<221> NAME/KEY: misc_feature
<222> LOCATION: (23)
<223> OTHER INFORMATION: Xaa at position 23 may be absent or may be
      substituted with a residue selected from the group consisting of
      G, A, I, L, Q, E, F, T, W, S, Y, and Kac and D-isoforms thereof,
      in no particular order

<400> SEQUENCE: 134

Val Glu Pro Asn Cys Asp Ile His Val Met Trp Glu Trp Xaa Cys Phe
1               5                   10                  15

Glu Arg Xaa Xaa Xaa Xaa Xaa
            20

<210> SEQ ID NO 135
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (19)
<223> OTHER INFORMATION: Xaa at position 19 may be substituted with any
      natural or unnatural hydrophobic amino acid or D-isomer thereof,
      in no particular order
<220> FEATURE:
<221> NAME/KEY: misc_feature
<222> LOCATION: (20)
<223> OTHER INFORMATION: Xaa at position 20 may be substituted with any
      neutral, hydrophobic or aromatic amino acid or D-isoforms thereof,
      in no particular order
<220> FEATURE:
<221> NAME/KEY: misc_feature
<222> LOCATION: (21)
<223> OTHER INFORMATION: Xaa at position 21 may be substituted with any
      neutral or positively charged amino acid or D-isoforms thereof, in
      no particular order
<220> FEATURE:
<221> NAME/KEY: misc_feature
<222> LOCATION: (22)
<223> OTHER INFORMATION: Xaa at position 22 may be absent, or may be
      substituted with a residue selected from the group consisting of
      G, V, L, I, P, S, T, W, F, E, epsilon acyl lysine, and D-isoforms
      thereof, in no particular order
<220> FEATURE:
<221> NAME/KEY: misc_feature
<222> LOCATION: (23)
```

```
<223> OTHER INFORMATION: Xaa at position 23 may be absent or may be
      substituted with a residue selected from the group consisting of
      G, A, I, L, Q, E, F, T, W, S, Y, and epsilon acyl lysine and
      D-isoforms thereof, in no particular order

<400> SEQUENCE: 135

Val Glu Pro Asn Cys Asp Ile His Val Met Trp Val Trp Glu Cys Phe
1               5                   10                  15

Glu Arg Xaa Xaa Xaa Xaa Xaa
            20

<210> SEQ ID NO 136
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (12)
<223> OTHER INFORMATION: Xaa is epsilon acyl lysine
<220> FEATURE:
<221> NAME/KEY: misc_feature
<222> LOCATION: (21)
<223> OTHER INFORMATION: Xaa is D-Ala
<220> FEATURE:
<221> NAME/KEY: misc_feature
<222> LOCATION: (23)
<223> OTHER INFORMATION: Xaa is D-Gln

<400> SEQUENCE: 136

Val Glu Pro Asn Cys Asp Ile His Val Met Trp Xaa Trp Glu Cys Phe
1               5                   10                  15

Glu Arg Leu Tyr Xaa Val Xaa
            20

<210> SEQ ID NO 137
<211> LENGTH: 22
<212> TYPE: PRT
<213> ORGANISM: Artificial Sequence
<220> FEATURE:
<223> OTHER INFORMATION: Synthetic

<400> SEQUENCE: 137

Gln Lys Tyr Gln Pro Leu Asp Glu Leu Asp Lys Thr Leu Tyr Asp Gln
1               5                   10                  15

Phe Met Leu Gln Gln Gly
            20

<210> SEQ ID NO 138
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine

<400> SEQUENCE: 138

Gln Xaa Tyr Gln Pro Leu Asp Glu Leu Asp Lys Thr Leu Tyr Asp Gln
1               5                   10                  15

Phe Met Leu Gln Gln Gly
            20

<210> SEQ ID NO 139
<211> LENGTH: 22
```

```
<212> TYPE: PRT
<213> ORGANISM: Artificial Sequence
<220> FEATURE:
<223> OTHER INFORMATION: Synthetic

<400> SEQUENCE: 139

Gln Asn Tyr Gln Pro Leu Asp Glu Leu Asp Lys Thr Leu Tyr Asp Gln
1               5                   10                  15

Phe Met Leu Gln Gln Gly
            20

<210> SEQ ID NO 140
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (11)
<223> OTHER INFORMATION: Xaa is epsilon acyl lysine

<400> SEQUENCE: 140

Gln Xaa Tyr Gln Pro Leu Asp Glu Lys Asp Xaa Thr Leu Tyr Asp Gln
1               5                   10                  15

Phe Met Leu Gln Gln Gly
            20

<210> SEQ ID NO 141
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine

<400> SEQUENCE: 141

Gln Xaa Tyr Gln Pro Leu Asp Glu Leu Asp Glu Thr Lys Tyr Asp Gln
1               5                   10                  15

Phe Met Leu Gln Gln Gly
            20

<210> SEQ ID NO 142
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (11)
<223> OTHER INFORMATION: Xaa is epsilon acyl lysine

<400> SEQUENCE: 142

Gln Xaa Tyr Gln Pro Leu Asp Glu Leu Asp Xaa Thr Lys Tyr Asp Gln
1               5                   10                  15

Phe Met Leu Gln Gln Gly
            20
```

<210> SEQ ID NO 143
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine

<400> SEQUENCE: 143

Gln Xaa Tyr Gln Pro Leu Asp Glu Lys Asp Glu Thr Leu Tyr Asp Gln
1               5                   10                  15

Phe Met Leu Gln Gln Gly
            20

<210> SEQ ID NO 144
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (5)
<223> OTHER INFORMATION: Xaa is dehydroxyproline

<400> SEQUENCE: 144

Gln Xaa Tyr Gln Xaa Leu Asp Glu Leu Asp Lys Thr Leu Tyr Asp Gln
1               5                   10                  15

Phe Met Leu Gln Gln Gly
            20

<210> SEQ ID NO 145
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (5)
<223> OTHER INFORMATION: Xaa is hydroxyproline

<400> SEQUENCE: 145

Gln Xaa Tyr Gln Xaa Leu Asp Glu Leu Asp Lys Thr Leu Tyr Asp Gln
1               5                   10                  15

Phe Met Leu Gln Gln Gly
            20

<210> SEQ ID NO 146
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine

<400> SEQUENCE: 146

Gln Xaa Tyr Gln Pro Leu Asp Glu Leu Asp Lys Thr Ile Tyr Asp Gln
1               5                   10                  15

Phe Met Leu Gln Gln Gly
            20

<210> SEQ ID NO 147
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine

<400> SEQUENCE: 147

Gln Xaa Tyr Gln Pro Leu Asp Glu Ile Asp Lys Thr Leu Tyr Asp Gln
1               5                   10                  15

Phe Met Leu Gln Gln Gly
            20

<210> SEQ ID NO 148
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (13)
<223> OTHER INFORMATION: Xaa is homocyclohexyl alanine

<400> SEQUENCE: 148

Gln Xaa Tyr Gln Pro Leu Asp Glu Leu Asp Lys Thr Xaa Tyr Asp Gln
1               5                   10                  15

Phe Met Leu Gln Gln Gly
            20

<210> SEQ ID NO 149
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (13)
<223> OTHER INFORMATION: Xaa is homophenyl alanine

<400> SEQUENCE: 149

Gln Xaa Tyr Gln Pro Leu Asp Glu Leu Asp Lys Thr Xaa Tyr Asp Gln
1               5                   10                  15

Phe Met Leu Gln Gln Gly
            20

<210> SEQ ID NO 150
<211> LENGTH: 22

```
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (13)
<223> OTHER INFORMATION: Xaa is thiazolyl alanine

<400> SEQUENCE: 150

Gln Xaa Tyr Gln Pro Leu Asp Glu Leu Asp Lys Thr Xaa Tyr Asp Gln
1               5                   10                  15

Phe Met Leu Gln Gln Gly
            20

<210> SEQ ID NO 151
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (13)
<223> OTHER INFORMATION: Xaa is norvaline

<400> SEQUENCE: 151

Gln Xaa Tyr Gln Pro Leu Asp Glu Leu Asp Lys Thr Xaa Tyr Asp Gln
1               5                   10                  15

Phe Met Leu Gln Gln Gly
            20

<210> SEQ ID NO 152
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (13)
<223> OTHER INFORMATION: Xaa is homoleucine

<400> SEQUENCE: 152

Gln Xaa Tyr Gln Pro Leu Asp Glu Leu Asp Lys Thr Xaa Tyr Asp Gln
1               5                   10                  15

Phe Met Leu Gln Gln Gly
            20

<210> SEQ ID NO 153
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
```

```
<220> FEATURE:
<221> NAME/KEY: misc_feature
<222> LOCATION: (9)
<223> OTHER INFORMATION: Xaa is epsilon acyl lysine

<400> SEQUENCE: 153

Gln Xaa Tyr Gln Pro Leu Asp Glu Xaa Asp Lys Thr Leu Tyr Asp Gln
1               5                   10                  15

Phe Met Leu Gln Gln Gly
            20

<210> SEQ ID NO 154
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine

<400> SEQUENCE: 154

Gln Xaa Tyr Gln Pro Leu Asp Glu Leu Asp Lys Thr Leu Phe Asp Gln
1               5                   10                  15

Phe Met Leu Gln Gln Gly
            20

<210> SEQ ID NO 155
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (5)
<223> OTHER INFORMATION: Xaa is hydroxyproline
<220> FEATURE:
<221> NAME/KEY: misc_feature
<222> LOCATION: (9)
<223> OTHER INFORMATION: Xaa is thienyl alanine
<220> FEATURE:
<221> NAME/KEY: misc_feature
<222> LOCATION: (14)
<223> OTHER INFORMATION: Xaa is 4-nitrophenylalanine

<400> SEQUENCE: 155

Gln Xaa Tyr Gln Xaa Leu Asp Glu Xaa Asp Lys Thr Leu Xaa Asp Gln
1               5                   10                  15

Phe Met Leu Gln Gln Gly
            20

<210> SEQ ID NO 156
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (5)
<223> OTHER INFORMATION: Xaa is hydroxyproline
```

```
<220> FEATURE:
<221> NAME/KEY: misc_feature
<222> LOCATION: (9)
<223> OTHER INFORMATION: Xaa is thienyl alanine
<220> FEATURE:
<221> NAME/KEY: misc_feature
<222> LOCATION: (14)
<223> OTHER INFORMATION: Xaa is 4-benzoyl phenylalanine

<400> SEQUENCE: 156

Gln Xaa Tyr Gln Xaa Leu Asp Glu Xaa Asp Lys Thr Leu Xaa Asp Gln
1               5                   10                  15

Phe Met Leu Gln Gln Gly
            20

<210> SEQ ID NO 157
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (5)
<223> OTHER INFORMATION: Xaa is hydroxyl proline
<220> FEATURE:
<221> NAME/KEY: misc_feature
<222> LOCATION: (9)
<223> OTHER INFORMATION: Xaa is thienyl alanine
<220> FEATURE:
<221> NAME/KEY: misc_feature
<222> LOCATION: (14)
<223> OTHER INFORMATION: Xaa is 4-carboxy phenylalanine

<400> SEQUENCE: 157

Gln Xaa Tyr Gln Xaa Leu Asp Glu Xaa Asp Lys Thr Leu Xaa Asp Gln
1               5                   10                  15

Phe Met Leu Gln Gln Gly
            20

<210> SEQ ID NO 158
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (9)
<223> OTHER INFORMATION: Xaa is epsilon acyl lysine
<220> FEATURE:
<221> NAME/KEY: misc_feature
<222> LOCATION: (14)
<223> OTHER INFORMATION: Xaa is 4-nitro phenylalanine

<400> SEQUENCE: 158

Gln Xaa Tyr Gln Pro Leu Asp Glu Xaa Asp Lys Thr Leu Xaa Asp Gln
1               5                   10                  15

Phe Met Leu Gln Gln Gly
            20

<210> SEQ ID NO 159
<211> LENGTH: 23
```

```
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)
<223> OTHER INFORMATION: Xaa is dichlorobenzoyl
<220> FEATURE:
<221> NAME/KEY: misc_feature
<222> LOCATION: (3)
<223> OTHER INFORMATION: Xaa is epsilon acyl lysine

<400> SEQUENCE: 159

Xaa Gln Xaa Tyr Gln Pro Leu Asp Glu Leu Asp Lys Thr Leu Tyr Asp
1               5                   10                  15

Gln Phe Met Leu Gln Gln Gly
            20

<210> SEQ ID NO 160
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)
<223> OTHER INFORMATION: Xaa is difluorobenzoyl
<220> FEATURE:
<221> NAME/KEY: misc_feature
<222> LOCATION: (3)
<223> OTHER INFORMATION: Xaa is epsilon acyl lysine

<400> SEQUENCE: 160

Xaa Gln Xaa Tyr Gln Pro Leu Asp Glu Leu Asp Lys Thr Leu Tyr Asp
1               5                   10                  15

Gln Phe Met Leu Gln Gln Gly
            20

<210> SEQ ID NO 161
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)
<223> OTHER INFORMATION: Xaa is pyridinyl carboxylete
<220> FEATURE:
<221> NAME/KEY: misc_feature
<222> LOCATION: (3)
<223> OTHER INFORMATION: Xaa is epsilon acyl lysine

<400> SEQUENCE: 161

Xaa Gln Xaa Tyr Gln Pro Leu Asp Glu Leu Asp Lys Thr Leu Tyr Asp
1               5                   10                  15

Gln Phe Met Leu Gln Gln Gly
            20

<210> SEQ ID NO 162
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)
<223> OTHER INFORMATION: Xaa is 3-[2-(2-Amido-ethoxy)-ethoxy]-
```

```
                propionamide
<220> FEATURE:
<221> NAME/KEY: misc_feature
<222> LOCATION: (3)
<223> OTHER INFORMATION: Xaa is epsilon acyl lysine

<400> SEQUENCE: 162

Xaa Gln Xaa Tyr Gln Pro Leu Asp Glu Leu Asp Lys Thr Leu Tyr Asp
1               5                   10                  15

Gln Phe Met Leu Gln Gln Gly
            20

<210> SEQ ID NO 163
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon chloro benzyl carbamate lysine

<400> SEQUENCE: 163

Gln Xaa Tyr Gln Pro Leu Asp Glu Leu Asp Lys Thr Leu Tyr Asp Gln
1               5                   10                  15

Phe Met Leu Gln Gln Gly
            20

<210> SEQ ID NO 164
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (11)
<223> OTHER INFORMATION: Xaa is diaminobutyric acid

<400> SEQUENCE: 164

Gln Xaa Tyr Gln Pro Leu Asp Glu Leu Asp Xaa Thr Leu Tyr Asp Gln
1               5                   10                  15

Phe Met Leu Gln Gln Gly
            20

<210> SEQ ID NO 165
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (11)
<223> OTHER INFORMATION: Xaa is diaminopropionic acid

<400> SEQUENCE: 165

Gln Xaa Tyr Gln Pro Leu Asp Glu Leu Asp Xaa Thr Leu Tyr Asp Gln
1               5                   10                  15

Phe Met Leu Gln Gln Gly
```

-continued

```
          20

<210> SEQ ID NO 166
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (14)
<223> OTHER INFORMATION: Xaa is 4-benzoyl phenylalanine

<400> SEQUENCE: 166

Gln Asn Tyr Gln Pro Leu Asp Glu Leu Asp Lys Thr Leu Xaa Asp Gln
1               5                   10                  15

Phe Met Leu Gln Gln Gly
          20

<210> SEQ ID NO 167
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (14)
<223> OTHER INFORMATION: Xaa is 4-carboxy phenalanine

<400> SEQUENCE: 167

Gln Asn Tyr Gln Pro Leu Asp Glu Leu Asp Lys Thr Leu Xaa Asp Gln
1               5                   10                  15

Phe Met Leu Gln Gln Gly
          20

<210> SEQ ID NO 168
<211> LENGTH: 22
<212> TYPE: PRT
<213> ORGANISM: Artificial Sequence
<220> FEATURE:
<223> OTHER INFORMATION: Synthetic

<400> SEQUENCE: 168

Gln Arg Tyr Gln Pro Leu Asp Glu Leu Asp Lys Thr Leu Tyr Asp Gln
1               5                   10                  15

Phe Met Leu Gln Gln Gly
          20

<210> SEQ ID NO 169
<211> LENGTH: 22
<212> TYPE: PRT
<213> ORGANISM: Artificial Sequence
<220> FEATURE:
<223> OTHER INFORMATION: Synthetic

<400> SEQUENCE: 169

Gln His Tyr Gln Pro Leu Asp Glu Leu Asp Lys Thr Leu Tyr Asp Gln
1               5                   10                  15

Phe Met Leu Gln Gln Gly
          20

<210> SEQ ID NO 170
<211> LENGTH: 22
<212> TYPE: PRT
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (2)
<223> OTHER INFORMATION: Xaa is nocotinyl lysine

<400> SEQUENCE: 170

Gln Xaa Tyr Gln Pro Leu Asp Glu Leu Asp Lys Thr Leu Tyr Asp Gln
1               5                   10                  15

Phe Met Leu Gln Gln Gly
            20

<210> SEQ ID NO 171
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (9)
<223> OTHER INFORMATION: Xaa is epsilon acyl lysine
<220> FEATURE:
<221> NAME/KEY: misc_feature
<222> LOCATION: (14)
<223> OTHER INFORMATION: Xaa is 4-carboxy phenylalanine

<400> SEQUENCE: 171

Gln Xaa Tyr Gln Pro Leu Asp Glu Xaa Asp Lys Thr Leu Xaa Asp Gln
1               5                   10                  15

Phe Met Leu Gln Gln Gly
            20

<210> SEQ ID NO 172
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (11)
<223> OTHER INFORMATION: Xaa is epsilon acyl lysine

<400> SEQUENCE: 172

Lys Xaa Tyr Gln Pro Leu Asp Glu Leu Asp Xaa Thr Leu Tyr Asp Gln
1               5                   10                  15

Phe Met Leu Gln Gln Gly
            20

<210> SEQ ID NO 173
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (11)
<223> OTHER INFORMATION: Xaa is epsilon acyl lysine

<400> SEQUENCE: 173
```

-continued

Gln Lys Tyr Gln Pro Leu Asp Glu Leu Asp Xaa Thr Leu Tyr Asp Gln
1               5                   10                  15

Phe Met Leu Gln Gln Gly
            20

<210> SEQ ID NO 174
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (11)
<223> OTHER INFORMATION: Xaa is epsilon acyl lysine

<400> SEQUENCE: 174

Gln Xaa Lys Gln Pro Leu Asp Glu Leu Asp Xaa Thr Leu Tyr Asp Gln
1               5                   10                  15

Phe Met Leu Gln Gln Gly
            20

<210> SEQ ID NO 175
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (11)
<223> OTHER INFORMATION: Xaa is epsilon acyl lysine

<400> SEQUENCE: 175

Gln Xaa Tyr Lys Pro Leu Asp Glu Leu Asp Xaa Thr Leu Tyr Asp Gln
1               5                   10                  15

Phe Met Leu Gln Gln Gly
            20

<210> SEQ ID NO 176
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (11)..(11)
<223> OTHER INFORMATION: Xaa is epsilon acyl lysine

<400> SEQUENCE: 176

Gln Xaa Tyr Gln Lys Leu Asp Glu Leu Asp Xaa Thr Leu Tyr Asp Gln
1               5                   10                  15

Phe Met Leu Gln Gln Gly
            20

<210> SEQ ID NO 177

```
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (11)
<223> OTHER INFORMATION: Xaa is epsilon acyl lysine

<400> SEQUENCE: 177

Gln Xaa Tyr Gln Pro Lys Asp Glu Leu Asp Xaa Thr Leu Tyr Asp Gln
1               5                   10                  15

Phe Met Leu Gln Gln Gly
            20

<210> SEQ ID NO 178
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (11)
<223> OTHER INFORMATION: Xaa is epsilon acyl lysine

<400> SEQUENCE: 178

Gln Xaa Tyr Gln Pro Leu Lys Glu Leu Asp Xaa Thr Leu Tyr Asp Gln
1               5                   10                  15

Phe Met Leu Gln Gln Gly
            20

<210> SEQ ID NO 179
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (11)
<223> OTHER INFORMATION: Xaa is epsilon acyl lysine

<400> SEQUENCE: 179

Gln Xaa Tyr Gln Pro Leu Asp Lys Leu Asp Xaa Thr Leu Tyr Asp Gln
1               5                   10                  15

Phe Met Leu Gln Gln Gly
            20

<210> SEQ ID NO 180
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
```

<223> OTHER INFORMATION: Xaa is epsilon acyl lysine
<220> FEATURE:
<221> NAME/KEY: misc_feature
<222> LOCATION: (11)
<223> OTHER INFORMATION: Xaa is epsilon acyl lysine

<400> SEQUENCE: 180

Gln Xaa Tyr Gln Pro Leu Asp Glu Leu Lys Xaa Thr Leu Tyr Asp Gln
1               5                   10                  15

Phe Met Leu Gln Gln Gly
            20

<210> SEQ ID NO 181
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (11)
<223> OTHER INFORMATION: Xaa is epsilon acyl lysine

<400> SEQUENCE: 181

Gln Xaa Tyr Gln Pro Leu Asp Glu Leu Asp Xaa Lys Leu Tyr Asp Gln
1               5                   10                  15

Phe Met Leu Gln Gln Gly
            20

<210> SEQ ID NO 182
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (11)
<223> OTHER INFORMATION: Xaa is epsilon acyl lysine

<400> SEQUENCE: 182

Gln Xaa Tyr Gln Pro Leu Asp Glu Leu Asp Xaa Thr Leu Lys Asp Gln
1               5                   10                  15

Phe Met Leu Gln Gln Gly
            20

<210> SEQ ID NO 183
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (11)
<223> OTHER INFORMATION: Xaa is epsilon acyl lysine

<400> SEQUENCE: 183

```
Gln Xaa Tyr Gln Pro Leu Asp Glu Leu Asp Xaa Thr Leu Tyr Lys Gln
1               5                   10                  15

Phe Met Leu Gln Gln Gly
            20
```

<210> SEQ ID NO 184
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (11)
<223> OTHER INFORMATION: Xaa is epsilon acyl lysine

<400> SEQUENCE: 184

```
Gln Xaa Tyr Gln Pro Leu Asp Glu Leu Asp Xaa Thr Leu Tyr Asp Lys
1               5                   10                  15

Phe Met Leu Gln Gln Gly
            20
```

<210> SEQ ID NO 185
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (11)
<223> OTHER INFORMATION: Xaa is epsilon acyl lysine

<400> SEQUENCE: 185

```
Gln Xaa Tyr Gln Pro Leu Asp Glu Leu Asp Xaa Thr Leu Tyr Asp Gln
1               5                   10                  15

Lys Met Leu Gln Gln Gly
            20
```

<210> SEQ ID NO 186
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (11)
<223> OTHER INFORMATION: Xaa is epsilon acyl lysine

<400> SEQUENCE: 186

```
Gln Xaa Tyr Gln Pro Leu Asp Glu Leu Asp Xaa Thr Leu Tyr Asp Gln
1               5                   10                  15

Phe Lys Leu Gln Gln Gly
            20
```

<210> SEQ ID NO 187

```
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (11)
<223> OTHER INFORMATION: Xaa is epsilon acyl lysine

<400> SEQUENCE: 187

Gln Xaa Tyr Gln Pro Leu Asp Glu Leu Asp Xaa Thr Leu Tyr Asp Gln
1               5                   10                  15

Phe Met Lys Gln Gln Gly
            20

<210> SEQ ID NO 188
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (11)
<223> OTHER INFORMATION: Xaa is epsilon acyl lysine

<400> SEQUENCE: 188

Gln Xaa Tyr Gln Pro Leu Asp Glu Leu Asp Xaa Thr Leu Tyr Asp Gln
1               5                   10                  15

Phe Met Leu Lys Gln Gly
            20

<210> SEQ ID NO 189
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is epsilon acyl lysine
<220> FEATURE:
<221> NAME/KEY: misc_feature
<222> LOCATION: (11)
<223> OTHER INFORMATION: Xaa is epsilon acyl lysine

<400> SEQUENCE: 189

Gln Xaa Tyr Gln Pro Leu Asp Glu Leu Asp Xaa Thr Leu Tyr Asp Gln
1               5                   10                  15

Phe Met Leu Gln Lys Gly
            20

<210> SEQ ID NO 190
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
```

<223> OTHER INFORMATION: Xaa is epsilon acyl lysine
<220> FEATURE:
<221> NAME/KEY: misc_feature
<222> LOCATION: (11)
<223> OTHER INFORMATION: Xaa is epsilon acyl lysine

<400> SEQUENCE: 190

Gln Xaa Tyr Gln Pro Leu Asp Glu Leu Asp Xaa Thr Leu Tyr Asp Gln
1               5                   10                  15

Phe Met Leu Gln Gln Lys
            20

<210> SEQ ID NO 191
<211> LENGTH: 18
<212> TYPE: PRT
<213> ORGANISM: Artificial Sequence
<220> FEATURE:
<223> OTHER INFORMATION: Synthetic

<400> SEQUENCE: 191

Pro Leu Asp Glu Leu Asp Lys Thr Leu Tyr Asp Gln Phe Met Leu Gln
1               5                   10                  15

Gln Gly

<210> SEQ ID NO 192
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (20)
<223> OTHER INFORMATION: Xaa is D-Leu
<220> FEATURE:
<221> NAME/KEY: misc_feature
<222> LOCATION: (21)
<223> OTHER INFORMATION: Xaa is epsilon acyl lysine

<400> SEQUENCE: 192

Val Glu Pro Asn Cys Asp Ile His Val Lys Trp Val Trp Glu Cys Phe
1               5                   10                  15

Glu Arg Leu Xaa Xaa
            20

<210> SEQ ID NO 193
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (22)
<223> OTHER INFORMATION: Xaa is D-Leu

<400> SEQUENCE: 193

Val Glu Pro Asn Cys Asp Ile His Val Lys Trp Val Trp Glu Cys Phe
1               5                   10                  15

Glu Arg Leu Tyr Gly Xaa Thr
            20

<210> SEQ ID NO 194
<211> LENGTH: 23
<212> TYPE: PRT
<213> ORGANISM: Artificial Sequence
<220> FEATURE:
<223> OTHER INFORMATION: Synthetic

<400> SEQUENCE: 194

Val Glu Pro Asn Cys Asp Ile His Val Lys Trp Val Trp Glu Cys Phe
1               5                   10                  15

Glu Arg Leu Tyr Gly Pro Leu
            20

<210> SEQ ID NO 195
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (21)
<223> OTHER INFORMATION: Xaa is D-Ala
<220> FEATURE:
<221> NAME/KEY: misc_feature
<222> LOCATION: (22)
<223> OTHER INFORMATION: Xaa is D-Leu

<400> SEQUENCE: 195

Val Glu Pro Asn Cys Asp Ile His Val Lys Trp Val Trp Glu Cys Phe
1               5                   10                  15

Glu Arg Leu Tyr Xaa Xaa
            20

<210> SEQ ID NO 196
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (20)
<223> OTHER INFORMATION: Xaa is D-Leu

<400> SEQUENCE: 196

Val Glu Pro Asn Cys Asp Ile His Val Met Trp Val Trp Glu Cys Phe
1               5                   10                  15

Glu Arg Leu Xaa Lys
            20

<210> SEQ ID NO 197
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (22)
<223> OTHER INFORMATION: Xaa is D-Leu

<400> SEQUENCE: 197

Val Glu Pro Asn Cys Asp Ile His Val Met Trp Val Trp Glu Cys Phe
1               5                   10                  15

Glu Arg Leu Tyr Gly Xaa Lys
            20

<210> SEQ ID NO 198
<211> LENGTH: 19
<212> TYPE: PRT
<213> ORGANISM: Artificial Sequence
<220> FEATURE:
<223> OTHER INFORMATION: Synthetic

```
<220> FEATURE:
<221> NAME/KEY: misc_feature
<222> LOCATION: (19)
<223> OTHER INFORMATION: Xaa is D-Leu

<400> SEQUENCE: 198

Val Glu Pro Asn Cys Asp Ile His Val Met Trp Glu Trp Glu Cys Phe
1               5                   10                  15

Lys Arg Xaa

<210> SEQ ID NO 199
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (17)
<223> OTHER INFORMATION: Xaa is N-methyl glutamate

<400> SEQUENCE: 199

Val Glu Pro Asn Cys Asp Ile His Val Lys Trp Glu Trp Glu Cys Phe
1               5                   10                  15

Xaa Arg Leu

<210> SEQ ID NO 200
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (17)
<223> OTHER INFORMATION: Xaa is D-Glu

<400> SEQUENCE: 200

Val Glu Pro Asn Cys Asp Ile His Val Lys Trp Val Glu Glu Cys Phe
1               5                   10                  15

Xaa Arg Leu

<210> SEQ ID NO 201
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (19)
<223> OTHER INFORMATION: Xaa is N-methyl arginine

<400> SEQUENCE: 201

Val Glu Pro Asn Cys Asp Ile His Val Lys Trp Glu Trp Glu Cys Phe
1               5                   10                  15

Glu Arg Xaa

<210> SEQ ID NO 202
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (19)
<223> OTHER INFORMATION: Xaa is D-Asn
```

<400> SEQUENCE: 202

Val Glu Pro Asn Cys Asp Ile His Val Lys Trp Glu Trp Glu Cys Phe
1               5                   10                  15

Glu Arg Xaa

<210> SEQ ID NO 203
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (19)
<223> OTHER INFORMATION: Xaa is 2-aminoisobutyric acid

<400> SEQUENCE: 203

Val Glu Pro Asn Cys Asp Ile His Val Lys Trp Glu Trp Glu Cys Phe
1               5                   10                  15

Glu Arg Xaa

<210> SEQ ID NO 204
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (17)
<223> OTHER INFORMATION: Xaa is 2-aminoisobutyric acid

<400> SEQUENCE: 204

Val Glu Pro Asn Cys Asp Ile His Val Lys Trp Glu Trp Glu Cys Phe
1               5                   10                  15

Xaa Arg Leu

<210> SEQ ID NO 205
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (16)
<223> OTHER INFORMATION: Xaa is Napthaline

<400> SEQUENCE: 205

Val Glu Pro Asn Cys Asp Ile His Val Lys Trp Glu Trp Glu Cys Xaa
1               5                   10                  15

Glu Arg Leu

<210> SEQ ID NO 206
<211> LENGTH: 22
<212> TYPE: PRT
<213> ORGANISM: Artificial Sequence
<220> FEATURE:
<223> OTHER INFORMATION: Synthetic

<400> SEQUENCE: 206

Val Glu Pro Asn Cys Asp Ile His Val Met Trp Val Glu Cys Phe Lys
1               5                   10                  15

Arg Leu Tyr Gly Leu Thr
            20

```
<210> SEQ ID NO 207
<211> LENGTH: 22
<212> TYPE: PRT
<213> ORGANISM: Artificial Sequence
<220> FEATURE:
<223> OTHER INFORMATION: Synthetic

<400> SEQUENCE: 207

Val Glu Pro Asn Cys Asp Ile His Val Met Trp Val Glu Cys Phe Glu
1               5                   10                  15

Arg Leu Tyr Lys Leu Glu
            20

<210> SEQ ID NO 208
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (19)
<223> OTHER INFORMATION: Xaa is D-Leu

<400> SEQUENCE: 208

Val Glu Pro Asn Cys Asp Ile His Val Met Trp Glu Trp Glu Cys Phe
1               5                   10                  15

Glu Arg Xaa

<210> SEQ ID NO 209
<211> LENGTH: 19
<212> TYPE: PRT
<213> ORGANISM: Artificial Sequence
<220> FEATURE:
<223> OTHER INFORMATION: Synthetic

<400> SEQUENCE: 209

Val Glu Pro Asn Cys Asp Ile His Val Glu Trp Glu Trp Glu Cys Phe
1               5                   10                  15

Lys Arg Leu

<210> SEQ ID NO 210
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (18)
<223> OTHER INFORMATION: Xaa is homoargenine
<220> FEATURE:
<221> NAME/KEY: misc_feature
<222> LOCATION: (21)
<223> OTHER INFORMATION: Xaa is D-Ala
<220> FEATURE:
<221> NAME/KEY: misc_feature
<222> LOCATION: (22)
<223> OTHER INFORMATION: Xaa is D-Leu

<400> SEQUENCE: 210

Val Glu Pro Asn Cys Asp Ile His Val Lys Trp Val Trp Glu Cys Phe
1               5                   10                  15

Glu Xaa Leu Tyr Xaa Xaa
            20
```

```
<210> SEQ ID NO 211
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (21)
<223> OTHER INFORMATION: Xaa is D-Leu

<400> SEQUENCE: 211

Val Glu Pro Asn Cys Asp Ile His Val Met Trp Lys Trp Glu Cys Phe
1               5                   10                  15

Glu Arg Tyr Gly Xaa Glu
            20

<210> SEQ ID NO 212
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (22)
<223> OTHER INFORMATION: Xaa is D-Leu

<400> SEQUENCE: 212

Val Glu Pro Asn Cys Asp Ile His Val Lys Trp Val Trp Glu Cys Phe
1               5                   10                  15

Glu Arg Leu Tyr Gly Xaa Glu
            20

<210> SEQ ID NO 213
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (21)
<223> OTHER INFORMATION: Xaa is 2-aminoisobutyric acid

<400> SEQUENCE: 213

Val Glu Pro Asn Cys Asp Ile His Val Lys Trp Val Trp Glu Cys Phe
1               5                   10                  15

Glu Arg Leu Tyr Xaa Leu Glu
            20

<210> SEQ ID NO 214
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (21)
<223> OTHER INFORMATION: Xaa is 2-aminoisobutyric acid

<400> SEQUENCE: 214

Val Glu Pro Asn Cys Asp Ile His Val Met Trp Lys Trp Glu Cys Phe
1               5                   10                  15

Glu Arg Leu Tyr Xaa Leu Glu
            20
```

```
<210> SEQ ID NO 215
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (19)
<223> OTHER INFORMATION: Xaa is D-Leu

<400> SEQUENCE: 215

Val Glu Pro Asn Cys Asp Ile His Val Met Trp Lys Trp Glu Cys Phe
1               5                   10                  15

Glu Arg Xaa Lys
            20

<210> SEQ ID NO 216
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (18)
<223> OTHER INFORMATION: Xaa is epsilon acyl lysine
<220> FEATURE:
<221> NAME/KEY: misc_feature
<222> LOCATION: (21)
<223> OTHER INFORMATION: Xaa is D-Ala
<220> FEATURE:
<221> NAME/KEY: misc_feature
<222> LOCATION: (22)
<223> OTHER INFORMATION: Xaa is D-Leu

<400> SEQUENCE: 216

Val Glu Pro Asn Cys Asp Ile His Val Lys Trp Val Trp Glu Cys Phe
1               5                   10                  15

Glu Xaa Leu Tyr Xaa Xaa
            20

<210> SEQ ID NO 217
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (18)
<223> OTHER INFORMATION: Xaa is epsilon acyl lysine
<220> FEATURE:
<221> NAME/KEY: misc_feature
<222> LOCATION: (19)
<223> OTHER INFORMATION: Xaa is cycloleucine
<220> FEATURE:
<221> NAME/KEY: misc_feature
<222> LOCATION: (21)
<223> OTHER INFORMATION: Xaa is D-Ala
<220> FEATURE:
<221> NAME/KEY: misc_feature
<222> LOCATION: (22)
<223> OTHER INFORMATION: Xaa is D-Leu

<400> SEQUENCE: 217

Val Glu Pro Asn Cys Asp Ile His Val Lys Trp Val Trp Glu Cys Phe
1               5                   10                  15

Glu Xaa Xaa Tyr Xaa Xaa
            20
```

```
<210> SEQ ID NO 218
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (18)
<223> OTHER INFORMATION: Xaa is epsilon acyl lysine
<220> FEATURE:
<221> NAME/KEY: misc_feature
<222> LOCATION: (19)
<223> OTHER INFORMATION: Xaa is 3-methyl valine
<220> FEATURE:
<221> NAME/KEY: misc_feature
<222> LOCATION: (21)
<223> OTHER INFORMATION: Xaa is D-Ala
<220> FEATURE:
<221> NAME/KEY: misc_feature
<222> LOCATION: (22)
<223> OTHER INFORMATION: Xaa is D-Leu

<400> SEQUENCE: 218

Val Glu Pro Asn Cys Asp Ile His Val Lys Trp Val Trp Glu Cys Phe
1               5                   10                  15

Glu Xaa Xaa Tyr Xaa Xaa
            20
```